US008324179B2

(12) United States Patent
Chen et al.

(10) Patent No.: US 8,324,179 B2
(45) Date of Patent: Dec. 4, 2012

(54) NUCLEOSIDE ANALOGS FOR ANTIVIRAL TREATMENT

(75) Inventors: James M. Chen, San Ramon, CA (US); Alan X. Huang, San Mateo, CA (US); Richard L. Mackman, Millbrae, CA (US); Jay Parrish, Redwood City, CA (US); Jason K. Perry, San Francisco, CA (US); Oliver L. Saunders, San Mateo, CA (US); David Sperandio, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 486 days.

(21) Appl. No.: 12/524,545

(22) PCT Filed: Feb. 8, 2008

(86) PCT No.: PCT/US2008/001743
§ 371 (c)(1),
(2), (4) Date: Nov. 30, 2009

(87) PCT Pub. No.: WO2008/100447
PCT Pub. Date: Aug. 21, 2008

(65) Prior Publication Data
US 2010/0104532 A1    Apr. 29, 2010

Related U.S. Application Data

(60) Provisional application No. 60/900,692, filed on Feb. 9, 2007.

(51) Int. Cl.
*A01N 43/04* (2006.01)
*A61K 31/70* (2006.01)
(52) U.S. Cl. ............... 514/43; 514/44 R; 514/45; 514/49
(58) Field of Classification Search .................. None
See application file for complete search history.

(56) References Cited

U.S. PATENT DOCUMENTS

| 5,672,697 | A | * | 9/1997 | Buhr et al. ................. 536/26.7 |
| 5,817,647 | A | | 10/1998 | Casara et al. |
| 5,892,024 | A | | 4/1999 | Chaturvedula et al. |
| 5,922,696 | A | | 7/1999 | Casara et al. |
| 5,952,478 | A | | 9/1999 | Baxter et al. |
| 6,087,490 | A | | 7/2000 | Baxter et al. |
| 2003/0004345 | A1 | | 1/2003 | Casara et al. |
| 2004/0023921 | A1 | | 2/2004 | Hong et al. |
| 2004/0059104 | A1 | | 3/2004 | Cook et al. |
| 2006/0074035 | A1 | | 4/2006 | Hong et al. |

FOREIGN PATENT DOCUMENTS

| EP | 0479640 A2 | 4/1992 |
| EP | 0 532 423 A1 | 3/1993 |
| EP | 0 618 214 A1 | 10/1994 |
| EP | 0 629 633 A2 | 12/1994 |
| WO | WO-94/22882 A1 | 10/1994 |
| WO | WO-96/07666 A1 | 3/1996 |
| WO | WO-03/073989 A2 | 9/2003 |
| WO | WO-2004/096286 A2 | 11/2004 |
| WO | WO-2006/015261 A2 | 2/2006 |

OTHER PUBLICATIONS

Lera et al. Organic Letters (2000), vol. 2, pp. 3873-3875.*
Abbas et al. (2000) "An Improved procedure for the synthesis of vinylphosphonate-linked nucleic acids," *Tetrahedron Letters* 41:4513-4517.
Abbas et al. (2001) "Commercially Available 5'-DMT Phosphoramidites as Reagents for the Synthesis of Vinylphosphonate-Linked Oligonucleic Acids," *Organic Letters* 3(21):3365-3367.
Abbas, S. et al (1999) "A Novel Palladium-Catalysed Coupling Strategy for the Rapid Synthesis of Nucleic Acid Analogues Bearing Modified Backbones," *Synlett* 7:1124-1126.
Almer et al. (1991) "Synthesis of a Phosphonomethyl Analogue of 3'-Deoxy-3'-fluorothymidine," *Acta Cheinica Scandinavica* 45:766-767.
Bertram et al. (2002) "Vinylphosphonate Internucleotide Linkages inhibit the Activity of PcrA DNA Helicase," *Biochemistry* 41:7725-7731.
Freeman et al. (1992) "3'-Azido-3',5'-dideoxythymidine-5'-methylphosphonic Acid Disphosphate: Synthesis and HIV-1 Reverse Transcriptase Inhibitors," *J. Med. Chem* 35:3192-3196.
Garvey et al. (1998) "Nucleotide and Nucleoside Analogues as Inhibitors of Cytosolic 5'-Nucleotidase I from Heart," *Biochemistry* 17:9043-9051.
Hai et al. (1982) "Species- or isozyme-Specific Enzyme Inhibitors. 7.[1] Selective Effects in Inhibitions of Rat Adenylate Kinase isozymes by Adenosine 5'-Phosphate Derivatives," *J. Med. Chem.* 25:806-812.
Hampton et al. (1976) "Evidence for the Conformation About the C(5') -O(5') Bond of AMP Complexed to AMP Kinase: Substrate Properties of a Vinyl Phosphonate Analog of AMP," *Bioorganic Chemistry* 5:31-35.
International Preliminary Report on Patentability for PCT/US2008/001743, issued Aug. 11, 2009.
International Search Report and Written Opinion for PCT/US2008/001743, mailed May 11, 2008.
Jones (1968) "The Synthesis of 6'-Deoxyhomonucleoside-6'-phosphonic Acids," *Journal of the American Chemical Society* 90:19 pp. 5337-5338.

(Continued)

*Primary Examiner* — Patrick Lewis
(74) *Attorney, Agent, or Firm* — Fitzpatrick, Cella, Harper & Scinto

(57) ABSTRACT

The invention provides unsaturated phosphonates of Formula I or a tautomer or pharmaceutically acceptable salt thereof, as described herein, as well as pharmaceutical compositions comprising the compounds, and therapeutic methods comprising administering the compounds. The compounds have anti-viral properties and are useful for treating viral infections (e.g. HCV) in animals (e.g. humans).

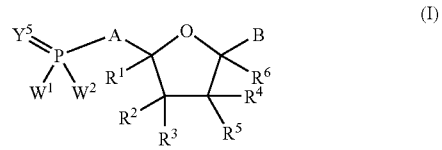

(I)

22 Claims, No Drawings

OTHER PUBLICATIONS

Jung et al. (2000) "Synthesis of Phosphonate Derivatives of Uridine, Cytidine, and Cytosine Arabinoside," *Bioorganic & Medicinal Chemistry* 8:2501-2509.

Kappler et al. (1985) "Use of a Vinyl Phosphonate Analog of ATP as a Rotationally Constrained Probe of the C5'-O5' Torsion Angle in ATP Complexed to Methionine Adenosyl Transferase," *Bioorganic Chemistry* 13:289-295.

Kers et al. (1999) "Preparation of nucleoside 5'-deoxy-5'-methylenephosphonates as building blocks for the synthesis of methylenephosphonate analogues," *J. Chem. Soc. Perkin Trans I* 2585-1590.

Koh et al. (2005) "Design, Synthesis, and Antiviral Activity of Adenosine 5'-Phosphonate Analogues as Chain Terminators against Hepatitis C Virus," *J Med Chem* 48:2867-2875.

Lera et al. (2001) "An Olefin Cross-Metathesis Approach to Vinylphophonate-Linked Nucleic Acids," *Organis Letters* 3(17):2765-2768.

Montgomery et al. (1979) "Phosphonate Analogue of 2'-Deoxy-5-fluorouridylic Acid," *Journal of Medicinal Chemistry* 22(1):109-111.

Szabo et al. (1995) "Synthesis and Some Conformational Features of the 5'-Deoxy-5-methylphosphonate Linked Dimmer, 5'-Deoxy-5'-C-(phosphonomethyl)thymidin-3'-yl(Thymidin-5'-yl)methylphosphonate [p(CH$_2$)T$_p$(CH$_2$)T]," *Tetrahedron* 51(14):4145-4160.

Zhao et al. (1996) "Synthesis and Preliminary Biochemical Studies with 5'-Deoxy-5'-methylidyne Phosphonate Linked Thymidine Oligonucleotides," *Tetrahedron Letters* 37(35):6239-6242.

\* cited by examiner

NUCLEOSIDE ANALOGS FOR ANTIVIRAL TREATMENT

RELATED APPLICATIONS

This application claims the benefit of U.S. Provisional Application Ser. No. 60/900,692 filed on Feb. 9, 2007, the entirety of which is incorporated herein by reference.

FIELD OF THE INVENTION

The invention relates generally to compounds with antiviral activity and more specifically to inhibitors of hepatitis C virus RNA-dependent RNA polymerase.

BACKGROUND OF THE INVENTION

The hepatitis C virus (HCV) is the leading cause of chronic liver disease worldwide (Boyer, N. et al. J Hepatol. 32:98-112, 2000). An estimated 170 million persons are infected with HCV worldwide. (Boyer, N. et al, J Hepatol. 32:98-112, 2000). A significant focus of current antiviral research is directed toward the development of improved methods of treatment of chronic HCV infections in humans (Di Besceglie, A. M. and Bacon, B. R., Scientific American, October: 80-85, (1999)). A number of HCV treatments are reviewed by Bymock et al. in Antiviral Chemistry & Chemotherapy, 11:2; 79-95 (2000).

Viral serine protease and the RNA-dependent RNA polymerase (RdRp) are the best studied targets for the development of novel HCV therapeutic agents. The NS5B polymerase is a target for inhibitors in early human clinical trials (Sommadossi, J., WO 01/90121 A2). These enzymes have been extensively characterized at the biochemical and structural level, with screening assays for identifying selective inhibitors (De Clercq, E. (2001) J. Pharmacol. Exp. Ther. 297:1-10; De Clercq, E. (2001) J. Clin. Virol. 22:73-89). Recent structural work on HCV RdRp has identified catalytic and regulatory nucleotide binding sites (Bressanelli S. et al (2002) J. Virol. 76:3482-92). Since HCV does not replicate in the laboratory, there are difficulties in developing cell-based assays and preclinical animal systems.

Currently, there are two primary antiviral compounds, ribavirin and interferon-alpha (α) (IFN) which are used for the treatment of chronic HCV infections in humans. Ribavirin alone is not effective in reducing viral RNA levels, has significant toxicity, and is known to induce anemia. The combination of IFN and ribavirin for the treatment of HCV infection has been reported to be effective in the treatment of IFN-naive patients (Battaglia, A. M. et al., Ann. Pharmacother. 34:487-494, 2000). Results are promising for this combination treatment both before hepatitis develops or when histological disease is present (Berenguer, M. et al. (1998) Antivir. Ther. 3 (Suppl. 3):125-136), but there is a need for improved anti-HCV therapeutic agents, i.e. drugs having improved antiviral and pharmacokinetic properties with enhanced activity against development of HCV resistance, improved oral bio-availability, greater efficacy, fewer undesirable side effects and extended effective half-life in vivo (De Francesco, R. et al (2003) Antiviral Research 58:1-16). The instant invention provides improved anti-HCV therapeutic agents.

Unsaturated linker phosphonate analogs of nucleotides have been disclosed in U.S. Pat. No. 5,672,697; WO 9607666; EP 629633; US 2006074035; *J. Med. Chem.* 2005, 48, 2867-2875; *Biochemistry* 2002, 41, 7725-7731; *Org. Lett.* 2001, 3, 3365-3367; *Org. Lett.* 2001, 3, 2756-2768; *Tetrahedron. Lett.* 2000, 41, 4513-4517; *Bioorg. & Med. Chem.* 2000, 8, 2501-2509; *J. Chem. Soc., Perkins Trans.* 1999, 2585-2590; *Synlett* 1999, 1124-1126; *Biochemistry* 1998, 37, 9043-9051; *Tetrahedron Lett.* 1996, 37, 6239-6242; *Tetrahedron* 1995, 51, 4145-4160; *Nucleic Acids Research* 1995, 23, 893-900; *Nucleosides Nucleotides* 1995, 14, 871-874; *Antiviral Chemistry Chemotherapy* 1994, 5, 221-228; *Tetrahedron Lett.* 1993, 34, 2723-2726; EP 479640; *J. Med. Chem.* 1992, 35, 3192-3196; *Nucleosides & Nucleotides* 1992, 11, 947-956; *Acta Chemica Scandinavica* 1991, 45, 766-767; *Bioorganic Chemistry* 1985, 13, 289-295; *J. Med. Chem.* 1982, 25, 806-812; *J. Med. Chem.* 1979, 22, 109-111; and *Bioorganic Chemistry* 1976, 5, 31-35. Unsaturated linker phosphonate derivatives of purine and pyrimidine compounds have been reported to be useful as antiviral agents (US 2003/0004345A1; EP 0532423A1; EP 0618214A1; EP 0701562B1; U.S. Pat. Nos. 5,817,647; 5,922,696; WO 94/22882).

SUMMARY OF THE INVENTION

In one aspect, this invention provides a compound of Formula I:

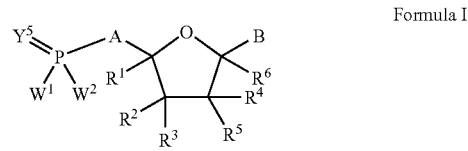

Formula I wherein:
A is $-CR^d=CR^d-$ or $$-C\equiv C-;$$

B is a nucleoside base which is optionally substituted;
each $R^1$, $R^2$, $R^3$, $R^4$, and $R^5$ is independently H, $OR^a$, $N(R^a)_2$, $N_3$, CN, $NO_2$, $SR^a$, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, or $C_2$-$C_8$ substituted alkynyl; or $R^2$ and $R^4$ are taken together along with the atoms to which they are attached to form a double bond; or $R^2$ and $R^3$ taken together are $=O$, $=NR^b$, or $=CR^cR^d$; or $R^2$ and $R^3$ taken together with the carbon atom to which they are attached form a 3-7 membered carbocyclic ring wherein one carbon atom can optionally be replaced with $-O-$, $-S-$ or $-NR^a-$;
$R^6$ is H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$alkynyl, or $C_2$-$C_8$ substituted alkynyl;
each $R^a$ is independently H, $(C_1$-$C_6)$alkyl, $(C_2$-$C_6)$alkenyl, $(C_2$-$C_6)$alkynyl or $(C_1$-$C_6)$alkanoyl;
each $R^b$ is independently H, $(C_1$-$C_6)$alkyl, $(C_2$-$C_6)$alkenyl, $(C_2$-$C_6)$alkynyl, $O-(C_1$-$C_6)$alkyl or OH;
each $R^c$ and $R^d$ is independently H, $(C_1$-$C_6)$alkyl, $(C_2$-$C_6)$alkenyl, $(C_2$-$C_6)$alkynyl or halo;
wherein each $(C_1$-$C_6)$alkyl, $(C_2$-$C_6)$alkenyl, or $(C_2$-$C_6)$alkynyl of $R^a$-$R^d$ is optionally substituted with one or more halo, hydroxy, or $(C_1$-$C_6)$alkoxy;
$Y^5$ is O, S, NR, $^+N(O)(R)$, $N(OR)$, $^+N(O)(OR)$, or $N-NR_2$;
each $Y^1$ is independently O, S, NR, $^+N(O)(R)$, $N(OR)$, $^+N(O)(OR)$, or $N-NR_2$;

$W^1$ and $W^2$ are each independently a group of the formula:

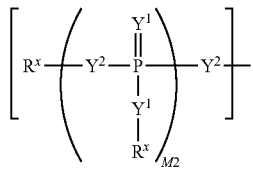

wherein:

each $Y^2$ is independently a bond, O, $CR_2$, NR, $^+N(O)(R)$, N(OR), $^+N(O)(OR)$, N—$NR_2$, S, S—S, S(O), or $S(O)_2$;

M2 is 0, 1 or 2;

each $R^y$ is independently H, F, Cl, Br, I, OH, R, —C($=Y^1$)R, —C($=Y^1$)OR, —C($=Y^1$)N(R)$_2$, —N(R)$_2$, —$^+$N(R)$_3$, —SR, —S(O)R, —S(O)$_2$R, —S(O)(OR), —S(O)$_2$(OR), —OC($=Y^1$)R, —OC($=Y^1$)OR, —OC($=Y^1$)(N(R)$_2$), —SC($=Y^1$)R, —SC($=Y^1$)OR, —SC($=Y^1$)(N(R)$_2$), —N(R)C($=Y^1$)R, —N(R)C($=Y^1$)OR, or —N(R)C($=Y^1$)N(R)$_2$, amino (—NH$_2$), ammonium (—NH$_3^+$), alkylamino, dialkylamino, trialkylammonium, $C_1$-$C_8$ alkyl, $C_1$-$C_8$ alkylhalide, carboxylate, sulfate, sulfamate, sulfonate, $C_1$-$C_8$ alkylsulfonate, $C_1$-$C_8$ alkylamino, $C_1$-$C_8$ alkylhydroxyl, $C_1$-$C_8$ alkylthiol, alkylsulfone (—SO$_2$R), sulfonamide (—SO$_2$NR$_2$), alkylsulfoxide (—SOR), ester (—C($=$O)OR), amido (—C($=$O)NR$_2$), nitrile (—CN), azido (—N$_3$), nitro (—NO$_2$), $C_1$-$C_8$ alkoxy (—OR), $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, a protecting group or $W^3$; or when taken together, two $R^y$ on the same carbon atom form a carbocyclic ring of 3 to 7 carbon atoms;

each $R^x$ is independently $R^y$, a protecting group, or the formula:

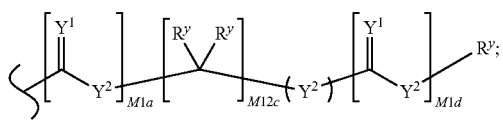

wherein:

M1a, M1c, and M1d are independently 0 or 1;

M12c is 0, 1, 2, 3, 4, 5, 6, 7, 8, 9, 10, 11 or 12; or when taken together, two $R^x$ are optionally substituted $C_2$-$C_4$ alkylene thereby forming a phosphorous-containing heterocycle;

each R is independently H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group;

$W^3$ is $W^4$ or $W^5$; $W^4$ is R, —C($Y^1$)$R^y$, —C($Y^1$)$W^5$, —SO$_2$$R^y$, or —SO$_2$$W^5$; and $W^5$ is a carbocycle or a heterocycle wherein $W^5$ is independently substituted with 0 to 3 $R^y$ groups; or or a pharmaceutically acceptable salt, thereof;

provided that $W^1$ or $W^2$ is not an oxygen-linked 2'-deoxynucleoside;

provided that when

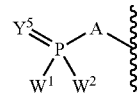

of Formula I is:

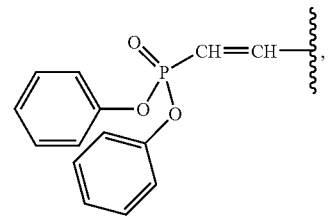

then

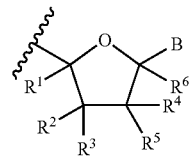

of Formula I is not:

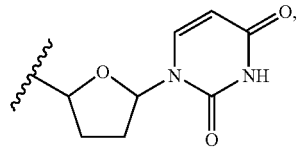

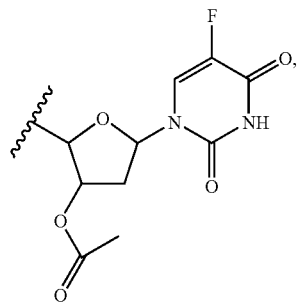

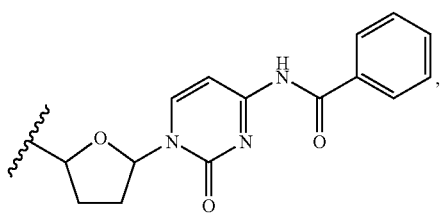

-continued

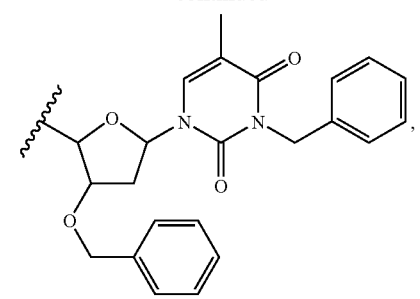

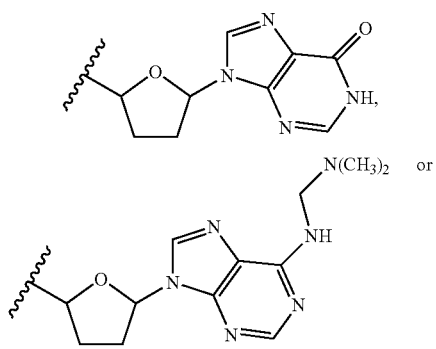

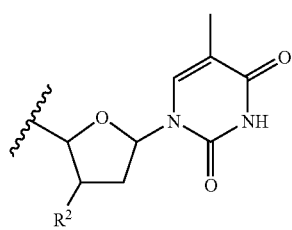

wherein $R^2$ is H, F or $N_3$;
provided that when

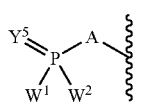

of Formula I is:

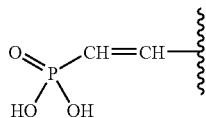

then

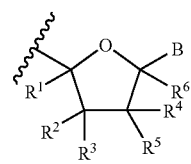

of Formula I is not:

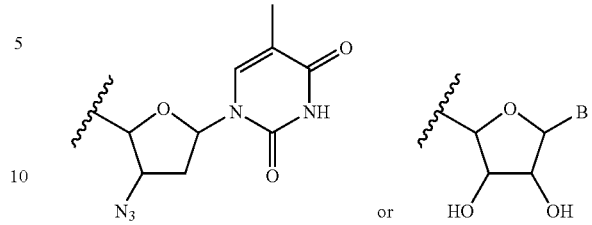

wherein B is:

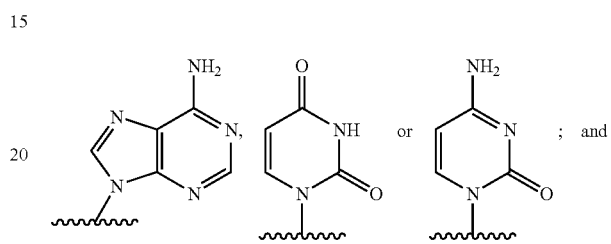

provided that the compound of Formula I is not:

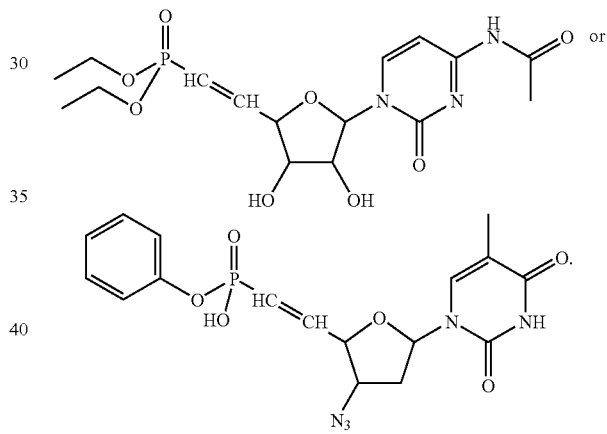

In another aspect, the present invention provides novel compounds with activity against infectious viruses. Without wishing to be bound by theory, the compounds of the invention may inhibit retroviral RNA-dependent RNA polymerase and thus inhibit the replication of the virus. They may be useful for treating human patients infected with a human retrovirus, such as hepatitis C.

In another aspect, the present invention relates generally to the accumulation or retention of therapeutic compounds inside cells. The invention is more particularly related to attaining high concentrations of active metabolite molecules in HCV infected cells. Intracellular targeting may be achieved by methods and compositions which allow accumulation or retention of biologically active agents inside cells. Such effective targeting may be applicable to a variety of therapeutic formulations and procedures.

In another aspect, the invention provides a pharmaceutical composition comprising an effective amount of a Formula I compound, or a pharmaceutically acceptable salt thereof, in combination with a pharmaceutically acceptable diluent or carrier.

In another embodiment, the present application provides for combination pharmaceutical agent comprising:
a) a first pharmaceutical composition comprising a compound of Formula I; or a pharmaceutically acceptable salt, solvate, or ester thereof; and
b) a second pharmaceutical composition comprising at least one additional therapeutic agent selected from the group consisting of interferons, ribavirin analogs, NS3 protease inhibitors, alpha-glucosidase 1 inhibitors, hepatoprotectants, non-nucleoside inhibitors of HCV, and other drugs for treating HCV.

In another embodiment, the present application provides for a method of inhibiting HCV polymerase, comprising contacting a cell infected with HCV with an effective amount of a compound of Formula I; or a pharmaceutically acceptable salts, solvate, and/or ester thereof.

In another embodiment, the present application provides for a method of inhibiting HCV polymerase, comprising contacting a cell infected with HCV with an effective amount of a compound of Formula I; or a pharmaceutically acceptable salts, solvate, and/or ester thereof; and at least one additional therapeutic agent.

In another embodiment, the present application provides for a method of treating HCV in a patient, comprising administering to said patient a therapeutically effective amount of a compound of Formula I; or a pharmaceutically acceptable salt, solvate, and/or ester thereof.

In another embodiment, the present application provides for a method of treating HCV in a patient, comprising administering to said patient a therapeutically effective amount of a compound of Formula I; or a pharmaceutically acceptable salt, solvate, and/or ester thereof; and at least one additional therapeutic agent.

Another aspect of the invention provides a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another aspect, this invention pertains to a method of increasing cellular accumulation and retention of drug compounds, thus improving their therapeutic and diagnostic value.

In another aspect, the invention also provides a method of inhibiting HCV, comprising administering to a mammal infected with HCV an amount of a Formula I compound, effective to inhibit the growth of said HCV infected cells.

In another aspect, the invention also provides processes and novel intermediates disclosed herein which are useful for preparing Formula I compounds of the invention.

In other aspects, novel methods for synthesis, analysis, separation, isolation, purification, characterization, and testing of the compounds of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

In one aspect, this invention provides a compound of Formula II:

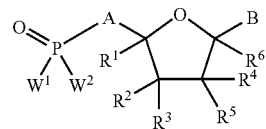

Formula II wherein:
A is —$CR^d$=$CR^d$— or

—C≡C—;

B is a nucleoside base which is optionally substituted;
each $R^1$, $R^2$, $R^3$, $R^4$, and $R^5$ is independently H, $OR^a$, $N(R^a)_2$, $N_3$, CN, $NO_2$, $SR^a$, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, or $C_2$-$C_8$ substituted alkynyl; or $R^2$ and $R^4$ are taken together along with the atoms to which they are attached to form a double bond; or $R^2$ and $R^3$ taken together are =O, =$NR^b$, or =$CR^cR^d$; or $R^2$ and $R^3$ taken together with the carbon atom to which they are attached form a 3-7 membered carbocyclic ring wherein one carbon atom can optionally be replaced with —O—, —S— or —$NR^a$—;
$R^6$ is H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, or $C_2$-$C_8$ substituted alkynyl;
each $R^a$ is independently H, ($C_1$-$C_6$)alkyl, ($C_2$-$C_6$)alkenyl, ($C_2$-$C_6$)alkynyl or ($C_1$-$C_6$)alkanoyl;
each $R^b$ is independently H, ($C_1$-$C_6$)alkyl, ($C_2$-$C_6$)alkenyl, ($C_2$-$C_6$)alkynyl, O—($C_1$-$C_6$)alkyl or OH;
each $R^c$ and $R^d$ is independently H, ($C_1$-$C_6$)alkyl, ($C_2$-$C_6$)alkenyl, ($C_2$-$C_6$)alkynyl or halo;
wherein each ($C_1$-$C_6$)alkyl, ($C_2$-$C_6$)alkenyl, or ($C_2$-$C_6$)alkynyl of $R^a$—$R^d$ is optionally substituted with one or more halo, hydroxy, or ($C_1$-$C_6$)alkoxy;
each $Y^1$ is independently O, S, NR, $^+$N(O)(R), N(OR), $^+$N(O)(OR), or N—$NR_2$;
$W^1$ and $W^2$ are each independently a group of the formula:

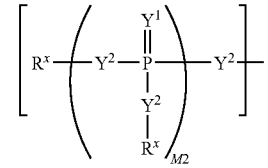

wherein:
each $Y^2$ is independently a bond, O, $CR_2$, NR, $^+$N(O)(R), N(OR), $^+$N(O)(OR), N—$NR_2$, S, S—S, S(O), or $S(O)_2$;
M2 is 0, 1 or 2;
each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, or —N(R)C(=$Y^1$)N(R)$_2$, amino (—NH$_2$), ammonium (—NH$_3^+$), alkylamino, dialkylamino, trialkylammonium, $C_1$-$C_8$ alkyl, $C_1$-$C_8$ alkylhalide, carboxylate, sulfate, sulfamate, sulfonate, $C_1$-$C_8$ alkylsulfonate, $C_1$-$C_8$ alkylamino, $C_1$-$C_8$ alkylhydroxyl, $C_1$-$C_8$ alkylthiol, alkylsulfone (—$SO_2R$), sulfonamide (—$SO_2NR_2$), alkylsulfoxide (—SOR), ester (—C(=O)OR), amido (—C(=O)$NR_2$), nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl $C_2$-$C_8$ substituted alkynyl, a protecting group, or $W^3$; or when taken together, two $R^y$ on the same carbon atom forms a carbocyclic ring of 3 to 7 carbon atoms;

each $R^x$ is independently $R^y$, a protecting group, or the formula:

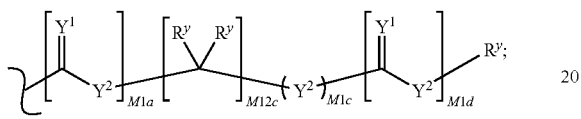

wherein:

M1a, M1c, and M1d are independently 0 or 1;

M12c is 0, 1, 2, 3, 4, 5, 6, 7, 8, 9, 10, 11 or 12; or when taken together, two $R^x$ are optionally substituted $C_2$-$C_4$ alkylene thereby forming a phosphorous-containing heterocycle;

each R is independently H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle or a protecting group;

$W^3$ is $W^4$ or $W^5$; $W^4$ is R, —C($Y^1$)$R^y$, —C($Y^1$)$W^5$, —$SO_2R^y$, or —$SO_2W^5$; and $W^5$ is a carbocycle or a heterocycle wherein $W^5$ is independently substituted with 0 to 3 $R^y$ groups; or or a pharmaceutically acceptable salt, thereof;

provided that $W^1$ or $W^2$ is not an oxygen-linked 2'-deoxynucleoside;

provided that when

of Formula II is:

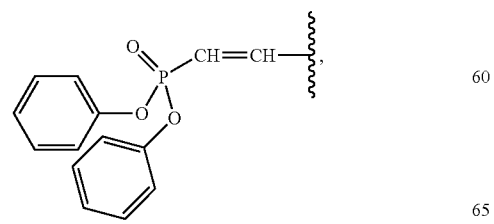

then

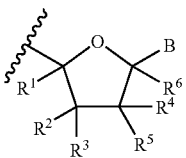

of Formula II is not:

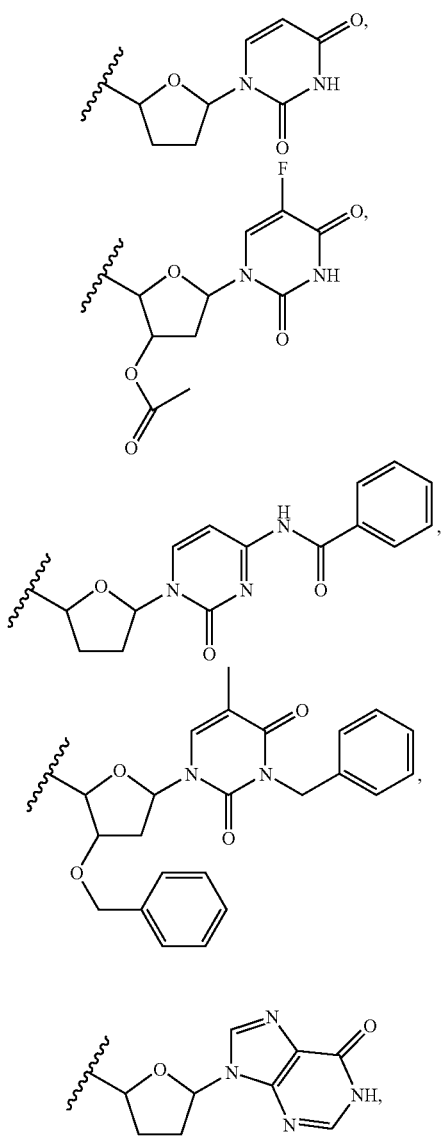

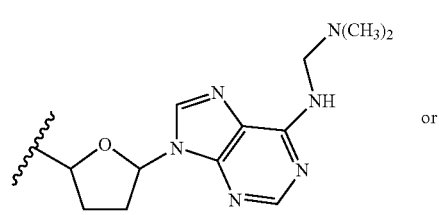

or

-continued

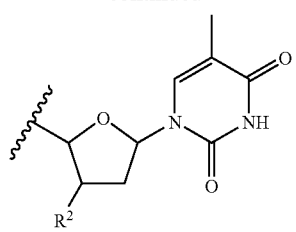

wherein $R^2$ is H, F or $N_3$;
provided that when

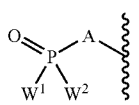

of Formula II is:

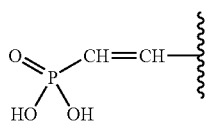

then

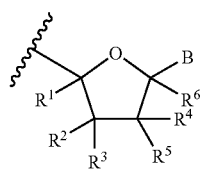

of Formula II is not:

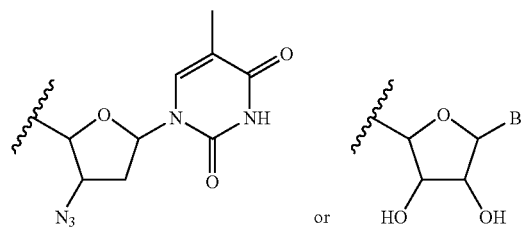

wherein B is:

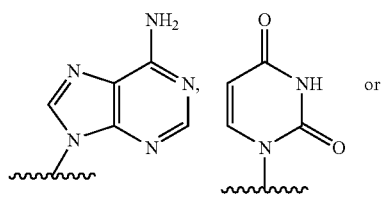

-continued

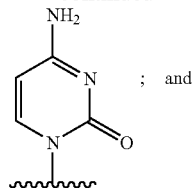; and provided that the compound of Formula II is not:

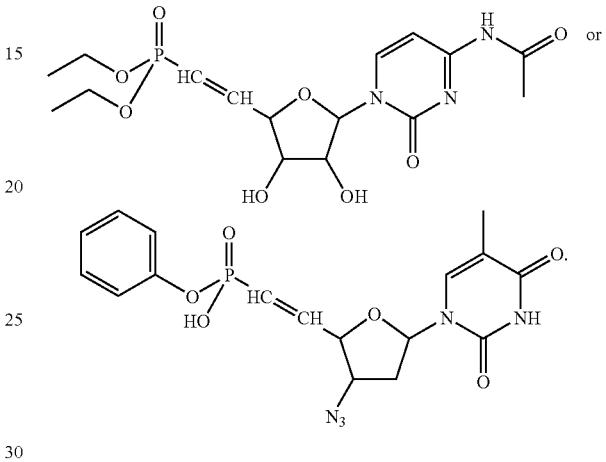

In one embodiment of the invention of Formula II, $R^1$ is H. In another embodiment, $R^1$ is not H. In another embodiment, $R^1$ is CN, $N_3$, methyl, $OR^a$, ethenyl, or ethynyl. In another embodiment $R^1$ is $N_3$.

In one embodiment of the invention of Formula II, $R^2$ and $R^3$ taken together are =O, =$NR^b$, or =$CR^cR^d$. In another embodiment, $R^2$ and $R^3$ taken together with the carbon atom to which they are attached form a 3-7 membered carbocyclic ring wherein one carbon atom can optionally be replaced with —O—, —S— or —$NR^a$—. In another embodiment, $R^2$ and $R^3$ are both H and at least one of $R^4$ and $R^5$ is not H. In another embodiment, $R^2$ and $R^3$ are both H and at least one of $R^4$ and $R^5$ is OH. In another embodiment, $R^2$ and $R^4$ are taken together along with the atoms to which they are attached to form a double bond. In another embodiment, each $R^3$ and $R^4$ is H, $R^2$ is H or F and $R^5$ is OH. In another embodiment $R^2$ and $R^4$ are H, $R^3$ is OH and $R^5$ is F.

In one embodiment of the invention of Formula II, $R^6$ is methyl, ethenyl, or ethynyl. In another embodiment, $R^6$ is H.

In one embodiment of the invention of Formula II, A is —$CR^d$=$CR^d$— wherein each $R^d$ is independently H, ($C_1$-$C_6$) alkyl, ($C_2$-$C_6$)alkenyl, ($C_2$-$C_6$)alkynyl or halo. In another embodiment A is

—C≡C—.

In a preferred embodiment A is —$CR^d$=$CR^d$— and each $R^d$ is H or halo. In a preferred embodiment, A is cis —CH=CH—. In another preferred embodiment, A is trans —CH=CH—. In another preferred embodiment, A is cis —CF=CH—. In another preferred embodiment, A is trans —CF=CH—. In another preferred embodiment, A is cis —CH=CF—. In another preferred embodiment, A is trans —CH=CF—.

In one embodiment of the invention of Formula II, $W^1$ or $W^2$ is not an oxygen-linked 2'-deoxynucleoside; when
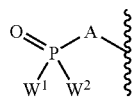
of Formula II is:
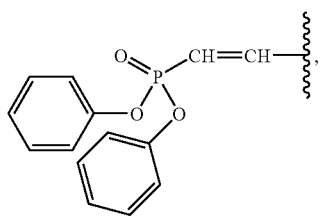
then
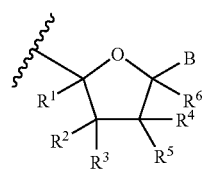
of Formula II is not:
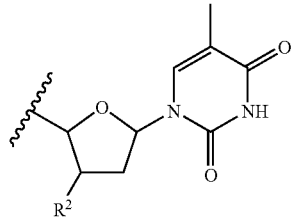
wherein $R^2$ is H, F or $N_3$,
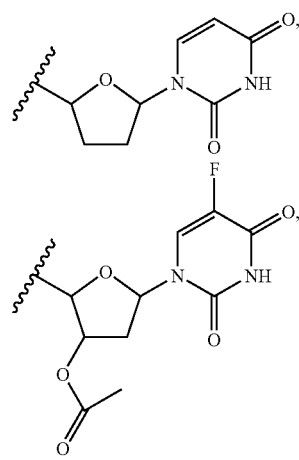
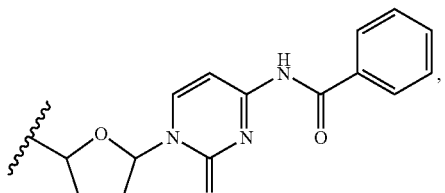
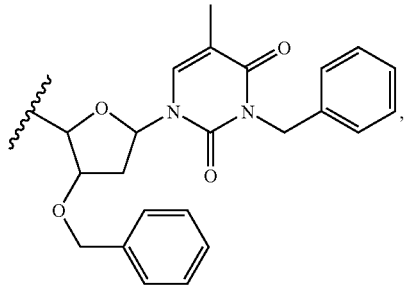
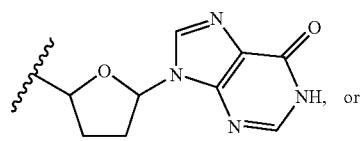
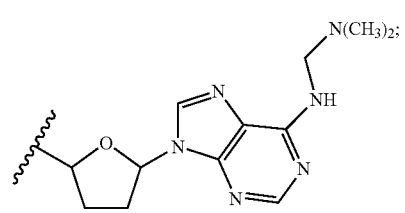
when
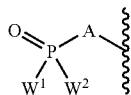
of Formula II is:
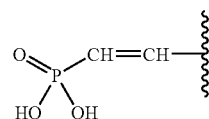
then
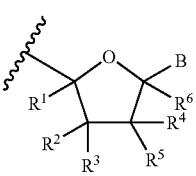

of Formula II is not:

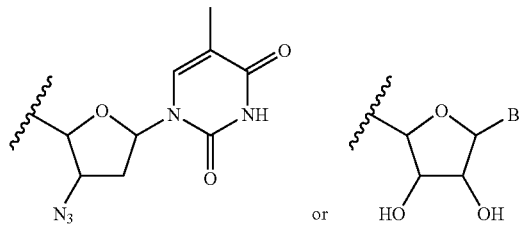

wherein B is:

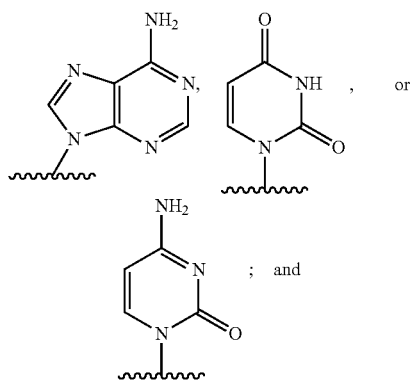

the compound of Formula II is not:

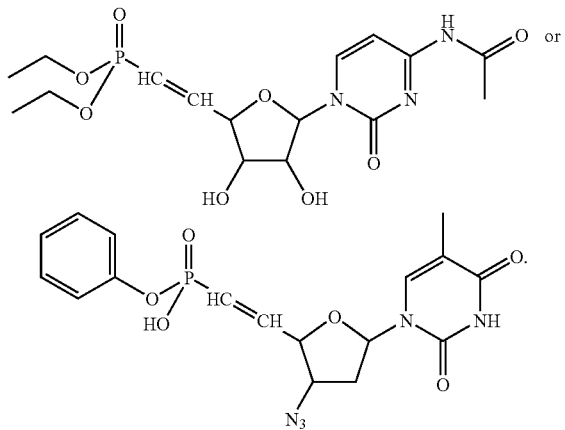

In another embodiment of the invention of Formula II, B has the following formula:

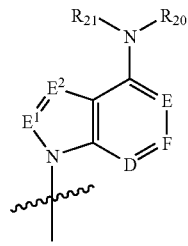

wherein:

$R_{20}$ is OH or $(C_1-C_6)$alkoxy that is optionally substituted with one or more $R_{22}$; and $R_{21}$ is H or $(C_1-C_6)$alkyl that is optionally substituted with one or more $R_{22}$; or $R_{20}$ and $R_{21}$ together with the nitrogen to which they are attached form a heterocyclic ring that is optionally subsitituted with one or more $R_{22}$;

each $R_{22}$ is independently $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, $NR_{23}R_{24}$, —C(=O)$NR_{23}R_{24}$, aryl, heteroaryl, cyano, halo, hydroxy, nitro, carboxy, or $(C_3-C_8)$cycloalkyl;

$R_{23}$ and $R_{24}$ are each independently H, $(C_1-C_6)$alkyl or $(C_1-C_6)$alkanoyl;

wherein each aryl or heteroaryl of $R_{22}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, $NR_{23}R_{24}$, —C(=O)$NR_{23}R_{24}$, cyano, halo, hydroxy, nitro, carboxy, $(C_3-C_8)$cycloalkyl, trifluoromethoxy, mercapto, or trifluoromethyl; and D, E, $E^1$, $E^2$, and F are each independently >N or >C—$R_{25}$;

each $R_{25}$ is independently H, cyano, nitro, $(C_1-C_6)$alkyl, $(C_1-C_6)$alkenyl, $(C_1-C_6)$alkynyl, —NHCONH$_2$, C(=O)$NR_{26}R_{27}$, COOR$_{28}$, hydroxy, $(C_1-C_6)$alkoxy, —$NR_{26}R_{27}$, halo, 1,3-oxazol-2-yl, 1,3-thiazol-2-yl, imidazol-2-yl, 2-oxo-[1,3]dithiol-4-yl, furan-2-yl, or 2H-[1,2,3]triazol-4-yl;

each $R_{26}$ and $R_{27}$ is independently H, $(C_1-C_6)$alkyl, $(C_1-C_6)$alkenyl, $(C_1-C_6)$alkynyl, $(C_3-C_8)$cycloalkyl, aryl, heterocycle, hydroxy, $(C_1-C_6)$alkoxy; or $R_{26}$ and $R_{27}$ together with the nitrogen to which they are attached form a heterocycle; and each $R_{28}$ is independently H, $(C_1-C_6)$alkyl, $(C_1-C_6)$alkenyl, $(C_1-C_6)$alkynyl, $(C_3-C_8)$cycloalkyl, aryl, or heterocycle;

wherein each $(C_1-C_6)$alkyl, $(C_1-C_6)$alkenyl, $(C_1-C_6)$alkynyl, $(C_3-C_8)$cycloalkyl, aryl, heterocycle, and $(C_1-C_6)$alkoxy of $R_{26}$ and $R_{27}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, NH$_2$, cyano, halo, hydroxy, nitro, carboxy, $(C_3-C_8)$cycloalkyl, $(C_3-C_8)$cycloalkoxy, trifluoromethoxy, or mercapto.

A specific value for $R_{20}$ is OH, methoxy, or propoxy; and for $R_{21}$ is H.

A specific value for $R_{20}$ and $R_{21}$ together with the nitrogen to which they are attached form a pyrrolidin-1-yl, 1,3,4,9-tetrahydro-beta-carbolin-2-yl, piperidinyl, azetidinyl, 3,6-dihydro-2H-pyridin-1-yl, or 3,4-dihydro-1H-isoquinolin-2-yl ring, which ring is optionally substituted with —C(=O)NH$_2$. In a preferred embodiment, $R^2$ and $R^3$ taken together are =O, =$NR^b$, or =$CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, N$_3$, methyl, $OR^a$, ethenyl, or ethynyl. In another preferred embodiment, $R^1$ is H. In another embodiment $R^1$ is N$_3$. In another embodiment, $R^6$ is methyl, ethenyl, or ethynyl. In another embodiment, $R^6$ is H.

In another embodiment of the invention of Formula II, B has the following formula:

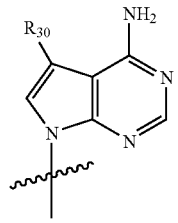

wherein:

R$_{30}$ is —C≡CR$_{31}$, —CH=CHR$_{32}$, formyl, —CH=NHNR$_{33}$, —CH=N(OR$_{33}$), —CH(OR$_{34}$), CN or —B(OR$_{33}$);

R$_{31}$ is H, tri(C$_1$-C$_6$)alkylsilyl, (C$_1$-C$_6$)alkoxy(C$_1$-C$_6$)alkyl, heteroaryl, aryl, carboxy, or (C$_1$-C$_6$)alkoxycarbonyl;

R$_{32}$ is hydrogen or cis-(C$_1$-C$_6$)alkoxy;

R$_{33}$ is H or (C$_1$-C$_6$)alkyl; and

R$_{34}$ is (C$_1$-C$_6$)alkyl;

wherein each aryl or heteroaryl of R$_{31}$ is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NR$_{35}$R$_{36}$, —C(=O)NR$_{35}$R$_{36}$, cyano, halo, hydroxy, nitro, carboxy, (C$_3$-C$_8$)cycloalkyl, (C$_3$-C$_8$)cycloalkoxy, guanidino, trifluoromethoxy, mercapto, —S(=O)$_m$R$_{37}$, or trifluoromethyl;

m is 0, 1, or 2;

R$_{35}$ and R$_{36}$ are each independently H, (C$_1$-C$_6$)alkyl or (C$_1$-C$_6$)alkanoyl;

R$_{37}$ is (C$_1$-C$_6$)alkyl, aryl, hetrocycle, or NR$_{38}$R$_{39}$; and

R$_{38}$ and R$_{39}$ are each independently H, (C$_1$-C$_6$)alkyl or (C$_1$-C$_6$)alkanoyl;

wherein each aryl or heterocycle of R$_{37}$ is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NR$_{35}$R$_{36}$, —C(=O)NR$_{35}$R$_{36}$, cyano, halo, hydroxy, nitro, carboxy, (C$_3$-C$_8$)cycloalkyl, (C$_3$-C$_8$)cycloalkoxy, guanidino, trifluoromethoxy, mercapto, or trifluoromethyl.

A specific value for R$_{30}$ is ethynyl, 2-trimethylsilylethynyl, 2-(2-pyridyl)ethynyl, 2-(4-pyridyl)ethynyl, 2-(4-methoxy)ethynyl, 2-(aminocarbonyl)ethynyl, 3,3-diethoxypropyn-1-yl, 2-(dimethylaminocarbonyl)ethynyl, 2-(N-amino(aminocarbonyl)ethynyl, 2-carboxyethynyl, 2-ethoxycarbonylethynyl, 2-methoxycarbonylethynyl, 2-phenylethynyl, 2-(4-fluorophenyl)ethynyl, 2-(4-methylphenyl)ethynyl, vinyl, 2-methoxyvinyl, formyl, —CH=N—NH$_2$, —CH=NOH, 1,1-diisopropoxymethyl, or —B(OH)$_2$. In a preferred embodiment, R$^2$ and R$^3$ taken together are =O, =NR$^b$, or =CR$^c$R$^d$. In another preferred embodiment R$^2$ and R$^3$ are both H and one of R$^4$ or R$^5$ is OH. In another embodiment, each R$^3$ and R$^4$ is H, R$^2$ is H or F and R$^5$ is OH. In another embodiment R$^2$ and R$^4$ are H, R$^3$ is OH and R$^5$ is F. In another preferred embodiment, R$^1$ is CN, N$_3$, methyl, OR$^a$, ethenyl, or ethynyl. In another preferred embodiment, R$^1$ is H. In another embodiment R$^1$ is N$_3$. In another embodiment, R$^6$ is methyl, ethenyl, or ethynyl. In another embodiment, R$^6$ is H.

In another embodiment of the invention of Formula II, B has the following formula:

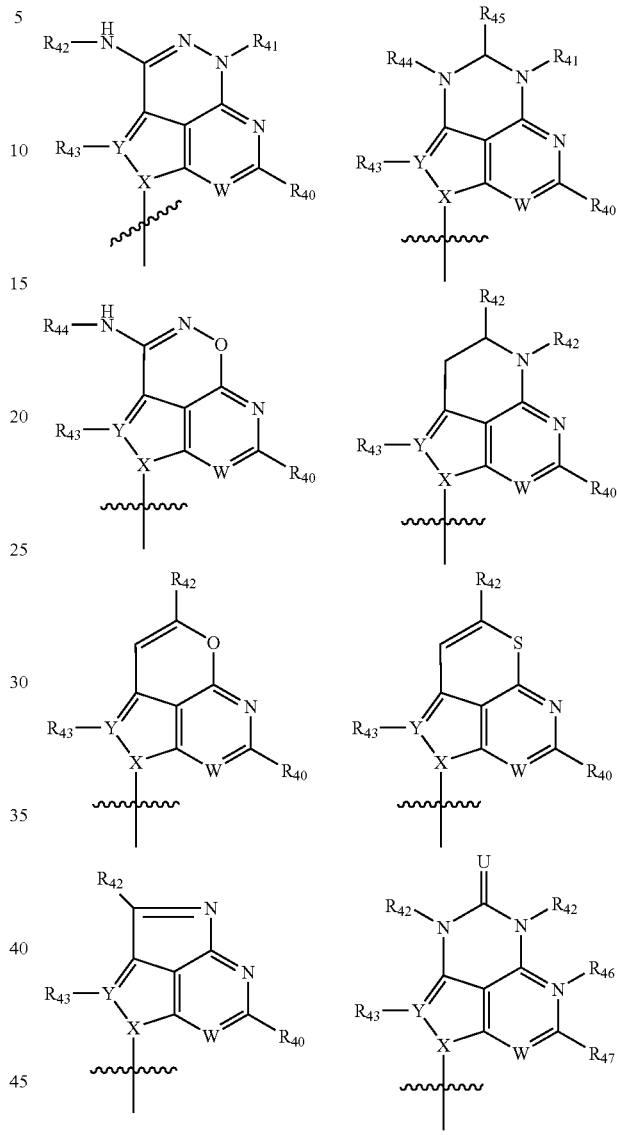

wherein:

R$_{40}$ is H, NR$_{4a}$R$_{4b}$, NHC(=O)R$_{4b}$, (C$_1$-C$_6$)alkylNR$_{4a}$R$_{4b}$, NHNH$_2$, cyano, (C$_1$-C$_6$)alkyl, (C$_2$-C$_6$)alkenyl, (C$_2$-C$_6$)alkynyl, aryl(C$_1$-C$_6$)alkyl, heterocycle(C$_1$-C$_6$)alkyl, halo, (C$_1$-C$_6$)alkylthio, (C$_1$-C$_6$)alkoxy, hydroxy, or mercapto;

R$_{41}$ is H, (C$_1$-C$_6$)alkyl, hydroxy(C$_1$-C$_6$)alkyl, (C$_2$-C$_6$)alkenyl, (C$_2$-C$_6$)alkynyl, heterocycle, aryl, aryl(C$_1$-C$_6$)alkyl;

each R$_{42}$ is independently H, hydroxy, mercapto, cyano, —SNR$_{4c}$R$_{4d}$, —C(NH)NR$_{4c}$R$_{4d}$, —C(=NH)NHOH, —C(NH)NHOR$_{4c}$, —C(=NH)NHNR$_{4c}$R$_{4d}$, NHCOR$_{4c}$, SR$_{4c}$, OR$_{4c}$, SOR$_{4c}$, SO$_2$R$_{4c}$, —C(=O)NR$_{4c}$R$_{4d}$, —C(=S)NR$_{4c}$R$_{4d}$, or R$_{4c}$;

R$_{43}$ is H, hydroxy, NR$_{4c}$R$_{4d}$, NHC(=O)R$_{4c}$, NHNHR$_{4c}$, (C$_1$-C$_6$)alkyl, (C$_2$-C$_6$)alkenyl, (C$_2$-C$_6$)alkynyl, heterocycle, aryl, aryl(C$_1$-C$_6$)alkyl, halo, COOR$_{4c}$, CONR$_{4c}$R$_{4d}$, or absent when Y is N;

$R_{4a}$ and $R_{4b}$ are each independently hydrogen, $(C_1\text{-}C_6)$alkyl, $(C_2\text{-}C_6)$alkenyl, $(C_2\text{-}C_6)$alkynyl, heterocycle, or aryl;

$R_{4c}$ and $R_{4d}$ are each independently hydrogen, $(C_1\text{-}C_6)$alkyl, $(C_2\text{-}C_6)$alkenyl, $(C_2\text{-}C_6)$alkynyl, heterocycle, or aryl;

X, Y, and W are each independently N, C, $CR_{4c}$, S or P;

$R_{44}$ is H, hydroxy, mercapto, cyano, —$SNR_{4c}R_{4d}$, —C(NH)$NR_{4c}R_{4d}$, —C(=NH)NHOH, —C(NH)$NHOR_{4c}$, —C(=NH)$NHNR_{4c}R_{4d}$, $NHCOR_{4c}$, $SR_{4c}$, $OR_{4c}$, $SOR_{4c}$, $SO_2R_{4c}$, —C(=O)$NR_{4c}R_{4d}$, —C(=S)$NR_{4c}R_{4d}$, or $R_{4c}$;

$R_{45}$ is H, hydroxy, mercapto, cyano, —$SNR_{4c}R_{4d}$, —C(NH)$NR_{4c}R_{4d}$, —C(=NH)NHOH, —C(NH)$NHOR_{4c}$, —C(=NH)$NHNR_{4c}R_{4d}$, $NHCOR_{4c}$, $SR_{4c}$, $OR_{4c}$, $SOR_{4c}$, $SO_2R_{4c}$, —C(=O)$R_{4c}R_{4d}$, —C(=S)$NR_{4c}R_{4d}$, or $R_{4c}$;

$R_{46}$ and $R_{47}$ together with the atoms to which they are attached form a heterocyclic ring; and U is S or O;

wherein each aryl or heterocycle is optionally substituted with one or more $(C_1\text{-}C_6)$alkyl, $(C_1\text{-}C_6)$alkylthio, $(C_1\text{-}C_6)$alkoxy, $(C_1\text{-}C_6)$alkanoyl, $(C_1\text{-}C_6)$alkanoyloxy, $(C_1\text{-}C_6)$alkoxycarbonyl, cyano, halo, hydroxy, nitro, carboxy, $(C_3\text{-}C_8)$cycloalkyl, $(C_3\text{-}C_8)$cycloalkoxy, trifluoromethoxy, mercapto, or trifluoromethyl.

In another embodiment of the invention of Formula II, B has the following formula:

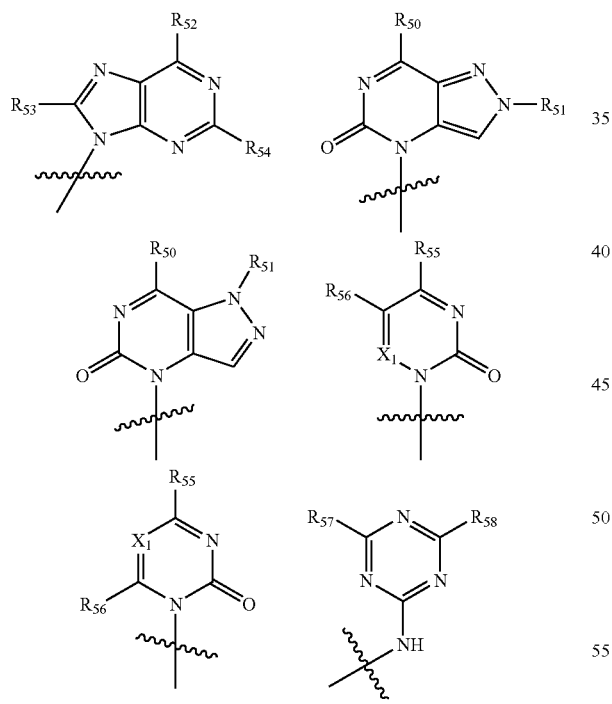

wherein:

$R_{50}$ is $NR_{5a}R_{5b}$, $ONR_{5a}R_{5b}$, $NR_{5a}NR_{5a}R_{5b}$, $SR_{5b}$, $OR_{5b}$, H, hydroxy, $(C_1\text{-}C_6)$alkyl, $(C_1\text{-}C_6)$alkenyl, $(C_1\text{-}C_6)$alkynyl, or aryl;

$R_{51}$ is $(C_1\text{-}C_6)$alkyl, $(C_1\text{-}C_6)$alkanoyl, or aryl;

$R_{52}$ is $(C_1\text{-}C_6)$alkyl, $(C_1\text{-}C_6)$alkenyl, $(C_1\text{-}C_6)$alkynyl, or aryl;

$R_{53}$ is H, halo, $(C_1\text{-}C_6)$alkyl, $(C_1\text{-}C_6)$alkenyl, $(C_1\text{-}C_6)$alkynyl, or aryl;

$R_{54}$ is H or $NH_2$;

$R_{55}$ is $NR_{5a}R_{5b}$, $ONR_{5a}R_{5b}$, $NR_{5a}NR_{5a}R_{5b}$, $SR_{5b}$, $OR_{5b}$, H, hydroxy, $(C_1\text{-}C_6)$alkyl, $(C_1\text{-}C_6)$alkenyl, $(C_1\text{-}C_6)$alkynyl, or aryl;

$R_{56}$ is H, halo, $(C_1\text{-}C_6)$alkyl, or $(C_1\text{-}C_6)$alkenyl;

$R_{57}$ and $R_{58}$ are each independently -L-$R_{5c}$;

each L is independently a direct bond, —$N(R_{5a})$—, O or S;

each $X_1$ is N or CH;

each $R_{5a}$ and $R_{5b}$ is independently H, hydroxy, $(C_1\text{-}C_6)$alkyl, $(C_1\text{-}C_6)$alkenyl, $(C_1\text{-}C_6)$alkynyl, or aryl; and each $R_{5c}$ is $NR_{5a}R_{5b}$, H, hydroxy, $(C_1\text{-}C_6)$alkyl, $(C_1\text{-}C_6)$alkenyl, $(C_1\text{-}C_6)$alkynyl, or aryl;

wherein each $(C_1\text{-}C_6)$alkyl, $(C_1\text{-}C_6)$alkenyl, $(C_1\text{-}C_6)$alkynyl, or aryl of $R_{50}$—$R_{58}$ and $R_{5a}$—$R_{5c}$ is optionally substituted with one or more $(C_1\text{-}C_6)$alkyl, $(C_1\text{-}C_6)$alkylthio, $(C_1\text{-}C_6)$alkoxy, $(C_1\text{-}C_6)$alkanoyl, $(C_1\text{-}C_6)$alkanoyloxy, $(C_1\text{-}C_6)$alkoxycarbonyl, cyano, halo, hydroxy, nitro, carboxy, $(C_3\text{-}C_8)$cycloalkyl, $(C_3\text{-}C_8)$cycloalkoxy, trifluoromethoxy, mercapto, or trifluoromethyl. In a preferred embodiment, $R^2$ and $R^3$ taken together are =O, =$NR^b$, or =$CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, $OR^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

In a preferred aspect, B is

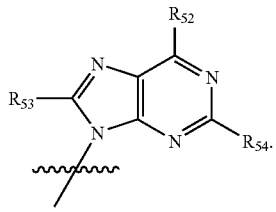

In another preferred aspect, B is

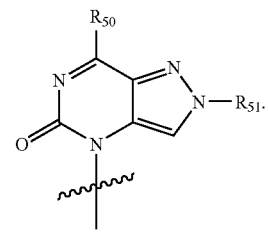

In another preferred aspect, B is

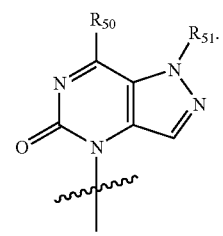

In another preferred aspect, $X_1$ is CH and B is

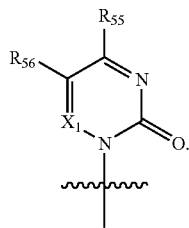

In another preferred aspect $X_1$ is N.
In another preferred aspect, $X_1$ is CH and B is

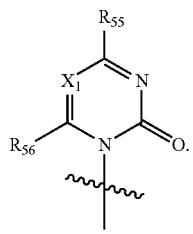

In another preferred aspect $X_1$ is N.
In another preferred aspect, B is

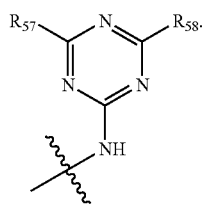

In another embodiment of the invention of Formula II, B has the following formula:

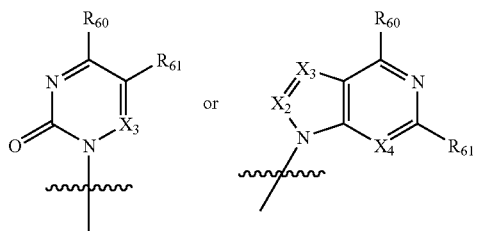

wherein:
$X_2$, $X_3$, and $X_4$ are each independently N, CH, or C—$R_{6a}$;
$R_{60}$, $R_{61}$, and $R_{6a}$ are each independently H, halo, $NR^{6b}R^{6c}$, hydroxyamino, $NR_{6b}NR_{6b}R_{6c}$, $N_3$, NO, $NO_2$, formyl, cyano, —C(=O)$NR_{6b}R_{6c}$, —C(=S)$NR_{6b}R_{6c}$, —C(=O)$OR_{6b}$, $R_{6b}$, $OR_{6b}$, or $SR_{6b}$; and
$R_{6b}$, and $R_{6c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, —S(O)$_2$($C_1$-$C_6$)alkyl or aryl($C_1$-$C_6$)alkyl. In a preferred embodiment, $R^2$ and $R^3$ taken together are =O, =$NR^b$, or =$CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, $OR^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

In a preferred aspect, $X_3$ is N and B of Formula II is

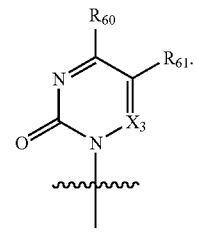

In another aspect, $X_3$ is CH. In another aspect $X_3$ is C—$R_{6a}$. In another aspect, $X_3$ is N. In a preferred embodiment, $X_3$ is CH and $R^2$ and $R^3$ taken together are =O, =$NR^b$, or =$CR^cR^d$. In another preferred embodiment, $X_3$ is CH and $R^2$ and $R^3$ are both H and one of $R^4$ or $R^5$ is OH. In another embodiment, $X_3$ is CH and $R^2$ and $R^4$ are H, $R^3$ is OH and $R^5$ is F. In another embodiment, $X_3$ is CH, each $R^3$ and $R^4$ is H, $R^2$ is H or F and $R^5$ is OH. In another preferred embodiment, $X_3$ is CH and $R^1$ is CN, $N_3$, methyl, $OR^a$, ethenyl, or ethynyl. In another embodiment, $X_3$ is CH and $R^1$ is $N_3$. In another embodiment, $R^6$ is methyl, ethenyl, or ethynyl.

In another preferred aspect, $X_2$ is N and B of Formula II is

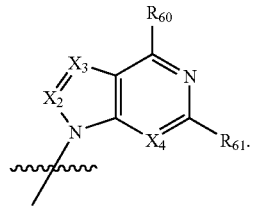

In another aspect, $X_2$ and $X_3$ are N. In another aspect $X_2$, $X_3$, and $X_4$ are N. In another aspect, $X_2$ and $X_4$ are N and $X_3$ is CH or C—$R_{6a}$. In another aspect, $X_3$ and $X_4$ are N. In a preferred embodiment, $X_3$ and $X_4$ are N and $R^2$ and $R^3$ taken together are =O, =$NR^b$, or =$CR^eR^d$. In another preferred embodiment, $X_3$ and $X_4$ are N and $R^2$ and $R^3$ are both H and one of $R^4$ or $R^5$ is OH. In another embodiment, $X_3$ and $X_4$ are N, each $R^3$ and $R^4$ is H, $R^2$ is H or F and $R^5$ is OH. In another embodiment, $X_3$ and $X_4$ are N and $R^2$ and $R^4$ are H, $R^3$ is OH and $R^5$ is F. In another preferred embodiment, $X_3$ and $X_4$ are N and $R^1$ is CN, $N_3$, methyl, $OR^a$, ethenyl, or ethynyl. In another embodiment, $X_3$ and $X_4$ are N and $R^1$ is $N_3$. In another embodiment, $R^6$ is methyl, ethenyl, or ethynyl.

In another embodiment of the invention of Formula II, B has the following formula:

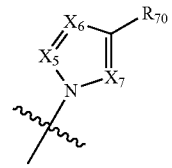

wherein:

$X_5$, $X_6$, and $X_7$, are each independently N, CH, or C—$R_{7a}$;

$R_{70}$ and $R_{7a}$ are each independently H, halo, $NR_{7b}R_{7c}$, hydroxyamino, $NR_{7b}NR_{7b}R_{7c}$, $N_3$, NO, $NO_2$, formyl, cyano, —C(=O)$NR_{7b}R_{7c}$, —C(=S)$NR_{7b}R_{7c}$, —C(=O)$OR_{7b}$, $R_{7b}$, $OR_{7b}$, or $SR_{7b}$; and $R_{7b}$, and $R_{7c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, or aryl($C_1$-$C_6$)alkyl. In a preferred embodiment, $R^2$ and $R^3$ taken together are =O, =$NR^b$, or =$CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, $OR^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H. In a preferred aspect, $X_5$ is CH and $X_6$ and $X_7$ are N. In a particularly preferred aspect, $X_5$ is CH, $X_6$ and $X_7$ are N, and $R_{70}$ is —C(=O)$NR_{7b}R_{7c}$.

In another embodiment of the invention of Formula II, B has the following formula:

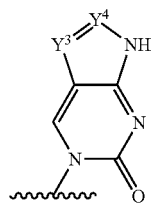

wherein:

$Y^3$=$Y^4$ is —N=N—, —N=$CR_{8a}$—, or —CH=$CR_{8a}$—; and each $R_{8a}$ is independently H, halo, or ($C_1$-$C_6$)alkyl.

In another embodiment of the invention of Formula II, B has the following formula:

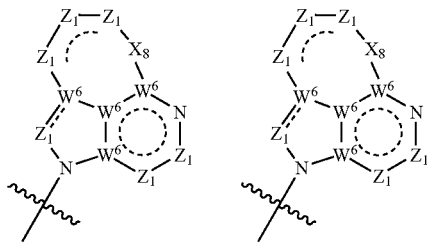

wherein:

each $Z_1$ is independently N, C—$R_{9a}$, O, S, $NR_{9b}$, >C=O, >C=S, >C=$NR_{9b}$, >S=O, >S(O)$_2$ or CH—$R_{9a}$; provided that if a $Z_1$ participates in an optional bond represented by a dotted line - - - in the formula, then that $Z_1$ is N or C—$R_{9a}$; and provided that if a $Z_1$ does not participate in an optional bond represented by a dotted line - - - in the formula, then that $Z_1$ is O, S, $NR_{9b}$, >C=O, >C=S, >C=$NR_{9b}$, >S=O, >S(O)$_2$ or CH—$R_{9a}$;

$X_8$ is O, S, SO, $SO_2$, Se, SeO, $SeO_2$ or $NR_{9b}$;

each $W^6$ is C, CH, or N; wherein if a $W^6$ participates in an optional bond represented by a dotted line - - - in the formula, then that $W^6$ is C; and if a $W^6$ does not participate in an optional bond represented by a dotted line - - - in the formula, then that $W^6$ is CH, or N;

each $R_{9a}$ is independently H, halo, $NR_{9c}R_{9d}$, hydroxyamino, $NR_{9c}NR_{9c}R_{9d}$, $N_3$, cyano, —C(=O)$NR_{9c}R_{9d}$, —C(=S)$NR_{9c}R_{9d}$, —C(=S)$NR_{9c}R_{9d}$, —C(=NH)$OR_{9c}$, $R_{9c}$, $OR_{9c}$, or $SR_{9c}$;

each $R_{9b}$ is independently H, ($C_1$-$C_6$)alkyl, ($C_1$-$C_6$)alkenyl, ($C_1$-$C_6$)alkynyl, aryl, ($C_1$-$C_6$)alkanoyl, or aryl($C_1$-$C_6$)alkyl; and $R_{9c}$, and $R_{9d}$ are each independently H, ($C_1$-$C_6$)alkyl, ($C_1$-$C_6$)alkenyl, ($C_1$-$C_6$)alkynyl, aryl, ($C_1$-$C_6$)alkanoyl, or aryl ($C_1$-$C_6$)alkyl. In a preferred embodiment, $R^2$ and $R^3$ taken together are =O, =$NR^b$, or =$CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, $OR^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

Another specific value for B has one of the following formulae:

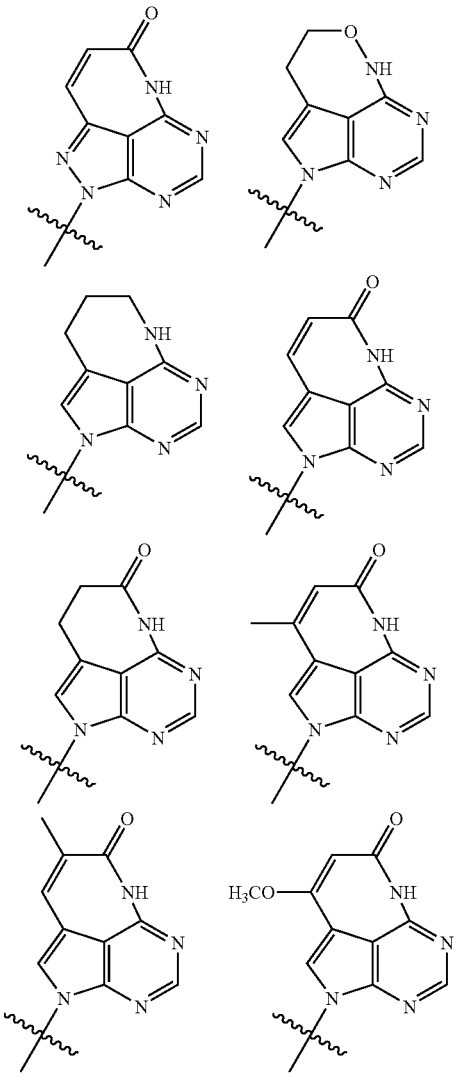

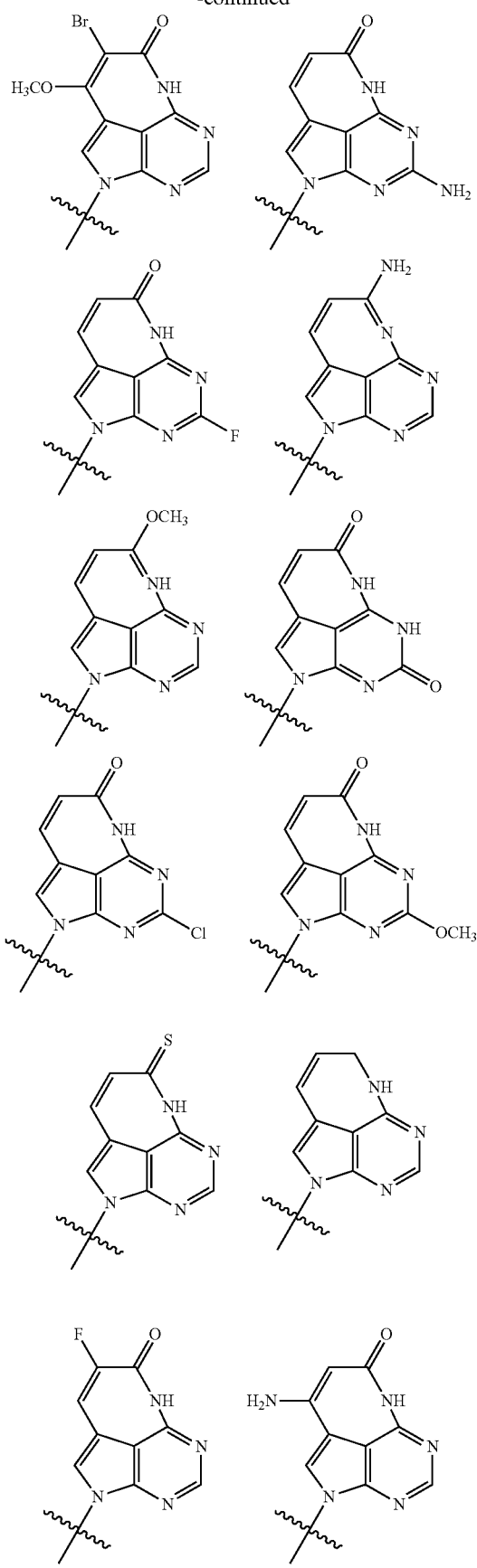

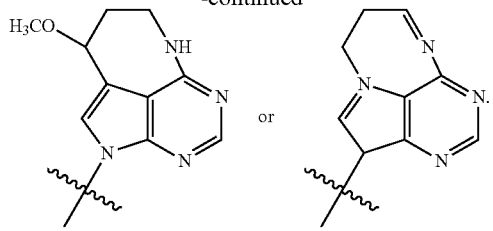

In another embodiment of the invention of Formula II, B has the following formula:

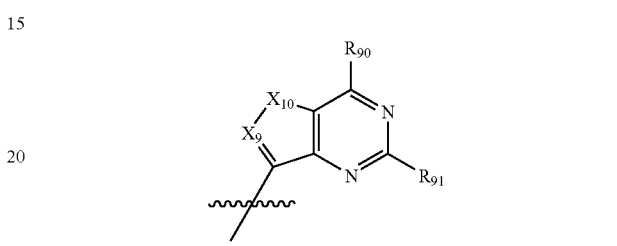

wherein:
X$_9$ is CR$_{90a}$ or N;
X$_{10}$ is O, S, or NR$_{91a}$;
R$_{90}$ and R$_{91}$ are each independently H, halo, hydroxy, (C$_1$-C$_6$)alkoxy, NR$_{90b}$R$_{91b}$, or heterocycle;
R$_{90a}$ is H, halo, methyl, azido, or amino;
R$_{91a}$ is H, or (C$_1$-C$_6$)alkyl; and
R$_{90b}$ and R$_{91b}$ are each independently H, (C$_1$-C$_6$)alkyl, (C$_3$-C$_8$)cycloalkyl, or aryl(C$_1$-C$_6$)alkyl;
wherein each (C$_1$-C$_6$)alkyl, (C$_3$-C$_8$)cycloalkyl, aryl(C$_1$-C$_6$)alkyl, and heterocycle of R$_{90}$—R$_{91}$, R$_{91a}$, and R$_{90b}$—R$_{91b}$ are optionally substituted with one or more (e.g. 1, 2, 3, or 4) halo, hydroxy, amino, (C$_1$-C$_6$)alkyl, and (C$_1$-C$_6$)alkoxy. In a preferred embodiment, R$^2$ and R$^3$ taken together are =O, =NR$^b$, or =CR$^c$R$^d$. In another preferred embodiment R$^2$ and R$^3$ are both H and one of R$^4$ or R$^5$ is OH. In another embodiment, each R$^3$ and R$^4$ is H, R$^2$ is H or F and R$^5$ is OH. In another preferred embodiment, R$^1$ is CN, N$_3$, methyl, OR$^a$, ethenyl, or ethynyl. In a preferred embodiment, X$_9$ is CR$_{90a}$. In another preferred embodiment, X$_9$ is N. In another preferred embodiment, X$_9$ is CR$_{90a}$ and X$_{10}$ is O. In another preferred embodiment, X$_9$ is CR$_{90a}$ and X$_{10}$ is S. In another preferred embodiment, X$_9$ is CR$_{90a}$ and X$_{10}$ is NR$_{91a}$. In another preferred embodiment, X$_9$ is N and X$_{10}$ is O. In another preferred embodiment, X$_9$ is N and X$_{10}$ is S. In another preferred embodiment, X$_9$ is N and X$_{10}$ is NR$_{91a}$.

In another embodiment of the invention of Formula II, B has the following formula:

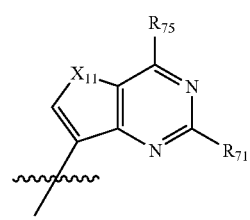

wherein:

$X_{11}$ is O, S, or $NR_{70a}$;

$R_{75}$ and $R_{71}$ are each independently H, halo, hydroxy, mercapto, aryl, heterocycle, $(C_1-C_6)$alkyl, $(C_1-C_6)$alkenyl, $(C_1-C_6)$alkynyl, $(C_1-C_6)$alkylthio, arylthio, —S(=O)$(C_1-C_6)$alkyl, —S(=O)$_2(C_1-C_6)$alkyl, —S(=O)$_2$NR$_{70b}$R$_{71b}$, $(C_1-C_6)$alkoxy, aryloxy, (heterocycle)oxy;

$R_{70a}$ is H, methyl, ethyl, or acetyl; and $R_{70b}$ and $R_{71b}$ are each independently H, $(C_1-C_6)$alkyl, aryl, aryl$(C_1-C_6)$alkyl, $(C_1-C_6)$alkanoyl, or aryl-C(=O)—.

In a preferred embodiment, $R^2$ and $R^3$ taken together are =O, =NR$^b$, or =CR$^c$R$^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another preferred embodiment, $R^1$ is CN, $N_3$, methyl, OR$^a$, ethenyl, or ethynyl. In a preferred embodiment, $X_{11}$ is O. In another preferred embodiment, $X_{11}$ is S. In another preferred embodiment, $X_{11}$ is $NR_{70a}$.

In another embodiment of the invention of Formula II, B has the following formula:

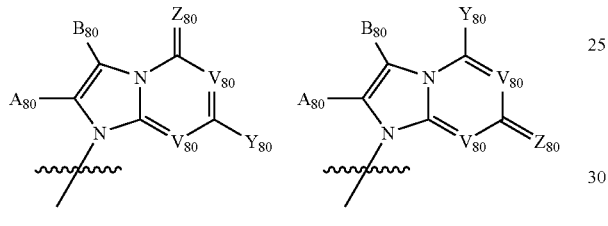

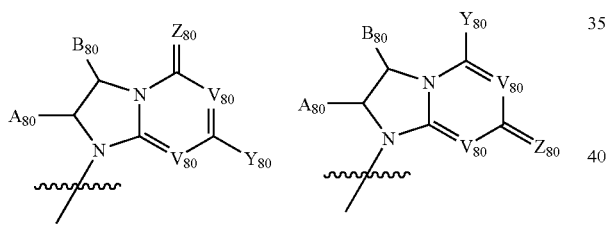

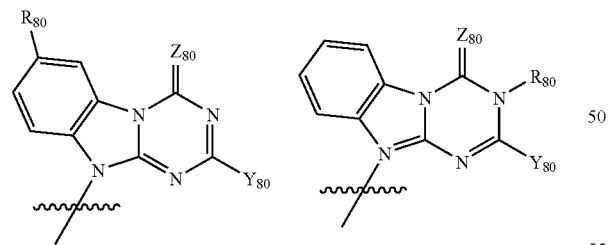

wherein:

$A_{80}$, $B_{80}$, and $Y_{80}$, are each independently H, halo, OR$_{80}$, S(O)$_n$R$_{80}$, NR$_{80}$R$_{81}$, cyano, trifluoromethyl, C(=W)OR$_{80}$, C(=W)SR$_{80}$, C(=W)NR$_{80}$R$_{81}$, nitro, azido, carbocyclic, $(C_1-C_6)$alkyl, $(C_1-C_6)$alkenyl, $(C_1-C_6)$alkynyl, aryl, aryl$(C_1-C_6)$alkyl, or heterocycle; or $A_{80}$ and $B_{80}$ taken together with the carbon atoms to which they are attached from a 4-7 membered carbocyclic or heterocyclic ring;

n is 0, 1, or 2

$Z_{80}$ is O, S, NR$_{80}$, or CR$_{80}$R$_{81}$;

each $V_{80}$ is independently N or CR$_{80}$; and each $R_{80}$ and $R_{81}$ is independently H, carbocycle, $(C_1-C_6)$alkyl, $(C_1-C_6)$alkenyl, $(C_1-C_6)$alkynyl, halo, $(C_1-C_6)$alkoxy, amino, methylamino, dimethylamino, cyano, $(C_1-C_6)$alkanoyl, aryl, aryl$(C_1-C_6)$alkyl, an amino acid residue (e.g. a naturally-occurring amino acid residue) or heterocycle; or $R_{80}$ and $R_{81}$ taken together with the atom(s) to which they are attached form a 3-7 membered carbocyclic or heterocyclic ring.

In another embodiment of the invention of Formula II, B has the following formula:

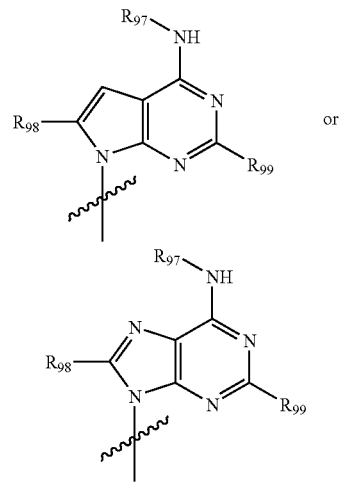

wherein:

$R_{97}$ is H, hydroxy, mercapto, $(C_1-C_6)$alkyl, $(C_1-C_6)$alkoxy, $(C_2-C_6)$alkenyl, $(C_3-C_8)$cycloalkyl, aryl$(C_1-C_6)$alkyl, aryl or $(C_2-C_6)$alkynyl;

$R_{98}$ is H, hydroxy, mercapto, or $(C_1-C_6)$alkyl;

$R_{99}$ is H, halo, azido, cyano, nitro, OR$_{99a}$, SR$_{99a}$, NR$_{99b}$R$_{99c}$, $(C_1-C_6)$alkyl, $(C_2-C_6)$alkenyl, $(C_3-C_8)$cycloalkyl, aryl$(C_1-C_6)$alkyl, aryl or $(C_2-C_6)$alkynyl;

each $R_{99a}$ is independently H, $(C_1-C_6)$alkyl, or $(C_1-C_6)$alkanoyl;

each $R_{99b}$ and $R_{99c}$ is independently H, $(C_1-C_6)$alkyl, or $(C_1-C_6)$alkanoyl;

wherein each $(C_1-C_6)$alkoxy $(C_1-C_6)$alkenyl, $(C_1-C_6)$alkynyl, $(C_3-C_8)$cycloalkyl, aryl, and aryl$(C_1-C_6)$alkyl of $R_{97}$, $R_{98}$, $R_{99}$, $R_{99a}$, $R_{99b}$, and $R_{99c}$, is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, NH$_2$, cyano, azido, halo, hydroxy, nitro, carboxy, trifluoromethoxy, aryl, or mercapto. In a preferred embodiment, $R^2$ and $R^3$ taken together are =O, =NR$^b$, or =CR$^c$R$^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, OR$^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

In a preferred embodiment, B of Formula II is

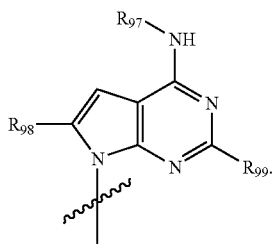

In another preferred embodiment, B of Formula II is

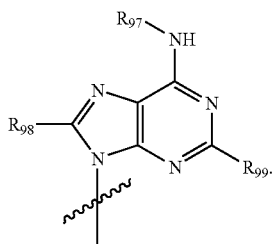

In a preferred embodiment, $R^2$ and $R^3$ taken together are $=O$, $=NR^b$, or $=CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl.

In another embodiment of the invention of Formula II, B is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, or pyrazolo[3,4-D]pyrimidine. In a preferred embodiment, $R^2$ and $R^3$ taken together are $=O$, $=NR^b$, or $=CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, $OR^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

In another embodiment of the invention of Formula II, B is 6-amino-2-chloro-purin-9-yl; 6-amino-2-iodo-purin-9-yl; 6-amino-2-fluoro-purin-9-yl; 6-amino-2-methylthio-purin-9-yl; 6-amino-purin-9-yl; or 4-amino-7H-pyrrolo[2,3-d]pyrimidin-7-yl.

In another embodiment of the invention of Formula II, B is adenine or cytosine, which adenine or cytosine is optionally substituted with one or more $(C_1-C_6)$alkyl, $(C_1-C_6)$alkylthio, $(C_1-C_6)$alkoxy, $(C_1-C_6)$alkanoyl, optionally substituted benzoyl, $(C_1-C_6)$alkanoyloxy, $(C_1-C_6)$alkoxycarbonyl, $NH_2$, cyano, halo, hydroxy, nitro, carboxy, trifluoromethoxy, aryl, or mercapto. In a preferred embodiment, $R^2$ and $R^3$ taken together are $=O$, $=NR^b$, or $=CR^cR^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, $OR^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

In a preferred embodiment of the invention of Formula II, B is adenine. In another embodiment, B is cytosine. In another embodiment, B is thymine. In another embodiment, B is guanine. In another embodiment, B is uracil. In another embodiment, B is not adenine, guanine, cytosine, thymine or uracil. In another preferred embodiment, B is adenine, guanine, cytosine, thymine, or uracil and $R^2$ and $R^3$ taken together are $=O$, $=NR^b$, or $=CR^cR^d$. In another preferred embodiment, B is adenine, guanine, cytosine, thymine, or uracil and $R^2$ and $R^3$ are both H and one of $R^4$ or $R^5$ is OH. In another preferred embodiment, B is adenine, guanine, cytosine, thymine, or uracil and each $R^3$ and $R^4$ is H, $R^2$ is H or F and $R^5$ is OH. In another preferred embodiment, B is adenine, guanine, cytosine, thymine, or uracil and $R^1$ is CN, $N_3$, methyl, $OR^a$, ethenyl, or ethynyl.

In another preferred embodiment of the invention of Formula II, B is

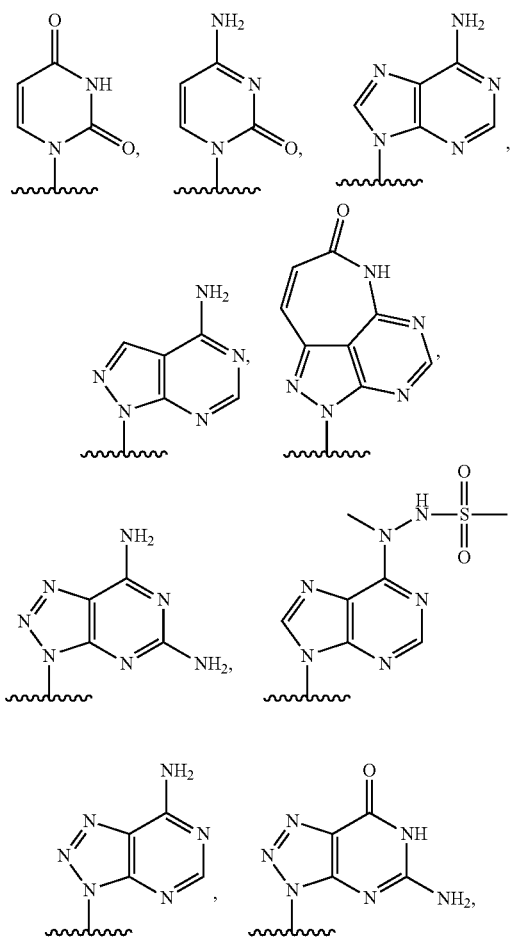

-continued

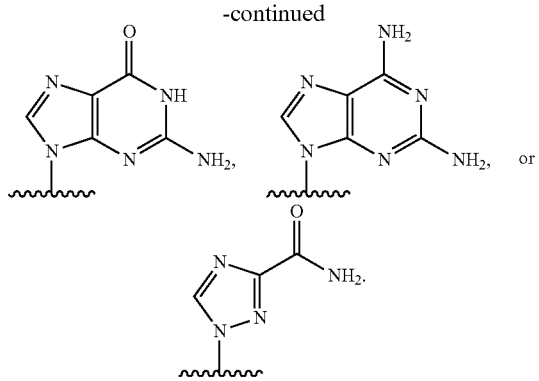

In a preferred embodiment, $R^2$ and $R^3$ taken together are =O, =NR$^b$, or =CR$^c$R$^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, OR$^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

In another embodiment of Formula II, $W^1$ and $W^2$ are not phenoxy or 2-chlorophenoxy. In another embodiment, $W^1$ and $W^2$ are not ethoxy. In another embodiment $W^1$ and $W^2$ are not OH. In another embodiment, $W^1$ is not phenoxy and $W^2$ is not OH.

In one embodiment of Formula II, $W^1$ or $W^2$ are selected from a nitrogen-linked naturally-occurring or unnatural α-aminoacid or α-aminoacid ester or an oxygen-linked naturally-occurring or unnatural α-hydroxycarboxylic acid or α-hydroxycarboxylic acid ester. In another embodiment, $W^1$ or $W^2$ is a nitrogen-linked alanine or an alanine ester. In another embodiment, $W^1$ and $W^2$ are each independently selected from a nitrogen-linked naturally-occurring or unnatural α-aminoacid or α-aminoacid ester or an oxygen-linked naturally-occurring or unnatural α-hydroxycarboxylic acid or α-hydroxycarboxylic acid ester. In another embodiment, $W^1$ and $W^2$ are each independently a nitrogen-linked alanine or an alanine ester. In another embodiment, $W^1$ or $W^2$ is $C_1$-$C_6$ alkoxy. In another embodiment $W^1$ or $W^2$ is aryloxy or substituted aryloxy.

In another embodiment of Formula II, $W^1$ and $W^2$ are independently a nitrogen-linked naturally-occurring or unnatural α-aminoacid or α-aminoacid ester. In a preferred embodiment, $R^2$ and $R^3$ taken together are =O, =NR$^b$, or =CR$^c$R$^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, OR$^a$, ethenyl, or ethynyl. In another preferred embodiment, $R^1$ is H. In another embodiment $R^1$ is $N_3$ In another embodiment, $R^6$ is methyl, ethenyl, or ethynyl. In another embodiment, $R^6$ is H. In another preferred embodiment, $W^1$ and $W^2$ are each independently a nitrogen-linked alanine or an alanine ester. In another preferred embodiment, $W^1$ and $W^2$ are each independently a nitrogen-linked alanine ester wherein the ester group is $C_1$-$C_6$ alkyl.

In another embodiment of Formula II, $W^1$ and $W^2$ are independently an oxygen-linked naturally-occurring or unnatural α-hydroxycarboxylic acid or α-hydroxycarboxylic acid ester. In a preferred embodiment, $R^2$ and $R^3$ taken together are =O, =NR$^b$, or =CR$^c$R$^d$. In another preferred embodiment $R^2$ and $R^3$ are both H and one of $R^4$ or $R^5$ is OH. In another embodiment, each $R^3$ and $R^4$ is H, $R^2$ is H or F and $R^5$ is OH. In another embodiment $R^2$ and $R^4$ are H, $R^3$ is OH and $R^5$ is F. In another preferred embodiment, $R^1$ is CN, $N_3$, methyl, OR$^a$, ethenyl, or ethynyl. In another preferred embodiment, $R^1$ is H. In another embodiment $R^1$ is $N_3$. In another embodiment, $R^6$ is methyl, ethenyl, or ethynyl. In another embodiment, $R^6$ is H.

In another embodiment of Formula II, R and R$^y$ are not protecting groups.

In another aspect, this invention provides a compound of Formula III or Formula IV:

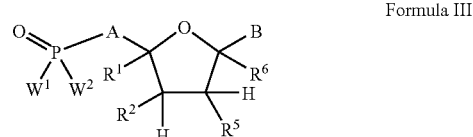

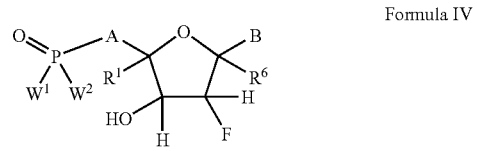

wherein:

A is —CR$^d$=CR$^d$— or

—C≡C—;

B is a nucleoside base which is optionally substituted;

$R^1$ is H, OR$^a$, N(R$^a$)$_2$, $N_3$, CN, NO$_2$, SR$^a$, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, or $C_2$-$C_8$ substituted alkynyl;

$R^2$ is H or F;

$R^5$ is OR$^a$, N(R$^a$)$_2$, $N_3$, CN, NO$_2$, SR$^a$, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, or $C_2$-$C_8$ substituted alkynyl;

$R^6$ is H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, or $C_2$-$C_8$ substituted alkynyl;

each R$^a$ is independently H, ($C_1$-$C_6$)alkyl, ($C_2$-$C_6$)alkenyl, ($C_2$-$C_6$)alkynyl or ($C_1$-$C_6$)alkanoyl;

each R$^b$ is independently H, ($C_1$-$C_6$)alkyl, ($C_2$-$C_6$)alkenyl, ($C_2$-$C_6$)alkynyl, O—($C_1$-$C_6$)alkyl or OH;

each R$^c$ and R$^d$ is independently H, ($C_1$-$C_6$)alkyl, ($C_2$-$C_6$)alkenyl, ($C_2$-$C_6$)alkynyl or halo;

wherein each ($C_1$-$C_6$)alkyl, ($C_2$-$C_6$)alkenyl, or ($C_2$-$C_6$)alkynyl of R$^a$—R$^d$ is optionally substituted with one or more halo, hydroxy, or ($C_1$-$C_6$)alkoxy;

each $Y^1$ is independently O, S, NR, $^+$N(O)(R), N(OR), $^+$N(O)(OR), or N—NR$_2$;

$W^1$ and $W^2$ are each independently a group of the formula:

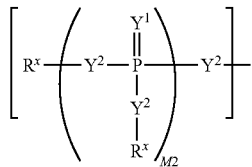

wherein:
each $Y^2$ is independently a bond, O, $CR_2$, NR, $^+N(O)(R)$, N(OR), $^+N(O)(OR)$, N—$NR_2$, S, S—S, S(O), or $S(O)_2$; M2 is 0, 1 or 2;
each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, or —N(R)C(=$Y^1$)N(R)$_2$, amino (—NH$_2$), ammonium (—NH$_3^+$), alkylamino, dialkylamino, trialkylammonium, $C_1$-$C_8$ alkyl, $C_1$-$C_8$ alkylhalide, carboxylate, sulfate, sulfamate, sulfonate, $C_1$-$C_8$ alkylsulfonate, $C_1$-$C_8$ alkylamino, $C_1$-$C_8$ alkylhydroxyl, $C_1$-$C_8$ alkylthiol, alkylsulfone (—SO$_2$R), sulfonamide (—SO$_2$NR$_2$), alkylsulfoxide (—SOR), ester (—C(=O)OR), amido (—C(=O)NR$_2$), nitrile (—CN), azido (—N$_3$), nitro (—NO$_2$), $C_1$-$C_8$ alkoxy (—OR), $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, a protecting group, or $W^3$; or when taken together, two $R^y$ on the same carbon atome form a carbocyclic ring of 3 to 7 carbon atoms;
each $R^x$ is independently $R^y$, a protecting group, or the formula:

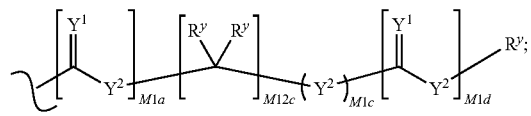

wherein:
M1a, M1c, and M1d are independently 0 or 1;
M12c is 0, 1, 2, 3, 4, 5, 6, 7, 8, 9, 10, 11 or 12; or
when taken together, two $R^x$ are optionally substituted $C_2$-$C_4$ alkylene thereby forming a phosphorous-containing heterocycle;
each R is independently H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle or a protecting group;
$W^3$ is $W^4$ or $W^5$; $W^4$ is R, —C($Y^1$)$R^y$, —C($Y^1$)$W^5$, —SO$_2$$R^y$, or —SO$_2$$W^5$; and $W^5$ is a carbocycle or a heterocycle wherein $W^5$ is independently substituted with 0 to 3 $R^y$ groups; or
or a pharmaceutically acceptable salt, thereof.

In another embodiment of Formula III, $R^2$ is H. In another embodiment $R^2$ is F.

In one embodiment of the invention of Formula III or Formula IV, $R^1$ is H. In another embodiment, $R^1$ is not H. In another embodiment, $R^1$ is CN, $N_3$, methyl, $OR^a$, ethenyl, or ethynyl. In another embodiment $R^1$ is $N_3$.

In one embodiment of the invention of Formula III or Formula IV, $R^6$ is methyl, ethenyl, or ethynyl. In another embodiment, $R^6$ is H.

In one embodiment of the invention of Formula III or Formula IV, A is —$CR^d$=$CR^d$— wherein each $R^d$ is independently H, ($C_1$-$C_6$)alkyl, ($C_2$-$C_6$)alkenyl, ($C_2$-$C_6$)alkynyl or halo. In another embodiment A is

In a preferred embodiment A is —$CR^d$=$CR^d$— and each $R^d$ is H or halo. In a preferred embodiment, A is cis —CH=CH—. In another preferred embodiment, A is trans —CH=CH—. In another preferred embodiment, A is cis —CF=CH—. In another preferred embodiment, A is trans —CF=CF—. In another preferred embodiment, A is cis —CH=CF—. In another preferred embodiment, A is trans —CH=CF—.

In another embodiment of the invention of Formula III or Formula IV, B has the following formula:

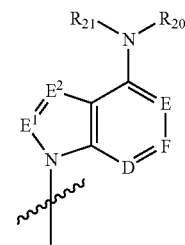

wherein:
$R_{20}$ is OH or ($C_1$-$C_6$)alkoxy that is optionally substituted with one or more $R_{22}$; and $R_{21}$ is H or ($C_1$-$C_6$)alkyl that is optionally substituted with one or more $R_{22}$; or $R_{20}$ and $R_{21}$ together with the nitrogen to which they are attached form a heterocyclic ring that is optionally subsitituted with one or more $R_{22}$;
each $R_{22}$ is independently ($C_1$-$C_6$)alkyl, ($C_1$-$C_6$)alkylthio, ($C_1$-$C_6$)alkoxy, ($C_1$-$C_6$)alkanoyl, ($C_1$-$C_6$)alkanoyloxy, ($C_1$-$C_6$)alkoxycarbonyl, NR$_{23}$R$_{24}$, —C(=O)NR$_{23}$R$_{24}$, aryl, heteroaryl, cyano, halo, hydroxy, nitro, carboxy, or ($C_3$-$C_8$)cycloalkyl;
$R_{23}$ and $R_{24}$ are each independently H, ($C_1$-$C_6$)alkyl or ($C_1$-$C_6$)alkanoyl;
wherein each aryl or heteroaryl of $R_{22}$ is optionally substituted with one or more ($C_1$-$C_6$)alkyl, ($C_1$-$C_6$)alkylthio, ($C_1$-$C_6$)alkoxy, ($C_1$-$C_6$)alkanoyl, ($C_1$-$C_6$)alkanoyloxy, ($C_1$-$C_6$)alkoxycarbonyl, NR$_{23}$R$_{24}$, —C(=O)NR$_{23}$R$_{24}$, cyano, halo, hydroxy, nitro, carboxy, ($C_3$-$C_8$)cycloalkyl, trifluoromethoxy, mercapto, or trifluoromethyl; and
D, E, $E^1$, $E^2$, and F are each independently >N or >C—$R_{25}$;
each $R_{25}$ is independently H, cyano, nitro, ($C_1$-$C_6$)alkyl, ($C_1$-$C_6$)alkenyl, ($C_1$-$C_6$)alkynyl, —NHCONH$_2$, C(=O)NR$_{26}$R$_{27}$, COOR$_{28}$, hydroxy, ($C_1$-$C_6$)alkoxy, —NR$_{26}$R$_{27}$, halo, 1,3-oxazol-2-yl, 1,3-oxazol-5-yl, 1,3-thiazol-2-yl, imidazol-2-yl, 2-oxo-[1,3]dithiol-4-yl, furan-2-yl, or 2H-[1,2,3]triazol-4-yl;
each $R_{26}$ and $R_{27}$ is independently H, ($C_1$-$C_6$)alkyl, ($C_1$-$C_6$)alkenyl, ($C_1$-$C_6$)alkynyl, ($C_3$-$C_8$)cycloalkyl, aryl, heterocycle, hydroxy, ($C_1$-$C_6$)alkoxy; or $R_{26}$ and $R_{27}$ together with the nitrogen to which they are attached form a heterocycle; and each $R_{28}$ is independently H, $(C_1-C_6)$alkyl, $(C_1-C_6)$alkenyl, $(C_1-C_6)$alkynyl, $(C_3-C_8)$cycloalkyl, aryl, or heterocycle;

wherein each $(C_1-C_6)$alkyl, $(C_1-C_6)$alkenyl, $(C_1-C_6)$alkynyl, $(C_3-C_8)$cycloalkyl, aryl, heterocycle, and $(C_1-C_6)$alkoxy of $R_{26}$ and $R_{27}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, $NH_2$, cyano, halo, hydroxy, nitro, carboxy, $(C_3-C_8)$cycloalkyl, $(C_3-C_8)$cycloalkoxy, trifluoromethoxy, or mercapto.

A specific value for $R_{20}$ is OH, methoxy, or propoxy; and for $R_{21}$ is H.

A specific value for $R_{20}$ and $R_{21}$ together with the nitrogen to which they are attached form a pyrrolidin-1-yl, 1,3,4,9-tetrahydro-beta-carbolin-2-yl, piperidinyl, azetidinyl, 3,6-dihydro-2H-pyridin-1-yl, or 3,4-dihydro-1H-isoquinolin-2-yl ring, which ring is optionally substituted with —C(=O)NH$_2$.

In another embodiment of the invention of Formula III or Formual IV, B has the following formula:

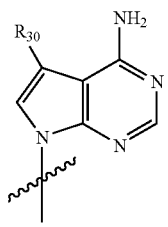

wherein:
$R_{30}$ is —C≡CR$_{31}$, —CH=CHR$_{32}$, formyl, —CH=NHNR$_{33}$, —CH=N(OR$_{33}$), —CH(OR$_{34}$), CN or —B(OR$_{33}$);
$R_{31}$ is H, tri$(C_1-C_6)$alkylsilyl, $(C_1-C_6)$alkoxy$(C_1-C_6)$alkyl, heteroaryl, aryl, carboxy, or $(C_1-C_6)$alkoxycarbonyl;
$R_{32}$ is hydrogen or cis-$(C_1-C_6)$alkoxy;
$R_{33}$ is H or $(C_1-C_6)$alkyl; and
$R_{34}$ is $(C_1-C_6)$alkyl;
wherein each aryl or heteroaryl of $R_{31}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, $NR_{35}R_{36}$, —C(=O)NR$_{35}$R$_{36}$, cyano, halo, hydroxy, nitro, carboxy, $(C_3-C_8)$cycloalkyl, $(C_3-C_8)$cycloalkoxy, guanidino, trifluoromethoxy, mercapto, —S(=O)$_m$R$_{37}$, or trifluoromethyl;
m is 0, 1, or 2;
$R_{35}$ and $R_{36}$ are each independently H, $(C_1-C_6)$alkyl or $(C_1-C_6)$alkanoyl;
$R_{37}$ is $(C_1-C_6)$alkyl, aryl, hetrocycle, or NR$_{38}$R$_{39}$; and
$R_{38}$ and $R_{39}$ are each independently H, $(C_1-C_6)$alkyl or $(C_1-C_6)$alkanoyl;
wherein each aryl or heterocycle of $R_{37}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, NR$_{35}$R$_{36}$, —C(=O)NR$_{35}$R$_{36}$, cyano, halo, hydroxy, nitro, carboxy, $(C_3-C_8)$cycloalkyl, $(C_3-C_8)$cycloalkoxy, guanidino, trifluoromethoxy, mercapto, or trifluoromethyl.

A specific value for $R_{30}$ is ethynyl, 2-trimethylsilylethynyl, 2-(2-pyridyl)ethynyl, 2-(4-pyridyl)ethynyl, 2-(4-methoxy)ethynyl, 2-(aminocarbonyl)ethynyl, 3,3-diethoxypropyn-1-yl, 2-(dimethylaminocarbonyl)ethynyl, 2-(N-amino(aminocarbonyl)ethynyl, 2-carboxyethynyl, 2-ethoxycarbonylethynyl, 2-methoxycarbonylethynyl, 2-phenylethynyl, 2-(4-fluorophenyl)ethynyl, 2-(4-methylphenyl)ethynyl, vinyl, 2-methoxyvinyl, formyl, —CH=N—NH$_2$, —CH=NOH, 1,1-diisopropoxymethyl, or —B(OH)$_2$.

In another embodiment of the invention of Formula III or Formula IV, B has the following formula:

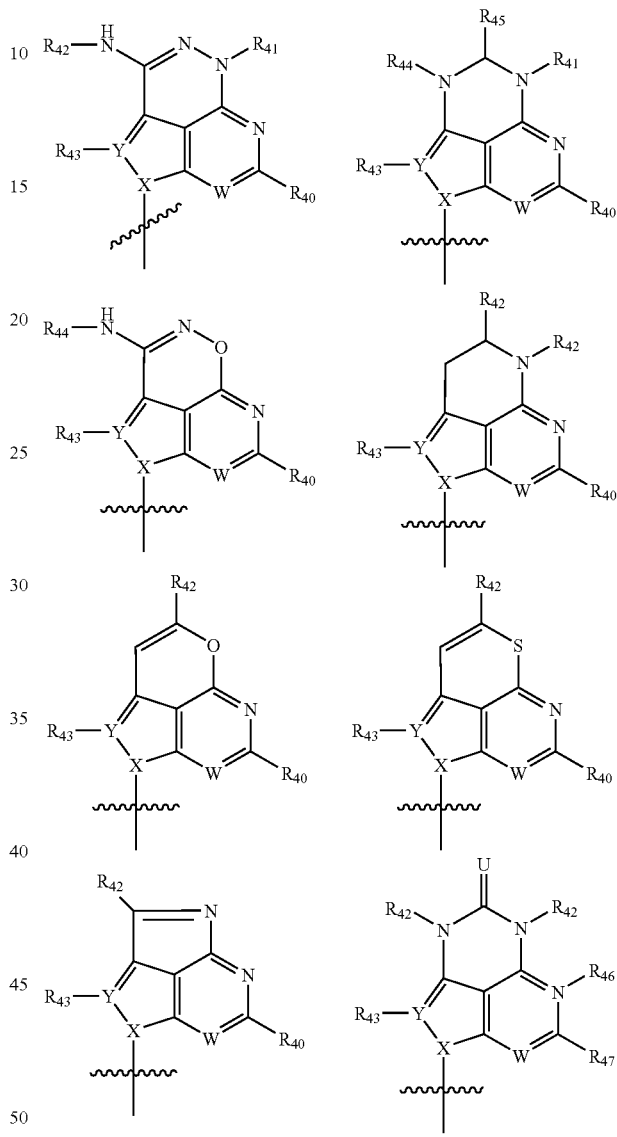

wherein:
$R_{40}$ is H, NR$_{4a}$R$_{4b}$, NHC(=O)R$_{4b}$, $(C_1-C_6)$alkylNR$_{4a}$R$_{4b}$, NHNH$_2$, cyano, $(C_1-C_6)$alkyl, $(C_2-C_6)$alkenyl, $(C_2-C_6)$alkynyl, aryl$(C_1-C_6)$alkyl, heterocycle$(C_1-C_6)$alkyl, halo, $(C_1-C_6)$alkylthio, $(C_1-C_6)$alkoxy, hydroxy, or mercapto;
$R_{41}$ is H, $(C_1-C_6)$alkyl, hydroxy$(C_1-C_6)$alkyl, $(C_2-C_6)$alkenyl, $(C_2-C_6)$alkynyl, heterocycle, aryl, aryl$(C_1-C_6)$alkyl;
each $R_{42}$ is independently H, hydroxy, mercapto, cyano, —SNR$_{4c}$R$_{4d}$, —C(NH)NR$_{4c}$R$_{4d}$, —C(=NH)NHOH, —C(NH)NHOR$_{4c}$, —C(=NH)NHNR$_{4c}$R$_{4d}$, NHCOR$_{4c}$, SR$_{4c}$, OR$_{4c}$, SOR$_{4c}$, SO$_2$R$_{4c}$, —C(=O)NR$_{4c}$R$_{4d}$, —C(=S)NR$_{4c}$R$_{4d}$, NHCOR$_{4c}$,
$R_{43}$ is H, hydroxy, NR$_{4c}$R$_{4d}$, NHC(=O)NR$_{4c}$, NHNHR$_{4c}$, $(C_1-C_6)$alkyl, $(C_2-C_6)$alkenyl, $(C_2-C_6)$alkynyl, heterocycle, aryl, aryl(C$_1$-C$_6$)alkyl, halo, COOR$_{4c}$, CONR$_{4c}$R$_{4d}$, or absent when Y is N;

R$_{4a}$ and R$_{4b}$ are each independently hydrogen, (C$_1$-C$_6$)alkyl, (C$_2$-C$_6$)alkenyl, (C$_2$-C$_6$)alkynyl, heterocycle, or aryl;

R$_{4c}$, and R$_{4d}$ are each independently hydrogen, (C$_1$-C$_6$)alkyl, (C$_2$-C$_6$)alkenyl, (C$_2$-C$_6$)alkynyl, heterocycle, or aryl;

X, Y, and W are each independently N, C, CR$_{4c}$, S or P;

R$_{44}$ is H, hydroxy, mercapto, cyano, —SNR$_{4c}$R$_{4d}$, —C(NH)NR$_{4c}$R$_{4d}$, —C(=NH)NHOH, —C(NH)NHOR$_{4c}$, —C(=NH)NHNR$_{4c}$R$_{4d}$, NHCOR$_{4c}$, SR$_{4c}$, OR$_{4c}$, SOR$_{4c}$, SO$_2$R$_{4c}$, —C(=O)NR$_{4c}$R$_{4d}$, —C(=S)NR$_{4c}$R$_{4d}$, or R$_{4c}$;

R$_{45}$ is H, hydroxy, mercapto, cyano, —SNR$_{4c}$R$_{4d}$, —C(NH)NR$_{4c}$R$_{4d}$, —C(=NH)NHOH, —C(NH)NHOR$_{4c}$, —C(=NH)NHNR$_{4c}$R$_{4d}$, NHCOR$_{4c}$, SR$_{4c}$, OR$_{4c}$, SOR$_{4c}$, SO$_2$R$_{4c}$, —C(=O)NR$_{4c}$R$_{4d}$, —C(=S)NR$_{4c}$R$_{4d}$, or R$_{4c}$;

R$_{46}$, and R$_{47}$ together with the atoms to which they are attached form a heterocyclic ring; and U is S or O;

wherein each aryl or heterocycle is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, halo, hydroxy, nitro, carboxy, (C$_3$-C$_8$)cycloalkyl, (C$_3$-C$_8$)cycloalkoxy, trifluoromethoxy, mercapto, or trifluoromethyl.

In another embodiment of the invention of Formula III or Formula IV, B has the following formula:

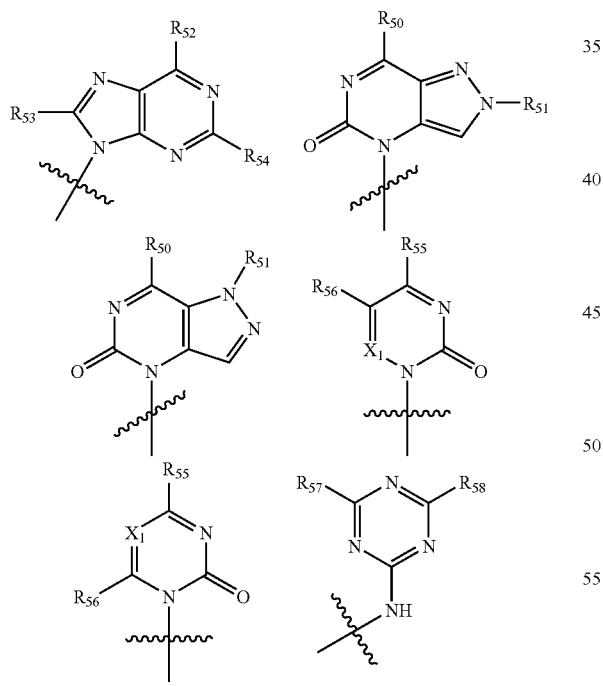

wherein:

R$_{50}$ is NR$_{5a}$R$_{5b}$, ONR$_{5a}$R$_{5b}$, NR$_{5a}$NR$_{5a}$R$_{5b}$, SR$_{5b}$, OR$_{5b}$, H, hydroxy, (C$_1$-C$_6$)alkyl, (C$_1$-C$_6$)alkenyl, (C$_1$-C$_6$)alkynyl, or aryl;

R$_{51}$ is (C$_1$-C$_6$)alkyl, (C$_1$-C$_6$)alkanoyl, or aryl;

R$_{52}$ is (C$_1$-C$_6$)alkyl, (C$_1$-C$_6$)alkenyl, (C$_1$-C$_6$)alkynyl, or aryl;

R$_{53}$ is H, halo, (C$_1$-C$_6$)alkyl, (C$_1$-C$_6$)alkenyl, (C$_1$-C$_6$)alkynyl, or aryl;

R$_{54}$ is H or NH$_2$;

R$_{55}$ is NR$_{5a}$R$_{5b}$, ONR$_{5a}$R$_{5b}$, NR$_{5a}$NR$_{5a}$R$_{5b}$, SR$_{5b}$, OR$_{5b}$, H, hydroxy, (C$_1$-C$_6$)alkyl, (C$_1$-C$_6$)alkenyl, (C$_1$-C$_6$)alkynyl, or aryl;

R$_{56}$ is H, halo, (C$_1$-C$_6$)alkyl, or (C$_1$-C$_6$)alkenyl;

R$_{57}$ and R$_{58}$ are each independently -L-R$_{5c}$;

each L is independently a direct bond, —N(R$_{5a}$)—, O or S;

each X$_1$ is N or CH;

each R$_{5a}$ and R$_{5b}$ is independently H, hydroxy, (C$_1$-C$_6$)alkyl, (C$_1$-C$_6$)alkenyl, (C$_1$-C$_6$)alkynyl, or aryl; and each R$_{5c}$ is NR$_{5a}$R$_{5b}$, H, hydroxy, (C$_1$-C$_6$)alkyl, (C$_1$-C$_6$)alkenyl, (C$_1$-C$_6$)alkynyl, or aryl;

wherein each (C$_1$-C$_6$)alkyl, (C$_1$-C$_6$)alkenyl, (C$_1$-C$_6$)alkynyl, or aryl of R$_{50}$—R$_{58}$ and R$_{5a}$—R$_{5c}$ is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, halo, hydroxy, nitro, carboxy, (C$_3$-C$_8$)cycloalkyl, (C$_3$-C$_8$)cycloalkoxy, trifluoromethoxy, mercapto, or trifluoromethyl.

In a preferred aspect, B is

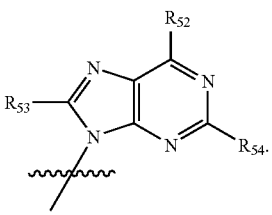

In another preferred aspect, B is

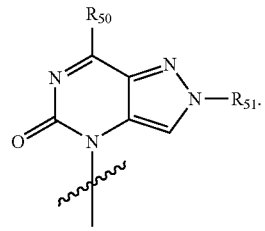

In another preferred aspect, B is

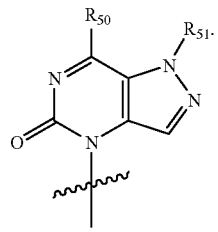

In another preferred aspect, X$_1$ is CH and B is

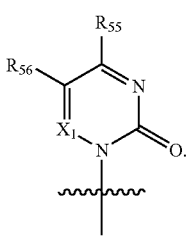

In another preferred aspect X$_1$ is N.

In another preferred aspect, $X_1$ is CH and B is

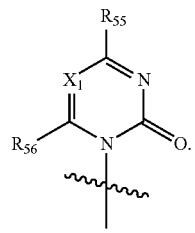

In another preferred aspect $X_1$ is N.
In another preferred aspect, B is

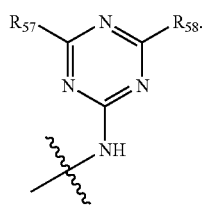

In another embodiment of the invention of Formula III or Formula IV, B has the following formula:

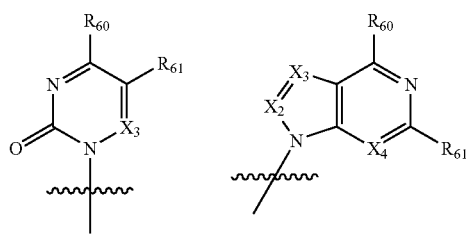

wherein:
$X_2$, $X_3$, and $X_4$ are each independently N, CH, or C—$R_{6a}$;
$R_{60}$, $R_{61}$, and $R_{6a}$ are each independently H, halo, $NR_{6b}R_{6c}$, hydroxyamino, $NR_{6b}NR_{6b}R_{6c}$, $N_3$, NO, $NO_2$, formyl, cyano, —C(=O)$NR_{6b}R_{6c}$, —C(=S)$NR_{6b}R_{6c}$, —C(=O)$OR_{6b}$, $R_{6b}$, $OR_{6b}$, or $SR_{6b}$; and
$R_{6b}$, and $R_{6c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, —S(O)$_2$($C_1$-$C_6$)alkyl or aryl($C_1$-$C_6$)alkyl. In on embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H.

In a preferred aspect, $X_3$ is N and B is

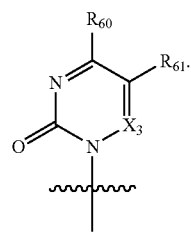

In another aspect, $X_3$ is CH. In another aspect $X_3$ is C—$R_{6a}$. In another embodiment $X_3$ is N.

In another preferred aspect, $X_2$ is N and B is

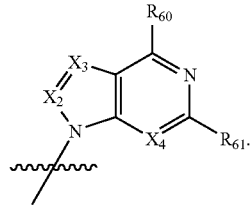

In another aspect, $X_2$ and $X_3$ are N. In another aspect $X_2$, $X_3$, and $X_4$ are N. In another aspect, $X_2$ and $X_4$ are N and $X_3$ is CH or C—$R_{6a}$. In another aspect, $X_3$ and $X_4$ are N.

In another embodiment of the invention of Formula III or Formula IV, B has the following formula:

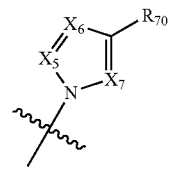

wherein:
$X_5$, $X_6$, and $X_7$, are each independently N, CH, or C—$R_{7a}$;
$R_{70}$ and $R_{7a}$ are each independently H, halo, $NR_{7b}R_{7c}$, hydroxyamino, $NR_{7b}NR_{7b}R_{7c}$, $N_3$, NO, $NO_2$, formyl, cyano, —C(=O)$NR_{7b}R_{7c}$, —C(=S)$NR_{7b}R_{7c}$, —C(=O)$OR_{7b}$, $R_{7b}$, $OR_{7b}$, or $SR_{7b}$; and
$R_{7b}$, and $R_{7c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, or aryl($C_1$-$C_6$)alkyl. In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H. In a preferred aspect, $X_5$ is CH and $X_6$ and $X_7$ are N. In a particularly preferred aspect, $X_5$ is CH, $X_6$ and $X_7$ are N, and $R_{70}$ is —C(=O)$NR_{7b}R_{7c}$.

In another embodiment of the invention of Formula III or Formula IV, B has the following formula:

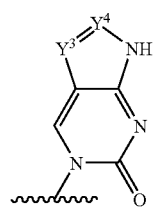

wherein:
$Y^3$=$Y^4$ is —N=N—, —CH=N—, —N=$CR_{8a}$—, or —CH=$CR_{8a}$—; and
each $R_{8a}$ is independently H, halo, or ($C_1$-$C_6$)alkyl.

In another embodiment of the invention of Formula III or Formula IV, B has the following formula:

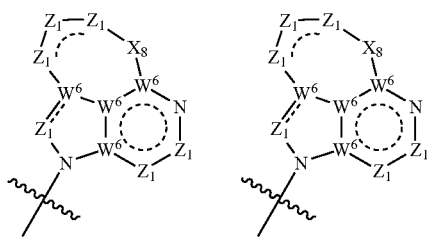

wherein:

each $Z_1$ is independently N, C—$R_{9a}$, O, S, $NR_{9b}$, >C=O, >C=S, >C=$NR_{9b}$, >S=O, >S(O)$_2$ or CH—$R_{9a}$; provided that if a $Z_1$ participates in an optional bond represented by a dotted line - - - in the formula, then that $Z_1$ is N or C—$R_{9a}$; and provided that if a $Z_1$ does not participate in an optional bond represented by a dotted line - - - in the formula, then that $Z_1$ is O, S, $NR_{9b}$, >C=O, >C=S, >C=$NR_{9b}$, >S=O, >S(O)$_2$ or CH—$R_{9a}$;

$X_8$ is O, S, SO, SO$_2$, Se, SeO, SeO$_2$ or $NR_{9b}$;

each $W^6$ is C, CH, or N; wherein if a $W^6$ participates in an optional bond represented by a dotted line - - - in the formula, then that $W^6$ is C; and if a $W^6$ does not participate in an optional bond represented by a dotted line - - - in the formula, then that $W^6$ is CH, or N;

each $R_{9a}$ is independently H, halo, $NR_{9c}R_{9d}$, hydroxyamino, $NR_{9c}NR_{9c}R_{9d}$, $N_3$, cyano, —C(=O)$NR_{9c}R_{9d}$, —C(=S)$NR_{9c}R_{9d}$, —C(=S)$NR_{9c}R_{9d}$, —C(=NH)$OR_{9c}$, $R_{9c}$, $OR_{9c}$, or $SR_{9c}$;

each $R_{9b}$ is independently H, (C$_1$-C$_6$)alkyl, (C$_1$-C$_6$)alkenyl, (C$_1$-C$_6$)alkynyl, aryl, (C$_1$-C$_6$)alkanoyl, or aryl(C$_1$-C$_6$)alkyl; and $R_{9c}$, and $R_{9d}$ are each independently H, (C$_1$-C$_6$)alkyl, (C$_1$-C$_6$)alkenyl, (C$_1$-C$_6$)alkynyl, aryl, (C$_1$-C$_6$)alkanoyl, or aryl(C$_1$-C$_6$)alkyl. In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H.

Another specific value for B has one of the following formulae:

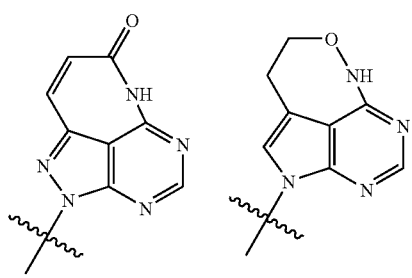

-continued

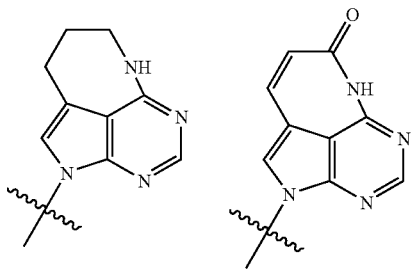

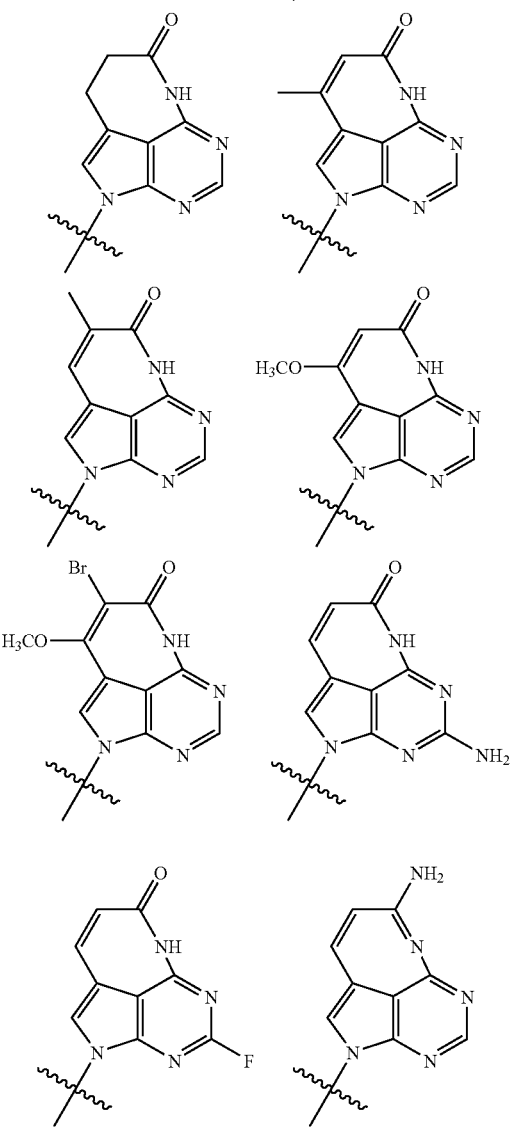

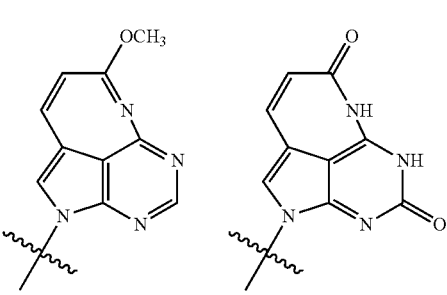

-continued

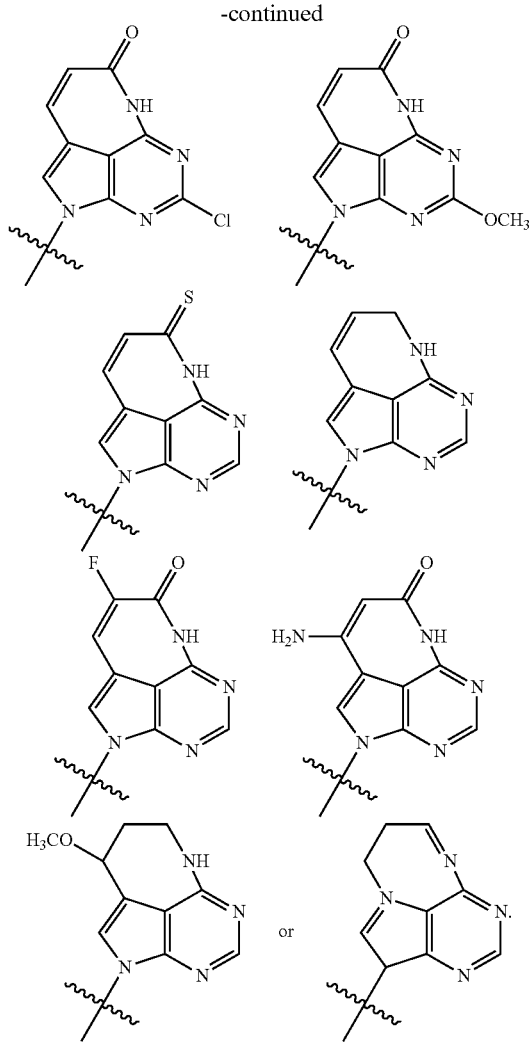

In another embodiment of the invention of Formula III or Formula IV, B has the following formula:

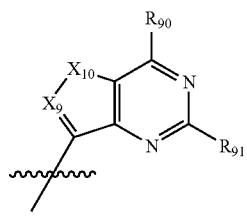

wherein:

$X_9$ is $CR_{90a}$ or N;

$X_{10}$ is O, S, or $NR_{91a}$;

$R_{90}$ and $R_{91}$ are each independently H, halo, hydroxy, ($C_1$-$C_6$)alkoxy, $NR_{90b}R_{91b}$, or heterocycle;

$R_{90a}$ is H, halo, methyl, azido, or amino;

$R_{91a}$ is H, or ($C_1$-$C_6$)alkyl; and $R_{90b}$ and $R_{91b}$ are each independently H, ($C_1$-$C_6$)alkyl, ($C_3$-$C_8$)cycloalkyl, or aryl($C_1$-$C_6$)alkyl;

wherein each ($C_1$-$C_6$)alkyl, ($C_3$-$C_8$)cycloalkyl, aryl($C_1$-$C_6$)alkyl, and heterocycle of $R_{90}$—$R_{91}$, $R_{91a}$, and $R_{90b}$—$R_{91b}$ are optionally substituted with one or more (e.g. 1, 2, 3, or 4) halo, hydroxy, amino, ($C_1$-$C_6$)alkyl, and ($C_1$-$C_6$)alkoxy.

In a preferred embodiment, $X_9$ is $CR_{90a}$. In another preferred embodiment, $X_9$ is N. In another preferred embodiment, $X_9$ is $CR_{90a}$ and $X_{10}$ is O. In another preferred embodiment, $X_9$ is $CR_{90a}$ and $X_{10}$ is S. In another preferred embodiment, $X_9$ is $CR_{90a}$ and $X_{10}$ is $NR_{91a}$. In another preferred embodiment, $X_9$ is N and $X_{10}$ is O. In another preferred embodiment, $X_9$ is N and $X_{10}$ is S. In another preferred embodiment, $X_9$ is N and $X_{10}$ is $NR_{91a}$.

In another embodiment of the invention of Formula III or Formula IV, B has the following formula:

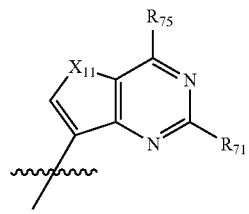

wherein:

$X_{11}$ is O, S, or $NR_{70a}$;

$R_{75}$ and $R_{71}$ are each independently H, halo, hydroxy, mercapto, aryl, heterocycle, ($C_1$-$C_6$)alkyl, ($C_1$-$C_6$)alkenyl, ($C_1$-$C_6$)alkynyl, ($C_1$-$C_6$)alkylthio, arylthio, —S(=O)($C_1$-$C_6$)alkyl, —S(=O)$_2$($C_1$-$C_6$)alkyl, —S(=O)$_2$$NR_{70b}R_{71b}$, $NR_{70b}R_{71b}$, ($C_1$-$C_6$)alkoxy, aryloxy, (heterocycle)oxy;

$R_{70a}$ is H, methyl, ethyl, or acetyl; and $R_{70b}$ and $R_{71b}$ are each independently H, ($C_1$-$C_6$)alkyl, aryl, aryl($C_1$-$C_6$)alkyl, ($C_1$-$C_6$)alkanoyl, or aryl-C(=O)—. In a preferred embodiment, $X_{11}$ is O. In another preferred embodiment, $X_{11}$ is S. In another preferred embodiment, $X_{11}$ is $NR_{70a}$.

In another embodiment of the invention of Formula III or Formula IV, B has the following formula:

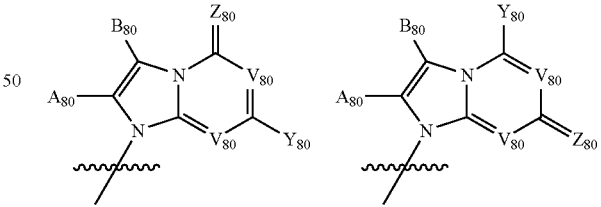

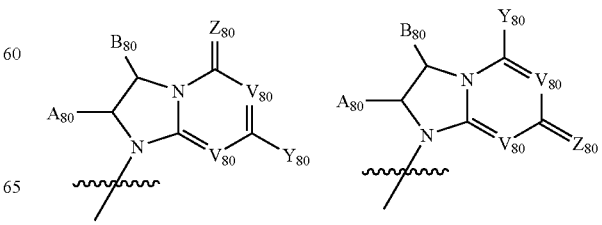

-continued

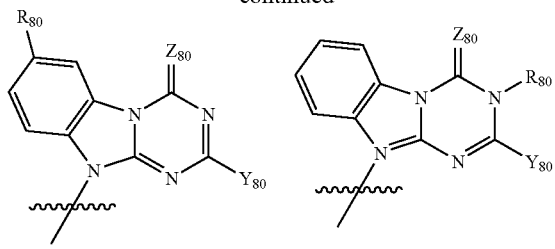

wherein:
- $A_{80}$, $B_{80}$, and $Y_{80}$, are each independently H, halo, $OR_{80}$, $S(O)_nR_{80}$, $NR_{80}R_{81}$, cyano, trifluoromethyl, $C(=W)OR_{80}$, $C(=W)SR_{80}$, $C(=W)NR_{80}R_{81}$, nitro, azido, carbocyclic, $(C_1-C_6)$alkyl, $(C_1-C_6)$alkenyl, $(C_1-C_6)$alkynyl, aryl, aryl$(C_1-C_6)$alkyl, or heterocycle; or $A_{80}$ and $B_{80}$ taken together with the carbon atoms to which they are attached from a 4-7 membered carbocyclic or heterocyclic ring;
- n is 0, 1, or 2
- $Z_{80}$ is O, S, $NR_{80}$, or $CR_{80}R_{81}$;
- each $V_{80}$ is independently N or $CR_{80}$; and
- each $R_{80}$ and $R_{81}$ is independently H, carbocycle, $(C_1-C_6)$alkyl, $(C_1-C_6)$alkenyl, $(C_1-C_6)$alkynyl, halo, $(C_1-C_6)$alkoxy, amino, methylamino, dimethylamino, cyano, $(C_1-C_6)$alkanoyl, aryl, aryl$(C_1-C_6)$alkyl, an amino acid residue (e.g. a naturally-occurring amino acid residue) or heterocycle; or $R_{80}$ and $R_{81}$ taken together with the atom(s) to which they are attached form a 3-7 membered carbocyclic or heterocyclic ring.

In another embodiment of the invention of Formula III or Formula IV, B has the following formula:

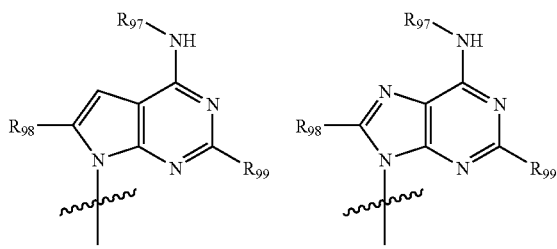

wherein:
- $R_{97}$ is H, hydroxy, mercapto, $(C_1-C_6)$alkyl, $(C_1-C_6)$alkoxy, $(C_2-C_6)$alkenyl, $(C_3-C_8)$cycloalkyl, aryl$(C_1-C_6)$alkyl, aryl or $(C_2-C_6)$alkynyl;
- $R_{98}$ is H, hydroxy, mercapto, or $(C_1-C_6)$alkyl;
- $R_{99}$ is H, halo, azido, cyano, nitro, $OR_{99a}$, $SR_{99a}$, $NR_{99b}R_{99c}$, $(C_1-C_6)$alkyl, $(C_2-C_6)$alkenyl, $(C_3-C_8)$cycloalkyl, aryl$(C_1-C_6)$alkyl, aryl or $(C_2-C_6)$alkynyl;
- each $R_{99a}$ is independently H, $(C_1-C_6)$alkyl, or $(C_1-C_6)$alkanoyl;
- each $R_{99b}$ and $R_{99c}$ is independently H, $(C_1-C_6)$alkyl, or $(C_1-C_6)$alkanoyl;
- wherein each $(C_1-C_6)$alkyl, $(C_1-C_6)$alkoxy $(C_1-C_6)$alkenyl, $(C_1-C_6)$alkynyl, $(C_3-C_8)$cycloalkyl, aryl, and aryl$(C_1-C_6)$alkyl of $R_{97}$, $R_{98}$, $R_{99}$, $R_{99a}$, $R_{99b}$, and $R_{99c}$, is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, $NH_2$, cyano, azido, halo, hydroxy, nitro, carboxy, trifluoromethoxy, aryl, or mercapto. In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H.

In a preferred embodiment, B is

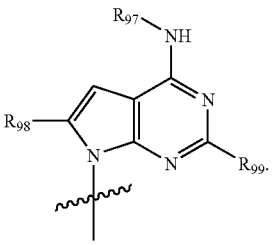

In another preferred embodiment, B is

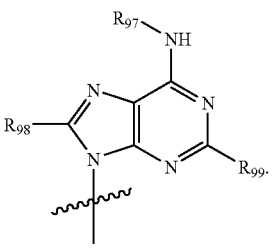

In another embodiment of the invention of Formula III or Formula IV, B is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, or pyrazolo[3,4-D]pyrimidine. In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H.

In another embodiment of the invention of Formula III or Formula IV, B is 6-amino-2-chloro-purin-9-yl; 6-amino-2-iodo-purin-9-yl; 6-amino-2-fluoro-purin-9-yl; 6-amino-2-methylthio-purin-9-yl; 6-amino-purin-9-yl; or 4-amino-7H-pyrrolo[2,3-d]pyrimidin-7-yl.

In another embodiment of the invention of Formula III or Formula IV, B is adenine or cytosine, which adenine or cytosine is optionally substituted with one or more $(C_1-C_6)$alkyl, $(C_1-C_6)$alkylthio, $(C_1-C_6)$alkoxy, $(C_1-C_6)$alkanoyl, optionally substituted benzoyl, $(C_1-C_6)$alkanoyloxy, $(C_1-C_6)$alkoxycarbonyl, $NH_2$, cyano, halo, hydroxy, nitro, carboxy, trifluoromethoxy, aryl, or mercapto. In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H.

In a preferred embodiment of the invention of Formula III or Formula IV, B is adenine. In another embodiment, B is cytosine. In another embodiment, B is thymine. In another embodiment, B is guanine. In another embodiment, B is uracil. In another embodiment, B is not adenine, guanine, cytosine, thymine or uracil.

In another preferred embodiment of the invention of Formula III or Formula IV, B is

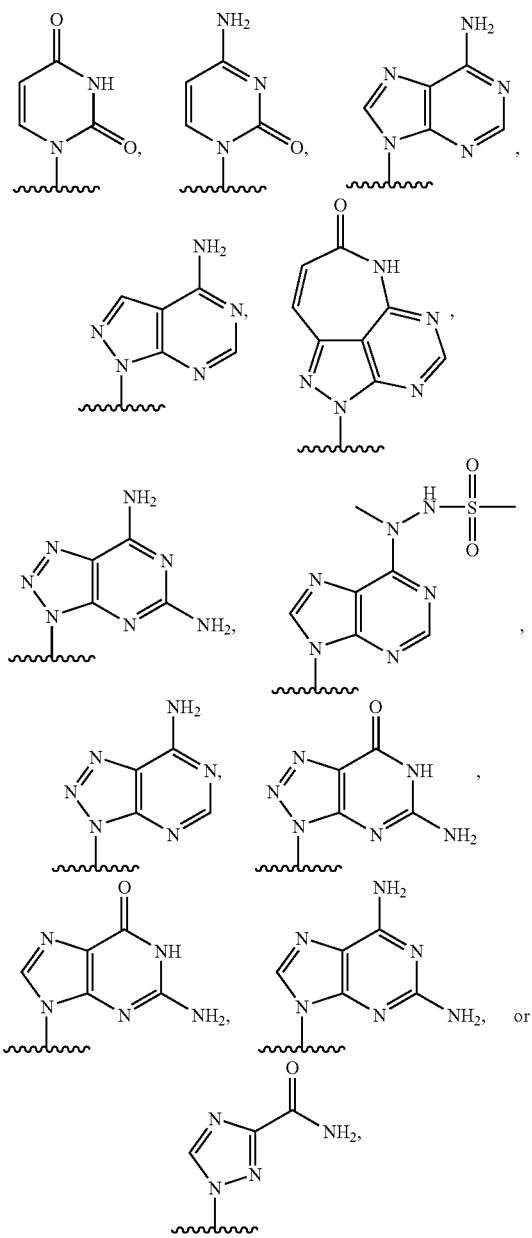

In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H.

In another embodiment of Formula III or Formula IV, $W^1$ and $W^2$ are independently a nitrogen-linked naturally-occurring or unnatural α-aminoacid or α-aminoacid ester. In another preferred embodiment, $W^1$ and $W^2$ are each independently a nitrogen-linked alanine or an alanine ester. In another preferred embodiment, $W^1$ and $W^2$ are each independently a nitrogen-linked alanine ester wherein the ester group is $C_1$-$C_6$ alkyl. In another embodiment, $W^1$ and $W^2$ are independently oxygen-linked optionally substituted aryloxy. In another embodiment, $W^1$ and $W^2$ are independently an oxygen-linked naturally-occurring or unnatural α-hydroxycarboxylic acid or α-hydroxycarboxylic acid ester.

In another embodiment of Formula III or Formula IV, $W^1$ and $W^2$ are independently a nitrogen-linked naturally-occurring or unnatural α-aminoacid or α-aminoacid ester. In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H. In another preferred embodiment, $W^1$ and $W^2$ are each independently a nitrogen-linked alanine or an alanine ester. In another preferred embodiment, $W^1$ and $W^2$ are each independently a nitrogen-linked alanine ester wherein the ester group is $C_1$-$C_6$ alkyl.

In another embodiment of Formula III or Formula IV, $W^1$ and $W^2$ are independently an oxygen-linked naturally-occurring or unnatural α-hydroxycarboxylic acid or α-hydroxycarboxylic acid ester. In one embodiment $R^1$ is H. In another embodiment, $R^1$ is CN, $N_3$, methyl, $OR^a$, ethenyl, or ethynyl. In another embodiment $R^1$ is $N_3$. In another embodiment, $R^6$ is methyl, ethenyl, or ethynyl. In another embodiment, $R^6$ is H.

In another embodiment of Formula III or Formula IV, R and $R^y$ are not protecting groups.

In another preferred aspect, a compound of the invention is

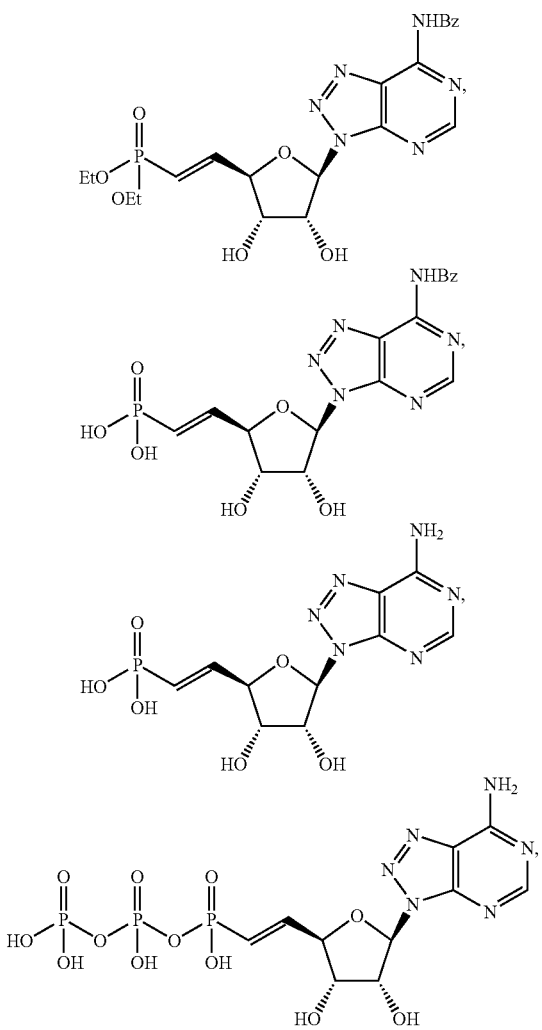

49
-continued
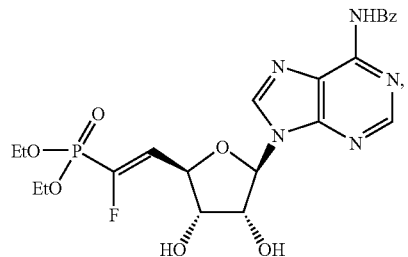
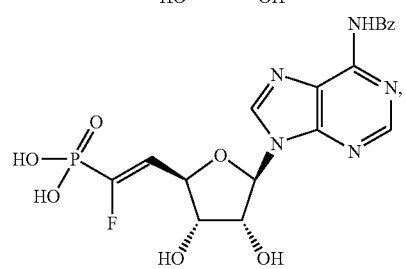
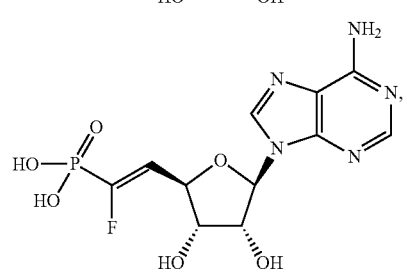
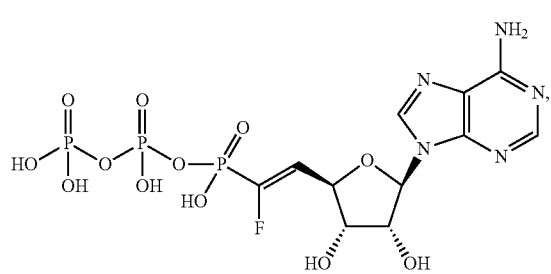
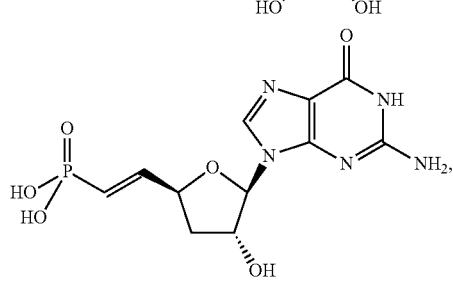
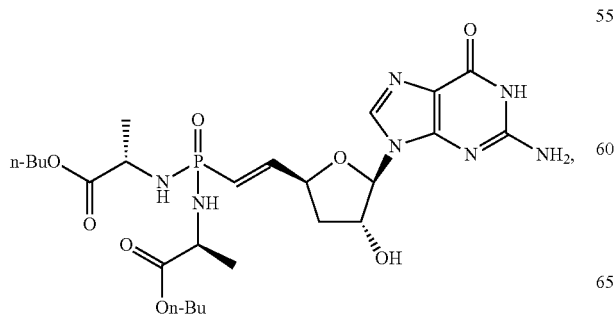
50
-continued
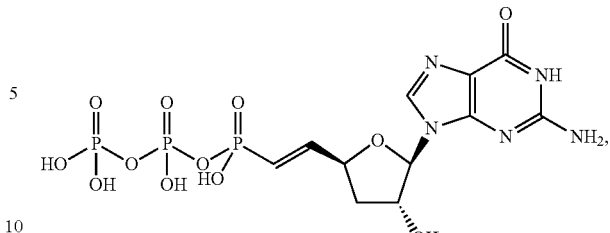
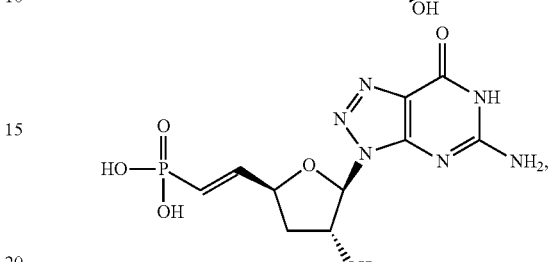
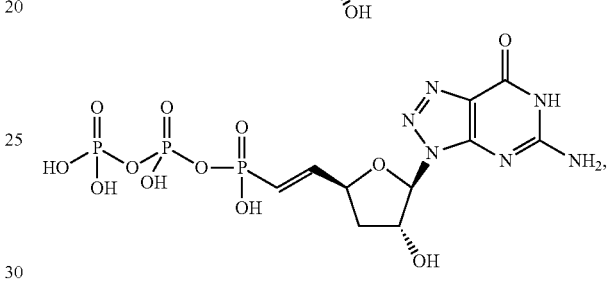
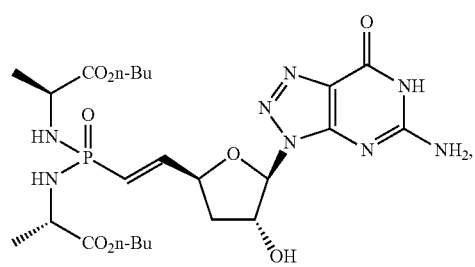
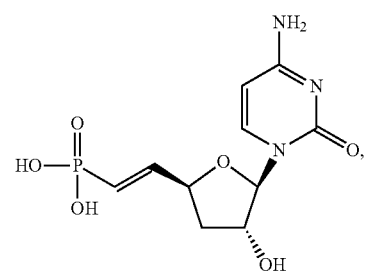
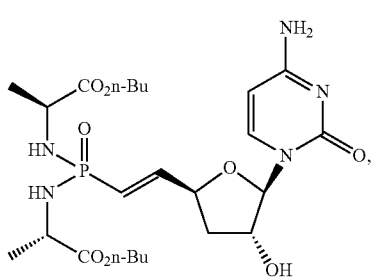

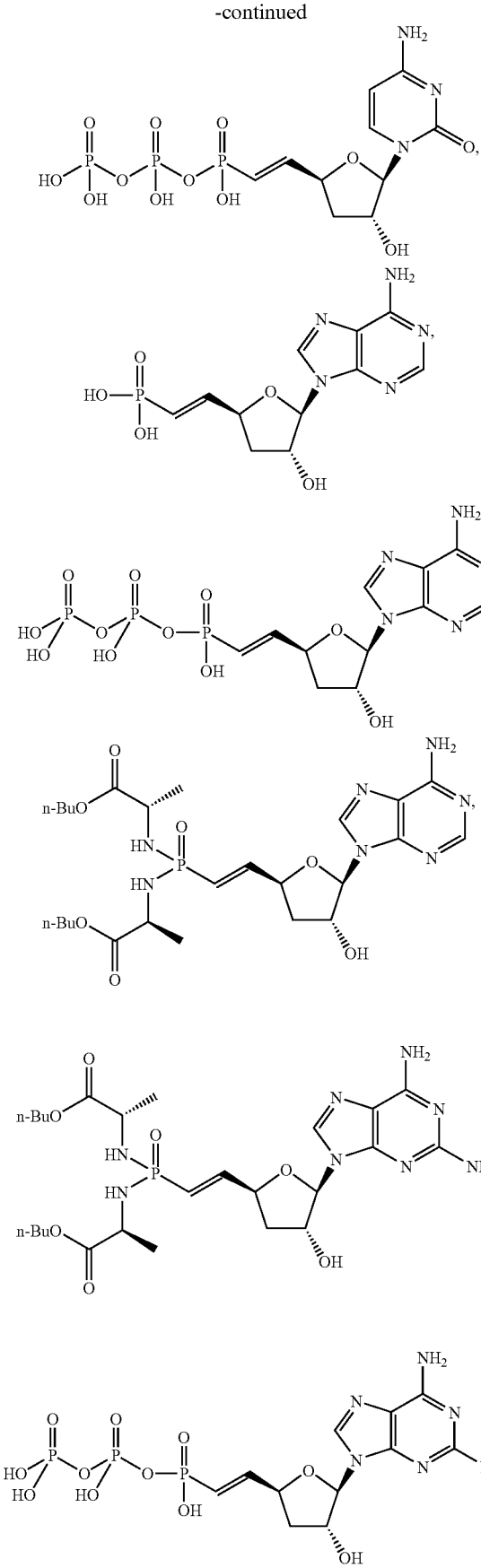
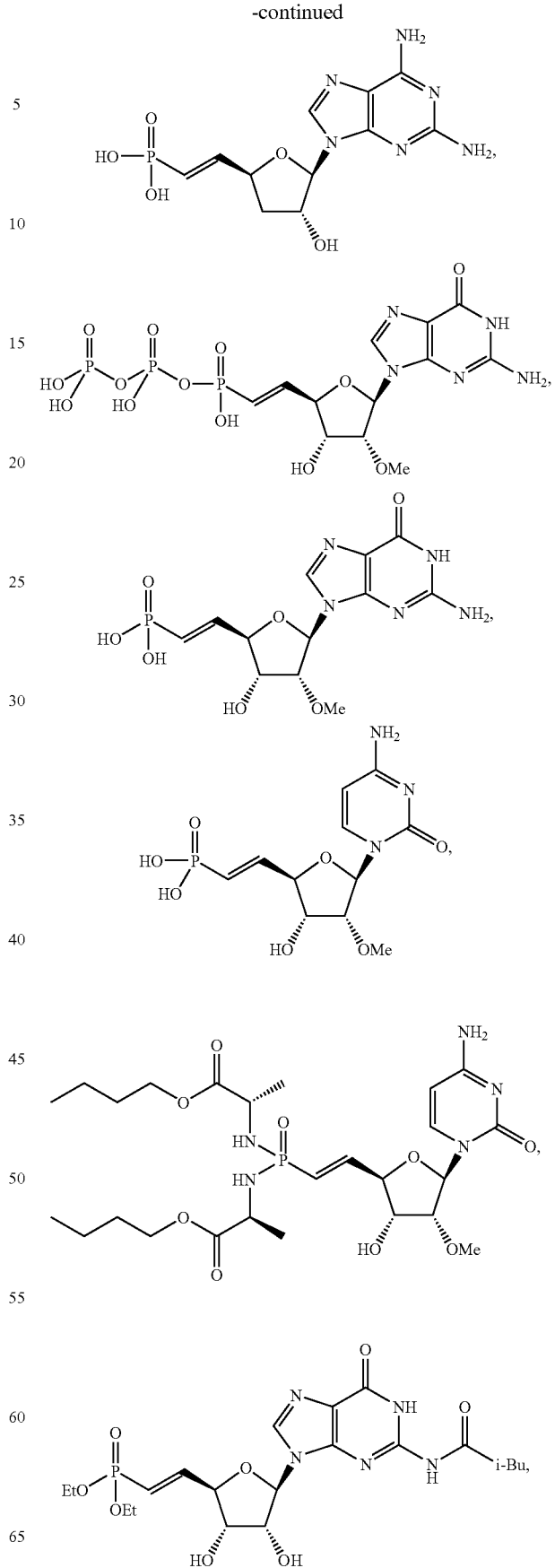

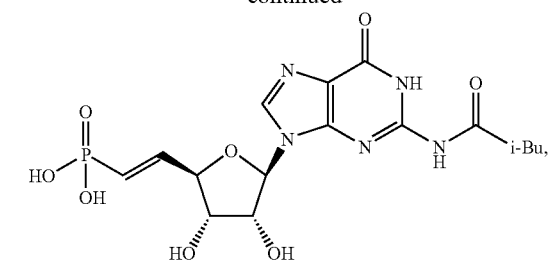
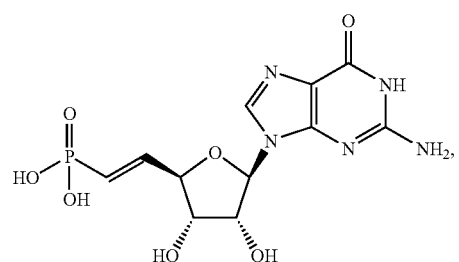
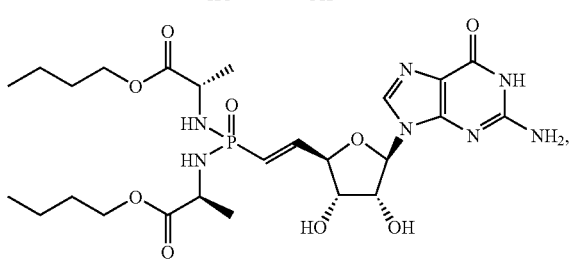
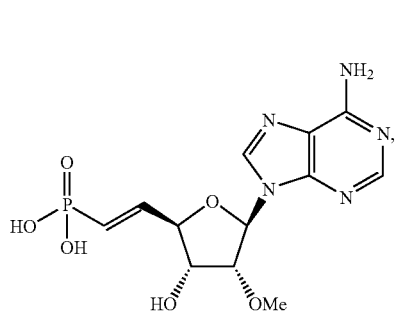
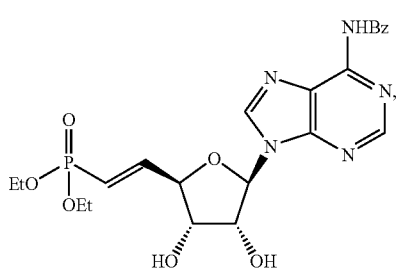
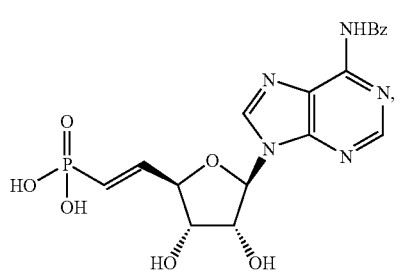
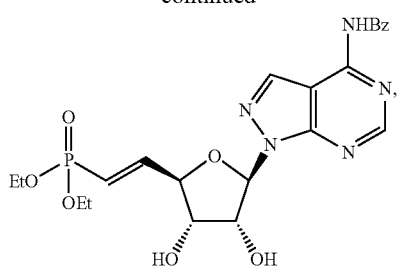
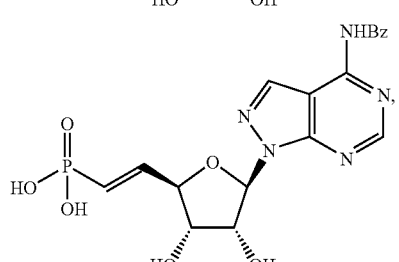
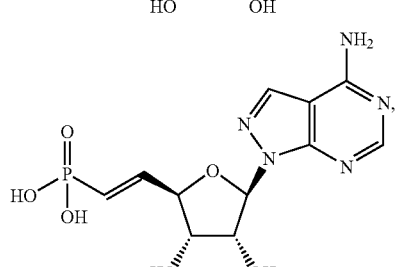
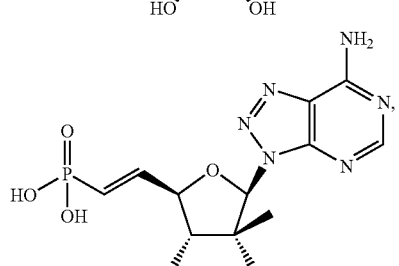
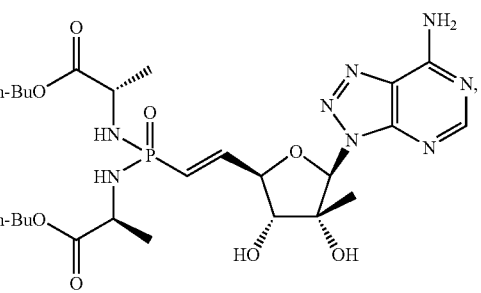
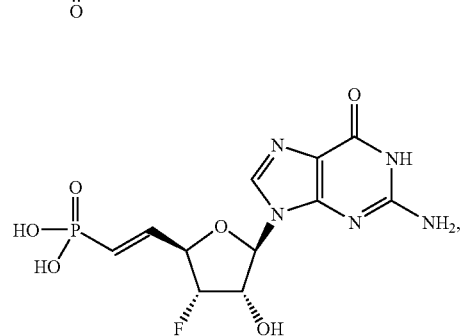

55
-continued
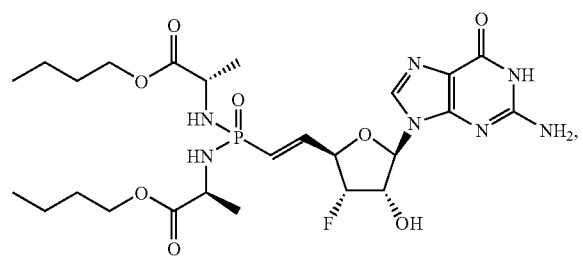
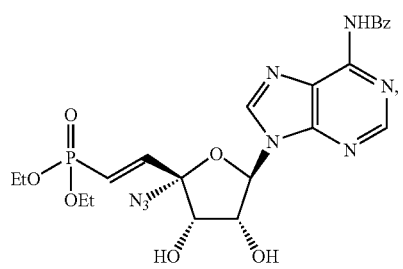
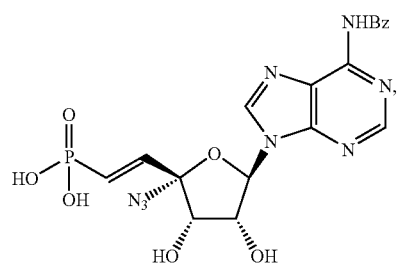
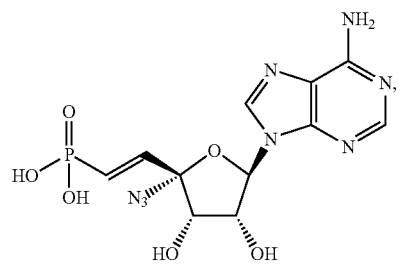
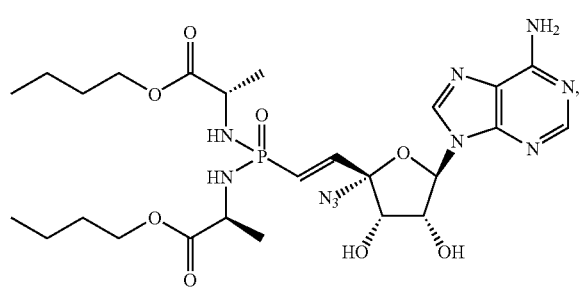
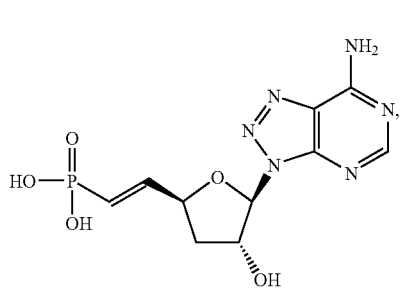
56
-continued
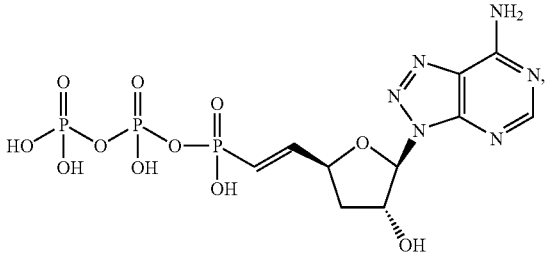
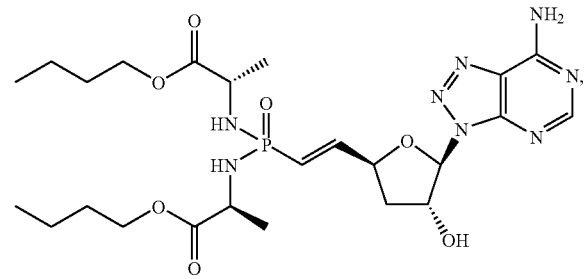
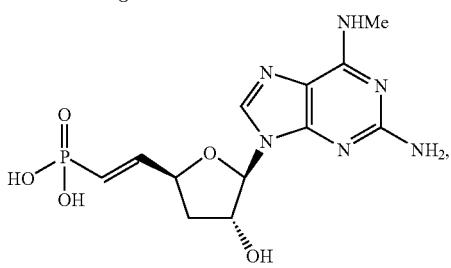
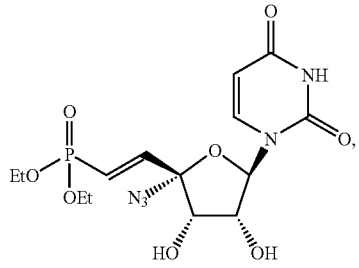
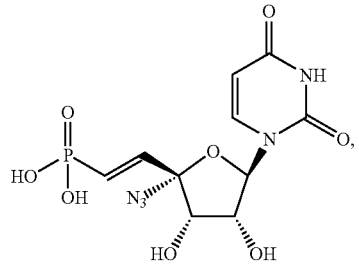
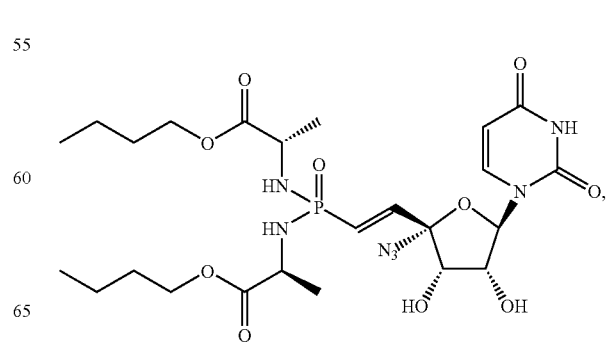

57
-continued
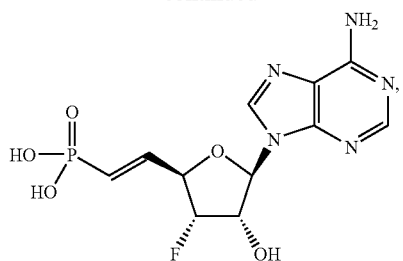
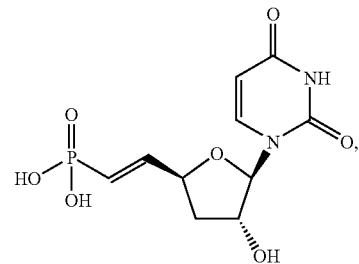
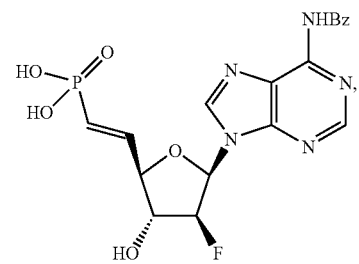
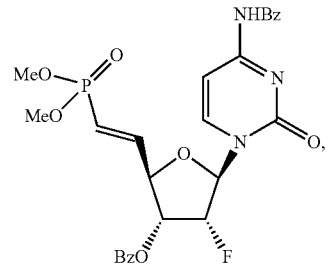
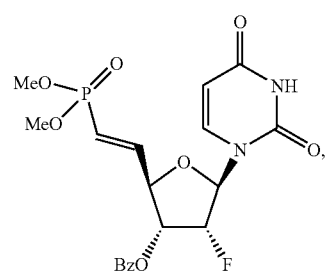
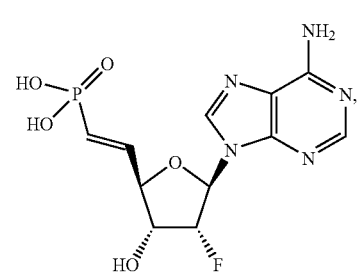
58
-continued
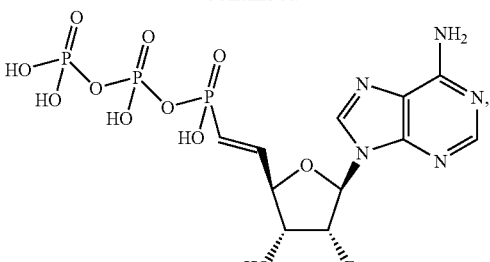
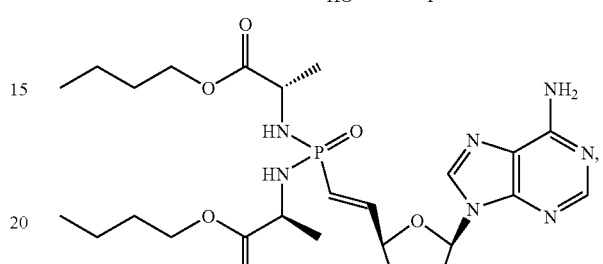
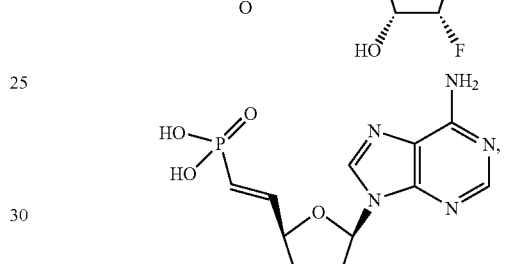
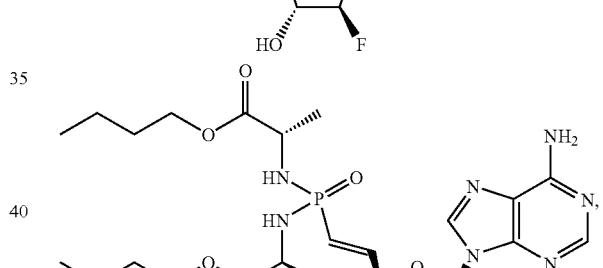
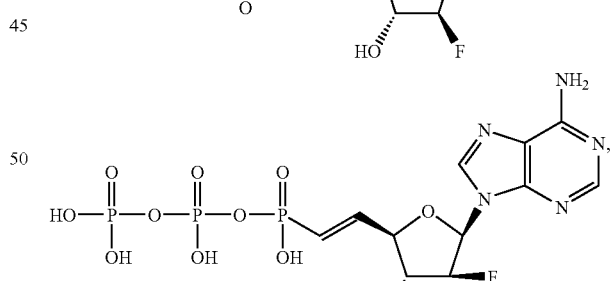
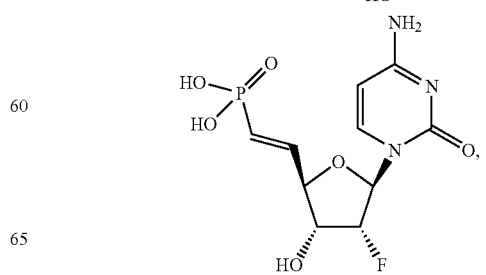

59
-continued
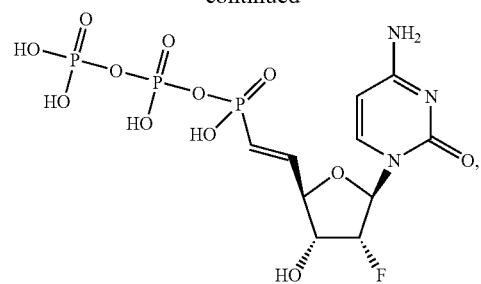
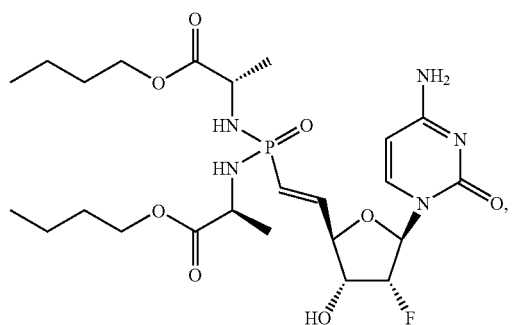
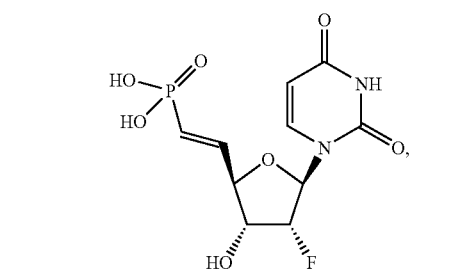
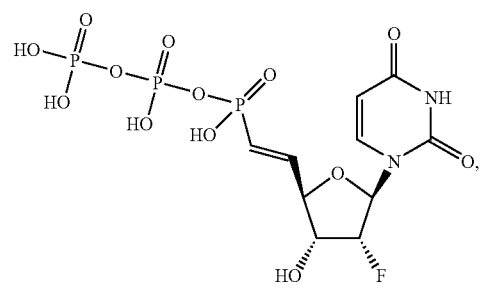
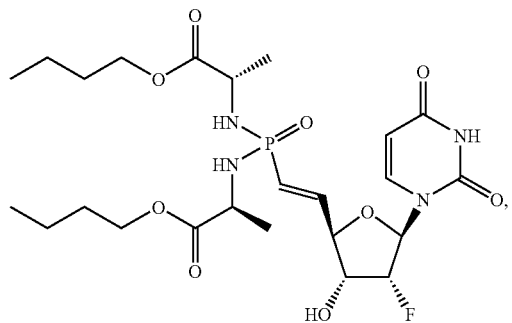
60
-continued
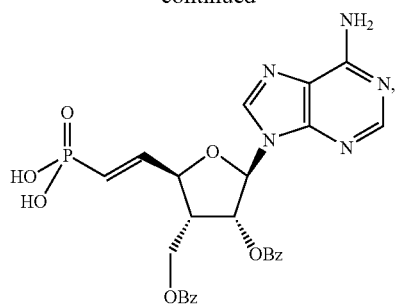
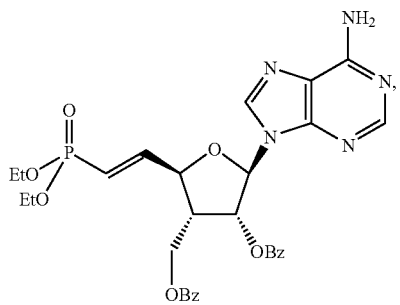
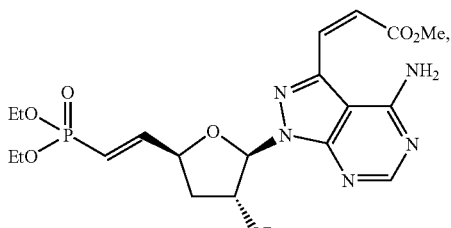
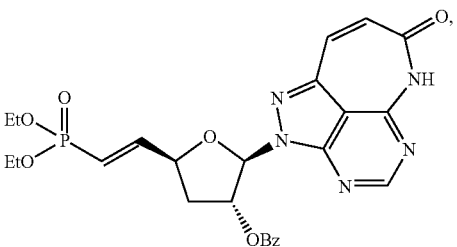
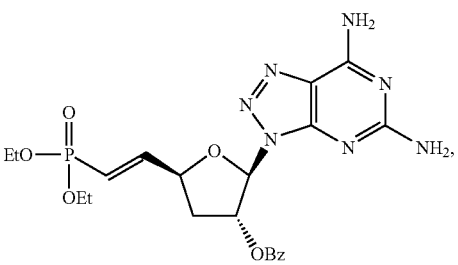
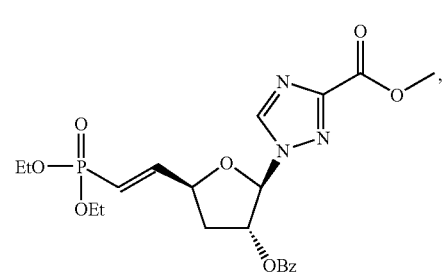

61
-continued
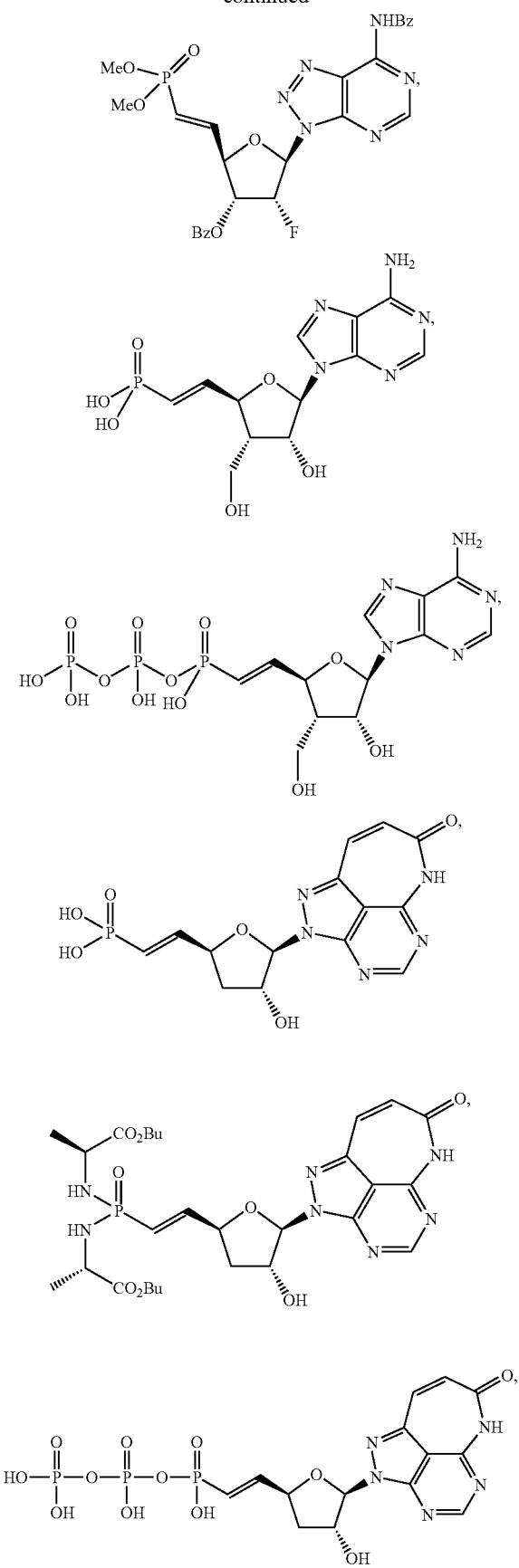
62
-continued
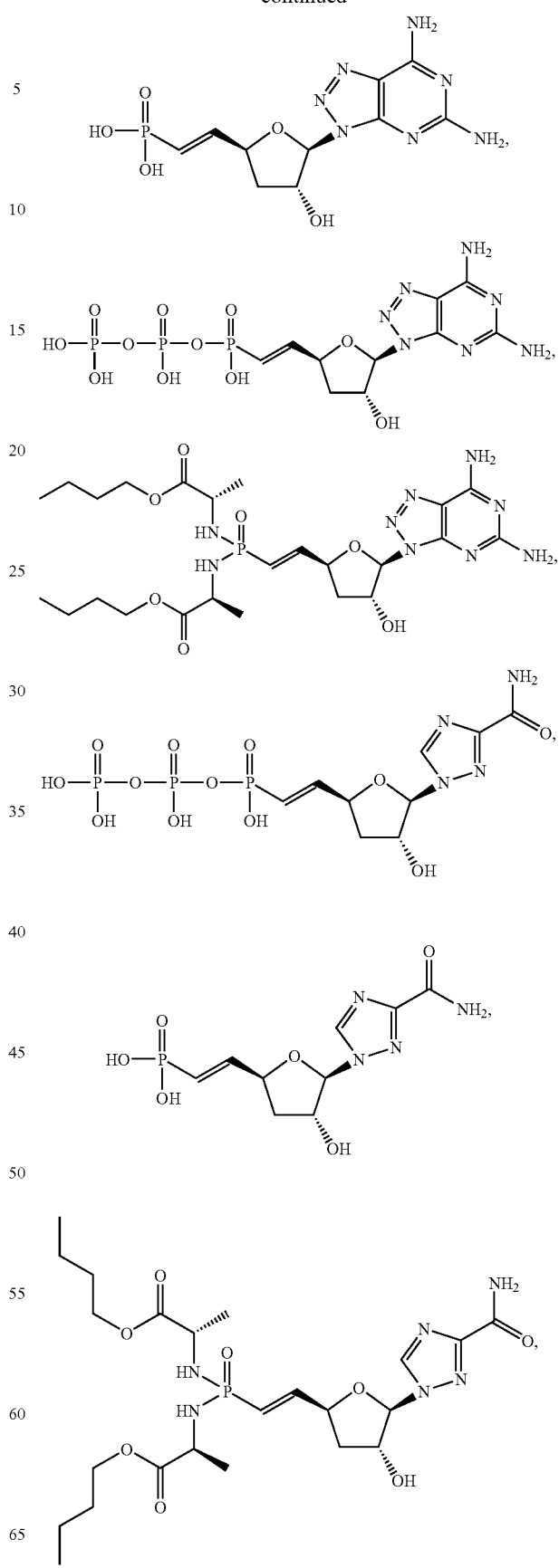

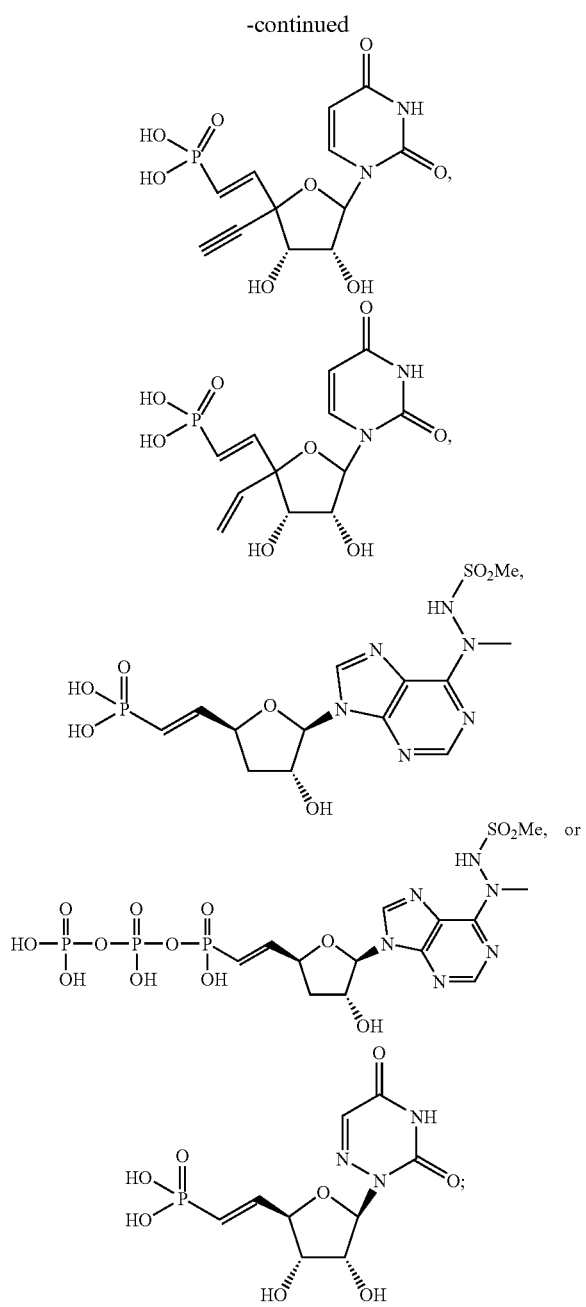

or a pharmaceutical acceptable salt thereof.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of Formula I" means a compound of Formula I or a pharmaceutically acceptable salt, solvate, or physiologically functional derivative thereof. Similarly, with respect to isolatable intermediates, the phrase "a compound of Formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms(i.e., $C_1$-$C_{12}$ alkoxy), or 1 to 6 carbon atoms(i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or -OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms(i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e. , $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2CH$=$CH_2$), cyclopentenyl (—$C_5H_7$), and 5-hexenyl (—$CH_2CH_2CH_2CH_2CH$=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2C$≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH$ ($CH_3$)—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡CH—).

"Amino" refers generally to a nitrogen radical which can be considered a derivative of ammonia, having the formula —$N(X)_2$, where each "X" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include —$NH_2$, —$N(alkyl)_2$, —NH(alkyl), —$N(carbocyclyl)_2$, —NH(carbocyclyl), —$N(heterocyclyl)_2$, —NH(heterocyclyl), —$N(aryl)_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —$NH_2$, —$NH(CH_3)$, —$N(CH_3)_2$, —NH($CH_2CH_3$), —$N(CH_2CH_3)_2$, —NH(phenyl), —$N(phenyl)_2$, —NH(benzyl), —$N(benzyl)_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or $sp^3$ carbon atom, but also an $sp^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or $sp^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —$O^-$, =O, —OR, —SR, —$S^-$, —$NR_2$, —$N^+R_3$, =NR, —$CX_3$, —CN, —OCN, —SCN, —N=C=O, —NCS, —NO, —$NO_2$, =$N_2$, —$N_3$, —NHC(=O)R, —C(=O)R, —C(=O)NRR—S(=O)$_2$—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)($O^-$)$_2$, —P(=O)(OH)$_2$, —P(O)(OR)($O^-$), —C(=O)R, —C(=O)X, —C(S)R, —C(O)OR, —C(O)$O^-$, –C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, or nitrogen substituents. These substituents may be part of a prodrug moiety. As defined herein, "phosphonate" and "phosphonate group" include molecules with phosphonic acid, phosphonic monoester, phosphonic diester, phosphonamidate, phosphondiamidate and phosphonthioate functional groups.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-IV should be selected in order to provide a compound which is sufficiently stable to provide a pharmaceutically useful compound which can be formulated into an acceptably stable pharmaceutical composition. Compounds of Formula I-IV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

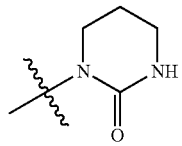

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

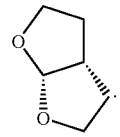

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or sp$^3$ carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or sp$^3$ carbon atom, but also a sp$^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is 5 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I-IV (e.g., an optionally substituted aryl group) refers to a moiety having 0, 1, 2, or more substituents.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

Certain $Y^1$ and $Y^2$ alternatives are nitrogen oxides such as $^+$N(O)(R) or $^+$N(O)(OR). These nitrogen oxides, as shown here attached to a carbon atom, can also be represented by charge separated groups such as

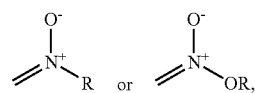

respectively, and are intended to be equivalent to the aforementioned representations for the purposes of describing this invention.

Unless otherwise specified, the carbon atoms of this invention are intended to have a valence of four. In some chemical structure representations where carbon atoms do not have a sufficient number of variables attached to produce a valence of four, the remaining carbon substitutents needed to provide a valence of four should be assumed to be hydrogen. For example,

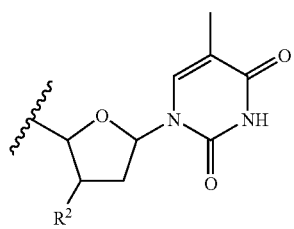

has the same meaning as

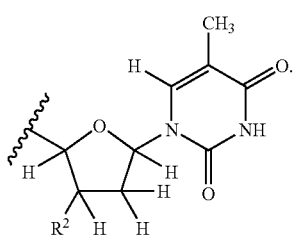

"Pharmaceutically acceptable prodrug" refers to a compound that is metabolized in the host, for example hydrolyzed or oxidized, by either enzymatic action or by general acid or base solvolysis, to form an active ingredient. Typical examples of prodrugs of the compounds of the invention have biologically labile protecting groups on a functional moiety of the compound. Prodrugs include compounds that can be oxidized, reduced, aminated, deaminated, esterified, deesterified, alkylated, dealkylated, acylated, deacylated, phosphorylated, dephosphorylated, photolyzed, hydrolyzed, or other functional group change or conversion involving forming or breaking chemical bonds on the prodrug.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

A prodrug moiety may include an active metabolite or drug itself.

Exemplary prodrug moieties include the hydrolytically sensitive or labile acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was used as a prodrug strategy for carboxylic acids and then applied to phosphates and phosphonates by Farquhar et al (1983) *J. Pharm. Sci.* 72: 324; also U.S. Pat. Nos. 4,816,570, 4,968,788, 5,663,159 and 5,792,756. In certain compounds of the invention, a prodrug moiety is part of a phosphonate group. The acyloxyalkyl ester may be used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (DeLambert et al (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al (1992) *J. Chem. Soc. Perkin Trans. I* 2345; Brook et al WO 91/19721. Still other benzylic prodrugs have been described containing a carboxylic ester-containing group attached to the benzylic methylene (Glazier et al WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al (1993) *Antiviral Res.*, 22: 155-174; Benzaria et al (1996) *J. Med Chem.* 39: 4958). Cyclic phosphonate esters have also been described as prodrugs of phosphorus-containing compounds (Erion et al, U.S. Pat. No. 6,312,662).

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

Any reference to any of the compounds of the invention also includes a reference to a physiologically acceptable salt thereof Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Nucleobase" or "nucleoside base" means any nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally-occurring nucleobases: adenine, guanine, cytosine, uracil, thymine, and analogs of the naturally-occurring nucleobases, e.g. 7-deazaadenine, substituted 7-deazapurines such as 7-alkynyl, 7-cyano, 7-carboxamido, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazine bases including 3-oxo-2-carboxamidopyrazine, 5-fluoro-3-oxo-2-carboxamidopyrazine, 6-fluoro-3-oxo-2-carboxamidopyrazine, pyrazolo[3,4-D]pyrimidines (U.S. Pat. Nos. 6,143,877 and 6,127,121; WO 01/38584), and ethenoadenine (Fasman (1989) in *Practical Handbook of Biochemistry and Molecular Biology*, pp. 385-394, CRC Press, Boca Raton, Fla.).

The invention provides compounds of Formula I-IV wherein B is a nucleoside base. The compounds may include any nucleoside base, provided the final compound possesses useful therapeutic (e.g. anti-viral) properties. Additional nucleoside bases that can be incorporated into the compounds of this invention are disclosed in United States Patent Application Publication Number 2004/0147464, United States Patent Application Publication Number 2005/0215511, International Patent Application Publication Number WO 03/061385, International Patent Application Publication Number WO 03/062257, International Patent Application Publication Number WO 03/072757, International Patent Application Publication Number WO 03/073989, International Patent Application Publication Number WO 2005/021568, International Patent Application Publication Number WO 2005/123087, International Patent Application Publication Number WO 2006/002231, and International Patent Application Publication Number WO 2006/000922.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Whenever a compound described herein is substituted with more than one of the same designated group, e.g., "R" or "$R^1$", then it will be understood that the groups may be the same or different, i.e., each group is independently selected. Wavy lines, ⁓, indicate the site of covalent bond attachments to the adjoining substructures, groups, moieties, or atoms.

The compounds of the Formula I-IV bear a phosphonate group, which may be a prodrug moiety

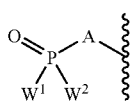

wherein $W^1$ and $W^2$ are each independently a group of the formula:

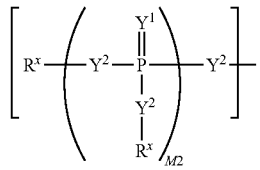

wherein:
each $Y^2$ is independently a bond, O, $CR_2$, NR, $^+N(O)(R)$, N(OR), $^+N(O)(OR)$, N—$NR_2$, S, S—S, S(O), or $S(O)_2$;
M2 is 0, 1 or 2;
each $R^y$ is independently H, F, Cl, Br, I, OH, R, —C(=$Y^1$)R, —C(=$Y^1$)OR, —C(=$Y^1$)N($R)_2$, —N($R)_2$, —$^+N(R)_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N($R)_2$), —SC(=$Y^1$)R, —SC(=$Y^1$)OR, —SC(=$Y^1$)(N($R)_2$), —N(R)C(=$Y^1$)R, —N(R)C(=$Y^1$)OR, or —N(R)C(=$Y^1$)N($R)_2$, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, $C_1$-$C_8$ alkylsulfonate, $C_1$-$C_8$ alkylamino, $C_1$-$C_8$ alkylhydroxyl, $C_1$-$C_8$ alkylthiol, alkylsulfone (—$SO_2$R), sulfonamide (—$SO_2NR_2$), alkylsulfoxide (—SOR), ester (—C(=O)OR), amido (—C(=O)$NR_2$), nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, a protecting group or $W^3$; or when taken together, two $R^y$ on the same carbon atom form a carbocyclic ring of 3 to 7 carbon atoms;
each $R^x$ is independently $R^y$, a protecting group, or the formula:

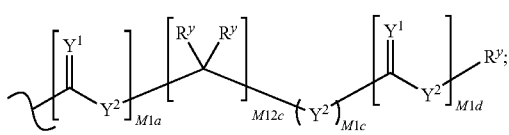

wherein:
M1a, M1c, and M1d are independently 0 or 1;
M12c is 0, 1, 2, 3, 4, 5, 6, 7, 8, 9, 10, 11 or 12; or
when taken together, two $R^x$ are optionally substituted $C_2$-$C_4$ alkylene thereby forming a phosphorous-containing heterocycle;
each R is H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group;

$W^3$ is $W^4$ or $W^5$; $W^4$ is R, —C($Y^1$)$R^y$, —C($Y^1$)$W^5$, —$SO_2R^y$, or —$SO_2W^5$; and $W^5$ is a carbocycle or a heterocycle wherein $W^5$ is independently substituted with 0 to 3 $R^y$ groups.

$W^5$ carbocycles and $W^5$ heterocycles may be independently substituted with 0 to 3 $R^y$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

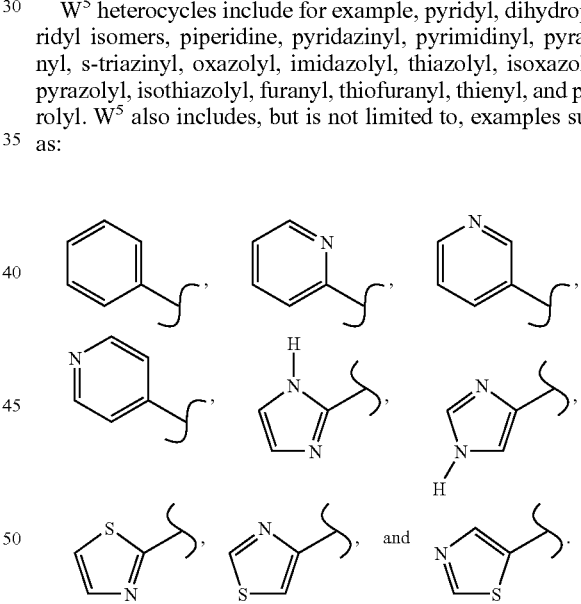

$W^5$ carbocycles and heterocycles may be independently substituted with 0 to 3 R groups, as defined above. For example, substituted $W^5$ carbocycles include:

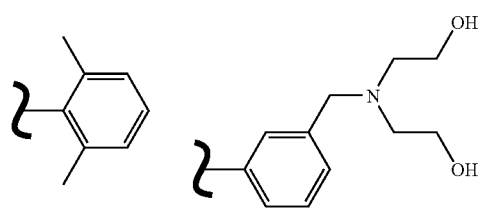

-continued

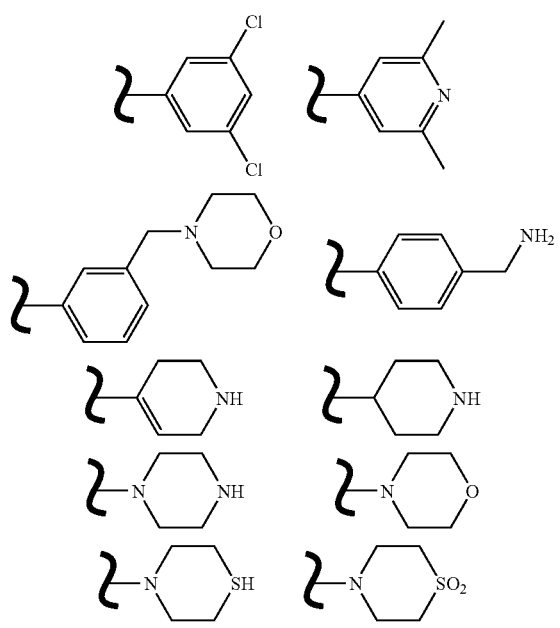

Examples of substituted phenyl carbocycles include:

Embodiments of

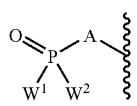

of Formula I-IV compounds include substructures such as:

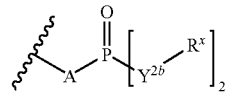

wherein each $Y^{2b}$ is, independently, O or N($R^x$).
Another embodiment of

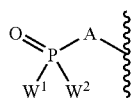

of Formula I-IV includes the substructures:

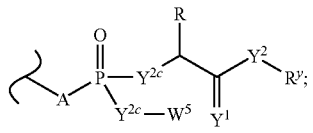

wherein each $Y^{2c}$ is, independently, O, N($R^y$) or S.
Another embodiment of

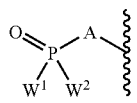

of Formula I-IV compounds includes the substructures:

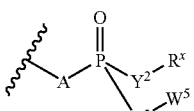

wherein $W^5$ is a carbocycle such as phenyl or substituted phenyl. Such a substructure includes:

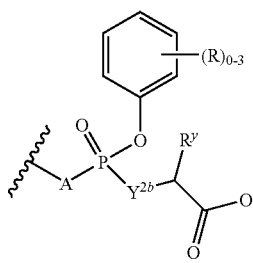

wherein $Y^{2b}$ is O or N($R^x$) and the phenyl carbocycle is substituted with 0 to 3 R groups.

An embodiment of

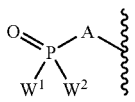

of Formula I-IV includes phenyl phosphonamidate amino acids, e.g. alanate esters and phenyl phosphonate-lactate esters:

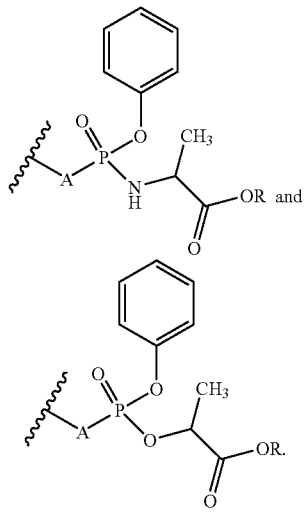

The chiral carbon of the amino acid and lactate moieties may be either the R or S configuration or the racemic mixture.

Another embodiment of

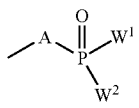

of Formula I-IV is

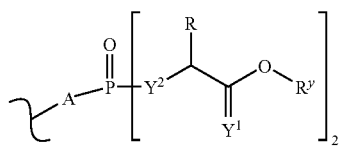

wherein each $Y^1$ is, independently, O or S and each $Y^2$ is, independently, —O— or —NH—. In a preferred embodiment $Y^1$ is O. In another preferred embodiment, $Y^1$ is O and $R^y$ is $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl or $C_2$-$C_8$ substituted alkynyl. In another preferred embodiment, $Y^1$ is O; $R^y$ is $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl or $C_2$-$C_8$ substituted alkynyl; and R is $CH_3$. In another preferred embodiment, $Y^1$ is O; $R^y$ is $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl or $C_2$-$C_8$ substituted alkynyl; R is $CH_3$; and each $Y^2$ is —NH—. In a preferred embodiment, $W^1$ and $W^2$ are, independently, nitrogen-linked, naturally occurring amino acids or naturally occurring amino acid esters. In another preferred embodiment, $W^1$ and $W^2$ are, independently, naturally occurring 2-hydroxy carboxylic acids or naturally occurring 2-hydroxy carboxylic acid esters wherein the acid or ester is linked to P through the 2-hydroxy group.

Another embodiment of

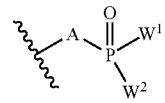

of Formula I, Formula II, Formula III or Formula IV is

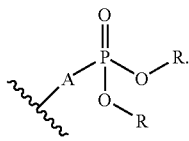

In one preferred embodiment each R is, independently, $C_1$-$C_8$ alkyl. In another preferred embodiment each R is, independently, $C_6$-$C_{20}$ aryl or $C_6$-$C_{20}$ substituted aryl.

Embodiments of $R^x$ include esters, carbamates, carbonates, thioesters, amides, thioamides, and urea groups:

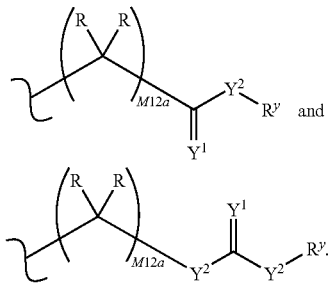

Cellular Accumulation

One aspect of the invention is HCV polymerase inhibitor compounds capable of accumulating in human PBMC (peripheral blood monocyte cells).

Optionally, the compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment, the intracellular half-life of a metabolite of the compound in human PBMC is improved when compared to an analog of the compound not having the phosphonate or phosphonate prodrug. In such embodiments, the metabolite is typically generated intracellularly, more typically, it is generated within human PBMC. Still more typically, the metabolite is a product of the cleavage of a phosphonate prodrug within human PBMCs. More typically yet, the phosphonate prodrug is cleaved to form a metabolite having at least one negative charge at physiological pH. Most typically, the phosphonate prodrug is enzymatically cleaved within human PBMC to form a phosphonate having at least one active hydrogen atom of the form P—OH.

Recursive Substituents

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, $R^x$ contains a $R^y$ substituent. $R^y$ can be R. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$ and $R^y$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $W^3$ will occur 0 to 8 times, $R^y$ will occur 0 to 6 times in a given embodiment. Even more typically, $W^3$ will occur 0 to 6 times, $R^y$ will occur 0 to 4 times and $R^3$ will occur 0 to 8 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Protecting Groups

In the context of the present invention, embodiments of protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PRT" will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect functional groups such as carboxyl, hydroxyl or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protection. For example, protecting groups for —OH groups (whether hydroxyl, carboxylic acid, phosphonic acid, or other functions) are embodiments of "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether-and Ester-forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may not be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary embodiment of a phosphonate ester-forming group is the phenyl carbocycle in a substructure having the formula:

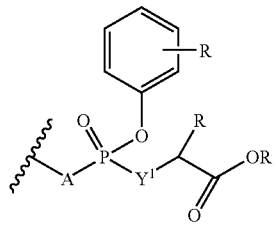

wherein the phenyl carbocycle is substituted with 0 to 3 R groups. Also, in this embodiment, where $Y^1$ is O, a lactate ester is formed. Alternatively, where $Y^1$ is NR, N—OR or N—N(R)$_2$, then phosphonamidate esters result. R susbstituents include H and $C_1$-$C_{12}$ alkyl.

In its ester-forming role, a protecting group typically is bound to any acidic group such as, by way of example and not limitation, a —CO$_2$H or —C(S)OH group, thereby resulting in —CO$_2$R$^x$ where R$^x$ is defined herein. Also, R$^x$ for example includes the enumerated ester groups of WO 95/07920.

Examples of protecting groups include (a)-(j):

(a) $C_3$-$C_{12}$ heterocycle (described above) or aryl. These aromatic groups optionally are polycyclic or monocyclic. Examples include phenyl, spiryl, 2-and 3-pyrrolyl, 2-and 3-thienyl, 2-and 4-imidazolyl, 2-, 4-and 5-oxazolyl, 3-and 4-isoxazolyl, 2-, 4-and 5-thiazolyl, 3-, 4-and 5-isothiazolyl, 3-and 4-pyrazolyl, 1-, 2-, 3-and 4-pyridinyl, and 1-, 2-, 4-and 5-pyrimidinyl.

(b) $C_3$-$C_{12}$ heterocycle or aryl substituted with halo, $R^1$, $R^1$—O—$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include, but are not limited to, 2-, 3- and 4-alkoxyphenyl ($C_1$-$C_{12}$ alkyl); 2-, 3- and 4-methoxyphenyl; 2-, 3- and 4-ethoxyphenyl; 2,3-, 2,4-, 2,5-, 2,6-, 3,4- and 3,5-diethoxyphenyl; 2- and 3-carboethoxy-4-hydroxyphenyl; 2- and 3-ethoxy-4-hydroxyphenyl; 2- and 3-ethoxy-5-hydroxyphenyl; 2- and 3-ethoxy-6-hydroxyphenyl; 2-, 3- and 4-O-acetylphenyl; 2-, 3- and 4-dimethylaminophenyl; 2-, 3- and 4-methylmercaptophenyl; 2-, 3- and 4-halophenyl (including 2-, 3- and 4-fluorophenyl and 2-, 3- and 4-chlorophenyl); 2,3-, 2,4-, 2,5-, 2,6-, 3,4- and 3,5-dimethylphenyl; 2,3-, 2,4-, 2,5-, 2,6-, 3,4- and 3,5-biscarboxyethylphenyl; 2,3-, 2,4-, 2,5-, 2,6-, 3,4- and 3,5-dimethoxyphenyl; 2,3-, 2,4-, 2,5-, 2,6-, 3,4- and 3,5-dihalophenyl (including 2,4-difluorophenyl and 3,5-difluorophenyl); 2-, 3- and 4-haloalkylphenyl (1 to 5 halogen atoms, $C_1$-$C_{12}$ alkyl including 4-trifluoromethylphenyl); 2-, 3- and 4-cyanophenyl; 2-, 3- and 4-nitrophenyl; 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl); 4-N-methylpiperidinyl; 3-N-methylpiperidinyl; 1-ethylpiperazinyl; benzyl; alkylsalicylphenyl ($C_1$-$C_4$ alkyl, including 2-, 3- and 4-ethylsalicylphenyl); 2-, 3- and 4-acetylphenyl; 1,8-dihydroxynaphthyl (—$C_{10}H_6$—OH) and aryloxy ethyl [$C_6$-$C_9$ aryl (including phenoxy ethyl)], 2,2'-dihydroxybiphenyl; 2-, 3- and 4-N,N-dialkylaminophenol; —$C_6H_4CH_2$—N($CH_3$)$_2$; trimethoxybenzyl; triethoxybenzyl; and 2-alkyl pyridinyl ($C_{1-4}$ alkyl).

(c)

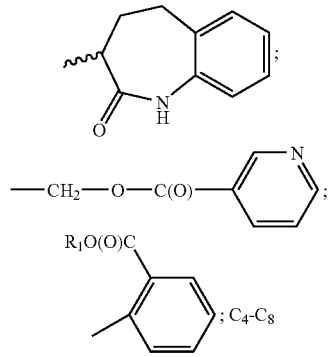

—$CH_2$—O—C(O)— 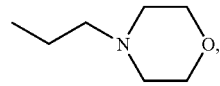 ;

$R_1O(O)C$ 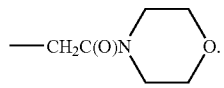 ; $C_4$-$C_8$ esters of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl.

(d) Alkoxy ethyl [$C_1$-$C_6$ alkyl including —$CH_2$—$CH_2$—O—$CH_3$ (methoxy ethyl)], alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, $CH_2CH_2F$, —$CH_2CH_2Cl$, —$CH_2CF_3$, and —$CH_2CCl_3$), —N-2-propylmorpholino, 2,3-dihydro-6-hydroxyindene, sesamol, catechol monoester, —$CH_2$—C(O)—N($R^1$)$_2$, —$CH_2$—S(O)($R^1$), —$CH_2$—S(O)$_2$($R^1$), —$CH_2$—CH(OC(O)$CH_2R^1$)—$CH_2$(OC(O)$CH_2R^1$), enolpyruvate (HOOC—C(=$CH_2$)—) or glycerol.

(e) A 5 or 6 carbon monosaccharide, disaccharide or oligosaccharide (3 to 9 monosaccharide residues).

(f) Triglycerides such as α-D-β-diglycerides (wherein the fatty acids composing glyceride lipids generally are naturally-occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

(g) Phospholipids linked to the carboxyl group through the phosphate of the phospholipid.

(h) Phthalidyl (shown in FIG. 1 of Clayton et al., *Antimicrob. Agents Chemo.* (1974) 5(6):670-671.

(i) Cyclic carbonates such as (5-$R_d$-2-oxo-1,3-dioxolen-4-yl)methyl esters (Sakamoto et al., *Chem. Pharm. Bull.* (1984) 32(6)2241-2248) where $R_d$ is $R_1$, $R_4$ or aryl.

(j)

—$CH_2C(O)N$⟨morpholino⟩O.

The hydroxyl groups of the compounds of this invention optionally are substituted with one of groups III, IV or V disclosed in WO 94/21604, or with isopropyl.

As further embodiments, Table A lists examples of protecting group ester moieties that for example can be bonded via oxygen to —C(O)O— and —P(O)(O—)$_2$ groups. Several amidates also are shown, which are bound directly to —C(O)— or —P(O)$_2$. Esters of structures 1-5, 8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| | |
|---|---|
| 1. | —$CH_2$—C(O)—N($R_1$)$_2$* |
| 2. | —$CH_2$—S(O)($R_1$) |
| 3. | —$CH_2$—S(O)$_2$($R_1$) |
| 4. | —$CH_2$—O—C(O)—$CH_2$—$C_6H_5$ |
| 5. | 3-cholesteryl |
| 6. | 3-pyridyl |
| 7. | N-ethylmorpholino |

TABLE A-continued

| | |
|---|---|
| 8. | —CH$_2$—O—C(O)—C$_6$H$_5$ |
| 9. | —CH$_2$—O—C(O)—CH$_2$CH$_3$ |
| 10. | —CH$_2$—O—C(O)—C(CH$_3$)$_3$ |
| 11. | —CH$_2$—CCl$_3$ |
| 12. | —C$_6$H$_5$ |
| 13. | —NH—CH$_2$—C(O)O—CH$_2$CH$_3$ |
| 14. | —N(CH$_3$)—CH$_2$—C(O)O—CH$_2$CH$_3$ |
| 15. | —NHR$_1$ |
| 16. | —CH$_2$—O—C(O)—C$_{10}$H$_{15}$ |
| 17. | —CH$_2$—O—C(O)—CH(CH$_3$)$_2$ |
| 18. | —CH$_2$C#H(OC(O)CH$_2$R$_1$)—CH$_2$—(OC(O)CH$_2$R$_1$)* |
| 19. | —CH$_2$C(O)N⟨morpholine⟩ |
| 20. | ⟨benzazepinone structure⟩ |
| 21. | ⟨sugar structure with HO, OH, HO, HO⟩ |
| 22. | —CH$_2$—O—C(O)-pyridyl |
| 23. | —CH$_2$CH$_2$-pyridyl |
| 24. | CH$_3$O(O)C-tolyl |
| 25. | CH$_3$CH$_2$O(O)C-tolyl |
| 26. | —CH$_2$-(3,4,5-trimethoxyphenyl) |

Other esters that are suitable for use herein are described in EP 632048.

Protecting groups also includes "double ester" forming profunctionalities such as —CH$_2$OC(O)OCH$_3$,

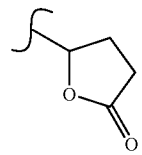

—CH$_2$SCOCH$_3$, —CH$_2$OCON(CH$_3$)$_2$, or alkyl- or aryl-acyloxyalkyl groups of the structure —CH(R$^1$ or W$^5$)O((CO)R$^{37}$) or —CH(R$^1$ or W$^5$)((CO)OR$^{38}$) (linked to oxygen of the acidic group) wherein R$^{37}$ and R$^{38}$ are alkyl, aryl, or alkylaryl groups (see U.S. Pat. No. 4,968,788). Frequently R$^{37}$ and R$^{38}$ are bulky groups such as branched alkyl, ortho-substituted aryl, meta-substituted aryl, or combinations thereof, including normal, secondary, iso-and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including —CH(CH$_2$CH$_2$OCH$_3$)OC(O)C(CH$_3$)$_3$,

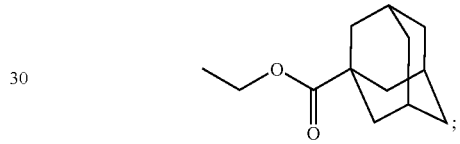

—CH$_2$OC(O)C$_{10}$H$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

For prodrug purposes, the ester typically chosen is one heretofore used for antibiotic drugs, in particular the cyclic carbonates, double esters, or the phthalidyl, aryl or alkyl esters.

In some embodiments the protected acidic group is an ester of the acidic group and is the residue of a hydroxyl-containing functionality. In other embodiments, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under R$^{31}$ or R$^{35}$), the table on page 105, and pages 21-23 (as R). Of particular interest are esters of unsubstituted aryl such as phenyl or arylalkyl such benzyl, or hydroxy-, halo-, alkoxy-, carboxy-and/or alkylestercarboxy-substituted aryl or alkylaryl, especially phenyl, ortho-ethoxyphenyl, or $C_1$-$C_4$ alkylestercarboxyphenyl (salicylate $C_1$-$C_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

A plurality of the acidic hydroxyls may be protected. If more than one acidic hydroxyl is protected then the same or a different protecting group is employed, e.g., the esters may be different or the same, or a mixed amidate and ester may be used.

Typical acid hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2-and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4''-Tris(4,5-dichlorophthalimidophenyl)methyl, 4,4',4''-Tris(levulinoyloxyphenyl)methyl, 4,4',4''-Tris(benzoyloxyphenyl)methyl, 3-(Imidazol-1-ylmethyl)bis(4',4''-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3-tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

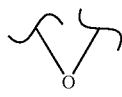 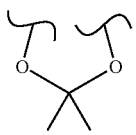

TABLE B-continued

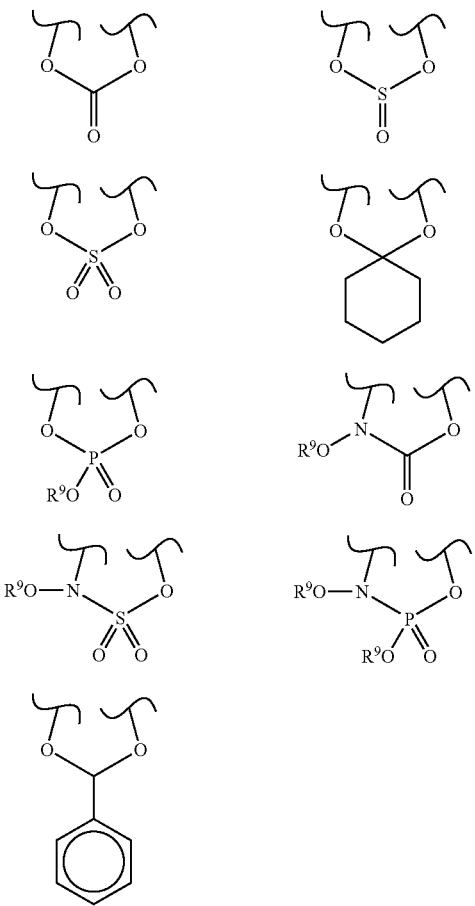

wherein $R^9$ is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'-and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl) propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl) phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N-N Derivatives: (N-nitro, N-nitroso, N-oxide);

N-P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

Protected amino groups include carbamates, amides and amidines, e.g. —NHC(O)OR$^1$, —NHC(O)R$^1$ or —N=CR$^1$N(R$^1$)$_2$. Another protecting group, also useful as a prodrug for amino or —NH(R$^5$), is:

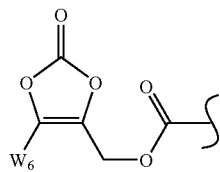

See for example Alexander, J. et al (1996) *J. Med. Chem.* 39:480-486.

Amino Acid and Polypeptide Protecting Group and Conjugates

An amino acid or polypeptide protecting group of a compound of the invention has the structure R$^{15}$NHCH(R$^{16}$)C(O)—, where R$^{15}$ is H, an amino acid or polypeptide residue, or R$^{15}$, and R$^{16}$ is defined below.

R$^{16}$ is lower alkyl or lower alkyl (C$_1$-C$_6$) substituted with amino, carboxyl, amide, carboxyl ester, hydroxyl, C$_6$-C$_7$ aryl, guanidinyl, imidazolyl, indolyl, sulfhydryl, sulfoxide, and/or alkylphosphate. R$^{16}$ also is taken together with the amino acid α-N to form a proline residue (R$^{16}$=—CH$_2$)$_3$—). However, R$^{16}$ is generally the side group of a naturally-occurring amino acid such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. R$^{16}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —NHSO$_2$R, NHC(O)R, —N(R)$_2$, NH$_2$ or —NH(R)(H), whereby for example a carboxylic acid is reacted, i.e. coupled, with the amine to form an amide, as in C(O)NR$_2$. A phosphonic acid may be reacted with the amine to form a phosphonamidate, as in —P(O)(OR)(NR$_2$).

Amino acids have the structure R$^{17}$C(O)CH(R$^{16}$)NH—, where R$^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono-or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted with substituents. These conjugates are generally produced by forming an amide bond between a carboxyl group of the amino acid (or C-terminal amino acid of a polypeptide for example). Generally, only one of any site in the scaffold drug-like compound is amidated with an amino acid as described herein, although it is within the scope of this invention to introduce amino acids at more than one permitted site. Usually, a carboxyl group of R$^3$ is amidated with an amino acid. In general, the α-amino or α-carboxyl group of the amino acid or the terminal amino or carboxyl group of a polypeptide are bonded to the scaffold, parental functionalities. Carboxyl or amino groups in the amino acid side chains generally may be used to form the amide bonds with the parental compound or these groups may need to be protected during synthesis of the conjugates as described further below.

With respect to the carboxyl-containing side chains of amino acids or polypeptides it will be understood that the carboxyl group optionally will be blocked, e.g. esterified or amidated with R.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro-and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may be immunogenic in an animal typically used to raise antibodies, e.g., rabbit, mouse, horse, or rat. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases, which digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In certain embodiments, a phosphonate group substituted with an amino acid or peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence -$X^{40}$-pro-$^{50}$-(where $X^{40}$ is any amino acid residue and $X^{50}$ is an amino acid residue, a carboxyl ester of proline, or hydrogen) will be cleaved by luminal carboxypeptidase to yield $X^{40}$ with a free carboxyl, which in turn is expected to autocatalytically cleave the phosphonoamidate bond. The carboxy group of $X^{50}$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) Pharm Res. 9:969-978. Transport competent peptides can thus be used to enhance bioavailability of the amidate compounds. Di- or tripeptides having one or more amino acids in the D configuration may be compatible with peptide transport. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Intracellular Targeting

The phosphonate group of Formula I-IV compounds may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in Formula I-IV compounds thus affords an unstable intermediate which releases a negatively charged "locked in" intermediate.

After passage inside a cell, intracellular enzymatic cleavage or modification of the phosphonate prodrug compound may result in an intracellular accumulation or retention of the cleaved or modified compound by a "trapping" mechanism. The cleaved or modified compound, i.e. active metabolite, may then be "locked-in" the cell, i.e. accumulate in the cell by a significant change in charge, polarity, or other physical property change which decreases the rate at which the cleaved or modified compound can exit the cell, relative to the rate at which it entered as the phosphonate prodrug. Other mechanisms by which a therapeutic effect is achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

It is known that the drug is activated in vivo by phosphorylation. Such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be converted, via the derivatives of this invention, to the active phosphorylated species.

From the foregoing, it will be apparent that many structurally different known approved and experimental HCV polymerase inhibitor drugs can be derivatized in accord with the present invention. Numerous such drugs are specifically mentioned herein. However, it should be understood that the discussion of drug families and their specific members for derivatization according to this invention is not intended to be exhaustive, but merely illustrative.

As another example, when the selected drug contains multiple reactive hydroxyl functions, a mixture of intermediates and final products may again be obtained. In the unusual case in which all hydroxy groups are approximately equally reactive, there is not expected to be a single, predominant product, as each mono-substituted product will be obtained in approximate by equal amounts, while a lesser amount of multiply-substituted product will also result. Generally speaking, however, one of the hydroxyl groups will be more susceptible to substitution than the other(s), e.g. a primary hydroxyl will be more reactive than a secondary hydroxyl, an unhindered hydroxyl will be more reactive than a hindered one. Consequently, the major product will be a mono-substituted one in which the most reactive hydroxyl has been derivatized while other mono-substituted and multiply-substituted products may be obtained as minor products.

Stereoisomers

The compounds of the invention, exemplified by Formula I, II, III or IV may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid.

Monovalent salts are preferred if a water soluble salt is desired.

Metal salts typically are prepared by treating a metal hydroxide with a compound of this invention. Examples of metal salts which are prepared in this way are salts containing $Li^+$, $Na^+$, and $K^+$. A less soluble metal salt may be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV Polymerase

Another aspect of the invention relates to methods of inhibiting the activity of HCV polymerase comprising the step of treating a sample suspected of containing HCV with a composition of the invention.

Compositions of the invention may act as inhibitors of HCV polymerase, as intermediates for such inhibitors or have other utilities as described below. The inhibitors will bind to locations on the surface or in a cavity of HCV polymerase having a geometry unique to HCV polymerase. Compositions binding HCV polymerase may bind with varying degrees of reversibility. Those compounds binding substantially irreversibly are ideal candidates for use in this method of the invention. Once labeled, the substantially irreversibly binding compositions are useful as probes for the detection of HCV polymerase. Accordingly, the invention relates to methods of detecting HCV polymerase in a sample suspected of containing HCV polymerase comprising the steps of: treating a sample suspected of containing HCV polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing HCV polymerase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HCV polymerase, frequently a pathogenic organism such as HCV. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HCV polymerase after application of the composition can be observed by any method including direct and indirect methods of detecting HCV polymerase activity. Quantitative, qualitative, and semiquantitative methods of determining HCV polymerase activity are all contemplated. Typically one of the screening methods described above are applied, however, any other method such as observation of the physiological properties of a living organism are also applicable.

Organisms that contain HCV polymerase include the HCV virus. The compounds of this invention are useful in the treatment or prophylaxis of HCV infections in animals or in man.

However, in screening compounds capable of inhibiting human immunodeficiency viruses, it should be kept in mind that the results of enzyme assays may not correlate with cell culture assays. Thus, a cell based assay should be the primary screening tool.

Screens for HCV Polymerase Inhibitors.

Compositions of the invention are screened for inhibitory activity against HCV polymerase by any of the conventional techniques for evaluating enzyme activity. Within the context of the invention, typically compositions are first screened for inhibition of HCV polymerase in vitro and compositions showing inhibitory activity are then screened for activity in vivo. Compositions having in vitro Ki (inhibitory constants) of less then about $5 \times 10^{-6}$ M, typically less than about $1 \times 10^{-7}$ M and preferably less than about $5 \times 10^{-8}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. Preferably, the other active therapeutic ingredients or agents are interferons, ribavirin analogs, NS3 protease inhibitors, alpha-glucosidase 1 inhibitors, hepatoprotectants, non-nucleoside inhibitors of HCV, and other drugs for treating HCV.

Combinations of the compounds of Formula I-IV are typically selected based on the condition to be treated, cross-reactivities of ingredients and pharmaco-properties of the combination. For example, when treating an infection (e.g., HCV), the compositions of the invention are combined with other active therapeutic agents (such as those described herein).

Suitable active therapeutic agents or ingredients which can be combined with the compounds of Formula I-IV can include interferons, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon; ribavirin analogs, e.g., rebetol, copegus, VX-497, and viramidine (taribavirin); NS5a inhibitors, e.g., A-831 and A-689; NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125; NS3 protease inhibitors, e.g., SCH-503034 (SCH-7), VX-950 (Telaprevir), ITMN-191, and BILN-2065; alpha-glucosidase 1 inhibitors, e.g., MX-3253 (celgosivir) and UT-231B; hepatoprotectants, e.g., IDN-6556, ME 3738, MitoQ, and LB-84451; non-nucleoside inhibitors of HCV, e.g., benzimidazole derivatives, benzo-1,2,4-thiadiazine derivatives, and phenylalanine derivatives; and other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or exipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, alpha-glucosidase 1 inhibitors, hepatoprotectants, non-nucleoside inhibitors of HCV, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of Formula I-IV and additional active therapeutic agents may be selected to treat patients infected with HCV and other conditions such as HIV infections. Accordingly, the compounds of Formula I-IV may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+)calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811, 19) pharmacokinetic enhancers, e.g., BAS-100 and SPI452, 20) RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, whereby HCV polymerase is inhibited.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, and at least one additional active therapeutic agent, whereby HCV polymerase is inhibited.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, and at least one additional active therapeutic agent selected from the group consisting of interferons, ribavirin analogs, NS3 protease inhibitors, alpha-glucosidase 1 inhibitors, hepatoprotectants, non-nucleoside inhibitors of HCV, and other drugs for treating HCV.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof, and at least one additional active therapeutic agent, whereby HCV polymerase is inhibited.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof, and at least one additional active therapeutic agent selected from the group consisting of interferons, ribavirin analogs, NS3 protease inhibitors, alpha-glucosidase 1 inhibitors, hepatoprotectants, non-nucleoside inhibitors of HCV, and other drugs for treating HCV.

In still yet another embodiment, the present application provides for the use of a compound of the present invention, or a pharmaceutically acceptable salt, solvate, and/or ester thereof, for the preparation of a medicament for treating an HCV infection in a patient.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV polymerase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but may be substantially hydrolyzed to the parental drug in the digestive lumen, liver or other metabolic organ, or within cells in general.

Exemplary Methods of Making the Compounds of the Invention.

The invention provides many methods of making the compositions of the invention. The compositions are prepared by any of the applicable techniques of organic synthesis. Many such techniques are well known in the art, such as those elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

Dialkyl phosphonates may be prepared according to the methods of: Quast et al (1974) *Synthesis* 490; Stowell et al (1990) *Tetrahedron Lett.* 3261; U.S. Pat. No. 5,663,159.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I,* 1577). Chlorophosphonate species may also be generated in situ from corresponding cyclic phosphites (Silverburg, et al., (1996) *Tetrahedron Lett.*, 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron Lett.*, 29:5763-66). Caution: fluorophosphonate compounds may be highly toxic!

Phosphonate prodrugs of the present invention may also be prepared from the precursor free acid by Mitsunobu reactions (Mitsunobu, (1981) *Synthesis,* 1; Campbell, (1992) *J. Org. Chem.*, 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.*, 2:145; Ohashi, et al, (1988) *Tetrahedron Lett.*, 29:1189), and benzotriazolyloxytris-(dimethylamino)phosphonium salts (Campagne, et al, (1993) *Tetrahedron Lett.*, 34:6743).

Aryl halides undergo $Ni^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis, et al, (1987) *J. Am. Chem. Soc.* 109:2831; Lu, et al, (1987) *Synthesis,* 726). In another method, aryl phosphonate esters are prepared from aryl phosphates under anionic rearrangement conditions (Melvin (1981) *Tetrahedron Lett.* 22:3375; Casteel, et al, (1991) *Synthesis,* 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethyl-carbodiimide hydrochloride (EDCI) can also be utilized for the synthesis of cyclic phosphonate prodrugs.

The carbamoyl group may be formed by reaction of a hydroxy group according to the methods known in the art, including the teachings of Ellis, US 2002/0103378 A1 and Hajima, U.S. Pat. No. 6,018,049.

Schemes and Examples

A number of exemplary methods for the preparation of the compositions of the invention are provided below. These methods are intended to illustrate the nature of such preparations are not intended to limit the scope of applicable methods.

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes above and in the examples (hereafter "exemplary schemes") leads to various analogs of the specific exemplary materials produce. The above cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g. (−)menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal-and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

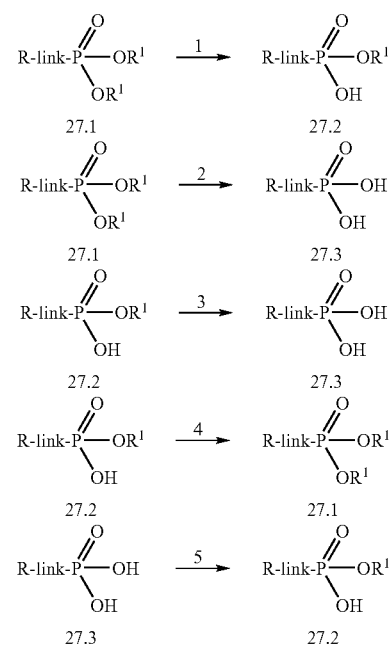

Scheme A

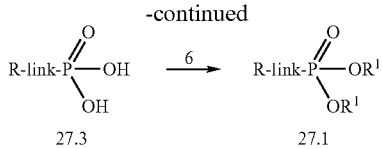

27.3    6→    27.1

Scheme A shows the general interconversions of certain phosphonate compounds: acids —P(O)(OH)$_2$; mono-esters —P(O)(OR$_1$)(OH); and diesters —P(O)(OR$_1$)$_2$ in which the R$^1$ groups are independently selected, and defined herein before, and the phosphorus is attached through a carbon moiety (link, i.e. linker), which is attached to the rest of the molecule, e.g. drug or drug intermediate (R). The R$^1$ groups attached to the phosphonate esters in Scheme 1 may be changed using established chemical transformations. The interconversions may be carried out in the precursor compounds or the final products using the methods described below. The methods employed for a given phosphonate transformation depend on the nature of the substituent R$^1$. The preparation and hydrolysis of phosphonate esters is described in *Organic Phosphorus Compounds*, G. M. Kosolapoff, L. Maeir, eds, Wiley, 1976, p. 9ff.

The conversion of a phosphonate diester 27.1 into the corresponding phosphonate monoester 27.2 (Scheme A, Reaction 1) can be accomplished by a number of methods. For example, the ester 27.1 in which R$^1$ is an arylalkyl group such as benzyl, can be converted into the monoester compound 27.2 by reaction with a tertiary organic base such as diazabicyclooctane (DABCO) or quinuclidine, as described in *J. Org. Chem.*, 1995, 60:2946. The reaction is performed in an inert hydrocarbon solvent such as toluene or xylene, at about 110° C. The conversion of the diester 27.1 in which R$^1$ is an aryl group such as phenyl, or an alkenyl group such as allyl, into the monoester 27.2 can be effected by treatment of the ester 27.1 with a base such as aqueous sodium hydroxide in acetonitrile or lithium hydroxide in aqueous tetrahydrofuran. Phosphonate diesters 27.2 in which one of the groups R$^1$ is arylalkyl, such as benzyl, and the other is alkyl, can be converted into the monoesters 27.2 in which R$^1$ is alkyl, by hydrogenation, for example using a palladium on carbon catalyst. Phosphonate diesters in which both of the groups R$^1$ are alkenyl, such as allyl, can be converted into the monoester 27.2 in which R$^1$ is alkenyl, by treatment with chlorotris (triphenylphosphine)rhodium (Wilkinson's catalyst) in aqueous ethanol at reflux, optionally in the presence of diazabicyclooctane, for example by using the procedure described in *J. Org. Chem.*, 38:3224 1973 for the cleavage of allyl carboxylates.

The conversion of a phosphonate diester 27.1 or a phosphonate monoester 27.2 into the corresponding phosphonic acid 27.3 (Scheme A, Reactions 2 and 3) can effected by reaction of the diester or the monoester with trimethylsilyl bromide, as described in *J. Chem. Soc., Chem. Comm.*, 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 27.2 in which R$^1$ is arylalkyl such as benzyl, can be converted into the corresponding phosphonic acid 27.3 by hydrogenation over a palladium catalyst, or by treatment with hydrogen chloride in an ethereal solvent such as dioxane. A phosphonate monoester 27.2 in which R$^1$ is alkenyl such as, for example, allyl, can be converted into the phosphonic acid 27.3 by reaction with Wilkinson's catalyst in an aqueous organic solvent, for example in 15% aqueous acetonitrile, or in aqueous ethanol, for example using the procedure described in *Helv. Chim. Acta.*, 68:618, 1985. Palladium catalyzed hydrogenolysis of phosphonate esters 27.1 in which R$^1$ is benzyl is described in *J. Org. Chem.*, 24:434, 1959. Platinum-catalyzed hydrogenolysis of phosphonate esters 27.1 in which R$^1$ is phenyl is described in *J. Amer. Chem. Soc.*, 78:2336, 1956.

The conversion of a phosphonate monoester 27.2 into a phosphonate diester 27.1 (Scheme A, Reaction 4) in which the newly introduced R$^1$ group is alkyl, arylalkyl, or haloalkyl such as chloroethyl, can be effected by a number of reactions in which the substrate 27.2 is reacted with a hydroxy compound R$^1$OH, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 27.1 to the diester 27.1 can be effected by the use of the Mitsunobu reaction. The substrate is reacted with the hydroxy compound R$^1$OH, in the presence of diethyl azodicarboxylate and a triarylphosphine such as triphenyl phosphine. Alternatively, the phosphonate monoester 27.2 can be transformed into the phosphonate diester 27.1, in which the introduced R$^1$ group is alkenyl or arylalkyl, by reaction of the monoester with the halide R$^1$Br, in which R$^1$ is as alkenyl or arylalkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 27.2 is transformed into the chloro analog —P(O)(OR$^1$)Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product —P(O)(OR$^1$)Cl is then reacted with the hydroxy compound R$^1$OH, in the presence of a base such as triethylamine, to afford the phosphonate diester 27.1.

A phosphonic acid —P(O)(OH)$_2$ can be transformed into a phosphonate monoester —P(O)(OR$^1$)(OH) (Scheme A, Reaction 5) by means of the methods described above of for the preparation of the phosphonate diester —P(O)(OR$^1$)$_2$ 27.1, except that only one molar proportion of the component R$^1$OH or R$^1$Br is employed.

A phosphonic acid —P(O)(OH)$_2$ 27.3 can be transformed into a phosphonate diester —P(O)(OR$^1$)$_2$ 27.1 (Scheme A, Reaction 6) by a coupling reaction with the hydroxy compound R$^1$OH, in the presence of a coupling agent such as Aldrithiol-2 (Aldrich) and triphenylphosphine. The reaction is conducted in a basic solvent such as pyridine. Alternatively, phosphonic acids 27.3 can be transformed into phosphonic esters 27.1 in which R$^1$ is aryl, such as phenyl, by means of a coupling reaction employing, for example, phenol and dicyclohexylcarbodiimide in pyridine at about 70° C. Alternatively, phosphonic acids 27.3 can be transformed into phosphonic esters 27.1 in which R$^1$ isalkenyl, by means of an alkylation reaction. The phosphonic acid is reacted with the alkenyl bromide R$^1$Br in a polar organic solvent such as acetonitrile solution at reflux temperature, in the presence of a base such as cesium carbonate, to afford the phosphonic ester 27.1.

Phosphonate prodrugs of the present invention may also be prepared from the precursor free acid by Mitsunobu reactions (Mitsunobu, (1981) *Synthesis*, 1; Campbell, (1992) *J. Org. Chem.*, 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.*, 2:145; Ohashi, et al, (1988) *Tetrahedron Lett.*, 29:1189), and benzotriazolyloxytris-(dimethylamino)phosphonium salts (Campagne, et al, (1993) *Tetrahedron Lett.*, 34:6743).

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in J. Gen. Chem. USSR, 1983, 53, 480, Zh. Obschei Khim., 1958, 28, 1063, or J. Org. Chem., 1994, 59, 6144, or by reaction with oxalyl chloride, as described in J. Am. Chem. Soc., 1994, 116, 3251, or J. Org. Chem., 1994, 59, 6144, or by reaction with phosphorus pentachloride, as described in J. Org. Chem., 2001, 66, 329, or in J. Med. Chem., 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in J. Chem. Soc., Chem. Comm., 1991, 312, or Nucleosides Nucleotides 2000, 19, 1885. Activated sulfonyloxy derivatives are obtained by the reaction of phosphonic acids with trichloromethylsulfonyl chloride, as described in J. Med. Chem. 1995, 38, 4958, or with triisopropylbenzenesulfonyl chloride, as described in Tet. Lett., 1996, 7857, or Bioorg. Med. Chem. Lett., 1998, 8, 663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in J. Chem. Soc., Chem. Comm., 1991, 312, or J. Med. Chem., 1980, 23, 1299 or Coll. Czech. Chem. Comm., 1987, 52, 2792. The use of ethyl dimethylaminopropyl carbodiimide for activation and coupling of phosphonic acids is described in Tet. Lett., 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in J. Org. Chem., 1995, 60, 5214, and J. Med. Chem., 1997, 40, 3842, mesitylene-2-sulfonyl-3-nitro-1,2,4-triazole (MSNT), as described in J. Med. Chem., 1996, 39, 4958, diphenylphosphoryl azide, as described in J. Org. Chem., 1984, 49, 1158, 1-(2,4,6-triisopropylbenzenesulfonyl-3-nitro-1,2,4-triazole (TPSNT) as described in Bioorg. Med. Chem. Lett., 1998, 8, 1013, bromotris(dimethylamino)phosphonium hexafluorophosphate (BroP), as described in Tet. Lett., 1996, 37, 3997, 2-chloro-5,5-dimethyl-2-oxo-1,3,2-dioxaphosphinane, as described in Nucleosides Nucleotides 1995, 14, 871, and diphenyl chlorophosphate, as described in J. Med. Chem., 1988, 31, 1305.

Phosphonic acids are converted into amidates and esters by means of the Mitsonobu reaction, in which the phosphonic acid and the amine or hydroxy reactant are combined in the presence of a triaryl phosphine and a dialkyl azodicarboxylate. The procedure is described in Org. Lett., 2001, 3, 643, or J. Med. Chem., 1997, 40, 3842.

Phosphonic esters are also obtained by the reaction between phosphonic acids and halo compounds, in the presence of a suitable base. The method is described, for example, in Anal. Chem., 1987, 59, 1056, or J. Chem. Soc. Perkin Trans., I, 1993, 19, 2303, or J. Med. Chem., 1995, 38, 1372, or Tet. Lett., 2002, 43, 1161.

Schemes 1-4 illustrate the conversion of phosphonate esters and phosphonic acids into carboalkoxy-substituted phosphorobisamidates (Scheme 1), phosphoroamidates (Scheme 2), phosphonate monoesters (Scheme 3) and phosphonate diesters, (Scheme 4).

Scheme 1 illustrates various methods for the conversion of phosphonate diesters 1.1 into phosphorobisamidates 1.5. The diester 1.1, prepared as described previously, is hydrolyzed, either to the monoester 1.2 or to the phosphonic acid 1.6. The methods employed for these transformations are described above. The monoester 1.2 is converted into the monoamidate 1.3 by reaction with an aminoester 1.9, in which the group $R^2$ is H or alkyl, the group $R^4$ is an alkylene moiety such as, for example, $CHCH_3$, $CHPr^1$, $CH(CH_2Ph)$, $CH_2CH(CH_3)$ and the like, or a group present in natural or modified aminoacids, and the group $R^5$ is alkyl. The reactants are combined in the presence of a coupling agent such as a carbodiimide, for example dicyclohexyl carbodiimide, as described in J. Am. Chem. Soc., 1957, 79, 3575, optionally in the presence of an activating agent such as hydroxybenztriazole, to yield the amidate product 1.3. The amidate-forming reaction is also effected in the presence of coupling agents such as BOP, as described in J. Org. Chem., 1995, 60, 5214, Aldrithiol, PYBOP and similar coupling agents used for the preparation of amides and esters. Alternatively, the reactants 1.2 and 1.9 are transformed into the monoamidate 1.3 by means of a Mitsonobu reaction. The preparation of amidates by means of the Mitsonobu reaction is described in J. Med. Chem., 1995, 38, 2742. Equimolar amounts of the reactants are combined in an inert solvent such as tetrahydrofuran in the presence of a triaryl phosphine and a dialkyl azodicarboxylate. The thus-obtained monoamidate ester 1.3 is then transformed into amidate phosphonic acid 1.4. The conditions used for the hydrolysis reaction depend on the nature of the $R^1$ group, as described previously. The phosphonic acid amidate 1.4 is then reacted with an aminoester 1.9, as described above, to yield the bisamidate product 1.5, in which the amino substituents are the same or different.

An example of this procedure is shown in Scheme 1, Example 1. In this procedure, a dibenzyl phosphonate 1.14 is reacted with diazabicyclooctane (DABCO) in toluene at reflux, as described in J. Org. Chem., 1995, 60, 2946, to afford the monobenzyl phosphonate 1.15. The product is then reacted with equimolar amounts of ethyl alaninate 1.16 and dicyclohexyl carbodiimide in pyridine, to yield the amidate product 1.17. The benzyl group is then removed, for example by hydrogenolysis over a palladium catalyst, to give the monoacid product 1.18. This compound is then reacted in a Mitsonobu reaction with ethyl leucinate 1.19, triphenyl phosphine and diethylazodicarboxylate, as described in J. Med. Chem., 1995, 38, 2742, to produce the bisamidate product 1.20.

Using the above procedures, but employing, in place of ethyl leucinate 1.19 or ethyl alaninate 1.16, different aminoesters 1.9, the corresponding products 1.5 are obtained.

Alternatively, the phosphonic acid 1.6 is converted into the bisamidate 1.5 by use of the coupling reactions described above. The reaction is performed in one step, in which case the nitrogen-related substituents present in the product 1.5 are the same, or in two steps, in which case the nitrogen-related substituents can be different. An example of the method is shown in Scheme 1, Example 2. In this procedure, a phosphonic acid 1.6 is reacted in pyridine solution with excess ethyl phenylalaninate 1.21 and dicyclohexylcarbodiimide, for example as described in J. Chem. Soc., Chem. Comm., 1991, 1063, to give the bisamidate product 1.22.

Using the above procedures, but employing, in place of ethyl phenylalaninate, different aminoesters 1.9, the corresponding products 1.5 are obtained.

As a further alternative, the phosphonic acid 1.6 is converted into the mono or bis-activated derivative 1.7, in which Lv is a leaving group such as chloro, imidazolyl, triisopropylbenzenesulfonyloxy etc. The conversion of phosphonic acids into chlorides 1.7 (Lv=Cl) is effected by reaction with thionyl chloride or oxalyl chloride and the like, as described in Organic Phosphorus Compounds, G. M. Kosolapoff, L. Maeir, eds, Wiley, 1976, p. 17. The conversion of phosphonic acids into monoimidazolides 1.7 (Lv=imidazolyl) is described in J. Med. Chem., 2002, 45, 1284 and in J. Chem. Soc. Chem. Comm., 1991, 312. Alternatively, the phosphonic acid is activated by reaction with triisopropylbenzenesulfonyl chloride, as described in Nucleosides and Nucleotides, 2000, 10, 1885. The activated product is then reacted with the aminoester 1.9, in the presence of a base, to give the bisamidate 1.5. The reaction is performed in one step, in which case the nitrogen substituents present in the product 1.5 are the same, or in two steps, via the intermediate 1.11, in which case the nitrogen substituents can be different.

Examples of these methods are shown in Scheme 1, Examples 3 and 5. In the procedure illustrated in Scheme 1, Example 3, a phosphonic acid 1.6 is reacted with ten molar equivalents of thionyl chloride, as described in Zh. Obschei Khim., 1958, 28, 1063, to give the dichloro compound 1.23. The product is then reacted at reflux temperature in a polar aprotic solvent such as acetonitrile, and in the presence of a base such as triethylamine, with butyl serinate 1.24 to afford the bisamidate product 1.25.

Using the above procedures, but employing, in place of butyl serinate 1.24, different aminoesters 1.9, the corresponding products 1.5 are obtained.

In the procedure illustrated in Scheme 1, Example 5, the phosphonic acid 1.6 is reacted, as described in J. Chem. Soc. Chem. Comm., 1991, 312, with carbonyl diimidazole to give the imidazolide 1.32. The product is then reacted in acetonitrile solution at ambient temperature, with one molar equivalent of ethyl alaninate 1.33 to yield the monodisplacement product 1.34. The latter compound is then reacted with carbonyl diimidazole to produce the activated intermediate 1.35, and the product is then reacted, under the same conditions, with ethyl N-methylalaninate 1.33a to give the bisamidate product 1.36.

Using the above procedures, but employing, in place of ethyl alaninate 1.33 or ethyl N-methylalaninate 1.33a, different aminoesters 1.9, the corresponding products 1.5 are obtained.

The intermediate monoamidate 1.3 is also prepared from the monoester 1.2 by first converting the monoester into the activated derivative 1.8 in which Lv is a leaving group such as halo, imidazolyl etc, using the procedures described above.

The product 1.8 is then reacted with an aminoester 1.9 in the presence of a base such as pyridine, to give an intermediate monoamidate product 1.3. The latter compound is then converted, by removal of the $R^1$ group and coupling of the product with the aminoester 1.9, as described above, into the bisamidate 1.5.

An example of this procedure, in which the phosphonic acid is activated by conversion to the chloro derivative 1.26, is shown in Scheme 1, Example 4. In this procedure, the phosphonic monobenzyl ester 1.15 is reacted, in dichloromethane, with thionyl chloride, as described in Tet. Let., 1994, 35, 4097, to afford the phosphoryl chloride 1.26. The product is then reacted in acetonitrile solution at ambient temperature with one molar equivalent of ethyl 3-amino-2-methylpropionate 1.27 to yield the monoamidate product 1.28. The latter compound is hydrogenated in ethyl acetate over a 5% palladium on carbon catalyst to produce the monoacid product 1.29. The product is subjected to a Mitsonobu coupling procedure, with equimolar amounts of butyl alaninate 1.30, triphenyl phosphine, diethylazodicarboxylate and triethylamine in tetrahydrofuran, to give the bisamidate product 1.31.

Using the above procedures, but employing, in place of ethyl 3-amino-2-methylpropionate 1.27 or butyl alaninate 1.30, different aminoesters 1.9, the corresponding products 1.5 are obtained.

The activated phosphonic acid derivative 1.7 is also converted into the bisamidate 1.5 via the diamino compound 1.10. The conversion of activated phosphonic acid derivatives such as phosphoryl chlorides into the corresponding amino analogs 1.10, by reaction with ammonia, is described in Organic Phosphorus Compounds, G. M. Kosolapoff, L. Maeir, eds, Wiley, 1976. The diamino compound 1.10 is then reacted at elevated temperature with a haloester 1.12, in a polar organic solvent such as dimethylformamide, in the presence of a base such as dimethylaminopyridine or potassium carbonate, to yield the bisamidate 1.5.

An example of this procedure is shown in Scheme 1, Example 6. In this method, a dichlorophosphonate 1.23 is reacted with ammonia to afford the diamide 1.37. The reaction is performed in aqueous, aqueous alcoholic or alcoholic solution, at reflux temperature. The resulting diamino compound is then reacted with two molar equivalents of ethyl 2-bromo-3-methylbutyrate 1.38, in a polar organic solvent such as N-methylpyrrolidinone at ca. 150° C., in the presence of a base such as potassium carbonate, and optionally in the presence of a catalytic amount of potassium iodide, to afford the bisamidate product 1.39.

Using the above procedures, but employing, in place of ethyl 2-bromo-3-methylbutyrate 1.38, different haloesters 1.12 the corresponding products 1.5 are obtained.

The procedures shown in Scheme 1 are also applicable to the preparation of bisamidates in which the aminoester moiety incorporates different functional groups. Scheme 1, Example 7 illustrates the preparation of bisamidates derived from tyrosine. In this procedure, the monoimidazolide 1.32 is reacted with propyl tyrosinate 1.40, as described in Example 5, to yield the monoamidate 1.41. The product is reacted with carbonyl diimidazole to give the imidazolide 1.42, and this material is reacted with a further molar equivalent of propyl tyrosinate to produce the bisamidate product 1.43.

Using the above procedures, but employing, in place of propyl tyrosinate 1.40, different aminoesters 1.9, the corresponding products 1.5 are obtained. The aminoesters employed in the two stages of the above procedure can be the same or different, so that bisamidates with the same or different amino substituents are prepared.

Scheme 2 illustrates methods for the preparation of phosphonate monoamidates. In one procedure, a phosphonate monoester 1.1 is converted, as described in Scheme 1, into the activated derivative 1.8. This compound is then reacted, as described above, with an aminoester 1.9, in the presence of a base, to afford the monoamidate product 2.1.

The procedure is illustrated in Scheme 2, Example 1. In this method, a monophenyl phosphonate 2.7 is reacted with, for example, thionyl chloride, as described in J. Gen. Chem. USSR., 1983, 32, 367, to give the chloro product 2.8. The product is then reacted, as described in Scheme 1, with ethyl alaninate 2.9, to yield the amidate 2.10.

Using the above procedures, but employing, in place of ethyl alaninate 2.9, different aminoesters 1.9, the corresponding products 2.1 are obtained.

Alternatively, the phosphonate monoester 1.1 is coupled, as described in Scheme 1, with an aminoester 1.9 to produce the amidate 2.1. If necessary, the $R^1$ substituent is then altered, by initial cleavage to afford the phosphonic acid 2.2. The procedures for this transformation depend on the nature of the $R^1$ group, and are described above. The phosphonic acid is then transformed into the ester amidate product 2.3, by reaction with the hydroxy compound $R^3OH$, in which the group $R^3$ is aryl, heteroaryl, alkyl, cycloalkyl, haloalkyl etc, using the same coupling procedures (carbodiimide, Aldrithiol-2, PYBOP, Mitsonobu reaction etc) described in Scheme 1 for the coupling of amines and phosphonic acids.

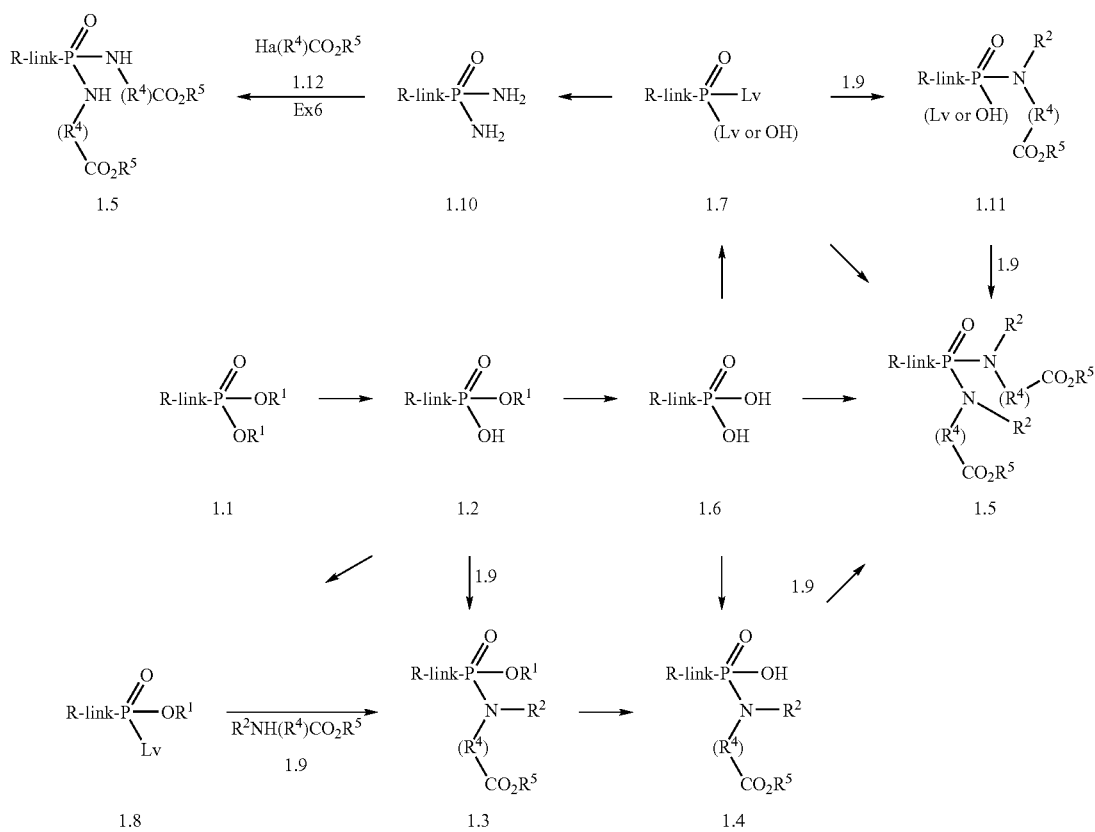

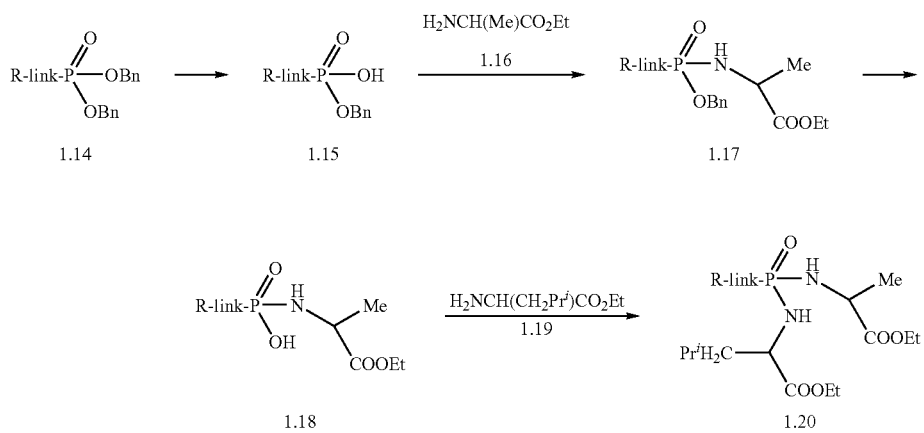

-continued
Scheme 1 Example 2
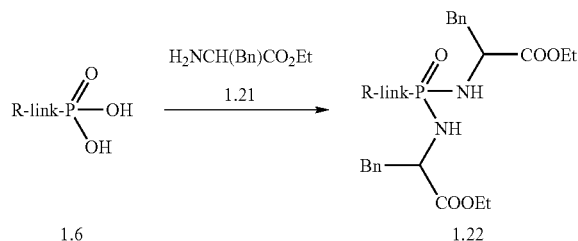
Scheme 1 Example 3
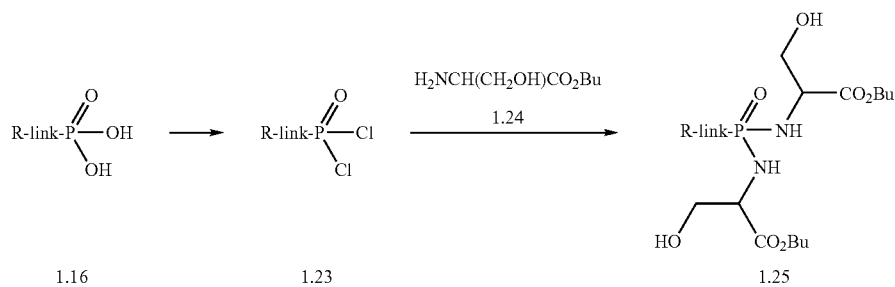
Scheme 1 Example 4
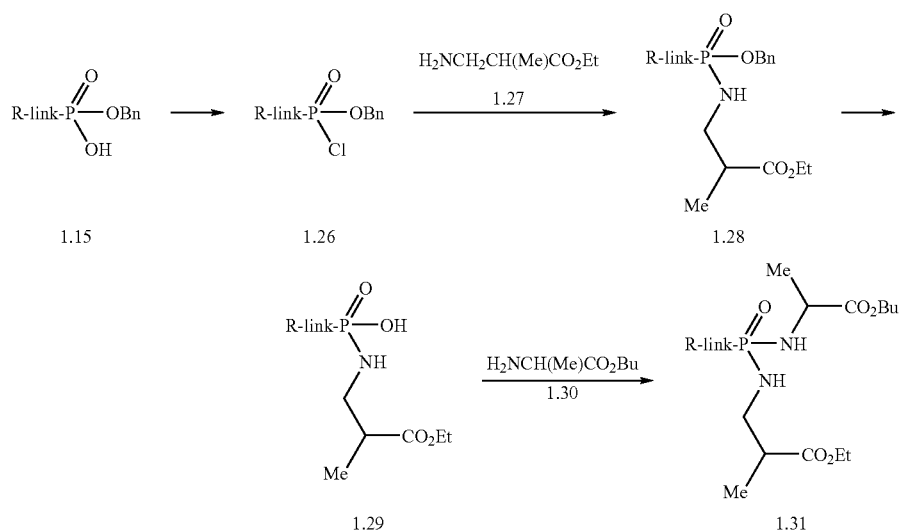
Scheme 1 Example 5
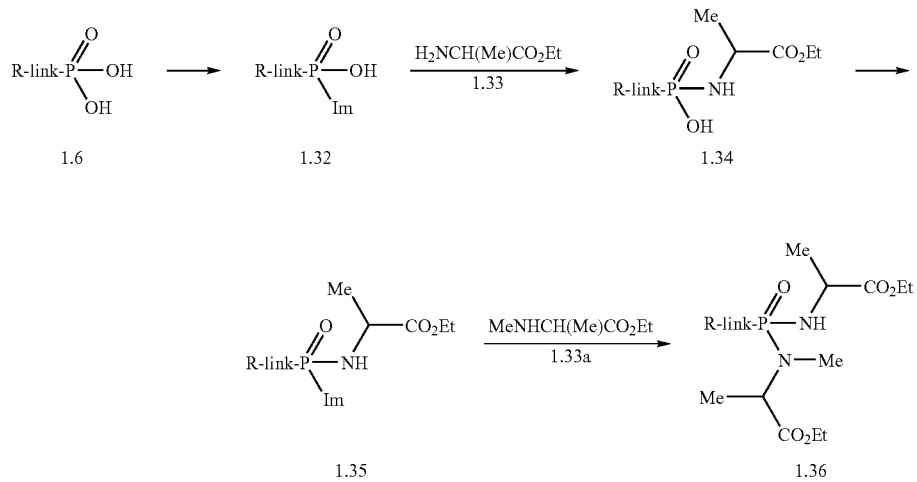

Scheme 1 Example 6

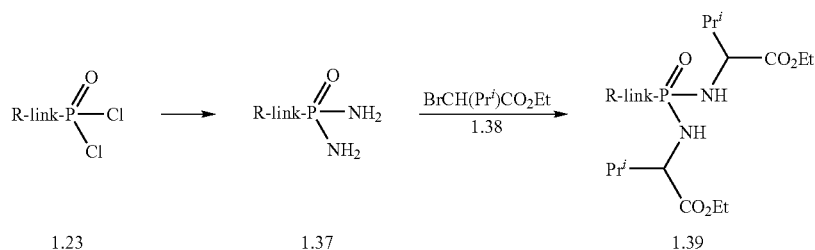

Scheme 1 Example 7

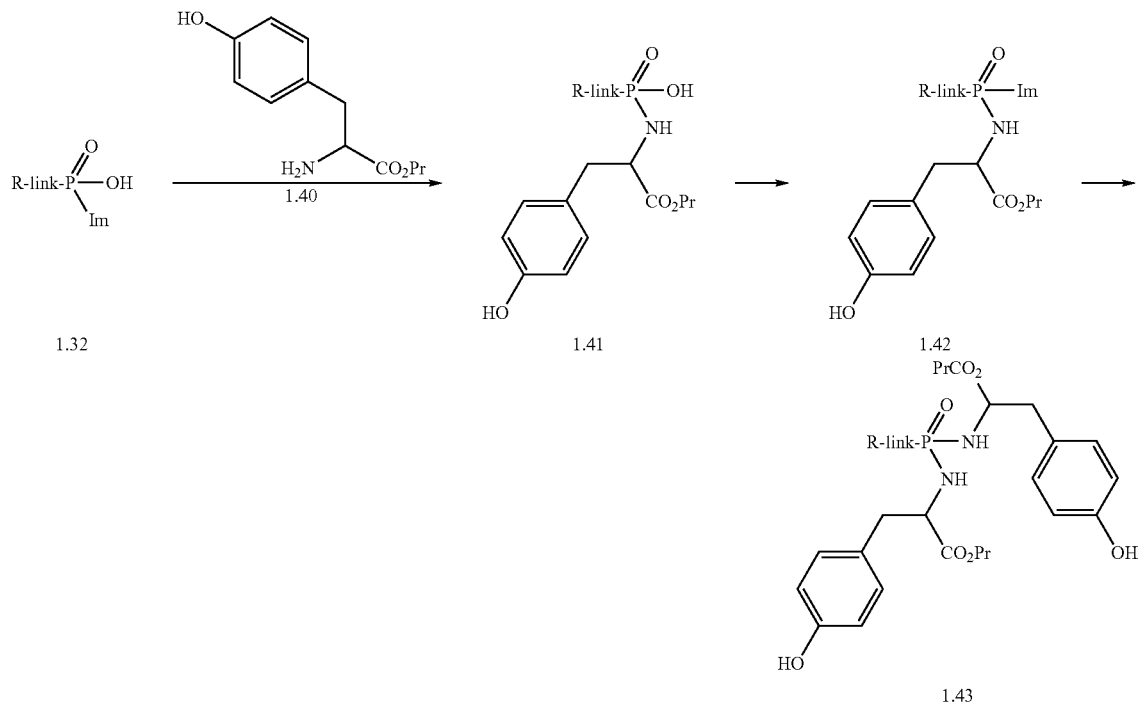

Examples of this method are shown in Scheme 2, Examples and 2 and 3. In the sequence shown in Example 2, a monobenzyl phosphonate 2.11 is transformed by reaction with ethyl alaninate, using one of the methods described above, into the monoamidate 2.12. The benzyl group is then removed by catalytic hydrogenation in ethyl acetate solution over a 5% palladium on carbon catalyst, to afford the phosphonic acid amidate 2.13. The product is then reacted in dichloromethane solution at ambient temperature with equimolar amounts of 1-(dimethylaminopropyl)-3-ethylcarbodiimide and trifluoroethanol 2.14, for example as described in Tet. Lett., 2001, 42, 8841, to yield the amidate ester 2.15.

In the sequence shown in Scheme 2, Example 3, the monoamidate 2.13 is coupled, in tetrahydrofuran solution at ambient temperature, with equimolar amounts of dicyclohexyl carbodiimide and 4-hydroxy-N-methylpiperidine 2.16, to produce the amidate ester product 2.17.

Using the above procedures, but employing, in place of the ethyl alaninate product 2.12 different monoacids 2.2, and in place of trifluoroethanol 2.14 or 4-hydroxy-N-methylpiperidine 2.16, different hydroxy compounds $R^3OH$, the corresponding products 2.3 are obtained.

Alternatively, the activated phosphonate ester 1.8 is reacted with ammonia to yield the amidate 2.4. The product is then reacted, as described in Scheme 1, with a haloester 2.5, in the presence of a base, to produce the amidate product 2.6. If appropriate, the nature of the $R^1$ group is changed, using the procedures described above, to give the product 2.3. The method is illustrated in Scheme 2, Example 4. In this sequence, the monophenyl phosphoryl chloride 2.18 is reacted, as described in Scheme 1, with ammonia, to yield the amino product 2.19. This material is then reacted in N-methylpyrrolidinone solution at 170° C. with butyl 2-bromo-3-phenylpropionate 2.20 and potassium carbonate, to afford the amidate product 2.21.

Using these procedures, but employing, in place of butyl 2-bromo-3-phenylpropionate 2.20, different haloesters 2.5, the corresponding products 2.6 are obtained.

The monoamidate products 2.3 are also prepared from the doubly activated phosphonate derivatives 1.7. In this procedure, examples of which are described in Synlett., 1998, 1, 73, the intermediate 1.7 is reacted with a limited amount of the aminoester 1.9 to give the mono-displacement product 1.11. The latter compound is then reacted with the hydroxy compound $R^3OH$ in a polar organic solvent such as dimethylformamide, in the presence of a base such as diisopropylethylamine, to yield the monoamidate ester 2.3.

The method is illustrated in Scheme 2, Example 5. In this method, the phosphoryl dichloride 2.22 is reacted in dichloromethane solution with one molar equivalent of ethyl N-methyl tyrosinate 2.23 and dimethylaminopyridine, to generate the monoamidate 2.24. The product is then reacted with phenol 2.25 in dimethylformamide containing potassium carbonate, to yield the ester amidate product 2.26.

Using these procedures, but employing, in place of ethyl N-methyl tyrosinate 2.23 or phenol 2.25, the aminoesters 1.9 and/or the hydroxy compounds $R^3OH$, the corresponding products 2.3 are obtained.

Scheme 2

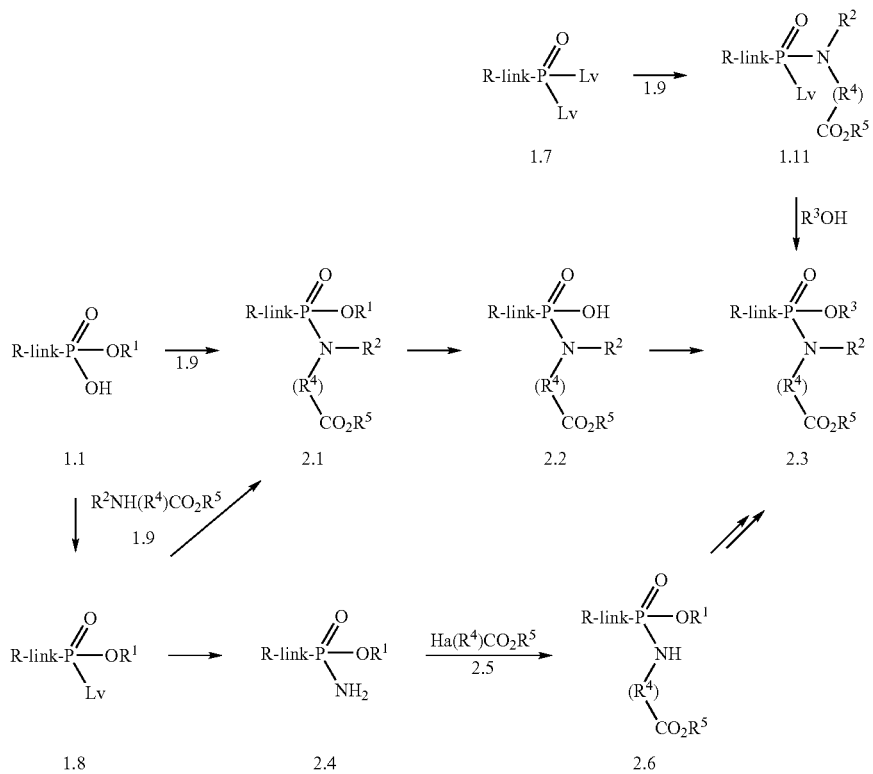

Scheme 2 Example 1

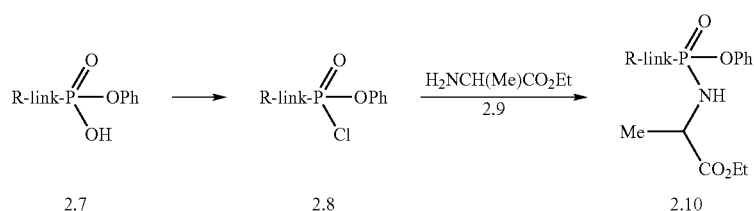

Scheme 2 Example 2

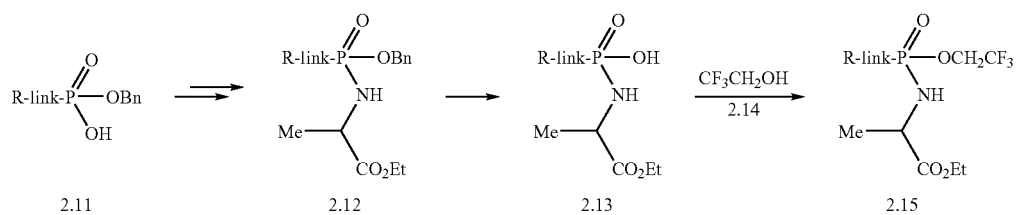

Scheme 2 Example 3

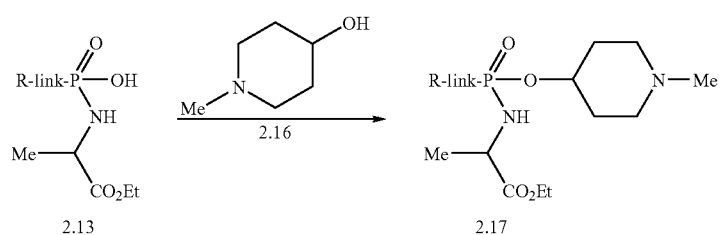

-continued

Scheme 2 Example 4

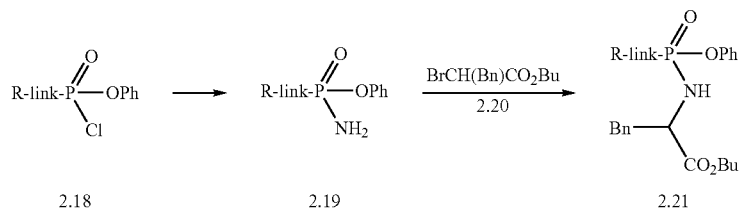

Scheme 2 Example 5

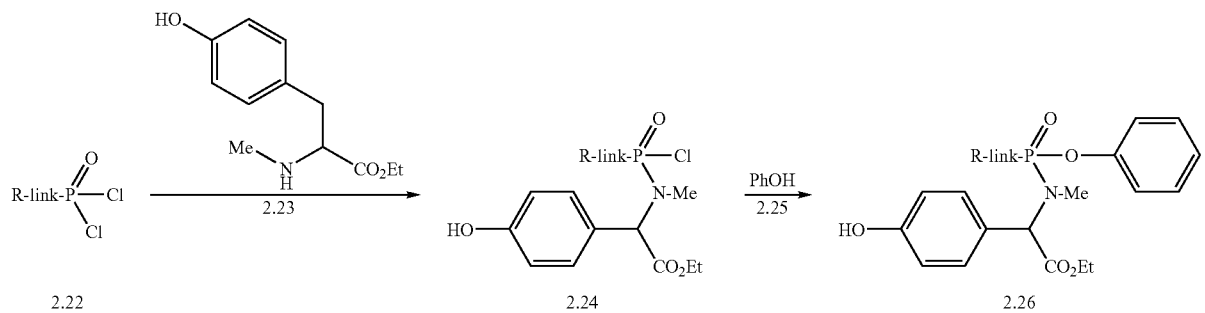

Scheme 3 illustrates methods for the preparation of carboalkoxy-substituted phosphonate diesters in which one of the ester groups incorporates a carboalkoxy substituent.

In one procedure, a phosphonate monoester 1.1, prepared as described above, is coupled, using one of the methods described above, with a hydroxyester 3.1, in which the groups $R^4$ and $R^5$ are as described in Scheme 1. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 3, Example 1. In this method, a monophenyl phosphonate 3.9 is coupled, in dichloromethane solution in the presence of dicyclohexyl carbodiimide, with ethyl 3-hydroxy-2-methylpropionate 3.10 to yield the phosphonate mixed diester 3.11.

Using this procedure, but employing, in place of ethyl 3-hydroxy-2-methylpropionate 3.10, different hydroxyesters 3.1, the corresponding products 3.2 are obtained.

The conversion of a phosphonate monoester 1.1 into a mixed diester 3.2 is also accomplished by means of a Mitsonobu coupling reaction with the hydroxyester 3.1, as described in Org. Lett., 2001, 643. In this method, the reactants 1.1 and 3.1 are combined in a polar solvent such as tetrahydrofuran, in the presence of a triarylphosphine and a dialkyl azodicarboxylate, to give the mixed diester 3.2. The $R^1$ substituent is varied by cleavage, using the methods described previously, to afford the monoacid product 3.3. The product is then coupled, for example using methods described above, with the hydroxy compound $R^3OH$, to give the diester product 3.4.

The procedure is illustrated in Scheme 3, Example 2. In this method, a monoallyl phosphonate 3.12 is coupled in tetrahydrofuran solution, in the presence of triphenylphosphine and diethylazodicarboxylate, with ethyl lactate 3.13 to give the mixed diester 3.14. The product is reacted with tris(triphenylphosphine)rhodium chloride (Wilkinson catalyst) in acetonitrile, as described previously, to remove the allyl group and produce the monoacid product 3.15. The latter compound is then coupled, in pyridine solution at ambient temperature, in the presence of dicyclohexyl carbodiimide, with one molar equivalent of 3-hydroxypyridine 3.16 to yield the mixed diester 3.17.

Using the above procedures, but employing, in place of the ethyl lactate 3.13 or 3-hydroxypyridine, a different hydroxyester 3.1 and/or a different hydroxy compound $R^3OH$, the corresponding products 3.4 are obtained.

The mixed diesters 3.2 are also obtained from the monoesters 1.1 via the intermediacy of the activated monoesters 3.5. In this procedure, the monoester 1.1 is converted into the activated compound 3.5 by reaction with, for example, phosphorus pentachloride, as described in J. Org. Chem., 2001, 66, 329, or with thionyl chloride or oxalyl chloride (Lv=Cl), or with triisopropylbenzenesulfonyl chloride in pyridine, as described in Nucleosides and Nucleotides, 2000, 19, 1885, or with carbonyl diimidazole, as described in J. Med. Chem., 2002, 45, 1284. The resultant activated monoester is then reacted with the hydroxyester 3.1, as described above, to yield the mixed diester 3.2.

The procedure is illustrated in Scheme 3, Example 3. In this sequence, a monophenyl phosphonate 3.9 is reacted, in acetonitrile solution at 70° C., with ten equivalents of thionyl chloride, so as to produce the phosphoryl chloride 3.19. The product is then reacted with ethyl 4-carbamoyl-2-hydroxybutyrate 3.20 in dichloromethane containing triethylamine, to give the mixed diester 3.21.

Using the above procedures, but employing, in place of ethyl 4-carbamoyl-2-hydroxybutyrate 3.20, different hydroxyesters 3.1, the corresponding products 3.2 are obtained.

The mixed phosphonate diesters are also obtained by an alternative route for incorporation of the $R^3O$ group into intermediates 3.3 in which the hydroxyester moiety is already incorporated. In this procedure, the monoacid intermediate 3.3 is converted into the activated derivative 3.6 in which Lv is a leaving group such as chloro, imidazole, and the like, as previously described. The activated intermediate is then reacted with the hydroxy compound $R^3OH$, in the presence of a base, to yield the mixed diester product 3.4.

The method is illustrated in Scheme 3, Example 4. In this sequence, the phosphonate monoacid 3.22 is reacted with trichloromethanesulfonyl chloride in tetrahydrofuran containing collidine, as described in J. Med. Chem., 1995, 38, 4648, to produce the trichloromethanesulfonyloxy product 3.23. This compound is reacted with 3-(morpholinomethyl) phenol 3.24 in dichloromethane containing triethylamine, to yield the mixed diester product 3.25.

Using the above procedures, but employing, in place of with 3-(morpholinomethyl)phenol 3.24, different carbinols $R^3OH$, the corresponding products 3.4 are obtained.

The phosphonate esters 3.4 are also obtained by means of alkylation reactions performed on the monoesters 1.1. The reaction between the monoacid 1.1 and the haloester 3.7 is performed in a polar solvent in the presence of a base such as diisopropylethylamine, as described in Anal. Chem., 1987, 59, 1056, or triethylamine, as described in J. Med. Chem., 1995, 38, 1372, or in a non-polar solvent such as benzene, in the presence of 18-crown-6, as described in Syn. Comm., 1995, 25, 3565.

The method is illustrated in Scheme 3, Example 5. In this procedure, the monoacid 3.26 is reacted with ethyl 2-bromo-3-phenylpropionate 3.27 and diisopropylethylamine in dimethylformamide at 80° C. to afford the mixed diester product 3.28.

Using the above procedure, but employing, in place of ethyl 2-bromo-3-phenylpropionate 3.27, different haloesters 3.7, the corresponding products 3.4 are obtained.

Scheme 3

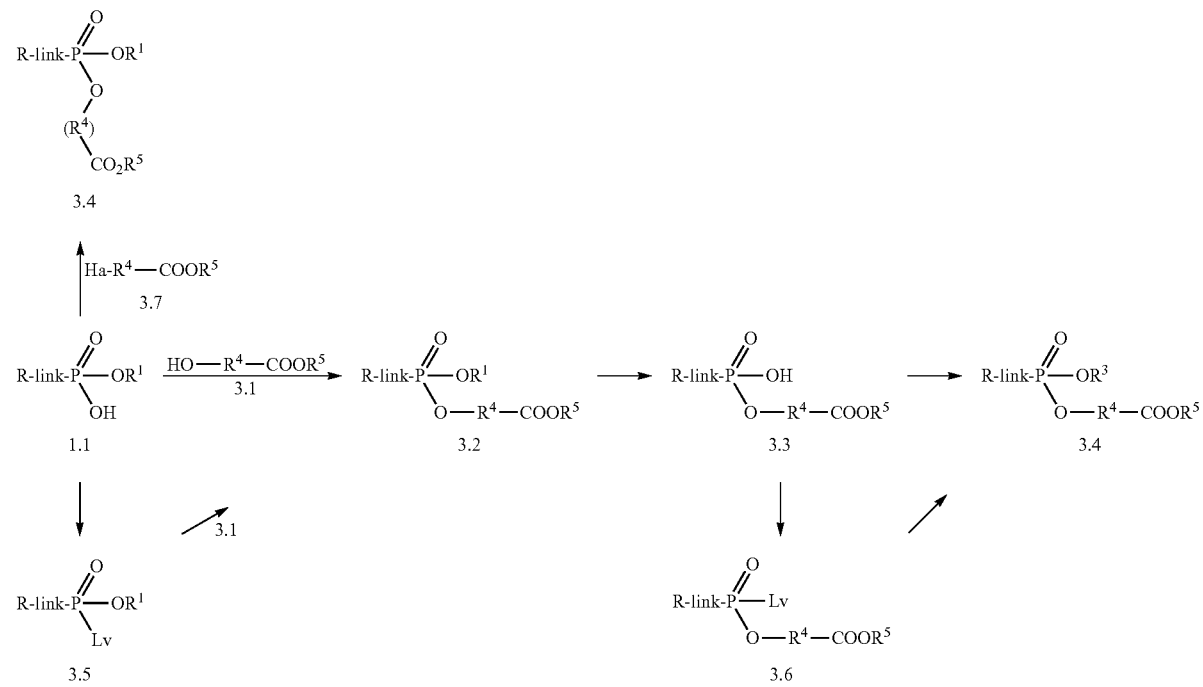

Scheme 3 Example 1

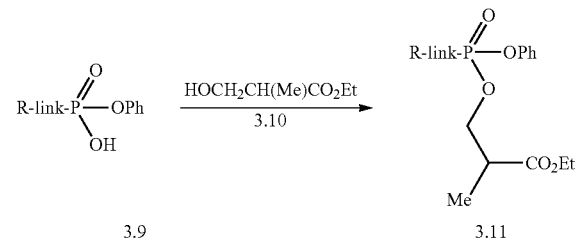

Scheme 3 Example 2

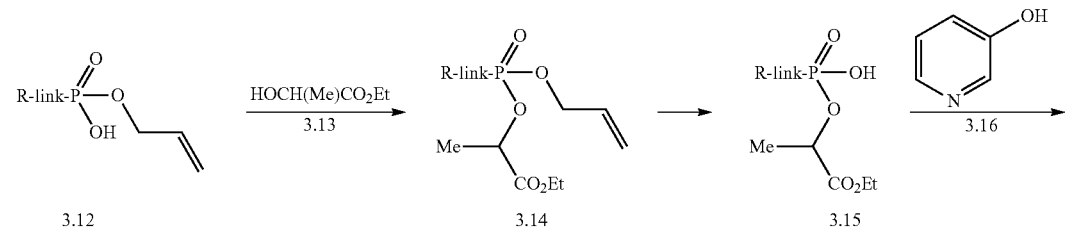

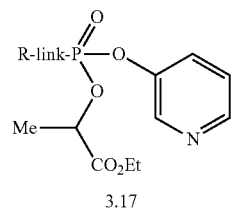

Scheme 3 Example 3

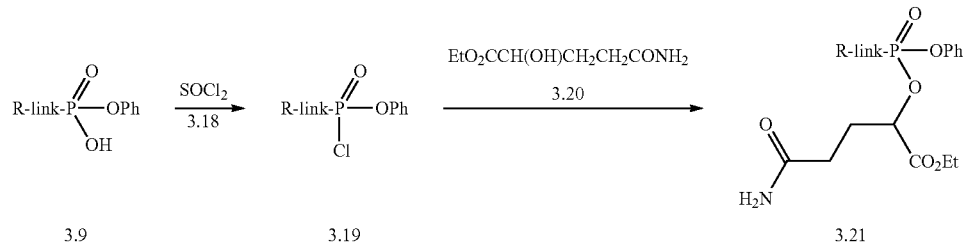

Scheme 3 Example 4

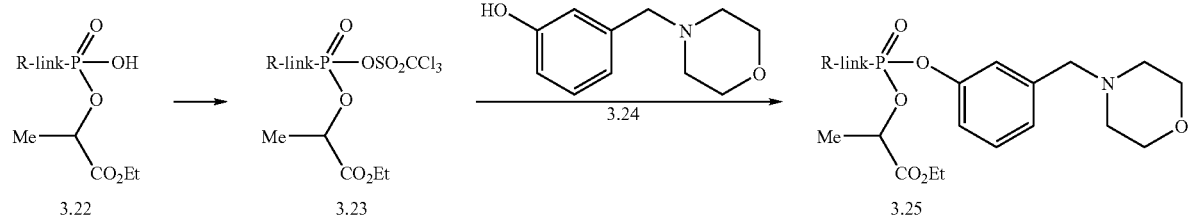

Scheme 3 Example 5

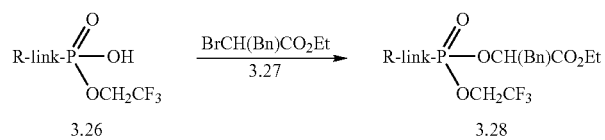

Scheme 4 illustrates methods for the preparation of phosphonate diesters in which both the ester substituents incorporate carboalkoxy groups.

The compounds are prepared directly or indirectly from the phosphonic acids 1.6. In one alternative, the phosphonic acid is coupled with the hydroxyester 4.2, using the conditions described previously in Schemes 1-3, such as coupling reactions using dicyclohexyl carbodiimide or similar reagents, or under the conditions of the Mitsonobu reaction, to afford the diester product 4.3 in which the ester substituents are identical.

This method is illustrated in Scheme 4, Example 1. In this procedure, the phosphonic acid 1.6 is reacted with three molar equivalents of butyl lactate 4.5 in the presence of Aldrithiol-2 and triphenyl phosphine in pyridine at ca. 70° C., to afford the diester 4.6.

Using the above procedure, but employing, in place of butyl lactate 4.5, different hydroxyesters 4.2, the corresponding products 4.3 are obtained.

Alternatively, the diesters 4.3 are obtained by alkylation of the phosphonic acid 1.6 with a haloester 4.1. The alkylation reaction is performed as described in Scheme 3 for the preparation of the esters 3.4.

This method is illustrated in Scheme 4, Example 2. In this procedure, the phosphonic acid 1.6 is reacted with excess ethyl 3-bromo-2-methylpropionate 4.7 and diisopropylethylamine in dimethylformamide at ca. 80° C., as described in Anal. Chem., 1987, 59, 1056, to produce the diester 4.8.

Using the above procedure, but employing, in place of ethyl 3-bromo-2-methylpropionate 4.7, different haloesters 4.1, the corresponding products 4.3 are obtained.

The diesters 4.3 are also obtained by displacement reactions of activated derivatives 1.7 of the phosphonic acid with the hydroxyesters 4.2. The displacement reaction is performed in a polar solvent in the presence of a suitable base, as described in Scheme 3. The displacement reaction is performed in the presence of an excess of the hydroxyester, to afford the diester product 4.3 in which the ester substituents are identical, or sequentially with limited amounts of different hydroxyesters, to prepare diesters 4.3 in which the ester substituents are different.

The methods are illustrated in Scheme 4, Examples 3 and 4. As shown in Example 3, the phosphoryl dichloride 2.22 is reacted with three molar equivalents of ethyl 3-hydroxy-2-(hydroxymethyl)propionate 4.9 in tetrahydrofuran containing potassium carbonate, to obtain the diester product 4.10.

Using the above procedure, but employing, in place of ethyl 3-hydroxy-2-(hydroxymethyl)propionate 4.9, different hydroxyesters 4.2, the corresponding products 4.3 are obtained.

Scheme 4, Example 4 depicts the displacement reaction between equimolar amounts of the phosphoryl dichloride 2.22 and ethyl 2-methyl-3-hydroxypropionate 4.11, to yield the monoester product 4.12. The reaction is conducted in acetonitrile at 70° C. in the presence of diisopropylethylamine. The product 4.12 is then reacted, under the same conditions, with one molar equivalent of ethyl lactate 4.13, to give the diester product 4.14.

Using the above procedures, but employing, in place of ethyl 2-methyl-3-hydroxypropionate 4.11 and ethyl lactate 4.13, sequential reactions with different hydroxyesters 4.2, the corresponding products 4.3 are obtained.

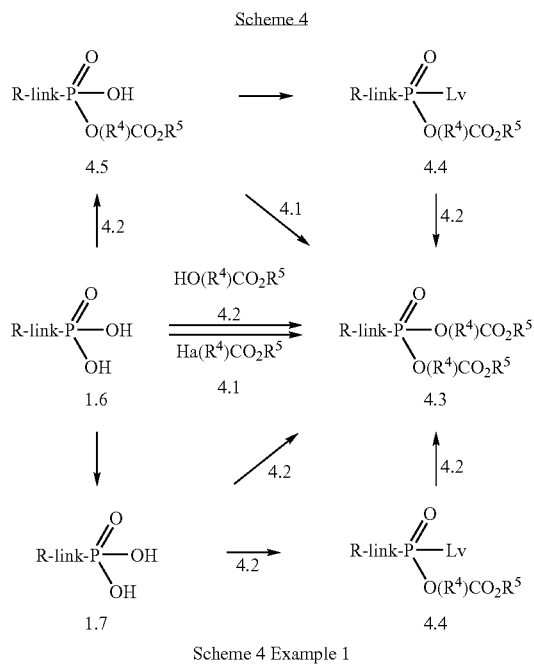

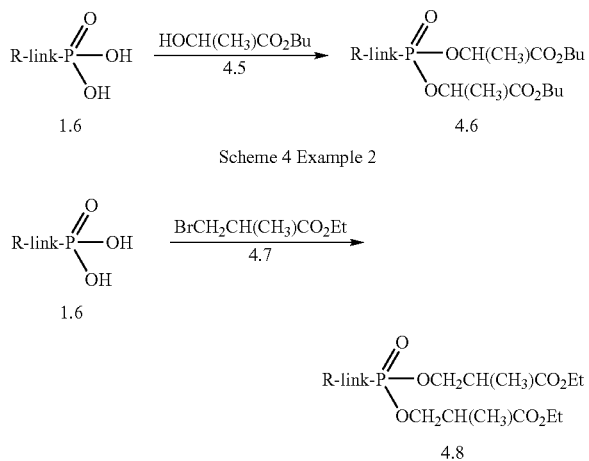

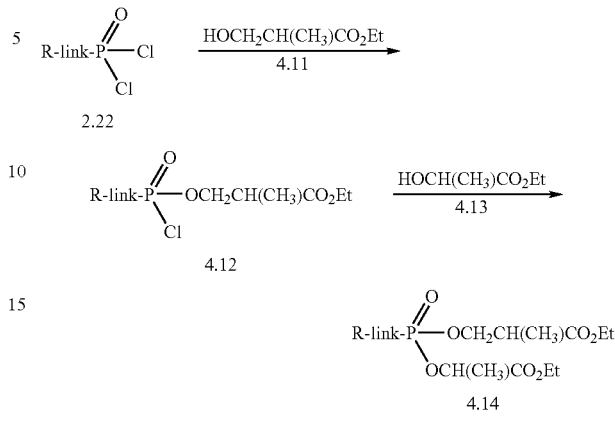

One skilled in the art will recognize that nucleobases can exist in tautomeric forms. For example, structures (a) and (b) can have equivalent tautomeric forms as shown below:

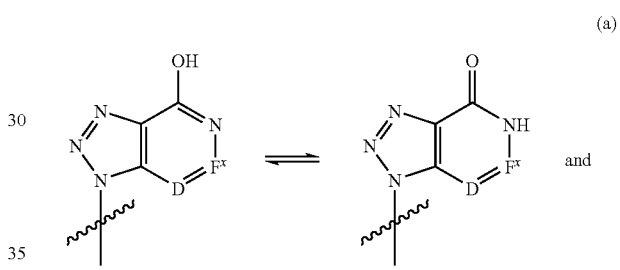

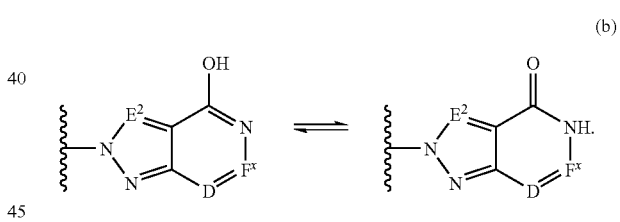

All possible tautomeric forms of the nucleobases of all of the embodiments are within the scope of the invention.

The compounds of Formula I-IV include all stereoisomers, and mixtures thereof. For example and not by way of limitation, the compounds of Formula I include at least the following stereoisomers:

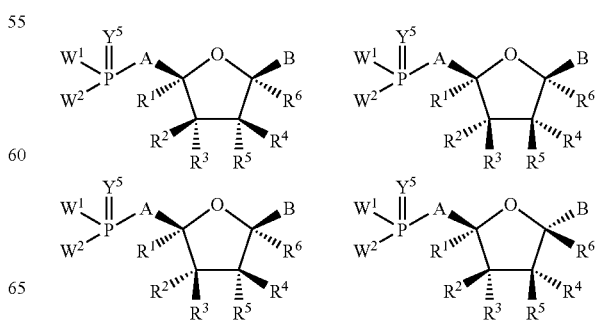

-continued

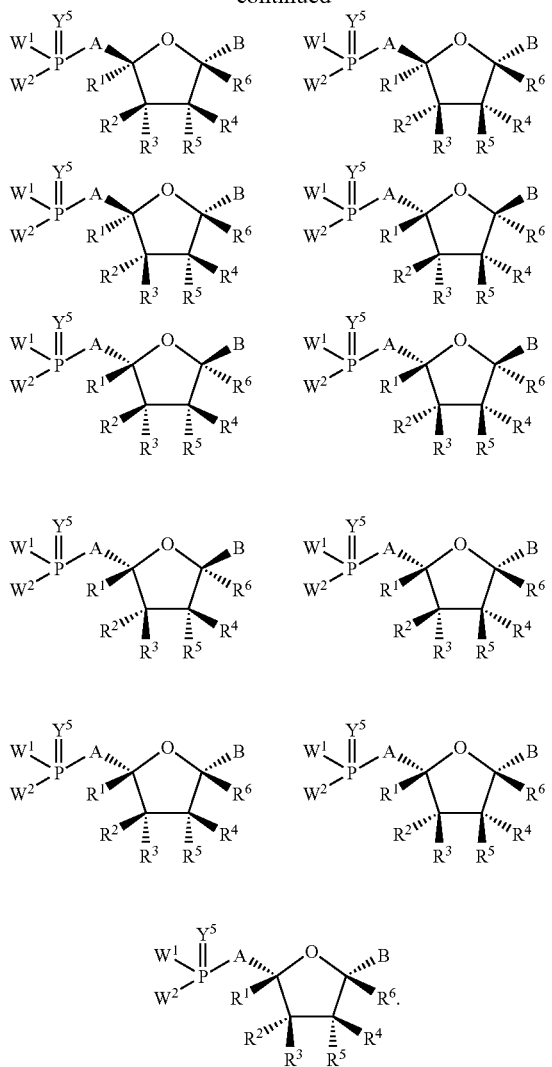

In still another embodiment, the compounds of Formula I, Formula II, Formula III or Formula IV are named below in tabular format (Table 6) as compounds of general Formula V:

Formula V

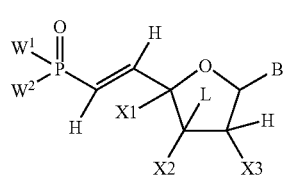

wherein X1, X2, X3, and L represent substituents attached to the tetrahydrofuranyl ring as defined in Tables 1-4, below; B is a purine defined in Table 5, below; and each $W^1$ and $W^2$ are as previously defined above.

The point of attachment of the core structure C is indicated in each of the structures of X1, X2, X3, L and B. Each structure in Tables 1-5 is represented by an alphanumeric "code". Each structure of a compound of Formula V can thus be designated in tabular form by combining the "code" representing each structural moiety using the following syntax: X1.X2.X3.L.B. Thus, for example, X1a.X2c.X3a.L1.B1 represents the following structure:

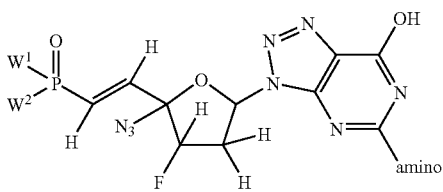

TABLE 1

X1 Structures

| Code | Structure |
|---|---|
| X1a | $N_3$ |
| X1b | ethylenyl |
| X1c | H |
| X1d | ethynyl |

TABLE 2

X2 Structures

| Code | Structure |
|---|---|
| X2a | H |
| X2b | OH |
| X2c | F |

TABLE 3

X3 Structures

| Code | Structure |
|---|---|
| X3a | H |
| X3b | OH |
| X3c | F |

TABLE 4

L Structures

| Code | Structure |
|---|---|
| L1 | H |
| L2 | $CH_3$ |
| L3 | —$CH_2OH$ |

TABLE 5

B Structures

| Code | Structure |
|------|-----------|
| B1 | 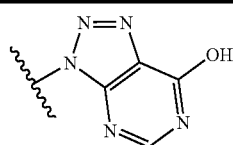 |
| B2 | 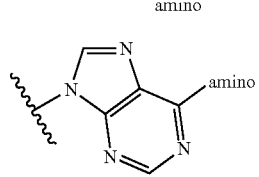 |

TABLE 5-continued

B Structures

| Code | Structure |
|------|-----------|
| B3 | 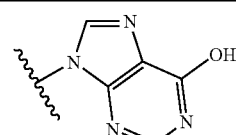 |
| B4 | 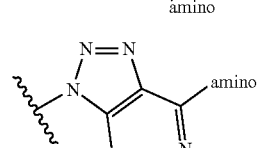 |

TABLE 6

List of Compounds of Formula V

X1a.X2a.X3a.L1.B1, X1a.X2a.X3a.L1.B2, X1a.X2a.X3a.L1.B3, X1a.X2a.X3a.L1.B4,
X1a.X2a.X3a.L2.B1, X1a.X2a.X3a.L2.B2, X1a.X2a.X3a.L2.B3, X1a.X2a.X3a.L2.B4,
X1a.X2a.X3a.L3.B1, X1a.X2a.X3a.L3.B2, X1a.X2a.X3a.L3.B3, X1a.X2a.X3a.L3.B4,
X1a.X2a.X3b.L1.B1, X1a.X2a.X3b.L1.B2, X1a.X2a.X3b.L1.B3, X1a.X2a.X3b.L1.B4,
X1a.X2a.X3b.L2.B1, X1a.X2a.X3b.L2.B2, X1a.X2a.X3b.L2.B3, X1a.X2a.X3b.L2.B4,
X1a.X2a.X3b.L3.B1, X1a.X2a.X3b.L3.B2, X1a.X2a.X3b.L3.B3, X1a.X2a.X3b.L3.B4,
X1a.X2a.X3c.L1.B1, X1a.X2a.X3c.L1.B2, X1a.X2a.X3c.L1.B3, X1a.X2a.X3c.L1.B4,
X1a.X2a.X3c.L2.B1, X1a.X2a.X3c.L2.B2, X1a.X2a.X3c.L2.B3, X1a.X2a.X3c.L2.B4,
X1a.X2a.X3c.L3.B1, X1a.X2a.X3c.L3.B2, X1a.X2a.X3c.L3.B3, X1a.X2a.X3c.L3.B4,
X1a.X2b.X3a.L1.B1, X1a.X2b.X3a.L1.B2, X1a.X2b.X3a.L1.B3, X1a.X2b.X3a.L1.B4,
X1a.X2b.X3a.L2.B1, X1a.X2b.X3a.L2.B2, X1a.X2b.X3a.L2.B3, X1a.X2b.X3a.L2.B4,
X1a.X2b.X3a.L3.B1, X1a.X2b.X3a.L3.B2, X1a.X2b.X3a.L3.B3, X1a.X2b.X3a.L3.B4,
X1a.X2b.X3b.L1.B1, X1a.X2b.X3b.L1.B2, X1a.X2b.X3b.L1.B3, X1a.X2b.X3b.L1.B4,
X1a.X2b.X3b.L2.B1, X1a.X2b.X3b.L2.B2, X1a.X2b.X3b.L2.B3, X1a.X2b.X3b.L2.B4,
X1a.X2b.X3b.L3.B1, X1a.X2b.X3b.L3.B2, X1a.X2b.X3b.L3.B3, X1a.X2b.X3b.L3.B4,
X1a.X2b.X3c.L1.B1, X1a.X2b.X3c.L1.B2, X1a.X2b.X3c.L1.B3, X1a.X2b.X3c.L1.B4,
X1a.X2b.X3c.L2.B1, X1a.X2b.X3c.L2.B2, X1a.X2b.X3c.L2.B3, X1a.X2b.X3c.L2.B4,
X1a.X2b.X3c.L3.B1, X1a.X2b.X3c.L3.B2, X1a.X2b.X3c.L3.B3, X1a.X2b.X3c.L3.B4,
X1a.X2c.X3a.L1.B1, X1a.X2c.X3a.L1.B2, X1a.X2c.X3a.L1.B3, X1a.X2c.X3a.L1.B4,
X1a.X2c.X3a.L2.B1, X1a.X2c.X3a.L2.B2, X1a.X2c.X3a.L2.B3, X1a.X2c.X3a.L2.B4,
X1a.X2c.X3a.L3.B1, X1a.X2c.X3a.L3.B2, X1a.X2c.X3a.L3.B3, X1a.X2c.X3a.L3.B4,
X1a.X2c.X3b.L1.B1, X1a.X2c.X3b.L1.B2, X1a.X2c.X3b.L1.B3, X1a.X2c.X3b.L1.B4,
X1a.X2c.X3b.L2.B1, X1a.X2c.X3b.L2.B2, X1a.X2c.X3b.L2.B3, X1a.X2c.X3b.L2.B4,
X1a.X2c.X3b.L3.B1, X1a.X2c.X3b.L3.B2, X1a.X2c.X3b.L3.B3, X1a.X2c.X3b.L3.B4,
X1a.X2c.X3c.L1.B1, X1a.X2c.X3c.L1.B2, X1a.X2c.X3c.L1.B3, X1a.X2c.X3c.L1.B4,
X1a.X2c.X3c.L2.B1, X1a.X2c.X3c.L2.B2, X1a.X2c.X3c.L2.B3, X1a.X2c.X3c.L2.B4,
X1a.X2c.X3c.L3.B1, X1a.X2c.X3c.L3.B2, X1a.X2c.X3c.L3.B3, X1a.X2c.X3c.L3.B4,
X1b.X2a.X3a.L1.B1, X1b.X2a.X3a.L1.B2, X1b.X2a.X3a.L1.B3, X1b.X2a.X3a.L1.B4,
X1b.X2a.X3a.L2.B1, X1b.X2a.X3a.L2.B2, X1b.X2a.X3a.L2.B3, X1b.X2a.X3a.L2.B4,
X1b.X2a.X3a.L3.B1, X1b.X2a.X3a.L3.B2, X1b.X2a.X3a.L3.B3, X1b.X2a.X3a.L3.B4,
X1b.X2a.X3b.L1.B1, X1b.X2a.X3b.L1.B2, X1b.X2a.X3b.L1.B3, X1b.X2a.X3b.L1.B4,
X1b.X2a.X3b.L2.B1, X1b.X2a.X3b.L2.B2, X1b.X2a.X3b.L2.B3, X1b.X2a.X3b.L2.B4,
X1b.X2a.X3b.L3.B1, X1b.X2a.X3b.L3.B2, X1b.X2a.X3b.L3.B3, X1b.X2a.X3b.L3.B4,
X1b.X2a.X3c.L1.B1, X1b.X2a.X3c.L1.B2, X1b.X2a.X3c.L1.B3, X1b.X2a.X3c.L1.B4,
X1b.X2a.X3c.L2.B1, X1b.X2a.X3c.L2.B2, X1b.X2a.X3c.L2.B3, X1b.X2a.X3c.L2.B4,
X1b.X2a.X3c.L3.B1, X1b.X2a.X3c.L3.B2, X1b.X2a.X3c.L3.B3, X1b.X2a.X3c.L3.B4,
X1b.X2b.X3a.L1.B1, X1b.X2b.X3a.L1.B2, X1b.X2b.X3a.L1.B3, X1b.X2b.X3a.L1.B4,
X1b.X2b.X3a.L2.B1, X1b.X2b.X3a.L2.B2, X1b.X2b.X3a.L2.B3, X1b.X2b.X3a.L2.B4,
X1b.X2b.X3a.L3.B1, X1b.X2b.X3a.L3.B2, X1b.X2b.X3a.L3.B3, X1b.X2b.X3a.L3.B4,
X1b.X2b.X3b.L1.B1, X1b.X2b.X3b.L1.B2, X1b.X2b.X3b.L1.B3,
X1b.X2b.X3b.L1.B4, X1b.X2b.X3b.L2.B1, X1b.X2b.X3b.L2.B2,
X1b.X2b.X3b.L2.B3, X1b.X2b.X3b.L2.B4, X1b.X2b.X3b.L3.B1,
X1b.X2b.X3b.L3.B2, X1b.X2b.X3b.L3.B3, X1b.X2b.X3b.L3.B4, X1b.X2b.X3c.L1.B1,
X1b.X2b.X3c.L1.B2, X1b.X2b.X3c.L1.B3, X1b.X2b.X3c.L1.B4, X1b.X2b.X3c.L2.B1,
X1b.X2b.X3c.L2.B2, X1b.X2b.X3c.L2.B3, X1b.X2b.X3c.L2.B4, X1b.X2b.X3c.L3.B1,
X1b.X2b.X3c.L3.B2, X1b.X2b.X3c.L3.B3, X1b.X2b.X3c.L3.B4, X1b.X2c.X3a.L1.B1,
X1b.X2c.X3a.L1.B2, X1b.X2c.X3a.L1.B3, X1b.X2c.X3a.L1.B4, X1b.X2c.X3a.L2.B1,
X1b.X2c.X3a.L2.B2, X1b.X2c.X3a.L2.B3, X1b.X2c.X3a.L2.B4, X1b.X2c.X3a.L3.B1,
X1b.X2c.X3a.L3.B2, X1b.X2c.X3a.L3.B3, X1b.X2c.X3a.L3.B4, X1b.X2c.X3b.L1.B1,
X1b.X2c.X3b.L1.B2, X1b.X2c.X3b.L1.B3, X1b.X2c.X3b.L1.B4, X1b.X2c.X3b.L2.B1,
X1b.X2c.X3b.L2.B2, X1b.X2c.X3b.L2.B3, X1b.X2c.X3b.L2.B4, X1b.X2c.X3b.L3.B1,
X1b.X2c.X3b.L3.B2, X1b.X2c.X3b.L3.B3, X1b.X2c.X3b.L3.B4, X1b.X2c.X3c.L1.B1,

TABLE 6-continued

List of Compounds of Formula V

X1b.X2c.X3c.L1.B2, X1b.X2c.X3c.L1.B3, X1b.X2c.X3c.L1.B4, X1b.X2c.X3c.L2.B1,
X1b.X2c.X3c.L2.B2, X1b.X2c.X3c.L2.B3, X1b.X2c.X3c.L2.B4, X1b.X2c.X3c.L3.B1,
X1b.X2c.X3c.L3.B2, X1b.X2c.X3c.L3.B3, X1b.X2c.X3c.L3.B4, X1c.X2a.X3a.L1.B1,
X1c.X2a.X3a.L1.B3, X1c.X2a.X3a.L1.B4, X1c.X2a.X3a.L2.B1, X1c.X2a.X3a.L2.B2,
X1c.X2a.X3a.L2.B3, X1c.X2a.X3a.L2.B4, X1c.X2a.X3a.L3.B1, X1c.X2a.X3a.L3.B2,
X1c.X2a.X3a.L3.B3, X1c.X2a.X3a.L3.B4, X1c.X2a.X3b.L1.B1, X1c.X2a.X3b.L1.B2,
X1c.X2a.X3b.L1.B3, X1c.X2a.X3b.L1.B4, X1c.X2a.X3b.L2.B1, X1c.X2a.X3b.L2.B2,
X1c.X2a.X3b.L2.B3, X1c.X2a.X3b.L2.B4, X1c.X2a.X3b.L3.B1, X1c.X2a.X3b.L3.B2,
X1c.X2a.X3b.L3.B3, X1c.X2a.X3b.L3.B4, X1c.X2a.X3c.L1.B1, X1c.X2a.X3c.L1.B2,
X1c.X2a.X3c.L1.B3, X1c.X2a.X3c.L1.B4, X1c.X2a.X3c.L2.B1, X1c.X2a.X3c.L2.B2,
X1c.X2a.X3c.L2.B3, X1c.X2a.X3c.L2.B4, X1c.X2a.X3c.L3.B1, X1c.X2a.X3c.L3.B2,
X1c.X2a.X3c.L3.B3, X1c.X2a.X3c.L3.B4, X1c.X2b.X3a.L1.B1, X1c.X2b.X3a.L1.B2,
X1c.X2b.X3a.L1.B3, X1c.X2b.X3a.L1.B4, X1c.X2b.X3a.L2.B1, X1c.X2b.X3a.L2.B2,
X1c.X2b.X3a.L2.B3, X1c.X2b.X3a.L2.B4, X1c.X2b.X3a.L3.B1, X1c.X2b.X3a.L3.B2,
X1c.X2b.X3a.L3.B3, X1c.X2b.X3a.L3.B4, X1c.X2b.X3b.L1.B1, X1c.X2b.X3b.L1.B3,
X1c.X2b.X3b.L1.B4, X1c.X2b.X3b.L2.B1, X1c.X2b.X3b.L2.B2, X1c.X2b.X3b.L2.B3,
X1c.X2b.X3b.L2.B4, X1c.X2b.X3b.L3.B1, X1c.X2b.X3b.L3.B2, X1c.X2b.X3b.L3.B3,
X1c.X2b.X3b.L3.B4, X1c.X2b.X3c.L1.B1, X1c.X2b.X3c.L1.B2, X1c.X2b.X3c.L1.B3,
X1c.X2b.X3c.L1.B4, X1c.X2b.X3c.L2.B1, X1c.X2b.X3c.L2.B2, X1c.X2b.X3c.L2.B3,
X1c.X2b.X3c.L2.B4, X1c.X2b.X3c.L3.B1, X1c.X2b.X3c.L3.B2, X1c.X2b.X3c.L3.B3,
X1c.X2b.X3c.L3.B4, X1c.X2c.X3a.L1.B1, X1c.X2c.X3a.L1.B2, X1c.X2c.X3a.L1.B3,
X1c.X2c.X3a.L1.B4, X1c.X2c.X3a.L2.B1, X1c.X2c.X3a.L2.B2, X1c.X2c.X3a.L2.B3,
X1c.X2c.X3a.L2.B4, X1c.X2c.X3a.L3.B1, X1c.X2c.X3a.L3.B2, X1c.X2c.X3a.L3.B3,
X1c.X2c.X3a.L3.B4, X1c.X2c.X3b.L1.B1, X1c.X2c.X3b.L1.B2, X1c.X2c.X3b.L1.B3,
X1c.X2c.X3b.L1.B4, X1c.X2c.X3b.L2.B1, X1c.X2c.X3b.L2.B2, X1c.X2c.X3b.L2.B3,
X1c.X2c.X3b.L2.B4, X1c.X2c.X3b.L3.B1, X1c.X2c.X3b.L3.B2, X1c.X2c.X3b.L3.B3,
X1c.X2c.X3b.L3.B4, X1c.X2c.X3c.L1.B1, X1c.X2c.X3c.L1.B2, X1c.X2c.X3c.L1.B3,
X1c.X2c.X3c.L1.B4, X1c.X2c.X3c.L2.B1, X1c.X2c.X3c.L2.B2, X1c.X2c.X3c.L2.B3,
X1c.X2c.X3c.L2.B4, X1c.X2c.X3c.L3.B1, X1c.X2c.X3c.L3.B2, X1c.X2c.X3c.L3.B3,
X1c.X2c.X3c.L3.B4,

Phosphonate Embodiments of Compounds of Formula I-IV

By way of example and not limitation, the phosphonate embodiments of Formula I-IV may be represented by the general formula "MBF":

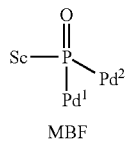

MBF

Each embodiment of MBF is depicted as a substituted nucleus (Sc). Sc is described in formulae A-G of Table 1.1 below, wherein Sc is a generic formula for a compound of Formula I, Formula II, Formula III or Formula IV and the point of attachment to —P(O)Pd$^1$Pd$^2$ is indicated with a wavy line.

TABLE 1.1

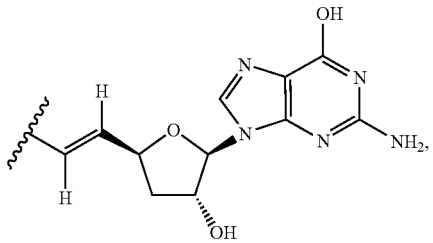

A

TABLE 1.1-continued

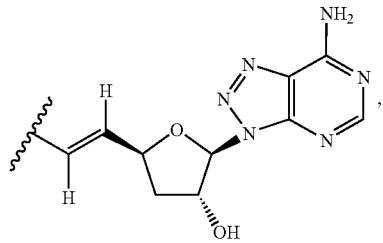

B

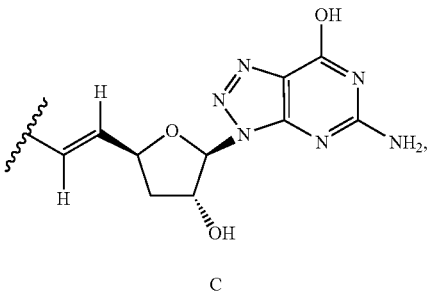

C

TABLE 1.1-continued

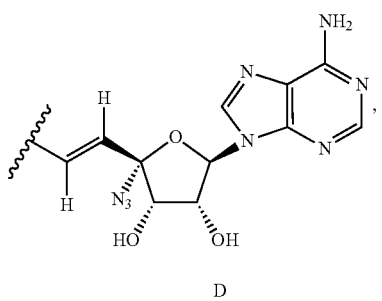

D

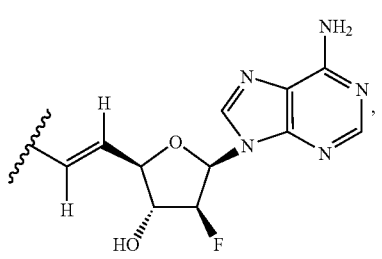

E

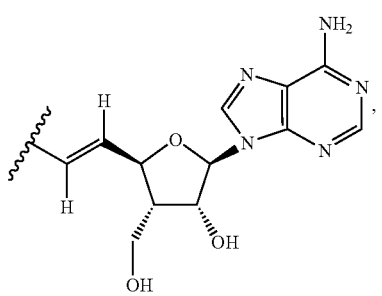

F

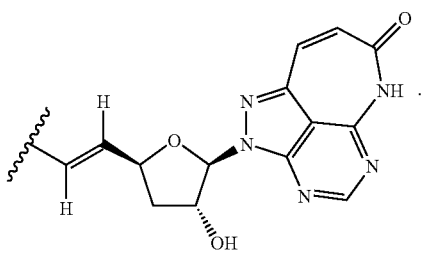

G

Pd$^1$ and Pd$^2$ are each independently selected from species in Tables 20.1 to 20.37. The definition of the variables used in Tables 20.1-20.37 (e.g., W$^3$, R$^1$, etc.) pertain only to Tables 20.1-20.37, unless otherwise indicated. Additional phosphonate groups are disclosed in U.S. patent publication No. 2004/100960, the entirety of which is incorporated herein by reference.

The variables used in Tables 20.1 to 20.37 have the following definitions and pertain only to those tables, unless otherwise indicated:

R$^1$ is independently H or alkyl of 1 to 18 carbon atoms;

R$^2$ is independently H, R$^1$, R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;

R$^{3a}$ is F, Cl, Br, I, —CN, N$_3$ or —NO$_2$;

R$^{3b}$ is Y$^1$;

R$^{3c}$ is —R$^x$, —N(R$^x$)(R$^x$), —SR$^x$, —S(O)R$^x$, —S(O)$_2$R$^x$, —S(O)(OR$^x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, —SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));

R$^{3d}$ is —C(Y$^1$)R$^x$, —C(Y$^1$)OR$^x$ or —C(Y$^1$)(N(R$^x$)(R$^x$));

R$^4$ is an alkyl of 1 to 18 carbon atoms, alkenyl of 2 to 18 carbon atoms, or alkynyl of 2 to 18 carbon atoms;

R$^5$ is R$^4$ wherein each R$^4$ is substituted with 0 to 3 R$^3$ groups;

R$^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 R$^3$ groups;

W$^3$ is W$^4$ or W$^5$;

W$^4$ is R$^5$, —C(Y$^1$)R$^5$, —C(Y$^1$)W$^5$, —SO$_2$R$^5$, or —SO$_2$W$^5$;

W$^5$ is carbocycle or heterocycle wherein W$^5$ is independently substituted with 0 to 3 R$^2$ groups;

TABLE 20.1

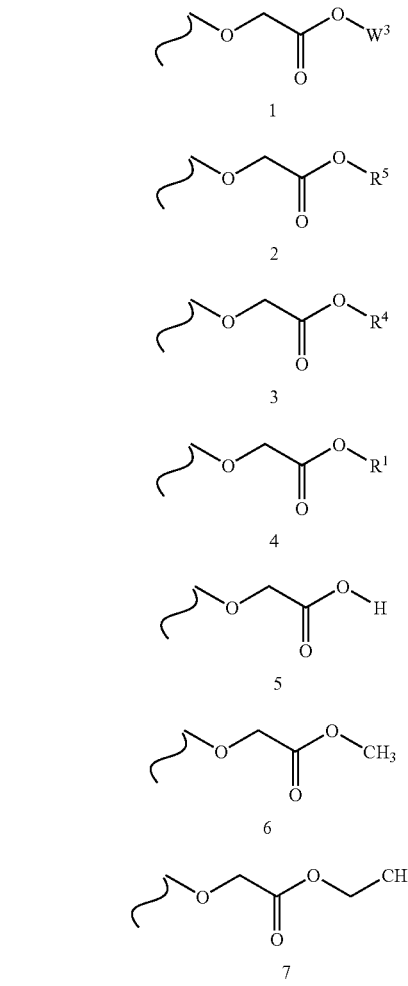

TABLE 20.1-continued
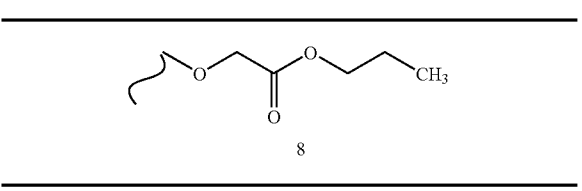
8
TABLE 20.2
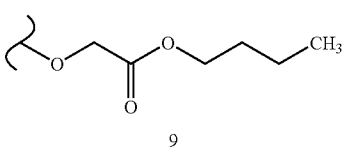
9
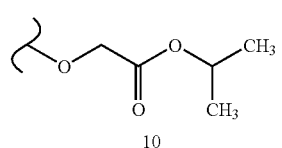
10
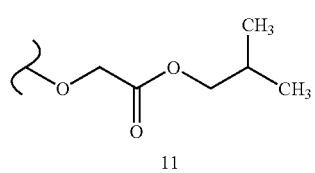
11
TABLE 20.3
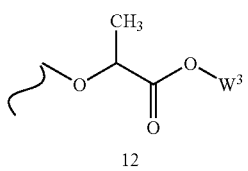
12
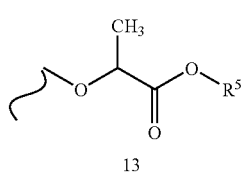
13
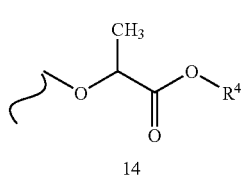
14
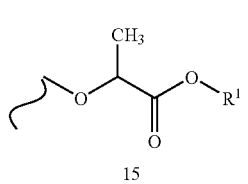
15
TABLE 20.3-continued
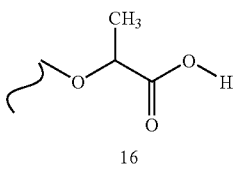
16
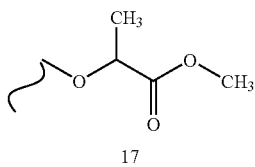
17
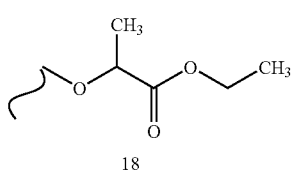
18
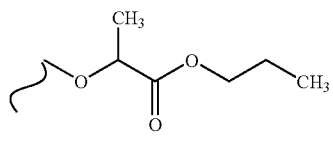
19
TABLE 20.4
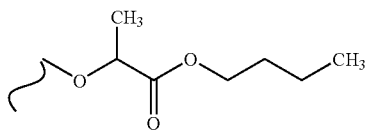
20
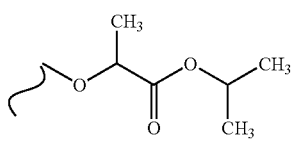
21
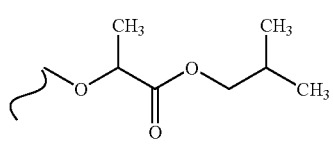
22
TABLE 20.5
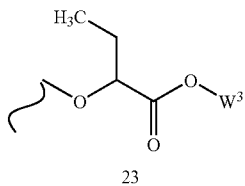
23

TABLE 20.5-continued
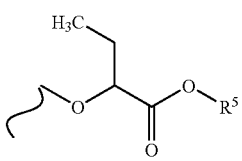
24
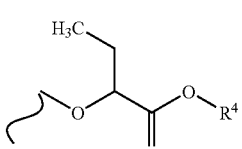
25
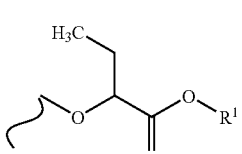
26
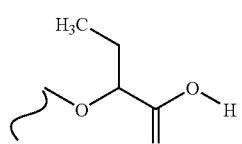
27
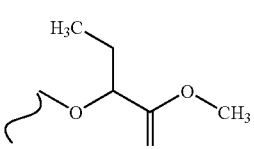
28
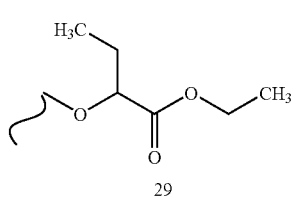
29
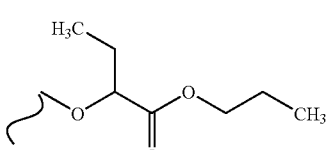
30
TABLE 20.6
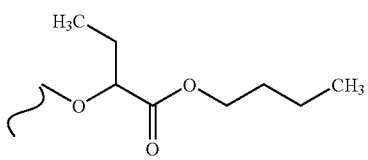
31
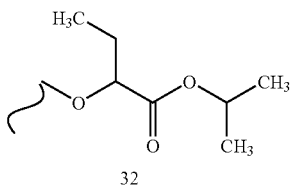
32
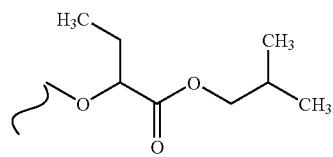
33
TABLE 20.7
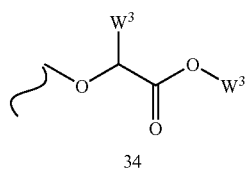
34
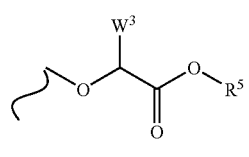
35
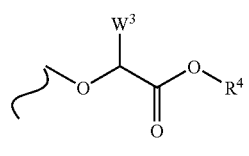
36
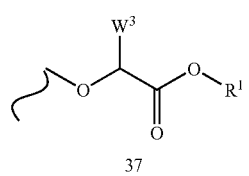
37
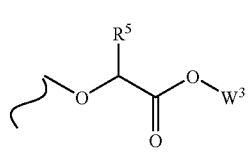
38

TABLE 20.7-continued
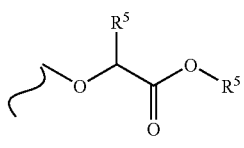
39
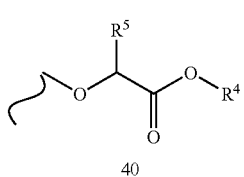
40
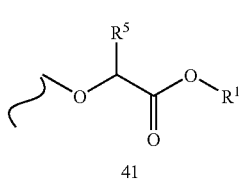
41
TABLE 20.8
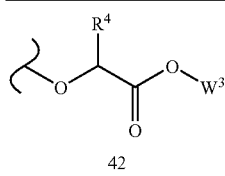    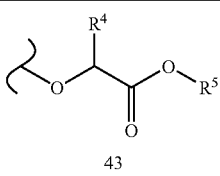
42             43
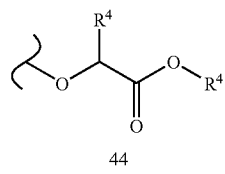    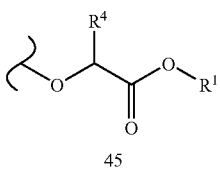
44             45
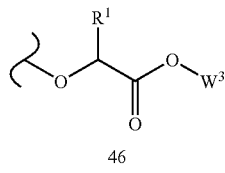    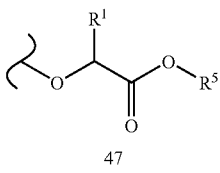
46             47
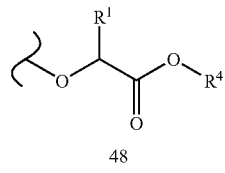    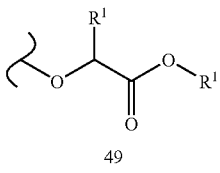
48             49
TABLE 20.9
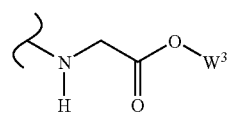
50
TABLE 20.9-continued
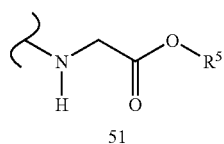
51
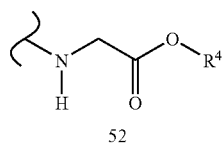
52
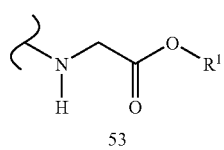
53
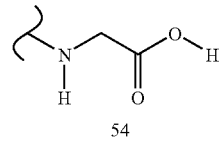
54
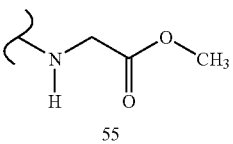
55
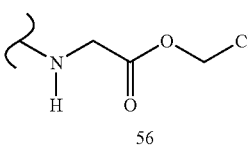
56
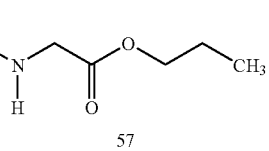
57
TABLE 20.10
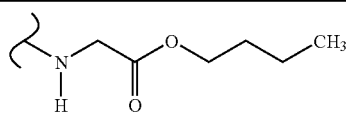
58
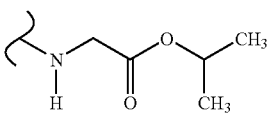
59

TABLE 20.10-continued
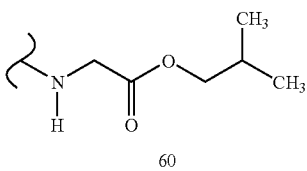
60
TABLE 20.11
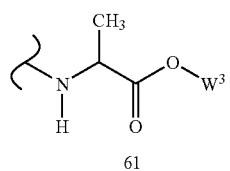
61
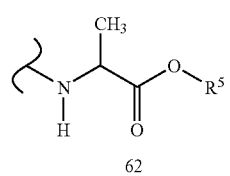
62
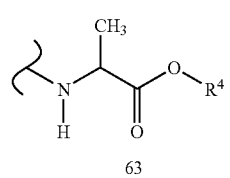
63
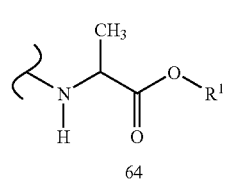
64
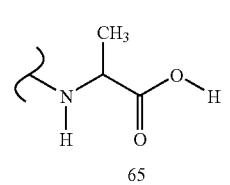
65
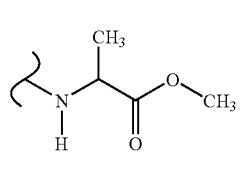
66
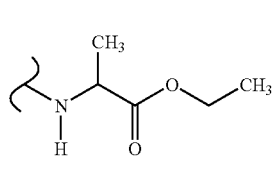
67
TABLE 20.11-continued
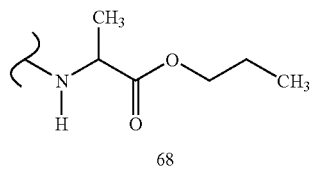
68
TABLE 20.12
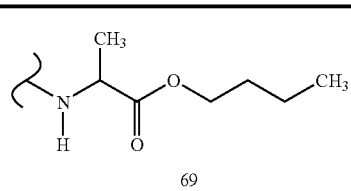
69
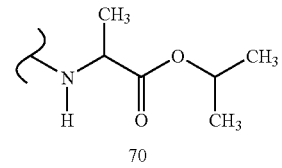
70
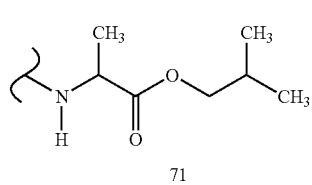
71
TABLE 20.13
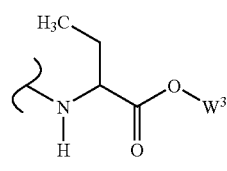
72
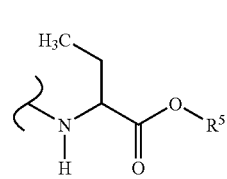
73
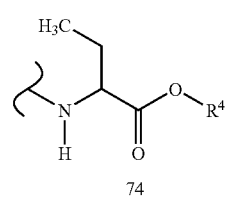
74

TABLE 20.13-continued
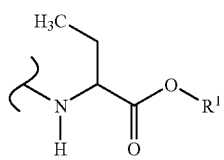
75
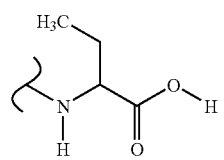
76
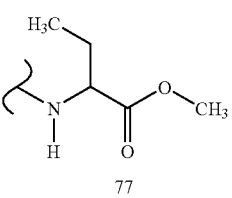
77
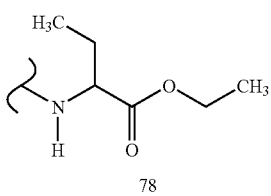
78
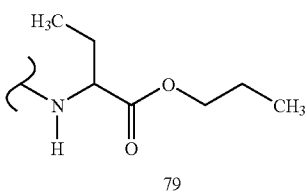
79
TABLE 20.14
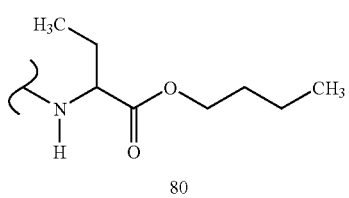
80
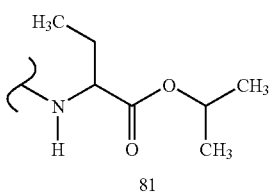
81
TABLE 20.14-continued
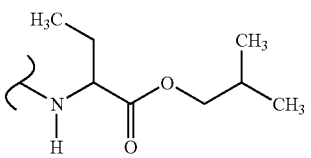
82
TABLE 20.15
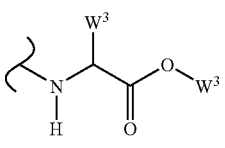 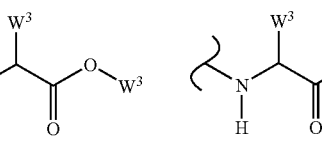
83  84
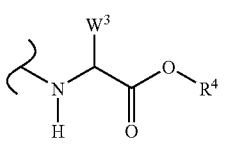
85  86
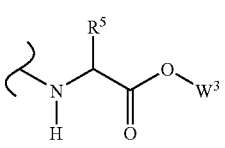
87  88
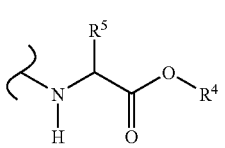
89  90
TABLE 20.16
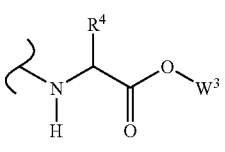 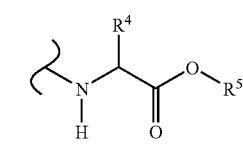
91  92
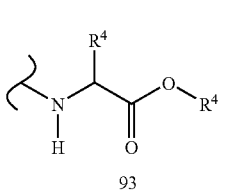 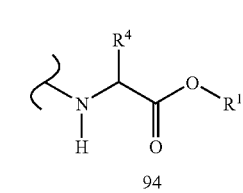
93  94

TABLE 20.16-continued
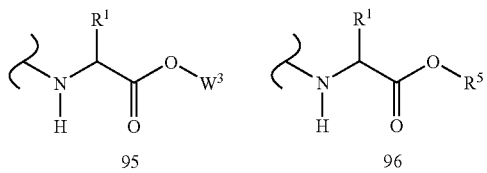
95
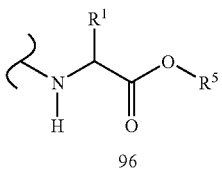
96
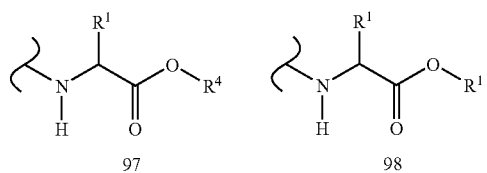
97
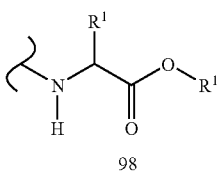
98
TABLE 20.17
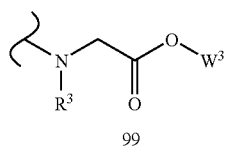
99
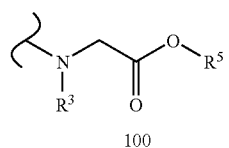
100
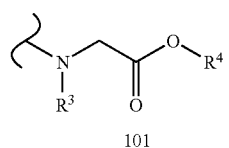
101
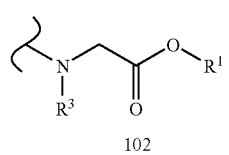
102
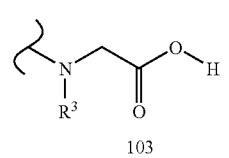
103
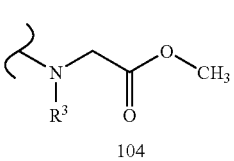
104
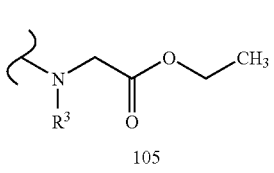
105
TABLE 20.17-continued
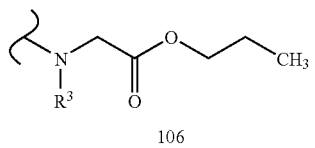
106
TABLE 20.18
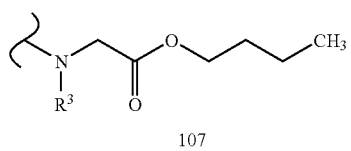
107
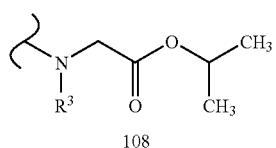
108
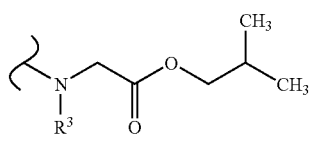
109
TABLE 20.19
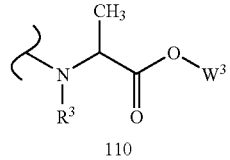
110
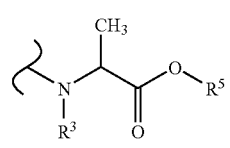
111
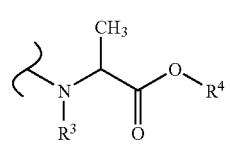
112
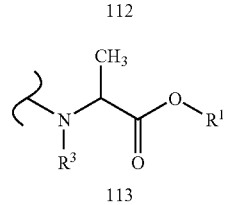
113

155
TABLE 20.19-continued
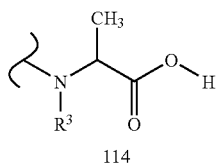
114
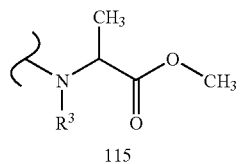
115
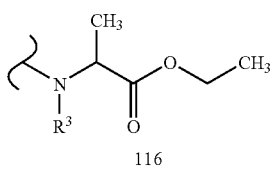
116
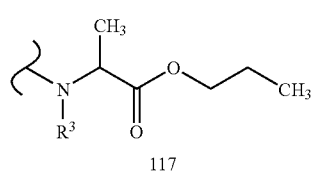
117
TABLE 20.20
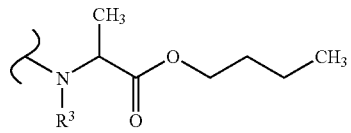
118
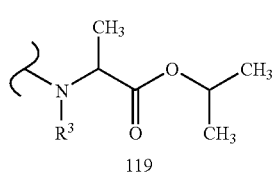
119
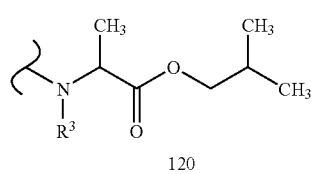
120
TABLE 20.21
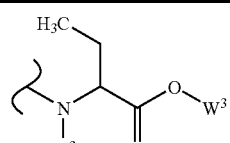
121
156
TABLE 20.21-continued
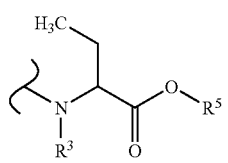
122
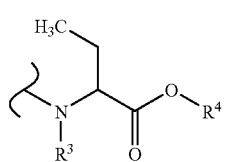
123
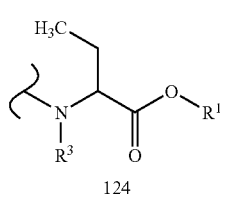
124
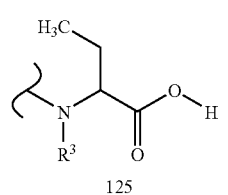
125
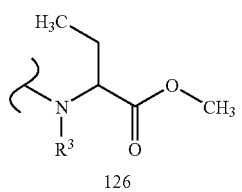
126
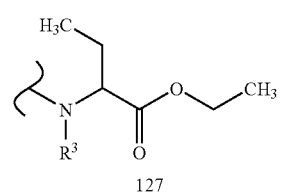
127
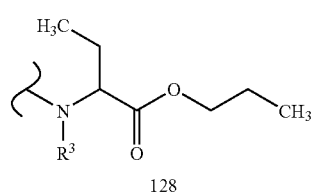
128

TABLE 20.22
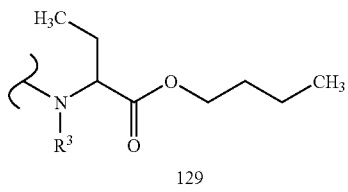
129
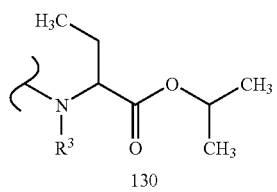
130
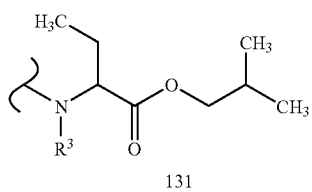
131
TABLE 20.23
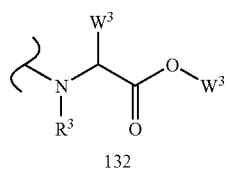 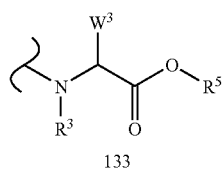
132    133
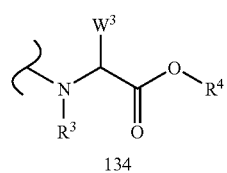 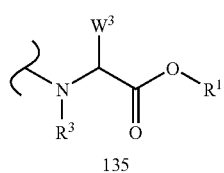
134    135
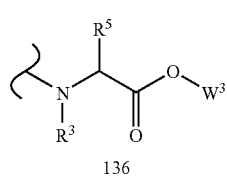 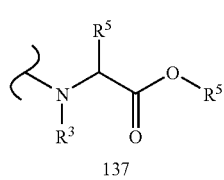
136    137
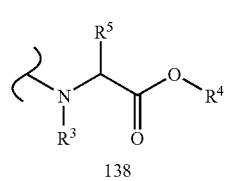 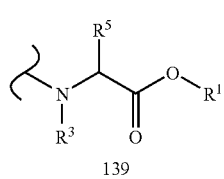
138    139
TABLE 20.24
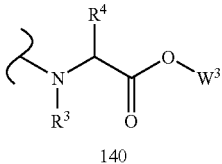 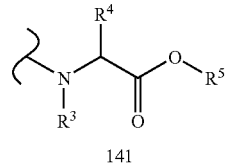
140    141
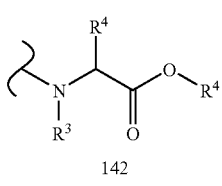 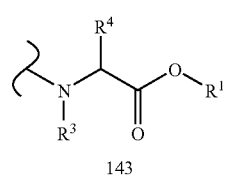
142    143
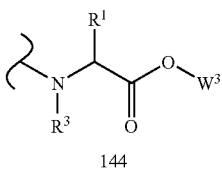 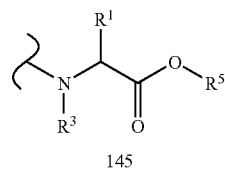
144    145
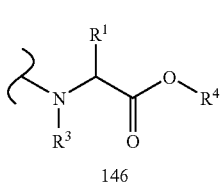 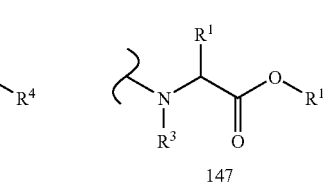
146    147
TABLE 20.25
  
148    149    150
  
151    152    153
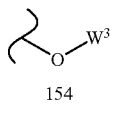 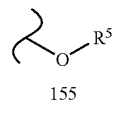 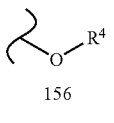
154    155    156
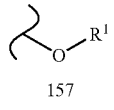 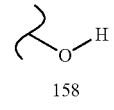 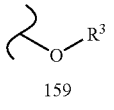
157    158    159
TABLE 20.26
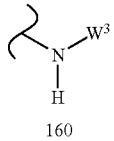 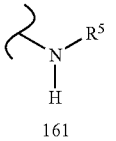 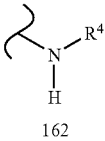
160    161    162

TABLE 20.26-continued
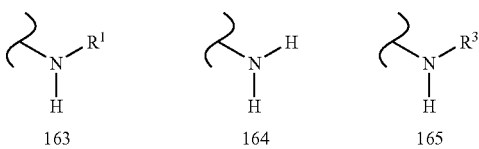
163 164 165
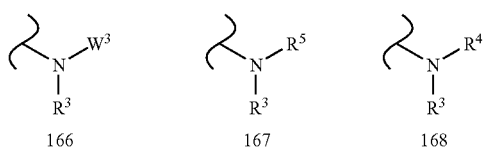
166 167 168
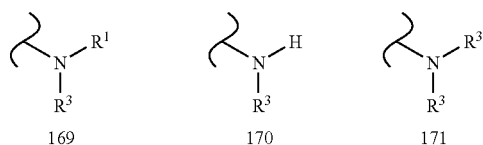
169 170 171
TABLE 20.27
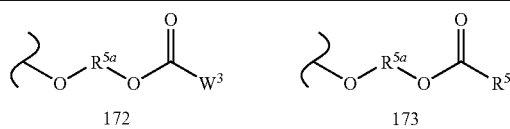
172 173
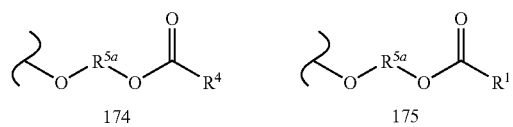
174 175
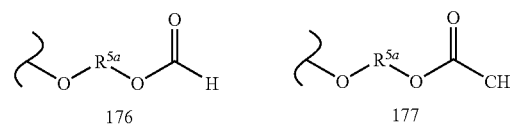
176 177
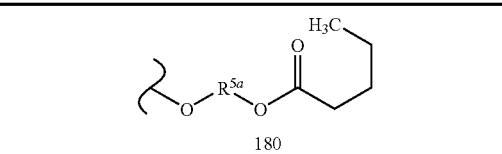
178 179
TABLE 20.28
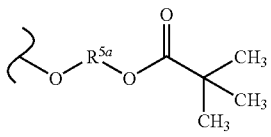
180
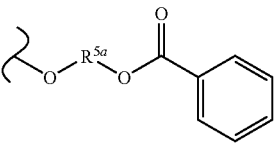
181
TABLE 20.28-continued
182
183
184
185
TABLE 20.29
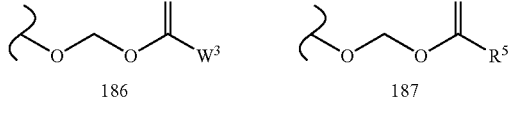
186 187
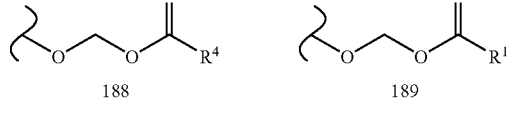
188 189
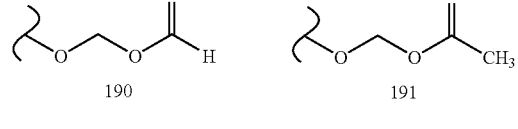
190 191
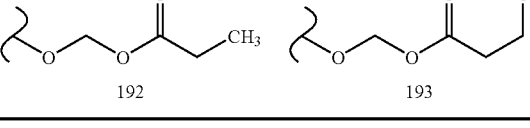
192 193
TABLE 20.30
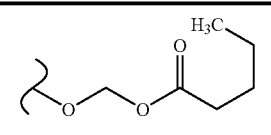
194

TABLE 20.30-continued
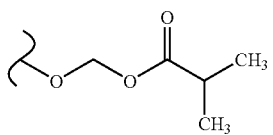
195
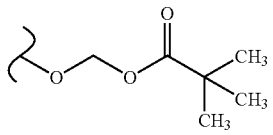
196
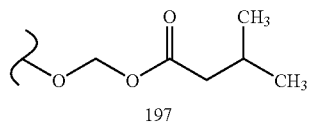
197
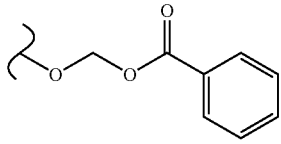
198
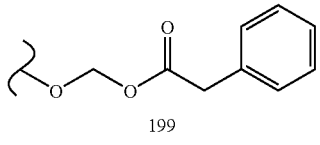
199
TABLE 20.31
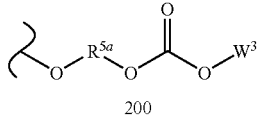
200
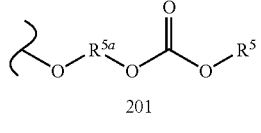
201
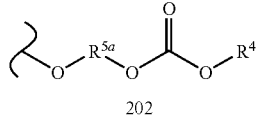
202
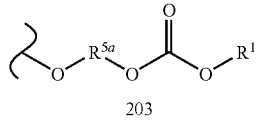
203
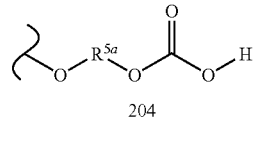
204
TABLE 20.31-continued
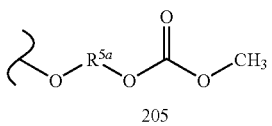
205
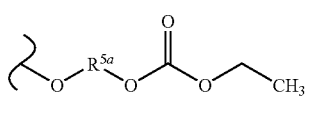
206
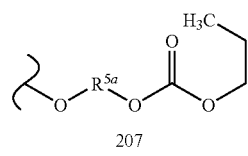
207
TABLE 20.32
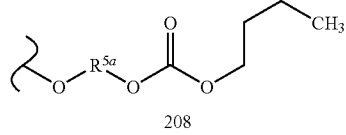
208
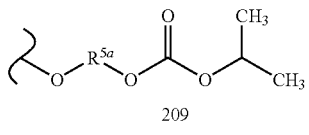
209
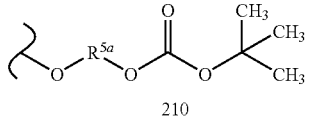
210
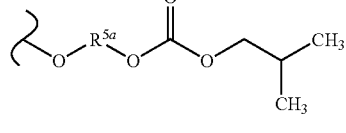
211
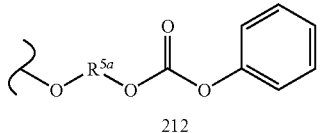
212
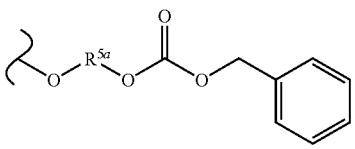
213

TABLE 20.33
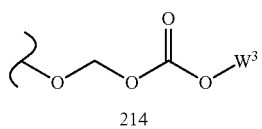
214
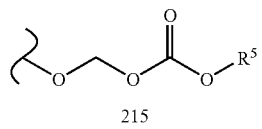
215
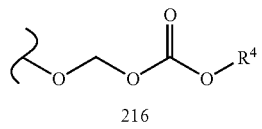
216
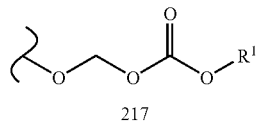
217
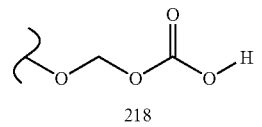
218
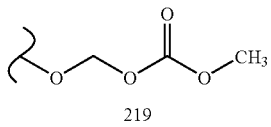
219
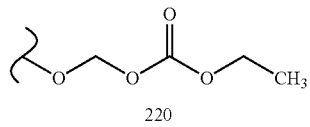
220
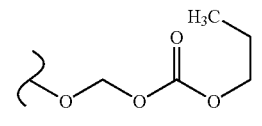
221
TABLE 20.34
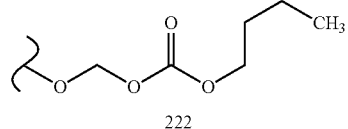
222
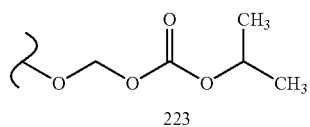
223
TABLE 20.34-continued
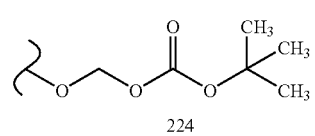
224
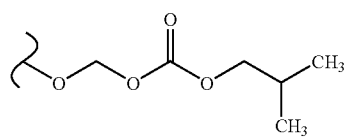
225
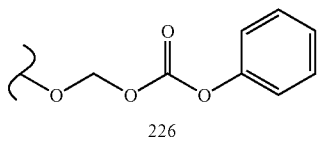
226
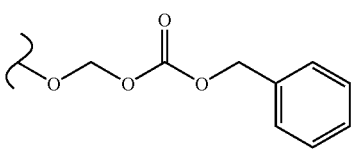
227
TABLE 20.35
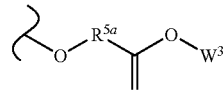
228
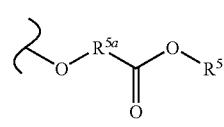
229
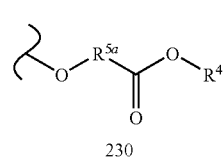
230
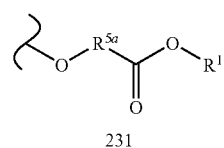
231
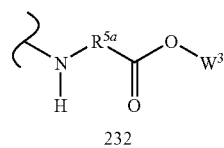
232

TABLE 20.35-continued
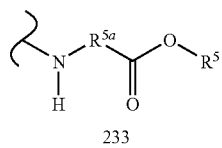
233
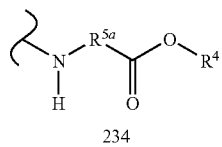
234
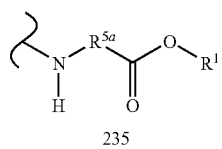
235
TABLE 20.36
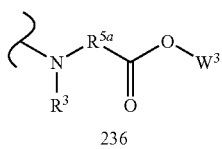   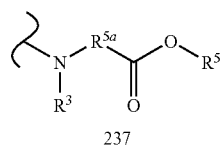
236           237
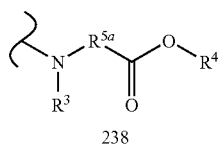   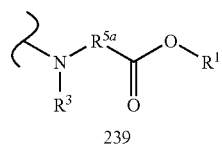
238           239
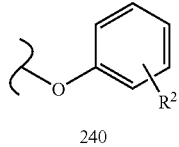   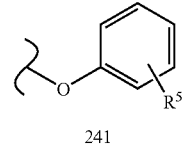
240           241
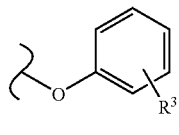  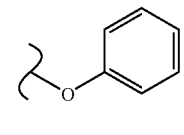
242           243
TABLE 20.37
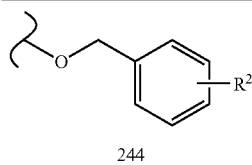  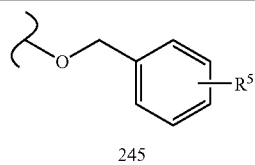
244           245
TABLE 20.37-continued
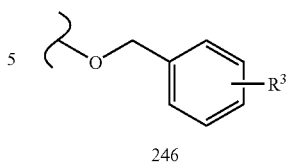   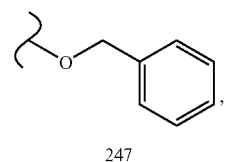
246            247
Pd$^1$ and Pd$^2$ of the "Sc" structures of Table 1.1 can also be independently selected from Table 30.1, below:
TABLE 30.1
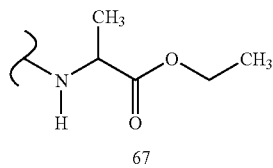
67
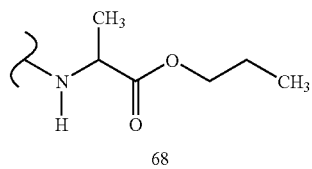
68
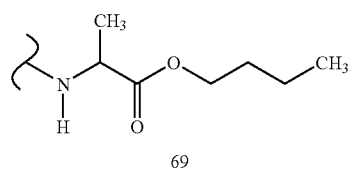
69
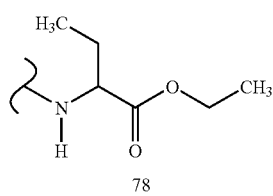
78
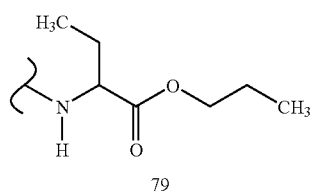
79
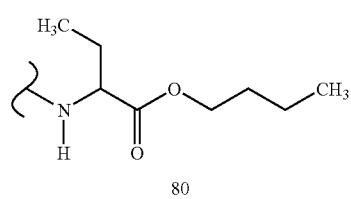
80

TABLE 30.1-continued

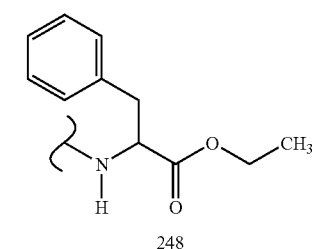
248

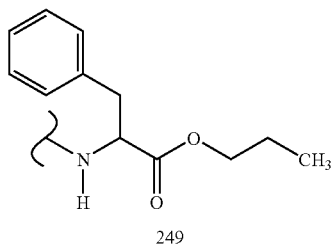
249

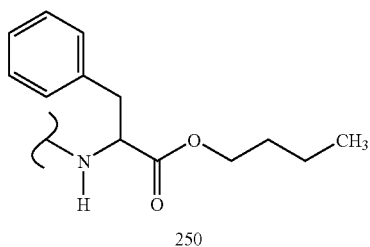
250

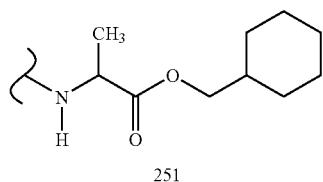
251

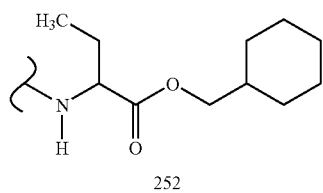
252

TABLE 30.1-continued

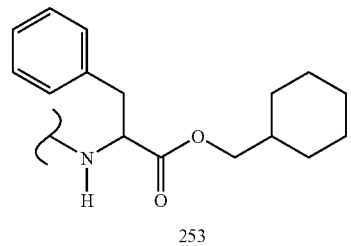
253

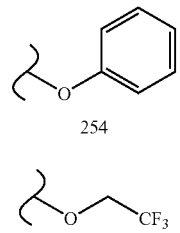
254

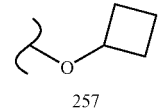
255

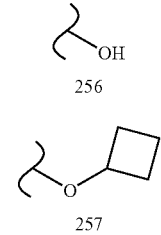
256

257

Combinations of "Sc" and Pd$^1$ and Pd$^2$ independently selected from table 30.1 can be expressed in the form of Sc.Pd$^1$.Pd$^2$, where Sc is represented by the respective letter A-G from Table 1.1 and Pd$^1$ and Pd$^2$ are represented by the respective number from Table 30.1. Thus, A.256.256 represents the following compound:

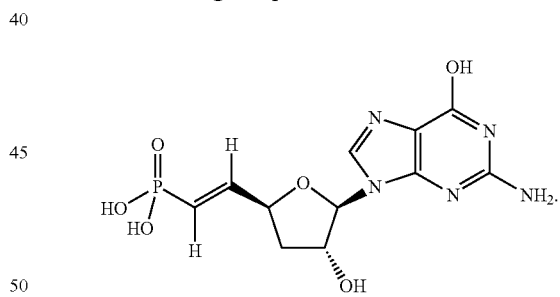

TABLE 7

List of Compounds of MBF

A.254.67, A.254.68, A.254.69, A.254.78, A.254.79, A.254.80, A.254.248, A.254.249, A.254.250, A.254.251, A.254.252, A.254.253, B.254.67, B.254.68, B.254.69, B.254.78, B.254.79, B.254.80, B.254.248, B.254.249, B.254.250, B.254.251, B.254.252, B.254.253, C.254.67, C.254.68, C.254.69, C.254.78, C.254.79, C.254.80, C.254.248, C.254.249, C.254.250, C.254.251, C.254.252, C.254.253, D.254.67, D.254.68, D.254.69, D.254.78, D.254.79, D.254.80, D.254.248, D.254.249, D.254.250, D.254.251, D.254.252, D.254.253, E.254.67, E.254.68, E.254.69, E.254.78, E.254.79, E.254.80, E.254.248, E.254.249, E.254.250, E.254.251, E.254.252, E.254.253, F.254.67, F.254.68, F.254.69, F.254.78, F.254.79, F.254.80, F.254.248, F.254.249, F.254.250, F.254.251, F.254.252, F.254.253, G.254.67, G.254.68, G.254.69, G.254.78, G.254.79, G.254.80, G.254.248, G.254.249, G.254.250, G.254.251, G.254.252, G.254.253, A.255.67, A.255.68, A.255.69, A.255.78, A.255.79, A.255.80, A.255.248,

TABLE 7-continued

List of Compounds of MBF

A.255.249, A.255.250, A.255.251, A.255.252, A.255.253, B.255.67, B.255.68,
B.255.69, B.255.78, B.255.79, B.255.80, B.255.248, B.255.249, B.255.250, B.255.251,
B.255.252, B.255.253, C.255.67, C.255.68, C.255.69, C.255.78, C.255.79, C.255.80,
C.255.248, C.255.249, C.255.250, C.255.251, C.255.252, C.255.253, D.255.67,
D.255.68, D.255.69, D.255.78, D.255.79, D.255.80, D.255.248, D.255.249, D.255.250,
D.255.251, D.255.252, D.255.253, E.255.67, E.255.68, E.255.69, E.255.78, E.255.79,
E.255.80, E.255.248, E.255.249, E.255.250, E.255.251, E.255.252, E.255.253,
F.255.67, F.255.68, F.255.69, F.255.78, F.255.79, F.255.80, F.255.248, F.255.249,
F.255.250, F.255.251, F.255.252, F.255.253, G.255.67, G.255.68, G.255.69, G.255.78,
G.255.79, G.255.80, G.255.248, G.255.249, G.255.250, G.255.251, G.255.252,
G.255.253, A.67.67, A.68.68, A.69.69, A.78.78, A.79.79, A.80.80, A.248.248,
A.249.249, A.250.250, A.251.251, A252.252, A.253.253, B.67.67, B.68.68, B.69.69,
B.78.78, B.79.79, B.80.80, B.248.248, B.249.249, B.250.250, B.251.251, B252.252,
B.253.253, C.67.67, C.68.68, C.69.69, C.78.78, C.79.79, C.80.80, C.248.248,
C.249.249, C.250.250, C.251.251, C252.252, C.253.253, D.67.67, D.68.68, D.69.69,
D.78.78, D.79.79, D.80.80, D.248.248, D.249.249, D.250.250, D.251.251, D252.252,
D.253.253, E.67.67, E.68.68, E.69.69, E.78.78, E.79.79, E.80.80, E.248.248, E.249.249,
E.250.250, E.251.251, E252.252, E.253.253, F.67.67, F.68.68, F.69.69, F.78.78,
F.79.79, F.80.80, F.248.248, F.249.249, F.250.250, F.251.251, F252.252, F.253.253,
G.67.67, G.68.68, G.69.69, G.78.78, G.79.79, G.80.80, G.248.248, G.249.249,
G.250.250, G.251.251, G252.252, G.253.253, A.256.257, B.256.257, C.256.257,
D.256.257, E.256.257, F.256.257, G.256.257.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| AIBN | 2,2'-azobis(2-methylpropionitrile) |
| BnBr | benzylbromide |
| BSA | bis(trimethylsilyl)acetamide |
| BzCl | benzoyl chloride |
| CDI | carbonyl diimidazole |
| DBU | 1,5-diazabicyclo[5.4.0]undecene-5 |
| DCA | dichloroacetamide |
| DCC | dicyclohexylcarbodiimide |
| DMAP | 4-dimethylaminopyridine |
| DME | 1,2-dimethoxyethane |
| DMTCl | dimethoxytrityl chloride |
| DMSO | dimethylsulfoxide |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| mCPBA | meta-chloroperbenzoic acid |
| MeOH | methanol |
| MMTC | mono methoxytrityl chloride |
| m/z or m/e | mass to charge ratio |
| MH+ | mass plus 1 |
| MH− | mass minus 1 |
| MsOH | methanesulfonic acid |
| MS or ms | mass spectrum |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TEA | triethylamine |
| TBA | tributylamine |
| TBAP | tributylammonium pyrophosphate |
| TBSCl | t-butyldimethylsilyl chloride |

TABLE 1-continued

List of abbreviations and acronyms.

| Abbreviation | Meaning |
|---|---|
| TEAB | triethylammonium bicarbonate |
| TFA | trifluoroacetic acid |
| TLC or tlc | thin layer chromatography |
| δ | parts per million down field from tetramethylsilane |

Example 1

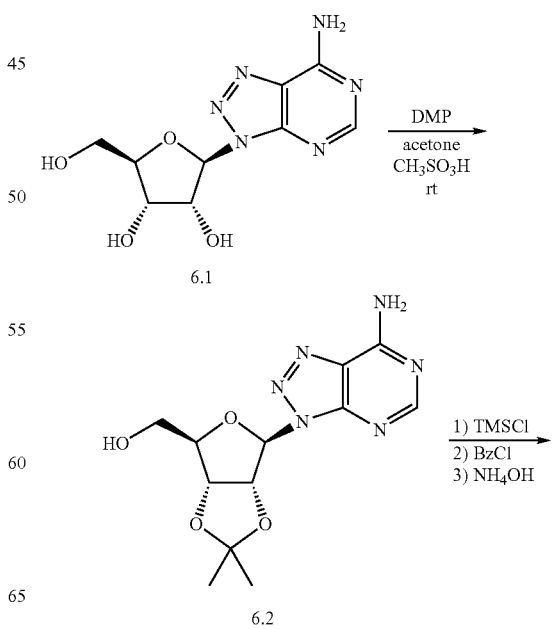

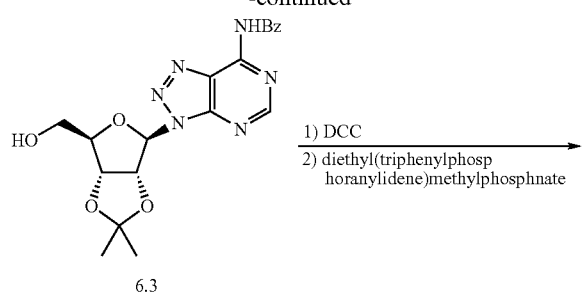

6.3

1) DCC
2) diethyl(triphenylphosphoranylidene)methylphosphnate

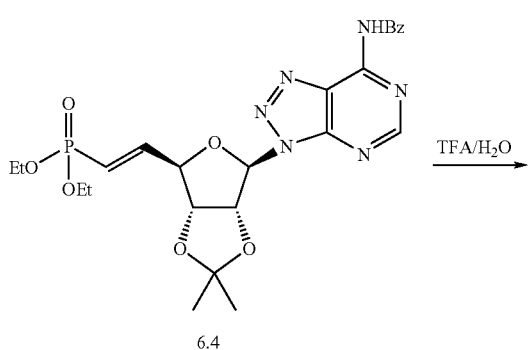

6.4

TFA/H₂O

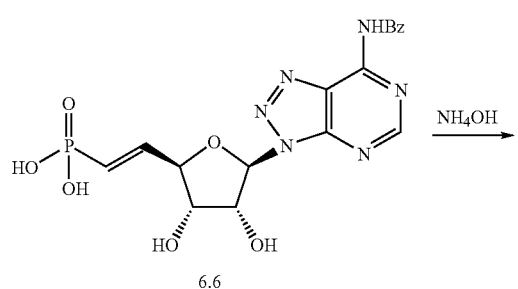

6.5

TMSBr
2,6-lutidine

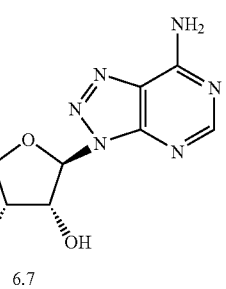

6.6

NH₄OH

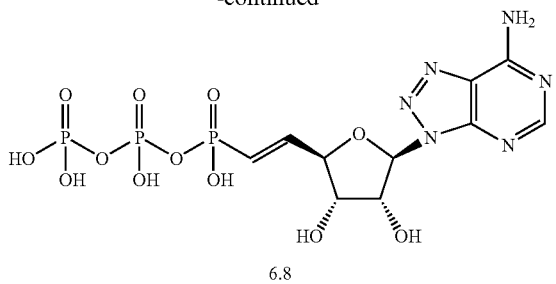

6.8

[6-(7-Amino-[1,2,3]triazolo[4,5-d]pyrimidin-3-yl)-2,2-dimethyl-tetrahydro-furo[3,4-d][1,3]dioxol-4-yl]-methanol (6.2)

Compound 6.1 (2 g, 7.46 mmol) was dissolved in 83 mL acetone, treated with 2,2-dimethoxypropane 50 mL and $CH_3SO_3H$ (0.5 mL, 7.46 mmol). The mixture was stirred for 3 h and then concentrated under reduced pressure. The residue was partitioned between $CH_2Cl_2$ and saturated $NaHCO_3$. The organic layer was separated, dried over $MgSO_4$, filtered and concentrated under reduced pressure. The residue was subjected to a silica gel column chromatography eluting with 0-5% MeOH in $CH_2Cl_2$ to yield compound 6.2 (2.2 g, 96% yield). ¹HNMR (300 MHz, CDCl₃) δ 1.41 (s, 3H), 1.69 (s, 3H), 3.77-4.00 (m, 2H), 4.61 (s, 1H), 5.12 (d, 1H, J=6), 5.25 (t, 1H, J=5.4), 6.57 (d, 1H, J=4.5), 8.46 (s, 1H). LRMS [M–H]⁻ $C_{12}H_{16}N_6O_4$ requires 307.1, Found 307.1.

N-[3-(6-Hydroxymethyl-2,2-dimethyl-tetrahydro-furo[3,4-d][1,3]dioxol-4-yl)-3H-[1,2,3]triazolo[4,5-d]pyrimidin-7-yl]-benzamide (6.3)

Compound 6.2 (2.2 g, 7.14 mmol) was dissolved in 30 mL pyridine and cooled to 0° C. To this was added TMSCl (2.7 mL, 21.4 mmol). The mixture was stirred at 0° C. for 30 min and then treated with BzCl (4.95 mL, 35.7 mmol). The mixture was stirred at 0° C. for 3 h and then treated with NH₄OH (7.3 mL), stirred at 0° C. for another 30 min. The mixture was concentrated under reduced pressure and the residue was partitioned between $CH_2Cl_2$ and 1N HCl. The water layer was extracted three times with $CH_2Cl_2$. The organic layer was combined, dried over $MgSO_4$, filtered and concentrated under reduced pressure. The residue was subjected to a silica gel column chromatography eluting with 80% EtOAc in Hexane to yield compound 6.3 (1.84 g, 63% yield). ¹HNMR (300 MHz, CDCl₃) δ 1.42 (s, 3H), 1.70 (s, 3H), 3.79-4.01 (m, 2H), 4.63 (s, 1H), 5.14-5.16 (m, 1H), 5.31-5.35 (m, 1H), 6.68 (d, 1H, J=4.2), 7.55-7.61 (m, 2H), 7.61-7.69 (m, 1H), 8.08 (d, 2H, J=7.2), 8.90 (s, 1H). LRMS (ESI) MH⁺ $C_{19}H_{20}N_6O_5$ requires 413.2. Found 412.9.

{2-[6-(7-Benzoylamino-[1,2,3]triazolo[4,5-d]pyrimidin-3-yl)-2,2-dimethyl-tetrahydro-furo[3,4-d][1,3]dioxol-4-yl]-vinyl}-phosphonic acid diethyl ester (6.4)

Compound 6.3 (1.2 g, 2.91 mmol) was dissolved in 23 mL DMSO, and treated with DCC (3.6 g, 17.5 mmol) and DCA (0.24 mL, 2.91 mmol). The mixture was stirred for 2 h and then treated with 0.3 mL pyridine. Diethyl(triphenylphosphoranylidene)methylphosphonate (2.9 g, 6.98 mmol) was dissolved in 5 mL $CH_2Cl_2$ and it was added to the mixture dropwise and the mixture was stirred for 3 h. The mixture was concentrated under reduced pressure and the residue was dissolved in EtOAc. The organic layer was washed with H₂O three times, dried over MgSO₄, filtered and concentrated down under reduced pressure. The residue was subjected to a silica gel column chromatography eluting with 100% EtOAc to 5% MeOH in EtOAc to give compound 6.4 (469 mg, 30% yield). ¹HNMR (300 MHz, CD₃OD) δ 1.17-1.35 (m, 6H), 1.46 (s, 3H), 1.64 (s, 3H), 3.85-3.97 (m, 4H), 4.04-4.12 (m, 1H), 5.01 (m, 1H), 5.33-5.45 (m, 2H), 5.81 (d, 1H, J=5.7), 6.63-6.77 (m, 1H), 7.57-8.12 (m, 5H), 8.87 (s, 1H). LRMS (ESI) MH⁺ C₂₄H₂₉N₆O₇P requires 545.2, Found 545.0.

{2-[5-(7-Benzoylamino-[1,2,3]triazolo[4,5-d]pyrimidin-3-yl)-3,4-dihydroxy-tetrahydro-furan-2-yl]-vinyl}-phosphonic acid diethyl ester (6.5)

Compound 6.4 (170 mg, 0.31 mmol) was dissolved in 90% TFA in H₂O (10 mL). The mixture was stirred for 30 min and concentrated down under reduced pressure. The residue was subjected to a silica gel column chromatography eluting with 10% MeOH in CH₂Cl₂ to yield compound 6.5 (110 mg, 70% yield). ¹HNMR (300 MHz, CD₃OD) δ 1.24-1.28 (m, 6H), 3.96-4.06 (m, 4H), 4.63 (t, 1H, J=5.1), 4.73 (s, 1H), 4.97 (t, 1H, J=4.2), 5.92-6.04 (m, 1H), 6.5 (d, 1H, J=3.9), 6.81-6.96 (m, 1H), 7.55-8.12 (m, 5H), 8.77 (s, 1H). LRMS (ESI) MH⁺ C₂₁H₂₅N₆O₇P requires 505.2. Found 504.9.

{2-[5-(7-Benzoylamino-[1,2,3]triazolo[4,5-d]pyrimidin-3-yl)-3,4-dihydroxy-tetrahydro-furan-2-yl]-vinyl}-phosphonic acid (6.6)

Compound 6.6 (190 mg, 0.38 mmol) was synthesized using the procedure described for the preparation of compound 1.10 (150 mg, 88% yield). ¹HNMR (300 MHz, D₂O) δ 4.52-4.55 (m, 1H), 5.03-5.06 (m, 1H), 5.79-5.91 (m, 1H), 6.26-6.40 (m, 1H), 6.44 (d, 1H, J=3.9), 7.43-7.91 (m, 5H), 8.76 (s, 1H). LRMS (ESI) MH⁺ C₁₇H₁₇N₆O₇P requires 449.1. Found 449.0.

{2-[5-(7-Amino-[1,2,3]triazolo[4,5-d]pyrimidin-3-yl)-3,4-dihydroxy-tetrahydro-furan-2-yl]-ethyl}-phosphonic acid (6.7)

Compound 6.6 (50 mg, 0.11 mmol) was dissolved in 15 mL NH₄OH and stirred under N2 for overnight. The mixture was concentrated under reduced pressure. The residue was subjected to reverse phase HPLC eluting with 0-25% CH₃CN in water to yield product 6.7 (34 mg, 89% yield). ¹HNMR (300 MHz, D₂O) δ 4.47-4.51 (m, 1H), 4.59-4.61 (m, 1H), 4.96-4.99 (m, 1H), 5.85 (t, 1H, J=17.1), 6.22-6.37 (m, 2H), 8.20 (s, 1H). ³¹P NMR: 10.98 ppm. LRMS (ESI) MH⁺ C₁₀H₁₃N₆O₆P requires 345.1. Found 345.8.

Diphosphophosphonate 6.8

Compound 6.7 (15 mg, 0.0436 mmol) was dissolved in 2 mL anhydrous DMF and treated with nBu₃N (21 μL, 0.0872 mmol) and CDI (71 mg, 0.436 mmol). The mixture was stirred for 20 min and then treated with MeOH (16 μL, 0.392 mmol), stirred for another 30 min. To this mixture was added 1 mL DMF solution of tetrabutylammonium pyrophosphate (250 mg, 0.436 mmol), stirred for 2 h and concentrated down under reduced pressure. The residue was subjected to ion exchange reverse phase HPLC eluting with 0-40% TEAB in water to yield product (7.9 mg, 36% yield). ¹HNMR (300 MHz, D₂O) δ 1.10-1.16 (m, 54H), 3.02-3.09 (m, 36H), 4.53 (t, 1H, J=5.1), 4.99 (t, 1H, J=4.8), 5.98 (t, 1H, J=17.7), 6.32 (d, 1H, J=4.2), 6.40-6.54 (m, 1H), 8.36 (s, 1H). ³¹P NMR: 4.39, 4.19, −10.62, −10.79, −23.31 ppm.

Example 2

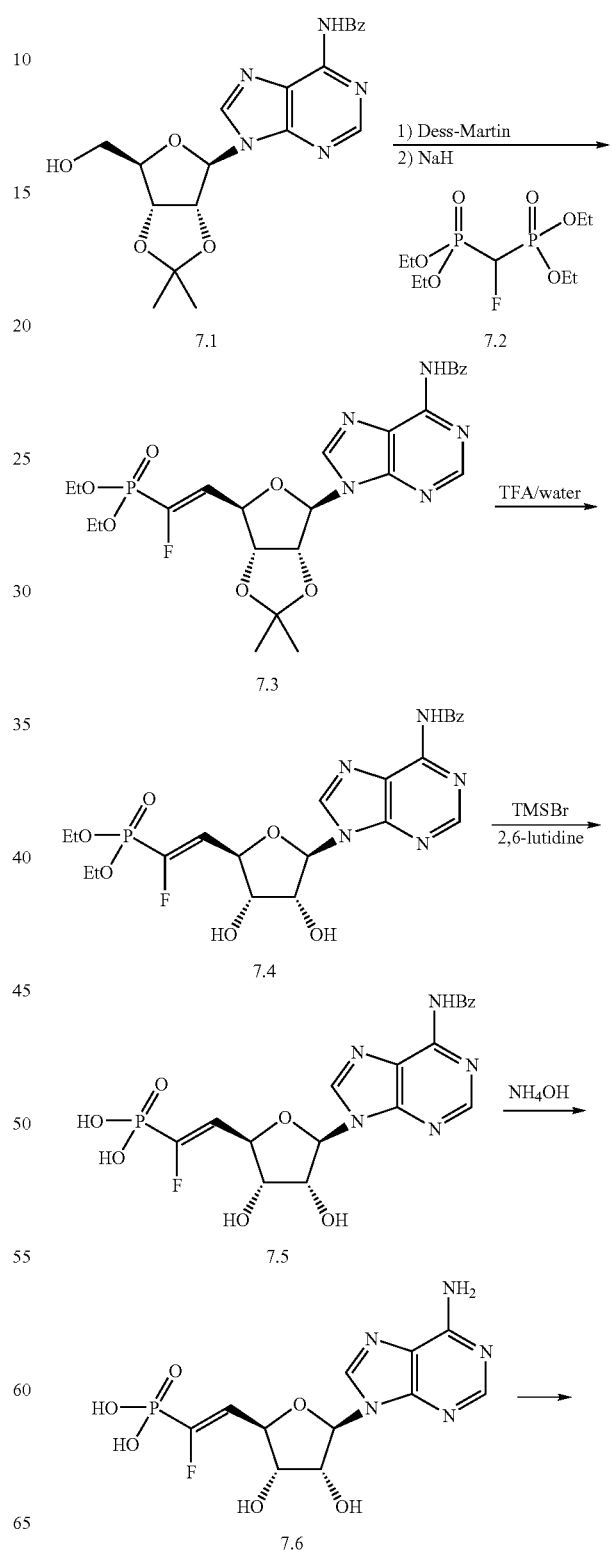

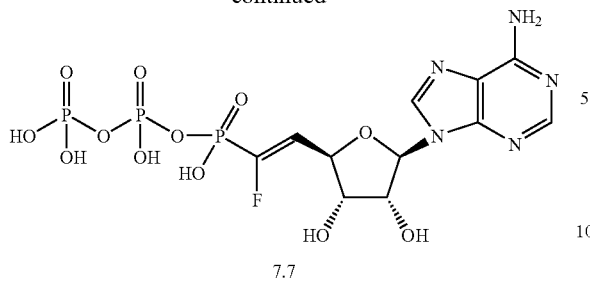

7.7

{2-[6-(6-Benzoylamino-purin-9-yl)-2,2-dimethyl-tetrahydro-furo[3,4-d][1,3]dioxol-4-yl]-1-fluoro-vinyl}-phosphonic acid diethyl ester (7.3)

Compound 7.1 (500 mg, 1.22 mmol) was dissolved in 5 mL anhydrous $CH_2Cl_2$ and treated with Dess-Martin reagent (670 mg, 1.59 mmol). The mixture was stirred for 2 h, filtered through a syringe filter, and concentrated down under reduced pressure. The residue was dissolved in EtOAc, filtered, concentrated down under reduced pressure and then dried on high vacuum. 60% NaH (150 mg, 3.66 mmol) was dissolved in 5 mL anhydrous THF at 0° C. and treated with compound 7.2 (1.8 g, 3.66 mmol). The mixture was stirred for 30 min at rt to generate the anion. The generated anion was then added to the aldehyde formed in the first step, and the mixture was stirred for 2 h. Water was added to quench the reaction, and the mixture was concentrated under reduced pressure. The residue was subjected to a silica gel column chromatography eluting with 50% EtOAc in Hexane to 100% EtOAc to yield compound 7.3 (100 mg, 15% yield). $^1$HNMR (300 MHz, $CD_3CN$) δ 1.22-1.40 (m, 6H), 1.41 (s, 3H), 1.63 (s, 3H), 3.97-4.17 (m, 4H), 5.21-5.29 (m, 2H), 5.64 (d, 1H, J=6), 5.93-6.12 (m, 1H), 6.30 (s, 1H), 7.55-8.05 (m, 5H), 8.28 (s, 1H), 8.70 (s, 1H). LRMS (ESI) MH$^+$ $C_{25}H_{29}FN_5O_7P$ requires 562.2. Found 562.2.

{2-[5-(6-Benzoylamino-purin-9-yl)-3,4-dihydroxy-tetrahydro-furan-2-yl]-1-fluoro-vinyl}-phosphonic acid diethyl ester (7.4)

Compound 7.4 (70 mg, 76% yield) was synthesized from compound 7.3 (100 mg) using the procedure described for the preparation for compound 6.5. $^1$HNMR (300 MHz, $CD_3CN$) δ 1.21-1.38 (m, 6H), 4.06-4.24 (m, 4H), 4.47 (s, 1H), 4.92 (s, 1H), 5.00 (s, 1H), 6.08 (d, 1H, J=4.8), 6.31-6.47 (m, 1H), 7.57-8.06 (m, 5H), 8.31 (s, 1H), 8.72 (s, 1H).

{2-[5-(6-Benzoylamino-purin-9-yl)-3,4-dihydroxy-tetrahydro-furan-2-yl]-1-fluoro-vinyl}-phosphonic acid (7.5)

Compound 7.5 (57 mg, 91% yield) was synthesized from compound 7.4 (70 mg) using the procedure described for the preparation for compound 1.10. $^1$HNMR (300 MHz, $D_2O$) δ 4.44 (t, 1H, J=4.8), 4.91 (t, 1H, J=4.8), 5.10-5.15 (m, 1H), 5.67-5.85 (m, 1H), 6.23 (d, 1H, J=5.1), 7.55-8.01 (m, 5H), 8.61 (s, 1H), 8.67 (s, 1H). LRMS (ESI) MH$^+$ $C_{18}H_{17}FN_5O_7P$ requires 466.1. Found 465.8.

{2-[5-(6-Amino-purin-9-yl)-3,4-dihydroxy-tetrahydro-furan-2-yl]-1-fluoro-vinyl}-phosphonic acid (7.6)

Compound 7.5 (50 mg, 0.11 mmol) was dissolved in 5 mL $NH_4OH$ and stirred under $N_2$ for overnight. The mixture was concentrated under reduced pressure and the residue was subjected to reverse phase HPLC eluting with 0-25% $CH_3CN$ in water to give compound 7.6 (22 mg, 57% yield). $^1$HNMR (300 MHz, $D_2O$) δ 4.24-4.27 (m, 1H), 4.69-4.71 (m, 1H), 4.96 (m, 1H), 5.54-5.68 (m, 1H), 5.97 (d, 1H, J=4.8), 8.11 (s, 1H), 8.21 (s, 1H). LRMS [M−H]$^−$ $C_{11}H_{13}FN_5O_6P$ requires 361.1. Found 361.5.

Diphosphophosphonate 7.7

The compound (3.9 mg, 29% yield) was synthesized from compound 7.6 (9.5 mg) using the procedure described for the preparation compound 6.8.

$^1$HNMR (300 MHz, $D_2O$) δ 1.11-1.16 (m, 63H), 3.05-3.22 (m, 42H), 4.31-4.34 (m, 1H), 4.71-4.74 (m, 1H), 4.98 (s, 1H), 5.78-5.96 (m, 1H), 5.99 (d, 1H, J=5.7), 8.14 (s, 1H), 8.27 (s, 1H). $^{31}$P NMR: −9.31, −9.50, −9.87, −10.04, −10.35, −10.65, −10.81, −23.00, −23.56 ppm. LRMS [M−H]$^−$ $C_{11}H_{15}FN_5O_{12}P_3$ requires 520.0. Found 519.9.

Example 3

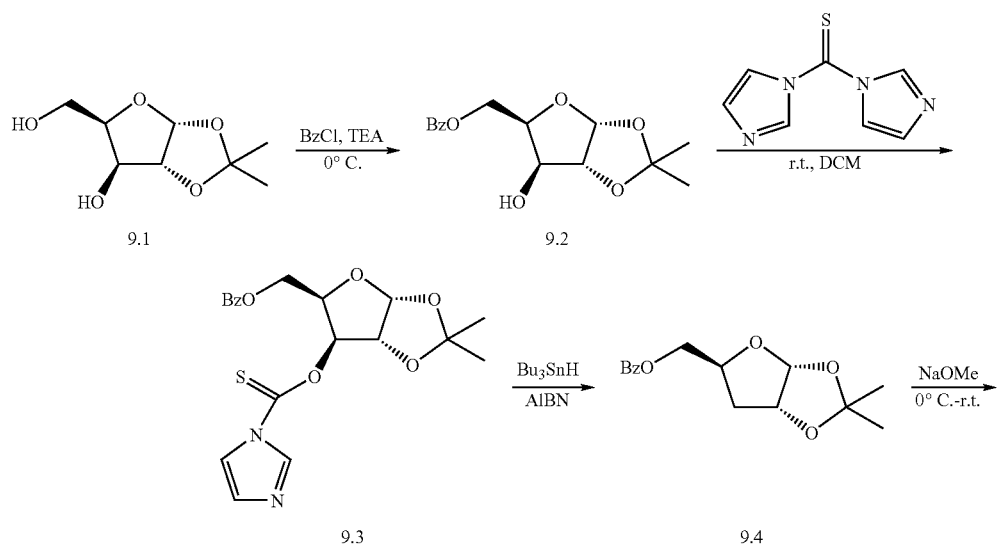

-continued

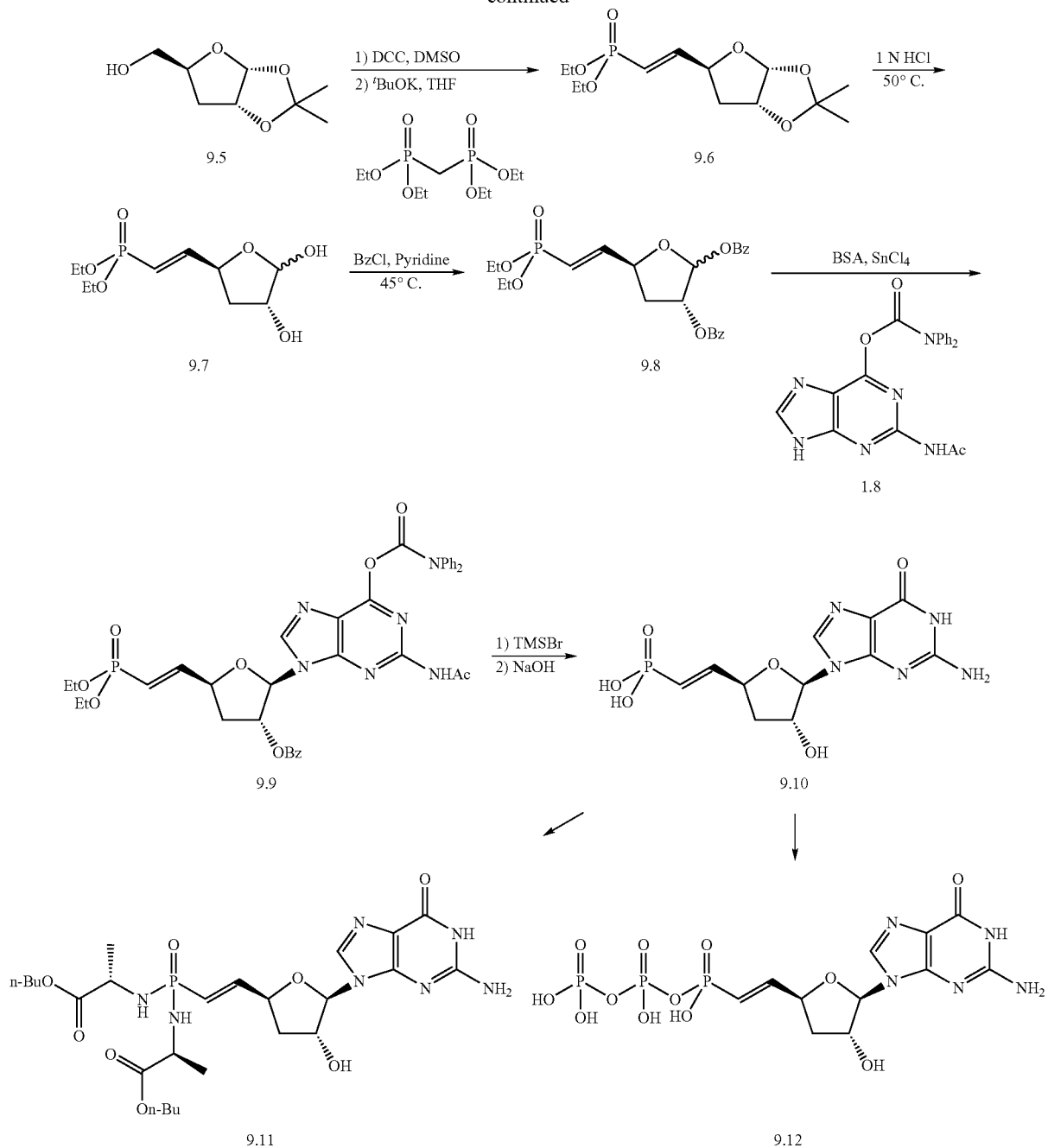

Benzoic acid 6-hydroxy-2,2-dimethyl-tetrahydro-furo[2,3-d][1,3]dioxol-5-ylmethyl ester (9.2)

1,2-O-Isopropylidene-α-D-xylofuranose (Aldrich, 20 g, 100 mmol) in $CH_2Cl_2$ (300 mL) and TEA (44 mL, 310 mmol) was cooled to 0° C. The solution was treated with benzoyl chloride (12.8 mL, 110 mmol) in $CH_2Cl_2$ (10 mL) dropwise and stirred for 2 h. The solution was diluted with $H_2O$ (30 mL) and washed with saturated $NaHCO_3$ (2×30 mL). The solution was dried over $MgSO_4$, filtered and concentrated in vacuo. The residue was treated to flash column chromatography ($SiO_2$, 4×20 cm, 0-100% EtOAc-hexanes gradient) to afford compound 9.2 (22.0 g, 71% yield). (Taken from: Johnson, C. R.; Bhumralkar, D. R. *Nucleosides & Nucleotides* 1995, 14, 185.)

Benzoic acid 6-(imidazole-1-carbothioyloxy)-2,2-dimethyl-tetrahydro-furo[2,3-d][1,3]dioxol-5-ylmethyl ester (9.3)

Compound 9.2 (3.0 g, 10 mmol) in $CH_2Cl_2$ (100 mL) was treated with 1,1-thiocarbonyldiimdazole (3.6 g, 20 mmol) and stirred for 2 h. The solution was concentrated in vacuo and treated to silica gel column chromatography ($SiO_2$, 4×20 cm, 35-65% EtOAc-hexanes gradient) to afford compound 9.3 (5.5 g, >100% yield). (Taken from: De Bernardo, S.; Tengi, J. P.; Sasso, G. J.; Weigele, M. *J. Org. Chem.* 1985, 50, 3457-3462.)

Benzoic acid 2,2-dimethyl-tetrahydro-furo[2,3-d][1, 3]dioxol-5-ylmethyl ester (9.4)

Compound 9.3 (5.5 g, 13.6 mmol) in toluene (20 mL) was added dropwise to a refluxing solution of $Bu_3SnH$ (6.7 mL, 24.0 mmol) and AIBN (300 mg, 1.8 mmol) in toluene (80 mL) under $N_2$. The mixture was stirred for 2 h then cooled. The solution was partitioned between MeCN (300 mL) and hexanes (3×200 mL). The combined hexanes fractions were extracted with MeCN (200 mL), then the combined MeCN fractions were concentrated in vacuo and the residue was treated to silica gel column chromatography ($SiO_2$, 4×20 cm, 35-75% EtOAc-hexanes gradient) to afford compound 9.4 (1.7 g, 46% yield). (Taken from: De Bernardo, S.; Tengi, J. P.; Sasso, G. J.; Weigele, *J. Org. Chem.* 1985, 50, 3457-3462.)

(2,2-Dimethyl-tetrahydro-furo[2,3-d][1,3]dioxol-5-yl)-methanol (9.5)

Compound 9.4 (11.0 g, 39.6 mmol) in MeOH (100 mL) at 0° C. was treated with NaOMe (4.3 M in MeOH, 3 mL, 20 mmol) and stirred for 30 min. The mixture was warmed to ambient temperature and stirred for 1 h. The mixture was cooled to 0° C. and treated with 1 N HCl (10 mL) then concentrated under reduced pressure. The residue was dissolved in EtOAc (100 mL) and stirred for 30 minutes, dried over $MgSO_4$, filtered, and concentrated in vacuo. The residue was subjected to a silica gel column chromatography ($SiO_2$, 4×20 cm, 20-50% EtOAc-hexanes gradient) to afford compound 9.5 (4.1 g, 60% yield).

[2-(2,2-Dimethyl-tetrahydro-furo[2,3-d][1,3]dioxol-5-yl)-vinyl]-phosphonic acid diethyl ester (9.6)

Compound 9.5 (4.0 g, 23 mmol) in DMSO (30 mL) was treated with DCC (7.1 g, 34.5 mmol) and pyridine-TFA (1.1 g, 5.7 mmol) and stirred for 5 h. $K_2CO_3$ (780 mg, 5.7 mmol) was added and the mixture was stirred for 30 min. The mixture was treated with a solution of tetraethyl ethylenediphosphonate (7.3 g, 25.3 mmol) and $^tBuOK$ (1 M in THF, 26 mL, 26 mmol) and stirred for 20 min. The mixture was cooled to 0° C. and 3 N HCl (6 mL) was added followed by EtOAc (100 mL). The organic layer was separated, dried over $MgSO_4$, filtered, and concentrated in vacuo. The residue was subjected to a silica gel column chromatography ($SiO_2$, 4×20 cm, 50-100% EtOAc-hexanes gradient) afforded compound 9.6 (3.6 g, 51% yield).

[2-(4,5-Dihydroxy-tetrahydro-furan-2-yl)-vinyl] phosphonic acid diethyl ester (9.7)

Compound 9.6 (3.6 g, 11.76 mmol) in MeCN (40 mL) was treated with 1 N HCl (10 mL) and stirred at 50° C. for 5 h with slow distillation of residual acetone. The solution was cooled to ambient temperature and treated with $NaHCO_3$ (1.0 g) then concentrated in vacuo. The residue was lyophilized overnight and MeOH (20 mL) was added and the solution was filtered. The solution was then co-evaporated with MeCN to afford crude compound 9.7 (3.5 g, >100% yield).

[2-(4,5-Dibenzoyl-tetrahydro-furan-2-yl)-vinyl]-phosphonic acid diethyl ester (9.8)

Compound 9.7 (3.1 g, 11.8 mmol) in pyridine (15 mL) was treated with benzoyl chloride (4.0 mL, 35 mmol) dropwise and the mixture was stirred at 45° C. for 1 h (significant exotherm upon BzCl addition). The mixture was cooled to 0° C. and EtOH (2 mL) was added dropwise and stirred for 10 minutes. The solution was concentrated in vacuo and the residue was dissolved in EtOAc (100 mL) and washed with 1 N HCl (10 mL) and brine (10 mL). The solution was dried over $MgSO_4$, filtered, and concentrated in vacuo. The residue was treated to silica gel column chromatography ($SiO_2$, 4×20 cm, 50-100% EtOAc-hexanes gradient) to afford compound 9.8 (4.2 g, 75% yield).

Benzoic acid 2-(2-acetylamino-6-diphenylcarbamoyloxy-purin-9-yl)-5-[2-(diethoxy-phosphoryl)-vinyl]-tetrahydro-furan-3-yl ester (9.9)

A suspension of $N^2$-acetyl-$O^6$-(diphenylcarbamoyl)guanine (582 mg, 1.5 mmol) in MeCN (10 mL) was treated with N,O-bis(trimethylsilyl)acetamide (0.45 mL, 1.84 mmol) and heated to 70° C. for 0.5 h. The solution was cooled down to room temperature and compound 9.8 (330 mg, 0.696 mmol) and $SnCl_4$ (2 mL, 1M in $CH_2Cl_2$) were added. The mixture was heated to 70° C. for 1.5 h, then cooled to 0° C., and $NaHCO_3$ (1.5 g) and water (0.5 mL) were added. After stirred at room temperature for 1 h, the mixture was filtered through a pad of silica gel and eluted with 50% EtOH in EtOAc. The filtrate was concentrated under reduced pressure and the residue was subjected to chromatography on silica gel (eluted with 5% EtOH in EtOAc) to give compound 9.9 as a colorless foam (128 mg, 24.8% yield).

Benzoic acid 2-(2-acetylamino-6-oxo-1,6-dihydro-purin-9-yl)-5-(2-phosphono-vinyl)-tetrahydro-furan-3-yl ester (9.10)

A suspension of compound 9.9 (128 mg, 0.173 mmol) in MeCN (5 mL) was treated with 2,6-lutidine (0.08 mL, 0.7 mmol) and bromotrimethylsilane (0.3 mL, 2.27 mmol) and stirred at room temperature for 2 h. The mixture was evaporated and co-evaporated with MeCN. The residue was dissolved in MeOH—$H_2O$ (1:1, 10 mL) and treated with NaOH (1 N, 3 mL). The mixture was stirred at room temperature for 16 h then at 45° C. for 1 h, and concentrated under reduced pressure. The residue was subjected to reverse phase HPLC eluting with 0-25% $CH_3CN$ in water to give the desired product 9.10 (32 mg, 48%). $^1H$ NMR ($D_2O$) δ 2.1 (m, 2H), 4.55 (m, 1H), 4.8 (m, 1H), 5.7 (d, 1H, J=1.5), 5.9 (m, 1H), 6.1(m, 1H), 7.7 (s, 1H). $^{31}P$ NMR ($D_2O$) d 17.17. LRMS (ESI) MH$^+$ $C_{11}H_{14}N_5O_6P$ requires 344.2. Found 344.0.

Bis-amidate prodrug 9.11

A solution of triphenylphosphine (48 mg, 0.183 mmol) and Aldrithiol-2 (38 mg, 0.173 mmol) in pyridine was treated with compound 9.10 (9.5 mg, 0.0245 mmol) and L-alanine n-butyl ester hydrochloride (35 mg, 0.193 mmol). The mixture was stirred at 60° C. for 1.5 h then concentrated under reduced pressure. The residue was subjected to reverse phase HPLC eluting with 20-70% $CH_3CN$ in water to give compound 9.11 (7.8 mg, 53% yield). $^1H$ NMR ($CD_3OD$) δ 0.95 (m, 6H), 1.4 (m, 10H), 1.6 (m, 4H), 2.3 (m, 2H), 3.95 (m, 2H), 4.15 (m, 4H), 4.7 (m, 1H), 4.98 (m, 1H), 5.85 (d, 1H, J=2.1 ), 6.1 (m, 1H), 6.8 (m, 1H), 7.8 (s, 1H). $^{31}P$ NMR ($CD_3OD$) d 18.77. LRMS (ESI) MH$^+$ $C_{25}H_{40}N_7O_8P$ requires 598.6. Found 598.1.

Diphosphophosphonate 9.12

Compound (5 mg) was synthesized from compound 9.10 (30 mg) using the procedure described for the preparation of the diphosphophosphonate 6.8. $^1H$ NMR ($D_2O$) δ 2.25 (m, 2H), 4.60 (m, 1H), 4.91 (m, 1H), 5.80 (d, 1H, J=2.1), 6.05 (m, 1H), 6.52 (m, 1H), 7.78 (s, 1H). LRMS [M–H]$^-$ $C_{11}H_{16}N_5O_{12}P_3$ requires 502.0. Found 502.0.

Example 4

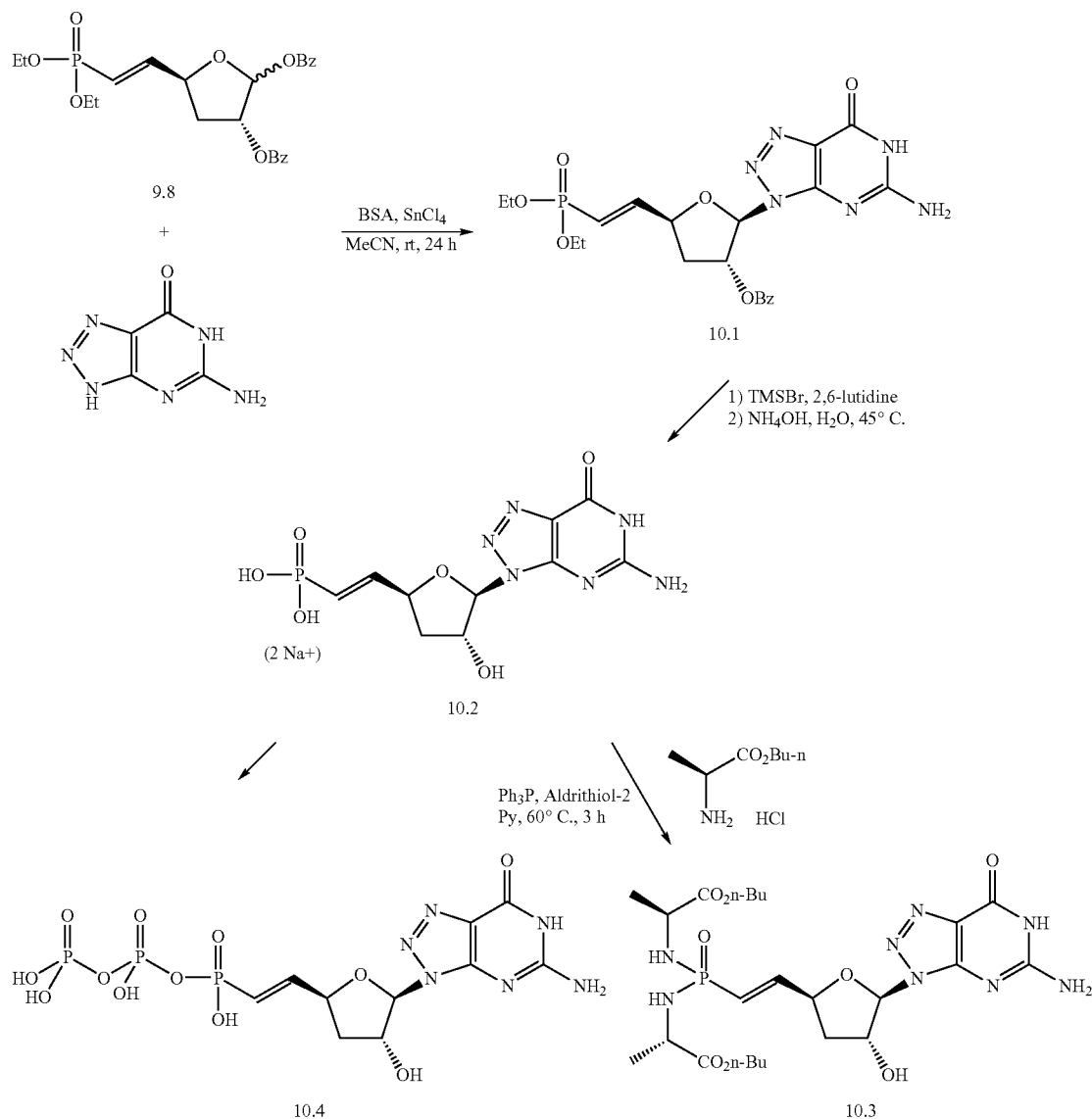

Benzoic acid 2-(5-amino-7-oxo-6,7-dihydro-[1,2,3] triazolo[4,5-d]pyrimidin-3-yl)-5-[2-(diethoxy-phosphoryl)-vinyl]-tetrahydro-furan-3-yl ester (10.1)

8-Azaguanine was persilylated first using the procedure described for the preparation of compound 9.9. Compound 9.8 (490 mg, 1.03 mmol) was dissolved in 20 mL anhydrous $CH_3CN$, and treated with 10 mL $CH_3CN$ solution of persilylated 8-azaguanine base (392.9 mg, 1.03 mmol), followed by addition of $SnCl_4$ (1M solution in $CH_2Cl_2$) (3 mL, 3 mmol). The mixture was stirred at r.t. for 24 h, cooled with ice-water and $NaHCO_3$, filtered, and concentrated down under reduced pressure. The residue was subjected to a silica gel column eluting with 10% EtOH in EtOAc to give compound 10.1 (430 mg, 83% yield).

{2-[5-(5-Amino-7-oxo-6,7-dihydro-[1,2,3]triazolo[4,5-d]pyrimidin-3-yl)-4-hydroxy-tetrahydro-furan-2-yl]-vinyl}-phosphonic acid (10.2)

Compound 10.1 (390 mg, 0.774 mmol) was dissolved in 15 mL $CH_3CN$, treated with 2,6-lutidine (0.3 mL, 2.59 mmol) and TMSBr (1.5 mL, 11.4 mmol). The mixture was stirred for 2 h and coevaporated with $CH_3CN$ under reduced pressure. The residue was treated with $NH_4OH$ (10 mL) and stirred at 45° C. for 1.5 h. The mixture was treated with 500 mg $NaHCO_3$ and concentrated down under reduced pressure. The residue was subjected to reverse phase HPLC eluting with 0-25% $CH_3CN$ in water to yield compound 10.2 (220 mg, 73% yield). $^1H$ NMR ($D_2O$) δ 2.28 (m, 1H), 2.45 (m, 1H), 4.90 (m, 2H), 5.8 (m, 1H), 6.15 (m, 1H). $^{31}P$ NMR ($D_2O$) d 18.77. LRMS (ESI) MH⁺ $C_{10}H_{13}N_6O_6P$ requires 345.2. Found 345.0.

Bis-amidate prodrug 10.3

Compound 10.3 (19.4 mg, 55% yield) was synthesized from compound 10.2 (23 mg) using the procedure described for the preparation of compound 9.11. $^1$H NMR (CD$_3$OD) δ 0.95 (m, 6H), 1.35 (m, 10H), 1.60 (m, 4H), 2.35 (m, 1H), 2.62 (m, 1H), 3.95 (m, 2H), 4.10 (m, 4H), 4.88 (m, 1H), 5.02 (m, 1H), 5.95 (m, 1H), 6.14 (m, 1H), 6.75 (m, 1H). $^{31}$P NMR (CD$_3$OD) d 18.94. LRMS (ESI) MH$^+$ C$_{24}$H$_{39}$N$_8$O$_8$P requires 599.6. Found 599.1.

Diphosphophosphonate 10.4

This compound (18 mg, 51.4% yield) was synthesized from compound 10.2 (27 mg, 0.07 mmol) using the procedure described for the preparation of compound 6.8. $^1$H NMR (300 MHz, D$_2$O): δ 2.25-2.50 (m, 2H), 4.87-4.95 (m, 2H), 5.95-6.05 (m, 2H), 6.30-6.42 (m, 1H). 31PNMR: 4.51, 4.33, −5.33, −5.50, −21.10, −21.27, −21.44 ppm. LRMS [M−H]$^-$ C$_{10}$H$_{15}$N$_6$O$_{12}$P$_3$ requires 503.0. Found 502.9.

Example 5

{2-[5-(4-Amino-2-oxo-2H-pyridin-1-yl)-4-hydroxy-tetrahydro-furan-2-yl]-vinyl}-phosphonic acid (11.2)

Compound 11.2 (97 mg, 86.5% yield) was synthesized from compound 11.1 (215 mg) using the procedure for the preparation of compound 10.2. $^1$H NMR (D$_2$O) δ 1.8 (m, 1H), 2.05 (m, 1H), 4.3 (d, 1H, J=4.8), 4.8 (m, 1H), 5.69 (s, 1H), 6.0 (m, 1H), 6.2 (m, 1H), 7.52 (d, 1H, J=7.8). $^{31}$P NMR (D$_2$O) d 9.8. LRMS (ESI) MH$^+$ C$_{10}$H$_{14}$N$_3$O$_6$P requires 304.2. Found 304.0.

Bis-amidate prodrug 11.3

Compound 11.3 (4.4 mg, 55% yield) was synthesized from compound 11.2 (5 mg) using the procedure for the preparation of compound 9.11. $^1$H NMR (300 MHz, CD$_3$OD) δ 0.95 (m, 6H), 1.4 (m, 10H), 1.65 (m, 4H), 1.85 (m, 1H), 2.1 (m, 1H), 3.95 (m, 2H), 4.15 (m, 4H), 4.32 (d, 1H, J=4.5), 4.98 (m, 1H), 5.8 (s, 1H), 5.95 (d, 1H, J=7.8), 6.1 (m, 1H), 7.64 (d, 1H,

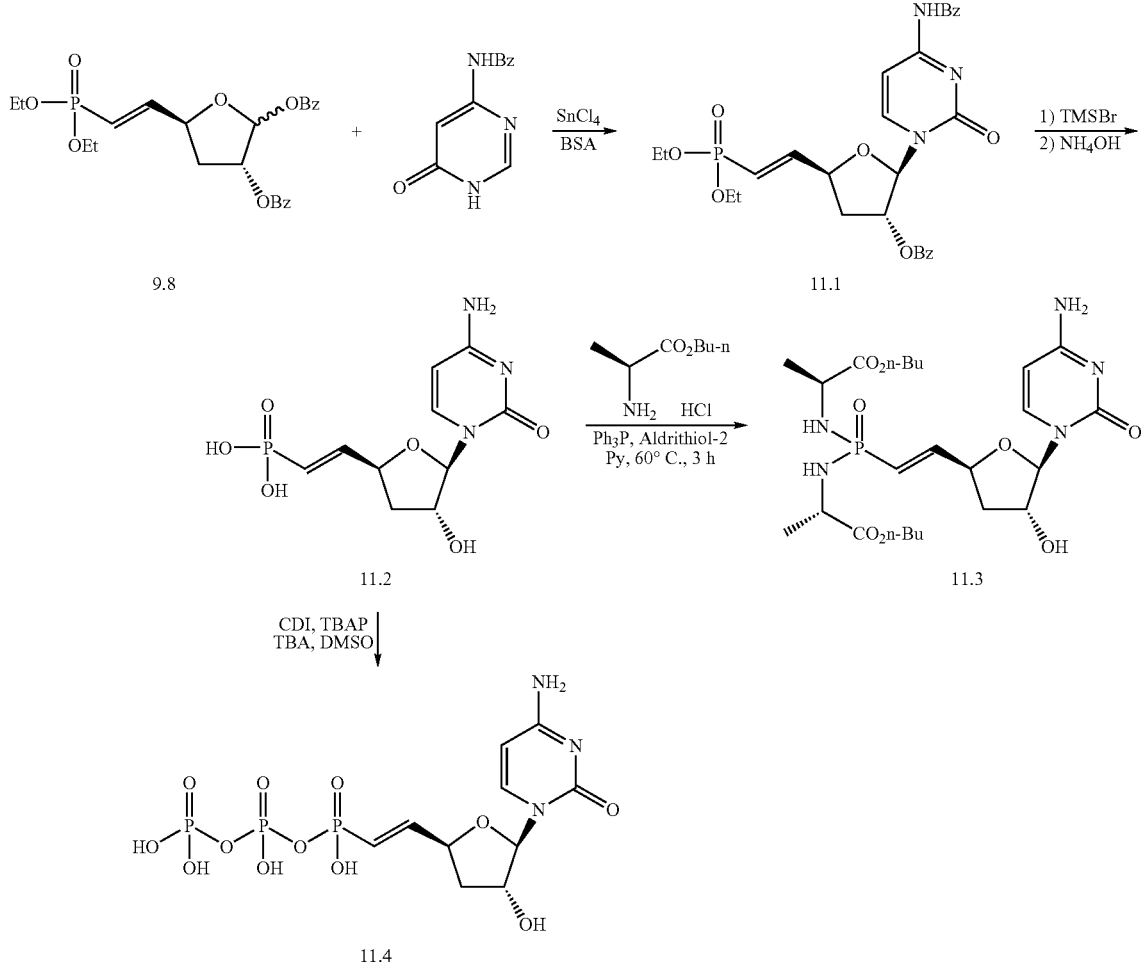

Benzoic acid 2-(4-benzoylamino-2-oxo-2H-pyridin-1-yl)-5-[2-(diethoxy-phosphoryl)-vinyl]-tetrahydro-furan-3-yl ester (11.1)

Compound 11.1 (215 mg, 60% yield) was synthesized from compound 9.8 (430 mg) using the procedure for the preparation of compound 9.9.

J=7.8). $^{31}$P NMR (CD$_3$OD) d 18.43. LRMS (ESI) MH$^+$ C$_{24}$H$_{40}$N$_5$O$_8$P requires 558.6. Found 558.1.

Diphosphophosphonate of 11.2. (11.4)

Compound 11.4 (5 mg, 19% yield) was synthesized from compound 11.2 (20 mg, 0.058 mmol) using the procedure described for the preparation of compound 6.8. $^1$H NMR (300

MHz, D$_2$O): δ 1.81-2.16 (m, 2H), 4.32 (d, 1H, J=4.8), 4.91 (s, 1H), 5.74 (s, 1H), 5.94 (d, 1H, J=7.8), 6.06-6.18 (t, 1H, J=18.3), 6.48-6.63 (m, 1H), 7.54 (d, 1H, J=7.5). 31PNMR: 4.40, 4.21, −9.52, −9.69, −22.68, −22.85, −23.03 ppm. LRMS [M−H]$^−$ C$_{10}$H$_{16}$N$_3$O$_{12}$P$_3$ requires 462.0. Found 461.9.

Example 6

{2-[5-(6-Amino-purin-9-yl)-4-hydroxy-tetrahydro-furan-2-yl]-vinyl}-phosphonic acid (12.2)

Compound 12.2 (103 mg, 68% yield) was synthesized from compound 12.1 (200 mg, 0.41 mmol) using the procedure for the preparation of compound 10.2. $^1$H NMR (D$_2$O) δ 2.10 (m, 1H), 2.19 (m, 1H), 4.62 (m, 1H), 4.87 (m, 1H), 5.95

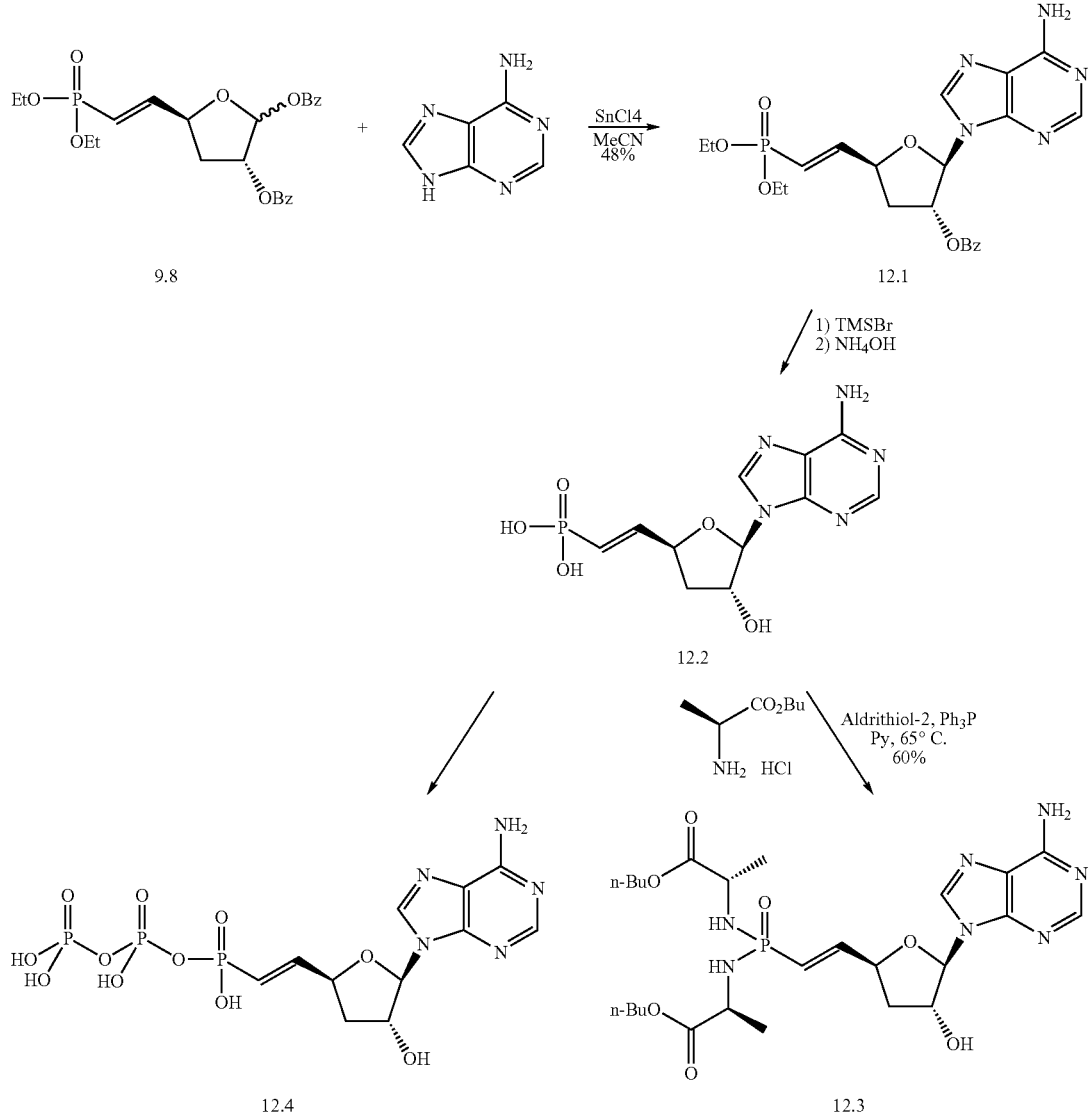

Benzoic acid 2-(6-amino-purin-9-yl)-5-[2-(diethoxy-phosphoryl)-vinyl]-tetrahydro-furan-3-yl ester (12.1)

Compound 9.8 (430 mg, 0.907 mmol) and adenine (135 mg, 1.0 mmol) was dissolved in 10 mL anhydrous CH$_3$CN. The mixture was treated with SnCl$_4$ (0.234 mL, 2.0 mmol) and stirred at r.t. for 20 h. The mixture was cooled to 0° C., treated with NaHCO$_3$ (2 g), water (2 mL), and stirred for 2 h. The mixture was diluted with CH$_3$CN, filtered, and concentrated under reduced pressure. The residue was subjected to a silica gel column chromatography eluting with EtOAc to 20% MeOH in EtOAc to yield compound 12.1 (210 mg, 48% yield).

(m, 2H), 6.16 (m, 1H), 8.03 (s, 1H), 8.09 (s, 1H). $^{31}$P NMR (D$_2$O) d 10.07. LRMS (ESI) MH$^+$ C$_{11}$H$_{14}$N$_5$O$_5$P requires 328.2. Found 328.0.

Bis-amidate prodrug 12.3

Compound 12.3 (11.5 mg, 61% yield) was synthesized from compound 12.2 (12 mg) using the procedure for the preparation of compound 9.11. $^1$H NMR (CD$_3$OD) δ 0.93 (m, 6H), 1.36 (m, 10H), 1.60 (m, 4H), 2.28 (m, 2H), 3.92 (m, 2H), 4.08 (m, 4H), 4.76 (s, 1H), 5.00 (m, 1H), 6.05 (m, 1H), 6.08 (m, 1H), 6.82 (m, 1H), 8.22 (s, 2H). $^{31}$P NMR (CD$_3$OD) d 19.63. LRMS (ESI) MH$^+$ C$_{25}$H$_{40}$N$_7$O$_7$P requires 582.6. Found 582.2.

Diphosphophosphonate 12.4

This compound (3 mg, 13.4% yield) was made from compound 12.2 (15 mg, 0.046 mmol) using the procedure described for the preparation of compound 6.8. $^1$H NMR (300 MHz, D$_2$O): δ 2.17-2.29 (m, 2H), 4.99 (s, 1H), 6.02-6.16 (m, 2H), 6.43-6.52 (m, 2H), 8.11 (s, 1H), 8.14 (s, 1H). 31PNMR: 4.37, 4.20, −5.41, −5.57, −21.32 ppm.

Example 7

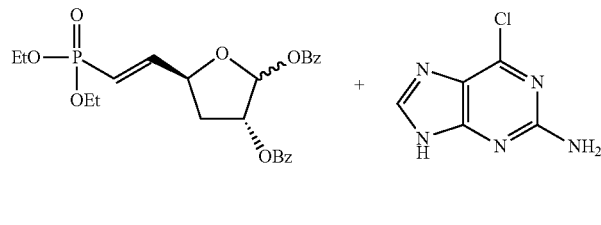

9.8

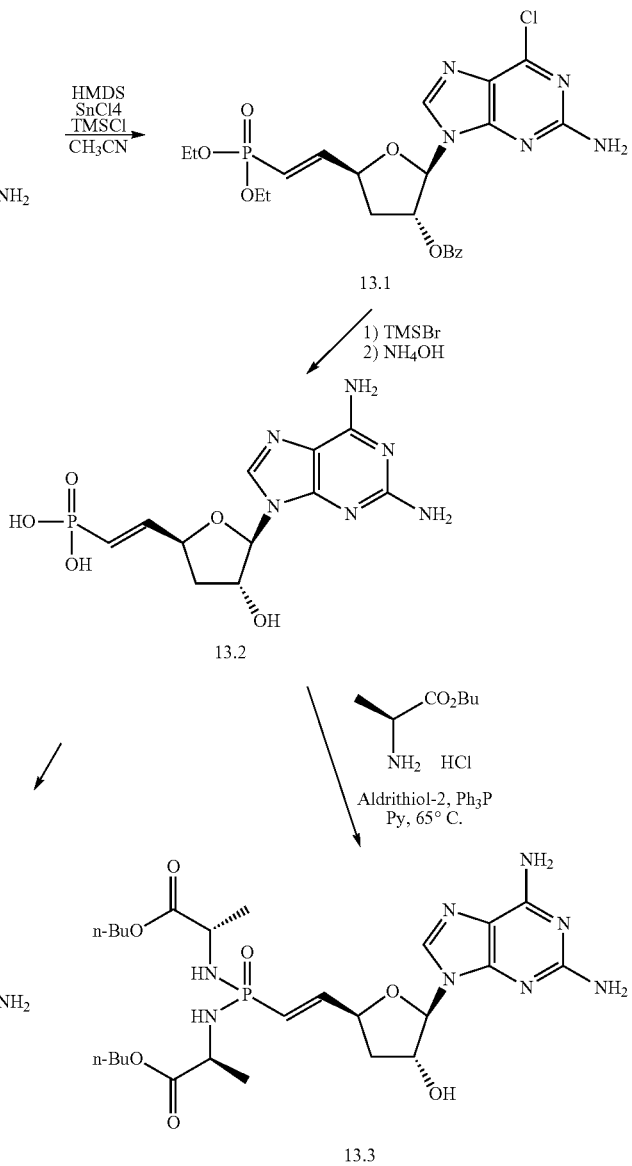

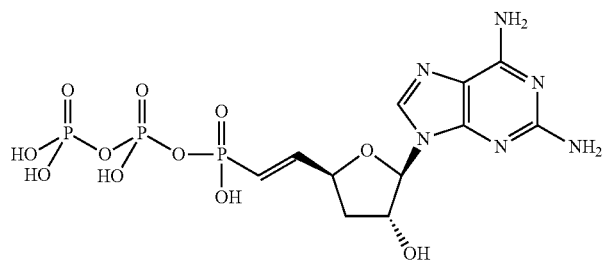

13.4

Benzoic acid 2-(2-amino-6-chloro-purin-9-yl)-5-[2-(diethoxy-phosphoryl)-vinyl]-tetrahydro-furan-3-yl ester (13.1)

Compound 9.8 (800 mg, 1.69 mmol) and 2-amino-6-chloropurine were dissolved in 15 mL anhydrous CH$_3$CN. The mixture was treated with HMDS (0.33 mL, 1.6 mmol), TMSCl (0.20 mL, 1.6 mmol), and then SnCl$_4$ (0.27 mL, 2.3 mmol). The mixture was stirred at 75° C. for 0.5 h and cooled to 0° C., treated with NaHCO$_3$ (2.4 g, 28.6 mmol), water (2 mL), and stirred at r.t for 1 h. The mixture was then filtered, concentrated under reduced pressure. The residue was subjected to a silica gel column chromatography eluting with EtOAc to yield compound 13.1 (295 mg, 33.5% yield). (Taken from: *J. Med. Chem* 1986, 29, 203-213.)

{2-[5-(2,6-Diamino-purin-9-yl)-4-hydroxy-tetrahydro-furan-2-yl]-vinyl}-phosphonic acid (13.2)

Compound 13.1 (147.5 mg, 0.283 mmol) was dissolved in 3 mL CH$_3$CN, treated with TMSBr (0.3 mL) and 2,6-lutidine (0.075 mL). The mixture was stirred at room temperature for 1.5 h, concentrated and coevaporated with CH$_3$CN under reduced pressure. The residue was dissolved in 30% NH$_3$ in water, and the mixture was stirred at 100° C. for 1.5 h. The mixture was then treated with NaHCO$_3$ (500 mg) and concentrated under reduced pressure. The residue was subjected to reverse phase HPLC eluting with 0-25% CH$_3$CN in water to yield compound 13.2 (81 mg, 74.3% yield). $^1$H NMR (D$_2$O) δ 2.05-2.25 (m, 2H), 4.58 (m, 1H), 5.8 (d, 1H, J=1.5), 5.95 (m, 1H), 6.15 (m, 1H), 7.8 (s, 1H). $^{31}$P NMR (D$_2$O) d 9.15. LRMS (ESI) MH$^+$ C$_{11}$H$_{15}$N$_6$O$_5$P requires 343.3. Found 343.1.

Bis-amidate prodrug 13.3

Compound 13.3 (9 mg, 46.8% yield) was synthesized from compound 13.2 (12.5 mg, 0.032 mmol) using the procedure for the preparation of compound 9.11. $^1$H NMR (CD$_3$OD) δ 0.92 (m, 6H), 1.35 (m, 10H), 1.60 (m, 4H), 2.28 (m, 2H), 3.95 (m, 2H), 4.10 (m, 4H), 4.72 (m, 1H), 4.95 (m, 1H), 5.88 (d, 1H, J=1.8), 6.84 (m, 1H), 7.85 (s, 1H). $^{31}$P NMR (CD$_3$OD) d 18.76. LRMS (ESI) MH$^+$ C$_{25}$H$_{41}$N$_8$O$_7$P requires 597.6 Found 597.2.

Diphosphophosphonate 13.4

Compound 13.3 (solium salt) (25 mg, 0.073 mmol) was dissovled in 2 mL water, treated with 1M HCl (0.2 mL). The solution was stirred for 10 min and then treated with 0.1 mL NH$_4$OH. It was then lyophilized to give 35 mg residue. The residue was dissovled in 2 mL DMSO, treated with TBA (60 mg), stirred for 30 min, then treated with CDI (60 mg), stirred for 1 h, the mixture was finally treated with TBAP (250 mg) in 2 mL DMF solution, and stirred for 2 h. The mixture was then concentrated under reduced pressure. The residue was dissolved in water, filtered through a C-18 column eluting with 2% NH$_3$.H$_2$O. The solvent was removed and the residue was purified by ion-exhange HPLC to give the desired compound (8.5 mg, 23% yield). $^1$H NMR (300 MHz, D$_2$O): δ 2.16-2.25 (m, 2H), 4.67 (s, 1H), 4.93 (s, 1H), 5.83 (s, 1H, J=1.8), 6.07 (t, 1H, J=18.3), 6.41-6.56 (m, 1H), 7.82 (s, 1H). 31PNMR: 4.30, 4.12, −5.87, −6.04, 31 21.79 ppm. LRMS [M−H]$^-$ C$_{11}$H$_{17}$N$_6$O$_{11}$P$_3$ requires 501.0. Found 501.0

Example 8

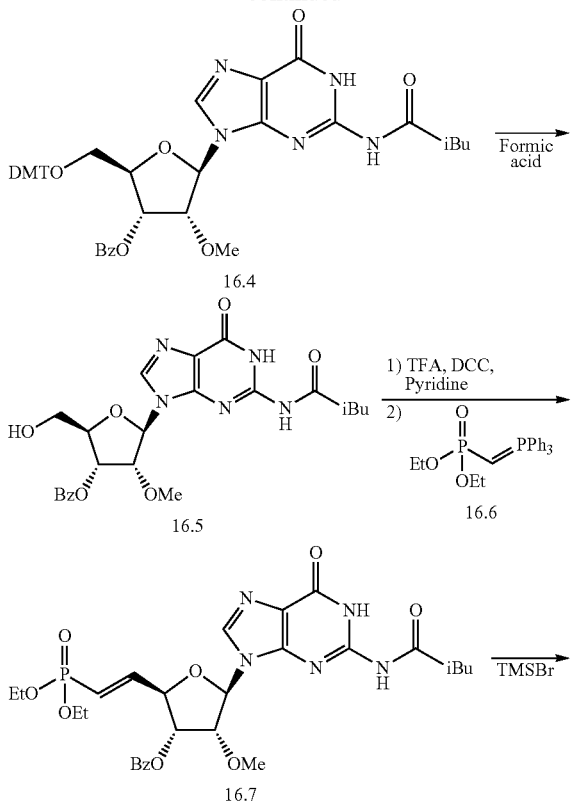
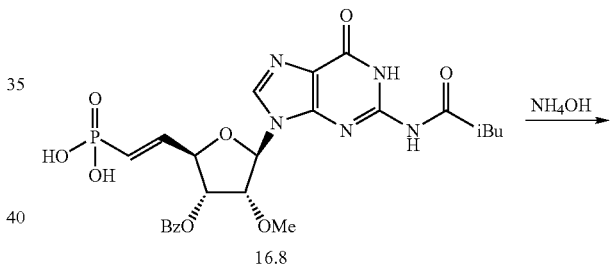
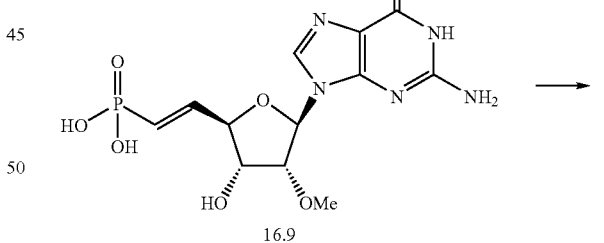
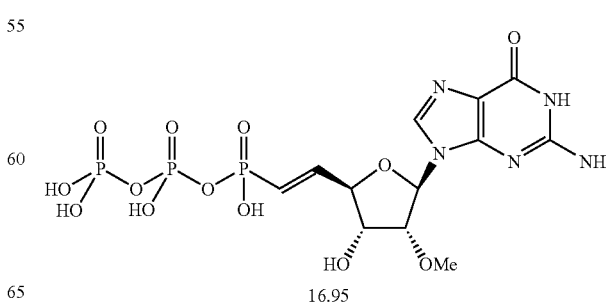
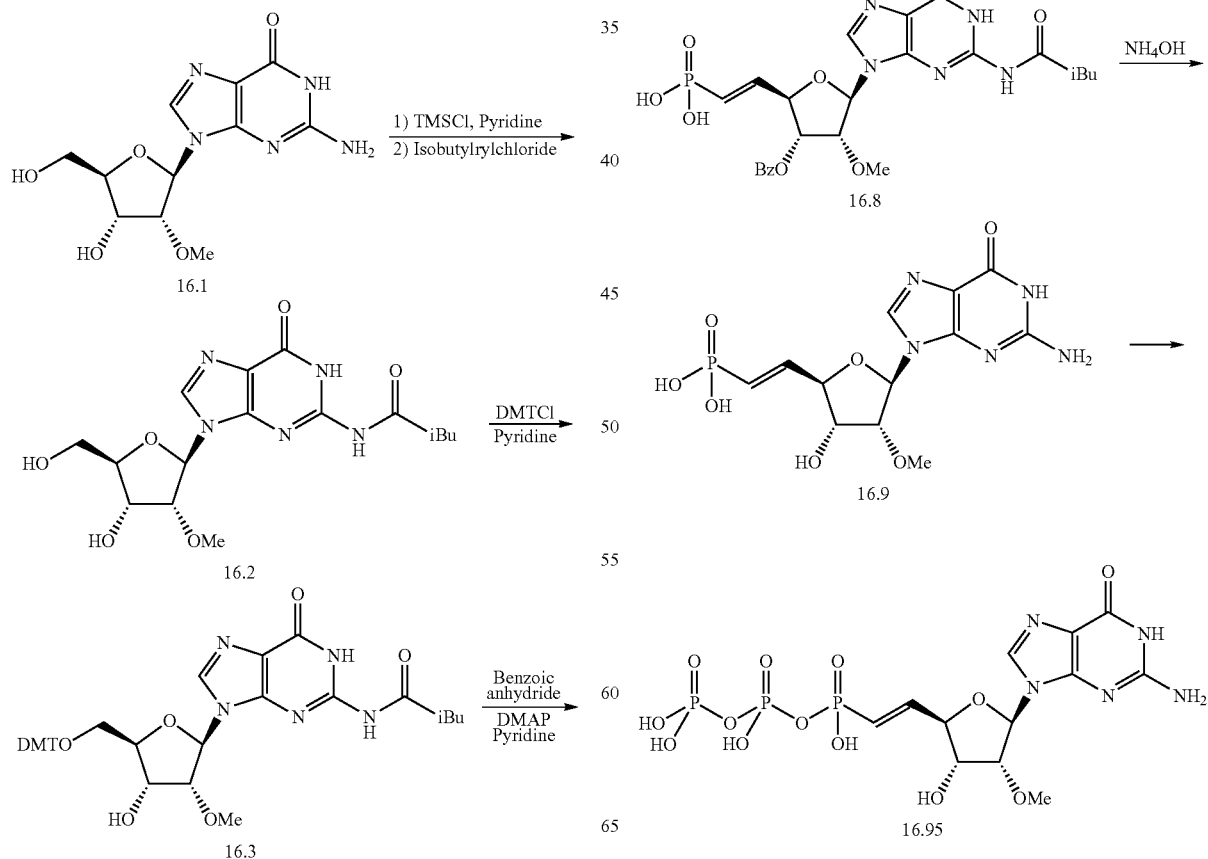

N-[9-(4-Hydroxy-5-hydroxymethyl-3-methoxy-tetrahydro-furan-2-yl)-6-oxo-6,9-dihydro-1H-purin-2-yl]-isobutyramide (16.2)

Compound 16.1 (5.0 g, 17.9 mmol) was dissolved in anhydrous pyridine 60 mL under nitrogen and cooled to 0° C. TMSCl (9.05 mL, 71.6 mmol) was added dropwise over a period of 10 min. The mixture was allowed to stir at r.t. for 1 h and cooled to 0° C., treated with isobutylryl chloride (2.06 mL, 19.7 mmol). The mixture was allowed to rise to r.t. and stirred for 3 h. MeOH (120 mL) was added to the mixture and stirred for 3 h to desilylate the product. The mixture was concentrated under reduced pressure and the residue was subjected to a quick plug of silica gel to give product 16.2 (6.18 g, 100% yield).

N-(9-{5-[Bis-(4-methoxy-phenyl)-phenyl-methoxymethyl]-4-hydroxy-3-methoxy-tetrahydro-furan-2-yl}-6-oxo-6,9-dihydro-1H-purin-2-yl)-isobutyramide (16.3)

Compound 16.2 (6.18 g, 17.19 mmol) was dissolved in 15 mL anhydrous pyridine, and treated with DMTCl (6.4 g, 18.91 mmol). The mixture was stirred for 12 h and poured on to 200 mL ice-water, filtered, and the solid was washed with 2×100 mL water. The solid was redissolved in 200 mL ethyl acetate. The organic layer was washed with 3×100 mL water, dried over MgSO$_4$, filtered, and concentrated down under reduced pressure. The residue was subjected to a silica gel column chromatography to yield product 16.3 (2.6 g, 23% yield).

Benzoic acid 2-[bis-(4-methoxy-phenyl)-phenylmethoxymethyl]-5-(2-isobutyrylamino-6-oxo-1,6-dihydro-purin-9-yl)-4-methoxy-tetrahydro-furan-3-yl ester (16.4)

Compound 16.3 (2.6 g, 3.9 mmol) was dissolved in 15 mL anhydrous pyridine, and treated with benzoic anhydride (17.62 g, 78 mmol), DMAP (95 mg, 0.78 mmol). The mixture was stirred for 4 h and poured on to 200 mL ice-water. The solid was collected by filtration and redissolved in 200 mL ethyl acetate. The organic layer was washed with 3×100 mL water, dried over MgSO$_4$, filtered and concentrated down under reduced pressure. The residue was subjected to a silica gel column chromatography to yield product 16.4 (1.5 g, 50% yield).

Benzoic acid 2-hydroxymethyl-5-(2-isobutyrylamino-6-oxo-1,6-dihydro-purin-9-yl)-4-methoxy-tetrahydro-furan-3-yl ester (16.5)

Compound 16.4 (1.5 g, 1.54 mmol) was dissolved in a mixture of 8 mL CH$_2$Cl$_2$ and 8 mL methanol, and treated with formic acid 16 mL. When the reaction was completed, 20 mL n-butanol was added to quench the reaction. The mixture was evaporated to dryness under reduced pressure and the byproducts were removed by washing the residue with hexane 3×200 mL. Compound 16.5 (840 mg, 92% yield) was obtained.

Benzoic acid 2-[2-(diethoxy-phosphoryl)-vinyl]-5-(2-isobutyrylamino-6-oxo-1,6-dihydro-purin-9-yl)-4-methoxy-tetrahydro-furan-3-yl ester (16.7)

Compound 16.5 (840 mg, 1.78 mmol) was dissolved in 6 mL anhydrous DMSO, treated with TFA (96 μL, 0.25 mmol), DCC (1.47 g, 7.12 mmol) and pyridine (0.20 mL, 2.49 mmol). The mixture was stirred for 16 h to form the aldehyde. Compound 16.6 (1.47 g, 3.56 mmol) dissolved in 6 mL anhydrous DMSO was added rapidly to the mixture and stirred for another 12 h. Oxalic acid anhydrate (0.3 g) dissolved in 2 mL MeOH was added to quench excess DCC. The mixture was stirred for 10 min and concentrated under reduced pressure. The residue was resuspended in EtOAc (100 mL) and filtered. The filtrated was washed with water (200 mL), Brine (200 mL), dried over MgSO$_4$, and concentrated under reduced pressure. The residue was subjected to a silica gel column chromatography to yield product 16.7 (460 mg, 43% yield).

Benzoic acid 5-(2-isobutyrylamino-6-oxo-1,6-dihydro-purin-9-yl)-4-methoxy-2-(2-phosphono-vinyl)-tetrahydro-furan-3-yl ester (16.8)

Compound 16.7 (460 mg, 0.763 mmol) was dissolved in 8 mL anhydrous DMF, treated with 2,6-lutidine (0.443 mL, 3.81 mmol) and TMSBr (1.5 mL, 11.4 mmol). The mixture was stirred at 80° C. for 4 h and quenched with MeOH. The mixture was concentrated under reduced pressure and the residue was subjected to reverse phase HPLC to yield product 16.8 (60 mg, 14.4% yield).

{2-[5-(2-Amino-6-oxo-1,6-dihydro-purin-9-yl)-3-hydroxy-4-methoxy-tetrahydro-furan-2-yl]-vinyl}-phosphonic acid (16.9)

Compound 16.9 (37.4 mg, 91% yield) was synthesized from compound 16.8 (60 mg, 0.11 mmol) using the procedure described for the preparation of compound 2.4. $^1$HNMR (D$_2$O, 300 MHz) δ 7.89 (bs, 1H), 6.45 (m, 1H), 6.07-5.85 (m, 2H), 4.55(bs, 1H), 4.41 (m, 2H), 3.32(s, 3H). $^{31}$PNMR (D$_2$O, 300 MHz) δ 11.23 ppm. LRMS (ESI) MH$^+$ C$_{12}$H$_{16}$N$_5$O$_7$P requires 374.1. Found 374.0.

Diphosphophosphonate 16.95

This compound (1 mg, 7% yield) was synthesized from compound 16.9 (10 mg, 0.027 mmol) using the procedure described for the preparation of diphosphophosphonate 6.8.

Example 9

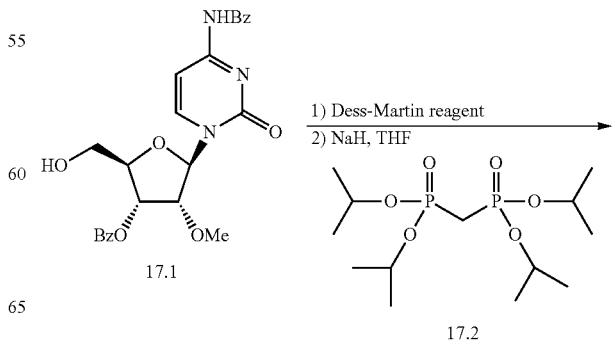

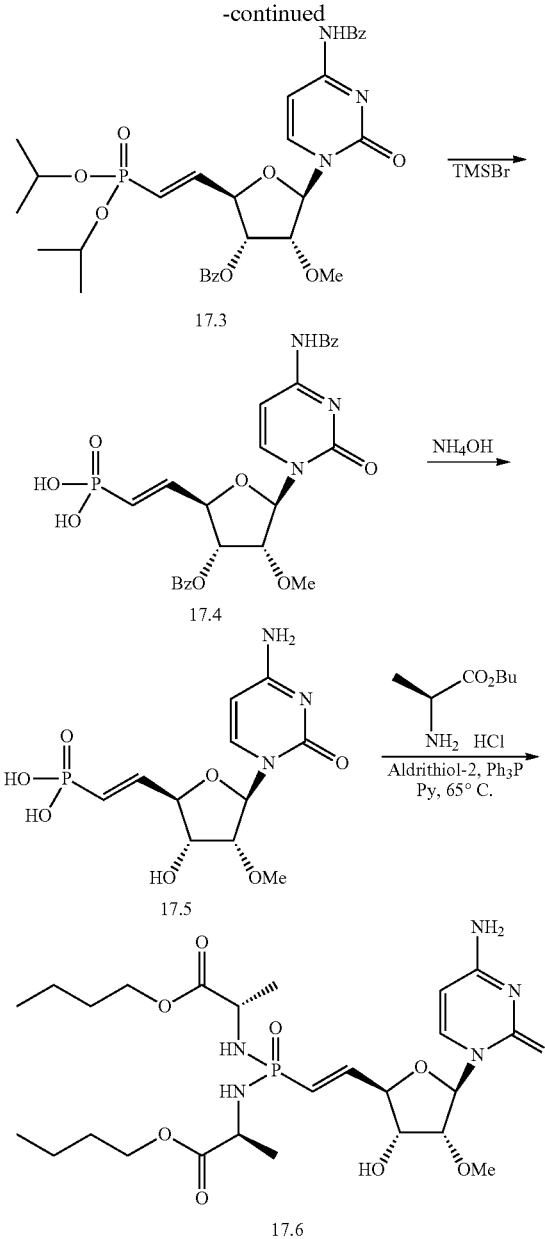

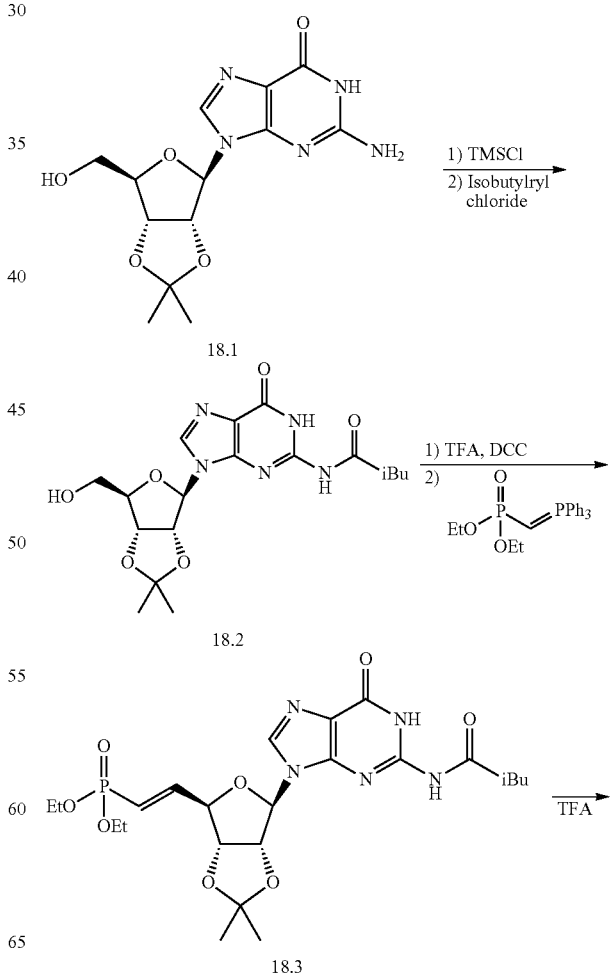

{2-[5-(4-Amino-2-oxo-2H-pyrimidin-1-yl)-3-hydroxy-4-methoxy-tetrahydro-furan-2-yl]-vinyl}-phosphonic acid (17.5)

Compound 17.5 (37 mg, 95% yield) was synthesized from compound 17.4 (62 mg, 0.11 mmol) by treating 17.4 with concentrated NH$_4$OH (10 ml) at 45° C. for 30 min. The reaction mixture was concentrated to dryness and purified by C-18 HPLC to afford compound 17.5. $^1$HNMR (D$_2$O, 300 MHz) δ 7.65 (d, 1H), 6.29-6.45 (m, 1H), 5.96-6.10 (m, 3H), 5.85 (d, 1H), 4.42 (t, 1H), 4.10 (t, 1H), 3.91 (m, 1H), 3.40 (s, 3H), $^{31}$PNMR (D$_2$O, 300 MHz): 0.90 ppm. LRMS [M–H]$^-$ C$_{11}$H$_{16}$N$_3$O$_7$P requires 332.1. Found 331.2.

Bis-amidate prodrug 17.6

Compound 17.6 (9 mg, 30% yield) was synthesized from compound 17.5 (17 mg, 0.05 mmol) using the procedure described for the preparation of compound 9.11. $^1$HNMR (CD$_3$CN, 300 MHz) δ 7.47 (d, 1H), 6.75 (m, 1H), 5.80-6.2 (m, 3H), 4.39 (m, 1H), 4.08 (m, 2H), 4.09 (m, 4H), 3.94 (m, 3H), 3.80 (m, 1H), 3.63 (m, 2H), 3.55 (s, 3H), 1.63 (m, 4H), 1.39 (m, 10H), 0.90 (m, 6H). $^{31}$PNMR (CD$_3$CN, 300 MHz): 15.019 ppm. LRMS (ESI) MH$^+$ C$_{25}$H$_{42}$N$_5$O$_9$P requires 588.3. Found 588.0.

Example 10

Benzoic acid 5-(4-benzoylamino-2-oxo-2H-pyrimidin-1-yl)-2-[2-(diisopropoxy-phosphoryl)-vinyl]-4-methoxy-tetrahydro-furan-3-yl ester (17.3)

Compound 17.3 (300 mg, 16% yield) was synthesized from compound 17.1 (1.41 g, 2.88 mmol) and compound 17.2 (3.96 g, 11.52 mmol) using the procedure described for the preparation of compound 7.3.

Benzoic acid 5-(4-benzoylamino-2-oxo-2H-pyrimidin-1-yl)-4-methoxy-2-(2-phosphono-vinyl)-tetrahydro-furan-3-yl ester (17.4)

Compound 17.4 (124 mg, 47.5% yield) was synthesized from compound 17.3 (300 mg, 0.462 mmol) using the procedure described for the preparation of compound 16.8.

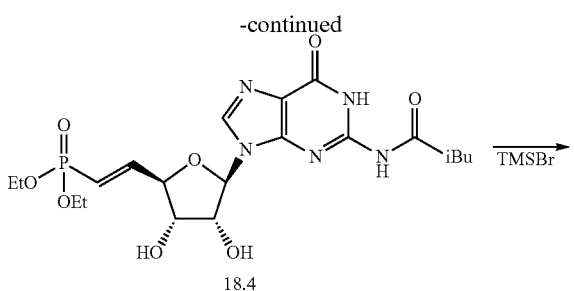

18.4

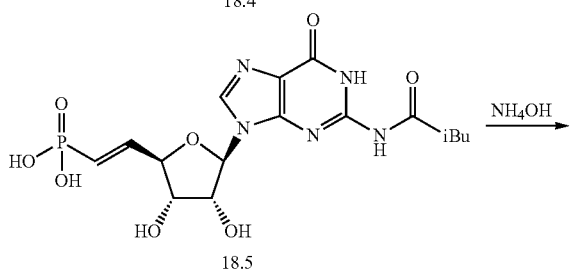

18.5

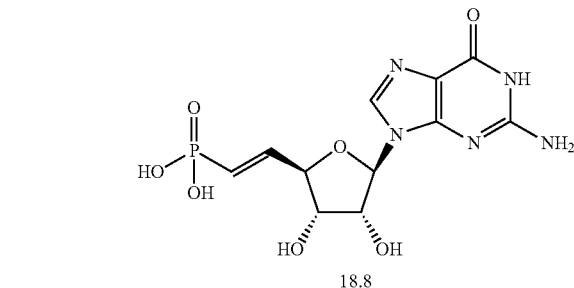

18.8

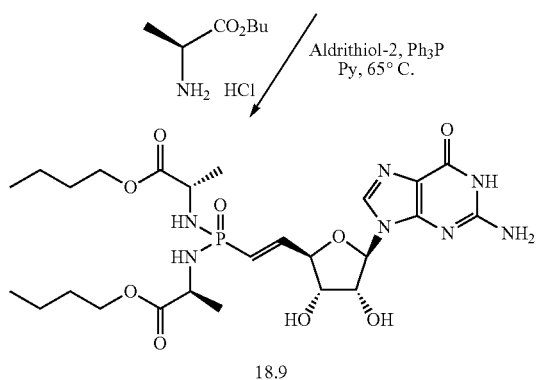

18.9

N-[9-(6-Hydroxymethyl-2,2-dimethyl-tetrahydro-furo[3,4-d][1,3]dioxol-4-yl)-6-oxo-6,9-dihydro-1H-purin-2-yl]isobutyramide (18.2)

Compound 18.2 (12.15 g, 100% yield) was synthesized from compound 18.1 (10.0 g, 30.93 mmol) using the procedure described for the preparation of compound 16.2.

{2-[6-(2-Isobutyrylamino-6-oxo-1,6-dihydro-purin-9-yl)-2,2-dimethyl-tetrahydro-furo[3,4-d][1,3]dioxol-4-yl]-vinyl}-phosphonic acid diethyl ester (18.3)

Compound 18.3 (1.7 g, 64% yield) was was synthesized from compound 18.2 (2.0 g, 5.09 mmol) using the procedure described for the preparation of compound 16.7.

{2-[3,4-Dihydroxy-5-(2-isobutyrylamino-6-oxo-1,6-dihydro-purin-9-yl)-tetrahydro-furan-2-yl]-vinyl}-phosphonic acid diethyl ester (18.4)

Compound 18.3 (850 mg, 1.62 mmol) was dissolved in 9 mL TFA and 1 mL water mixture, stirred for 1.5 h. The mixture was concentrated under reduced pressure, and the residue was subjected to a silica gel column chromatography eluting with 10% MeOH in CH$_2$Cl$_2$ to give compound 18.4 (680 mg, 86.4% yield).

{2-[3,4-Dihydroxy-5-(2-isobutyrylamino-6-oxo-1,6-dihydro-purin-9-yl)-tetrahydro-furan-2-yl]-vinyl}-phosphonic acid (18.5)

Compound 18.5 (400 mg, 67% yield) was synthesized from compound 18.4 (680 mg, 1.4 mmol) using the procedure described for the preparation of compound 16.8.

{2-[5-(2-Amino-6-oxo-1,6-dihydro-purin-9-yl)-3,4-dihydroxy-tetrahydro-furan-2-yl]-vinyl}-phosphonic acid (18.8)

Compound 18.8 (180 mg, 54% yield) was synthesized from compound 18.5 (400 mg, 0.932 mmol) by treating 18.5 with concentrated NH$_4$OH (10 ml) at 45° C. for 30 min. $^1$H NMR (D$_2$O, 300 MHz) 7.98 (s, 1H), 6.41 (m, 1H), 5.95 (m, 1H), 5.75 (d, J=5.4 Hz, 1H), 4.63 (m, 1H), 4.49 (m, 1H), 4.19 (t, J=4.5 Hz, 1H), $^{31}$P NMR (D$_2$O, 121.4 MHz) 9.7; MS (ESI) m/z 360 [M+H]$^+$ Bis-amidate prodrug 18.9

Compound 18.9 (2 mg, 3% yield) was synthesized from compound 18.8 (400 mg, 0.932 mmol) using the procedure described for the preparation of compound 9.11.

Example 11

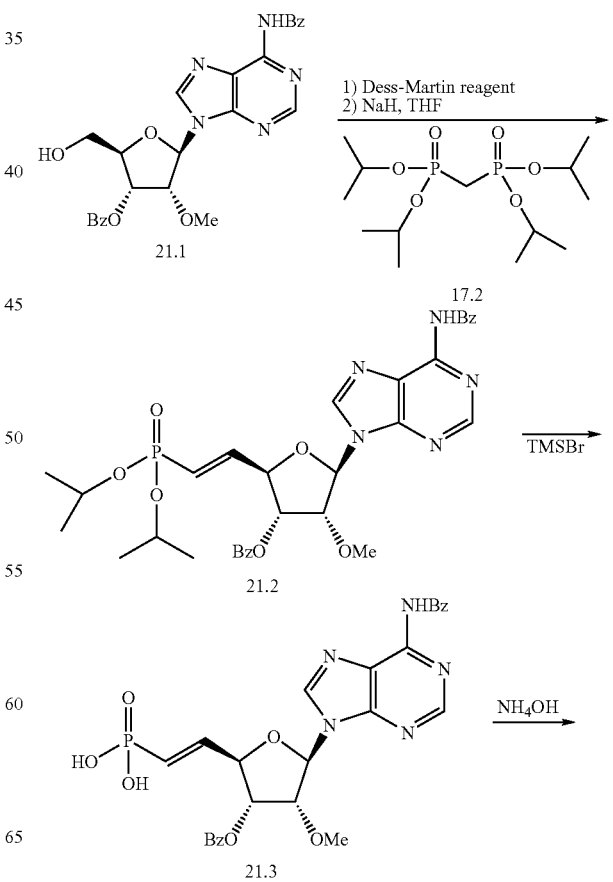

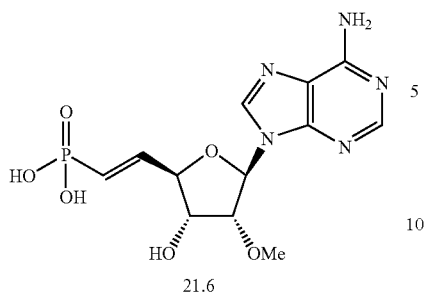

21.6

(2R,3R,4R,5R)-5-(6-benzamido-9H-purin-9-yl)-2-((E)-2-(diisopropoxyphosphoryl)vinyl)-4-methoxy-tetrahydrofuran-3-yl benzoate (21.2)

Compound 21.2 (300 mg, 16% yield) was synthesized from compound 21.1 (1.41 g, 2.88 mmol) using the procedure described for the synthesis of compound 7.3.

(E)-2-((2R,3R,4R,5R)-5-(6-benzamido-9H-purin-9-yl)-3-(benzoyloxy)-4-methoxy-tetrahydrofuran-2-yl)vinylphosphonic acid (21.3)

Compound 21.3 (124 mg, 47.5% yield) was synthesized from compound 21.2 (300 mg, 0.462 mmol) using the procedure described for the synthesis of compound 16.8.

2-((2R,3R,4R,5R)-5-(6-amino-9H-purin-9-yl)-3-hydroxy-4-methoxy-tetrahydrofuran-2-yl)ethylphosphonic acid (21.6)

Compound 21.6 (37 mg, 95% yield) was synthesized from compound 21.3 (62 mg, 0.11 mmol) by treating 21.3 with concentrated NH$_4$OH (10 ml) at 45° C. for 30 min. $^1$HNMR (D$_2$O, 300 MHz) δ 8.17 (s, 1H), 8.05 (s, 1H), 6.4 (m, 1H), 6.02-5.87 (m, 2H), 4.65(bs, 2H), 4.37 (m, 2H), 3.32(s, 3H). $^{31}$PNMR (D$_2$O, 300 MHz) δ 11.001 ppm. LRMS (ESI) MH$^+$ C$_{12}$H$_{16}$N$_5$O$_6$P requires 358.1. Found 358.0.

Example 12

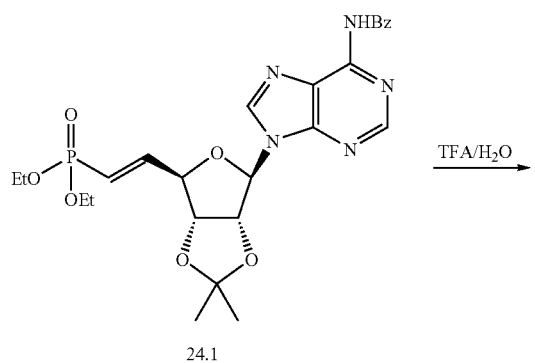

24.1

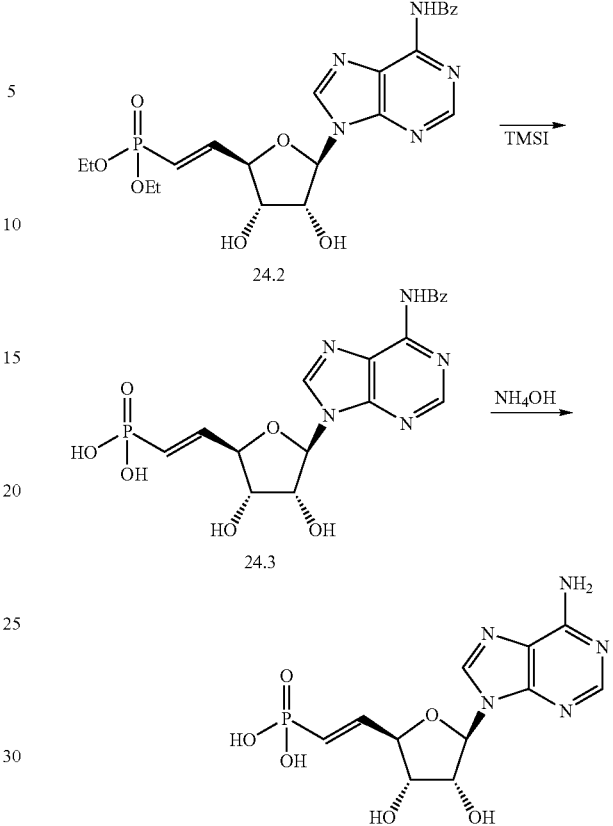

diethyl (E)-2-(3aR,4R,6R,6aR)-6-(6-benzamido-9H-purin-9-yl)-2,2-dimethyl-tetrahydrofuro[3,4-d][1,3]dioxol-4-yl)vinylphosphonate (24.2)

Compound 24.1 was synthesized in the same manner as compound 6.4. Compound 24.1 (271 mg, 0.499 mmol) was treated with TFA (1600 µL) and H$_2$O (200 µL) and stirred at room temperature for 30 min and the solvent was removed in vacuo. The residue was subjected to a silica gel column chromatography eluting with 0-20% MeOH—CH$_2$Cl$_2$ to afford compound 24.2 (243 mg, 97% yield) as a white solid: $^1$H NMR (CDCl$_3$, 300 MHz) 9.73 (br s, 1H), 8.71 (s, 2H), 7.91 (d, J=7.2 Hz, 2H), 7.50 (t, J=7.5 Hz, 1H), 7.35 (t, J=7.5 Hz, 2H), 6.89 (m, 1H), 6.15 (br s, 1H), 5.94 (m, 1H), 4.78 (m, 1H), 4.62 (m, 1H), 4.36 (m, 1H), 3.96 (m, 4H), 1.21 (m, 6H), $^{31}$P NMR (CDCl$_3$, 121.4 MHz) 15.8; MS (ESI) m/z 504 [M+H]$^+$.

(E)-2-((2R,3S,4R,5R)-5-(6-benzamido-9H-purin-9-yl)-3,4-dihydroxy-tetrahydrofuran-2-yl)vinylphosphonic acid (24.3)

Compound 24.2 (243 mg, 0.483 mmol) in CH$_3$CN (4.80 mL, 0.1 M) was treated with 2,6-lutidine (840 µL, 7.24 mmol) and TMSI (688 µL, 4.83 mmol). The mixture was stirred at room temperature for 1 h and the solvent was removed in vacuo. The residue was treated with concentrated NH$_4$OH (2 mL) and the solvent was removed in vacuo (×3). The residue was treated with 1% AcOH (2 mL) and treated to reverse phase HPLC to afford compound 24.3 (47.6 mg, 22% yield) as a white solid: $^1$H NMR (DMSO-d$_6$, 300 MHz) 8.71 (s, 1H), 8.61 (s, 1H), 7.99 (d, J=7.8 Hz, 2H), 7.57 (t, J=7.2 Hz, 1H), 7.48 (t, J=7.2 Hz, 2H), 6.37 (m, 1H), 6.00 (d, J=5.7 Hz, 1H), 5.85 (m, 1H), 4.69 (m, 1H), 4.37 (m, 1H), 4.15 (m, 1H), 3.52 (br m, 2H), $^{31}$P NMR (CDCl$_3$, 121.4 MHz) 8.2; MS (ESI) m/z 448 [M+H]$^+$.

(E)-2-((2R,3S,4R,5R)-5-(6-amino-9H-purin-9-yl)-3,4-dihydroxy-tetrahydrofuran-2-yl)vinylphosphonic acid (24.4)

Compound 24.3 (43 mg, 0.961 mmol) was treated with concentrated NH$_4$OH (4.85 mL, 0.02 M) and stirred at room temperature for 16 h. The solvent was removed in vacuo and the residue was treated with 1% AcOH (2 mL). Reverse phase HPLC afforded compound 24.4 (23 mg, 70% yield) as a white solid: $^1$H NMR (D$_2$O, 300 MHz) 8.21 (s, 1H), 8.11 (s, 1H), 6.41 (m, 1H), 5.97 (d, J=5.7 Hz, 1H), 5.84 (m, 1H), 4.66 (appt t, J=4.8 Hz, 1H), 4.53 (m, 1H), 4.22 (t, J=4.8 Hz, 1H); $^{31}$P NMR (D$_2$O, 121.4 MHz) 9.4; MS (ESI) m/z 344 [M+H]$^+$.

Example 13

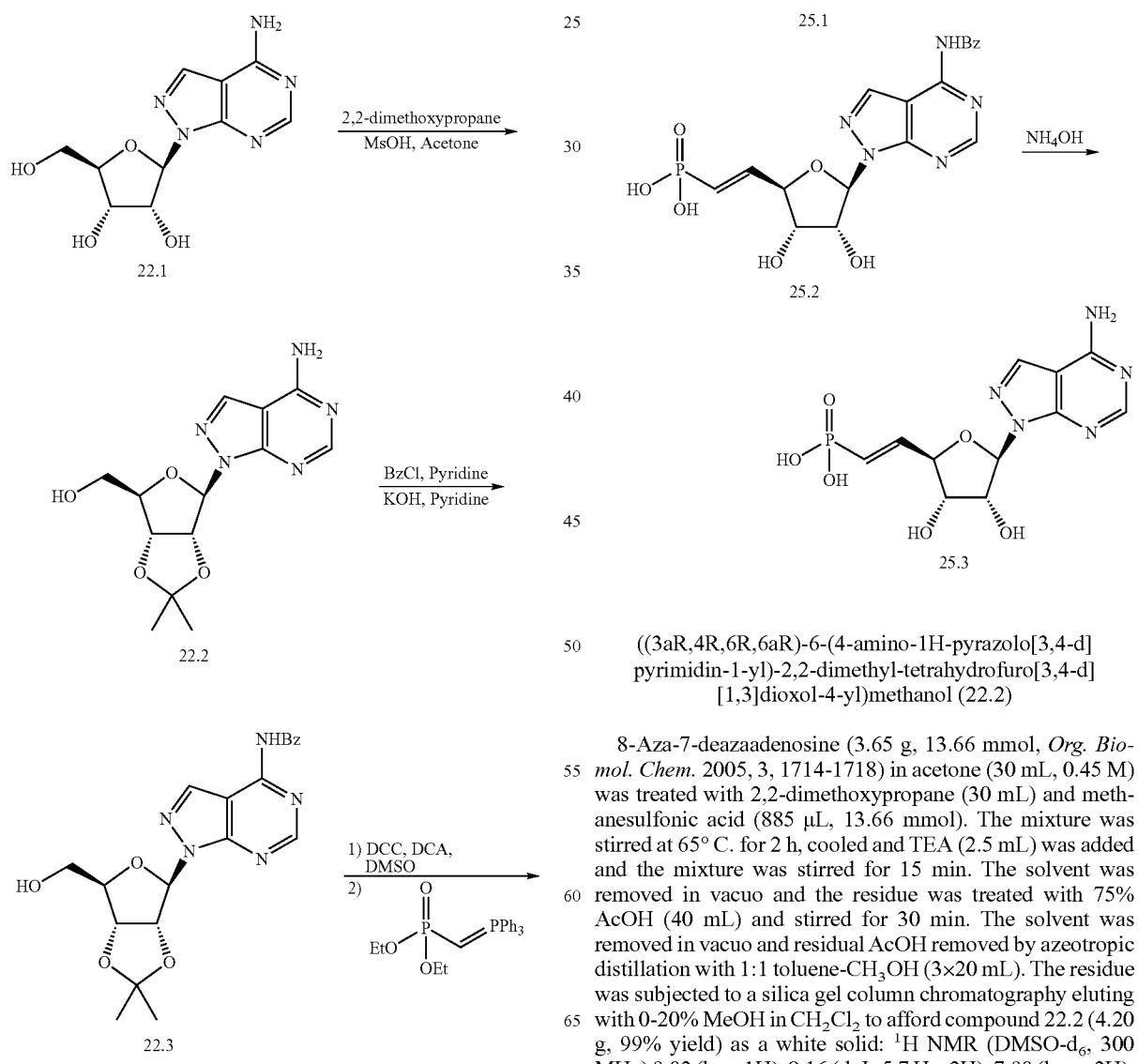

((3aR,4R,6R,6aR)-6-(4-amino-1H-pyrazolo[3,4-d]pyrimidin-1-yl)-2,2-dimethyl-tetrahydrofuro[3,4-d][1,3]dioxol-4-yl)methanol (22.2)

8-Aza-7-deazaadenosine (3.65 g, 13.66 mmol, *Org. Biomol. Chem.* 2005, 3, 1714-1718) in acetone (30 mL, 0.45 M) was treated with 2,2-dimethoxypropane (30 mL) and methanesulfonic acid (885 μL, 13.66 mmol). The mixture was stirred at 65° C. for 2 h, cooled and TEA (2.5 mL) was added and the mixture was stirred for 15 min. The solvent was removed in vacuo and the residue was treated with 75% AcOH (40 mL) and stirred for 30 min. The solvent was removed in vacuo and residual AcOH removed by azeotropic distillation with 1:1 toluene-CH$_3$OH (3×20 mL). The residue was subjected to a silica gel column chromatography eluting with 0-20% MeOH in CH$_2$Cl$_2$ to afford compound 22.2 (4.20 g, 99% yield) as a white solid: $^1$H NMR (DMSO-d$_6$, 300 MHz) 9.02 (br s, 1H), 8.16 (d, J=5.7 Hz, 2H), 7.90 (br m, 2H), 6.25 (s, 1H), 5.25 (app d, J=5.1 Hz, 1H), 4.88 (app d, J=4.5 Hz, 2H), 4.07 (m, 1H), 3.46 (m, 1H), 3.33 (m, 1H), 1.45 (s, 3H), 1.26 (s, 3H); MS (ESI) m/z 308 [M+H]$^+$.

N-(1-((3aR,4R,6R,6aR)-6-(hydroxymethyl)-2,2-dimethyl-tetrahydrofuro[3,4-d][1,3]dioxol-4-yl)-1H-pyrazolo[3,4-d]pyrimidin-4-yl)benzamide (22.3)

Compound 22.2 (4.20 g, 13.66 mmol) in pyridine (40 mL, 0.33 M) was cooled to 0° C. and treated with benzoyl chloride (12.68 mL, 109.3 mmol) The mixture was warmed to room temperature and stirred for 16 h. The solvent was removed in vacuo and the residue was treated with 2.5 N KOH (40 mL) in pyridine (40 mL) and stirred for 20 min. The mixture was cooled to 0° C. and AcOH was added (6 mL). The solvent was removed in vacuo and the residue was dissolved in EtOAc (150 mL) and washed with H$_2$O (100 mL), saturated NaHCO$_3$ (2×100 mL), and brine (100 mL). The organic layer was dried over Na$_2$SO$_4$, filtered, and concentrated under reduced pressure to afford compound 22.3 (2.74 g, 49% yield) as a white solid: $^1$H NMR (CDCl$_3$, 300 MHz) 9.02 (br s, 1H), 8.80 (s, 1H), 8.55 (s, 1H), 7.97 (d, J=7.5 Hz, 2H), 7.62 (app t, J=7.5 Hz, 1H), 7.52 (t, J=7.5 Hz, 2H), 6.65 (s, 1H), 5.25 (m, 1H), 5.07 (d, J=6.0 Hz, 1H), 4.99 (br s, 1H), 4.53 (m, 1H), 3.91 (m, 1H), 3.77 (m, 1H), 1.61 (s, 3H), 1.35 (s, 3H); MS (ESI) m/z 412 [M+H]$^+$.

diethyl (E)-2-((3aR,4R,6R,6aR)-6-(4-benzamido-1H-pyrazolo[3,4-d]pyrimidin-1-yl)-2,2-dimethyl-tetrahydrofuro[3,4-d][1,3]dioxol-4-yl)vinylphosphonate (22.4)

Compound 22.3 (2.03 g, 4.93 mmol) in anhydrous dimethyl sulfoxide (25 mL, 0.2 M) was treated with dichloroacetic acid (400 μL, 4.93 mmol) and DCC (2.04 g, 9.67 mmol). The solution was stirred at room temperature for 2 h. [(Diethoxyphosphinyl)methylidene]triphenylphosphorane (2.0 g, 4.93 mmol, *J. Org. Chem.* 1996, 61, 7697-7701) was added and the mixture was stirred overnight. MeOH (25 mL) and H$_2$O (25 mL) were added and the mixture was filtered over a plug of SiO$_2$ and washed with MeOH (3×25 mL). The solvent was removed in vacuo and residue was suspended in CH$_2$Cl$_2$ and filtered over a plug of SiO$_2$, and the solvent removed in vacuo. The residue was subjected to a column chromatography eluting with 0-100% EtOAc-hexanes, followed by 0-20% MeOH—CH$_2$Cl$_2$ to afford compound 22.4 (734 mg, 27% yield, E/Z ratio not determined) as a white solid (data for major isomer): $^1$H NMR (CDCl$_3$, 300 MHz) 9.73 (br s, 1H), 8.71 (s, 2H), 7.91 (d, J=7.8 Hz, 2H), 7.50 (m, 1H), 7.35 (t, J=7.5 Hz, 2H), 6.89 (m, 1H), 6.15 (br s, 1H), 5.95 (m, 1H), 4.78 (m, 1H), 4.62 (m, 1H), 4.36 (m, 1H), 4.01 (m, 4H), 1.23 (m, 12H); $^{31}$P NMR (DMSO-d$_6$, 121.4 MHz) 15.9; MS (ESI) m/z 544 [M+H]$^+$].

diethyl (E)-2-((2R,3S,4R,5R)-5-(4-benzamido-1H-pyrazolo[3,4-d]pyrimidin-1-yl)-3,4-dihydroxy-tetrahydrofuran-2-yl)vinylphosphonate (25.1)

Compound 22.4 (163 mg, 0.299 mmol) was treated with TFA (1000 μL) and H$_2$O (100 μL) and stirred at room temperature for 2 h. The solvent was removed in vacuo and the residue was subjected to a silica gel column chromatography eluting with 0-20% MeOH—CH$_2$Cl$_2$ to afford compound 25.1 (65 mg, 43% yield) as a white solid: $^1$H NMR (CDCl$_3$, 300 MHz) 9.51 (br s, 1H), 8.65 (s, 1H), 8.47 (s, 1H), 7.90 (d, J=7.5 Hz, 2H), 7.51 (t, J=7.5 Hz, 1H), 7.43 (t, J=7.5 Hz, 2H), 6.88 (m, 1H), 6.61 (s, 1H), 5.98 (m, 1H), 4.85 (m, 1H), 4.67 (m, 1H), 4.60 (m, 1H), 3.89 (m, 4H), 1.20 (t, 6H); $^{31}$P NMR (CDCl$_3$, 121.4 MHz) 16.6; MS (ESI) m/z 504 [M+H]$^+$.

(E)-2-((2R,3S,4R,5R)-5-(4-benzamido-1H-pyrazolo[3,4-d]pyrimidin-1-yl)-3,4-dihydroxy-tetrahydrofuran-2-yl)vinylphosphonic acid (25.2)

Compound 25.1 (62.2 mg, 0.124 mmol) in CH$_3$CN (1.25 mL, 0.1 M) was treated with 2,6-lutidine (215 μL, 1.85 mmol) and TMSI (176 μL, 1.24 mmol). The mixture was stirred at room temperature for 1 h and the solvent was removed in vacuo. The residue was treated with concentrated NH$_4$OH (2 mL) and the solvent was removed in vacuo (×3). The residue was treated with 1% AcOH (2 mL) and treated to reverse phase HPLC to afford compound 25.2 (19.3 mg, 35% yield) as a white solid: MS (ESI) m/z 448 [M+H]$^+$.

(E)-2-((2R,3S,4R,5R)-5-(4-amino-1H-pyrazolo[3,4-d]pyrimidin-1-yl)-3,4-dihydroxy-tetrahydrofuran-2-yl)vinylphosphonic acid (25.3)

Compound 25.2 (19.3 mg, 0.431 mmol) was treated with concentrated NH$_4$OH (2.2 mL, 0.02 M) and stirred at room temperature for 16 h. The solvent was removed in vacuo and the residue was treated with 1% AcOH (2 mL). Reverse phase HPLC afforded compound 25.3 (7.0 mg, 47% yield) as a white solid: $^1$H NMR (D$_2$O, 300 MHz) 8.10 (s, 2H), 6.26 (m, 1H), 6.19 (m, 1H), 5.85 (m, 1H), 4.77 (m, 1H), 4.51 (m, 1H), 4.31 (m, 1H); $^{31}$P NMR (D$_2$O, 121.4 MHz) 9.6; MS (ESI) m/z 344 [M+H]$^+$.

Example 14

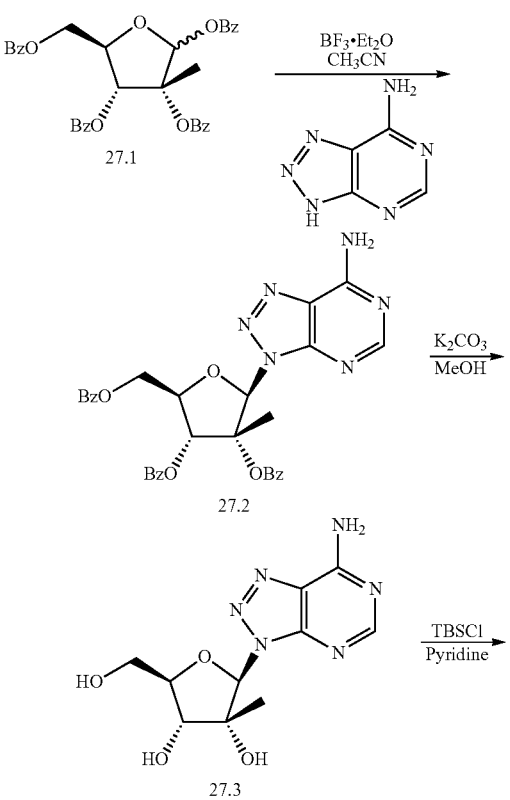

-continued

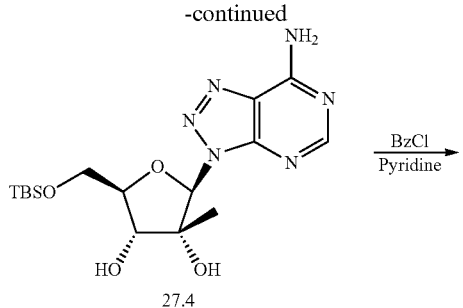

27.4

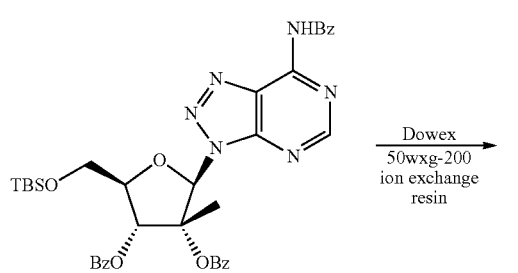

27.5

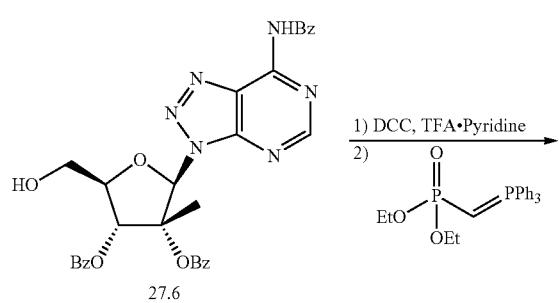

27.6

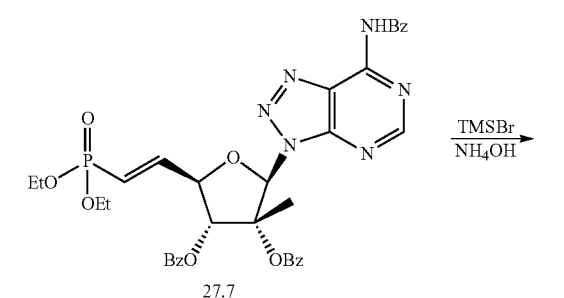

27.8

-continued

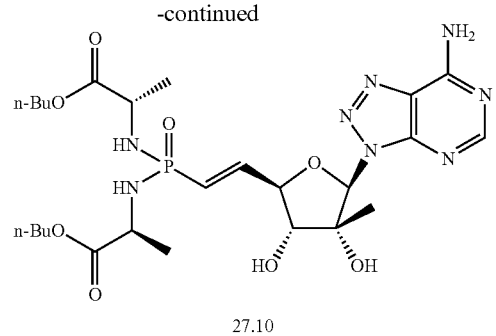

27.10

Compound 27.2

Compound 27.1 (4.19 g, 7.22 mmol) and 8-azaadenine (983 mg, 7.22 mmol) were dissolved in 70 mL anhydrous CH$_3$CN and cooled to 0° C. The mixture was treated with BF$_3$.OEt$_2$ (2.3 mL, 18.05 mmol), stirred at r.t. for 5.5 h. The mixture was then cooled to 0° C., treated with saturated NaHCO$_3$, and extracted with EtOAc. The organic layer was dried over Na$_2$SO$_4$, filtered and concentrated down under reduced pressure. The residue was subjected to a silica gel column chromatography eluting with 50% EtOAc in hexane to 100% EtOAc to give compound 27.2 (1.6 g, 37% yield).

(2R,3R,4R,5R)-2-(7-amino-3H-[1,2,3]triazolo[4,5-d] pyrimidin-3-yl)-5-(hydroxymethyl)-3-methyl-tetrahydrofuran-3,4-diol (27.3)

Compound 27.2 (1.6 g, 2.75 mmol) was dissolved in 25 mL anhydrous MeOH, and treated with K$_2$CO$_3$ (190 mg, 1.38 mmol). The mixture was stirred for 2 h and concentrated sown under reduced pressure. The resulting solid was washed three times with Hexane, dissolved in H$_2$O and neutralized with HCl to PH=8. The water solution was concentrated down under reduced pressure and the residue was dried under high vacuo to give compound 27.3 (654 mg, 84% yield) without further purification.

(2R,3R,4R,5R)-2-(7-amino-3H-[1,2,3]triazolo[4,5-d] pyrimidin-3-yl)-5-((tert-butyldimethylsilyloxy)methyl)-3-methyl-tetrahydrofuran-3,4-diol (27.4)

Mixed compound 27.3 (969 mg, 3.4 mmol) with pyridine and concentrated under reduced pressure. The resulting solid was suspended in pyridine 5 mL, treated with TBSCl (615 mg, 4.1 mmol) and the mixture was stirred at r.t. for overnight. The mixture was concentrated down under reduced pressure and water was added to give solid. The suspension was stirred for 30 min, filtered and the solid was dried under reduced pressure to give compound 27.4 (1.33 g, 98% yield).

Compound 27.5

Compound 27.4 (1.33 g, 3.35 mmol) was dissolved in pyridine 10 mL and treated with BzCl (1.16 mL, 10.0 mmol). The mixture was stirred at r.t. for overnight, concentrated down under reduced pressure, and dissolved in EtOAc, washed with saturated NaHCO$_3$, Brine, dried over Na$_2$SO$_4$, filtered and concentrated down under reduced pressure. The residue was subjected to a column chromatography eluting with 0-40% EtOAc in Hexane to give compound 27.5 (1.67 g, 70% yield).

Compound 27.6

Compound 27.5 (1 g, 1.66 mmol) was dissolved in MeOH 15 mL, treated with Dowex H$^+$ resin and stirred overnight. The mixture was filtered and concentrated under reduced pressure. The residue was subjected to a silica gel column chromatography eluting with 0-60% EtOAc in Hexane to give compound 27.6 (583 mg, 61% yield).

Compound 27.7

Compound 27.6 (349 mg, 0.588 mmol) was dissolved in 3 mL anhydrous DMSO, and treated with DCC (606 mg, 0.588 mmol). The mixture was stirred for 20 min, treated with TFA.Pyridine (114 mg, 0.588 mmol) and stirred for another 2 h. The mixture was diluted with EtOAc, washed with Brine, dried over $MgSO_4$, filtered and concentrated down under reduced pressure. The residue was dissolved in 5 mL anhydrous $CH_3CN$, treated with Wittig reagent (342 mg, 0.829 mmol) dissolved in 2 mL $CH_3CN$, and stirred for overnight. The mixture was concentrated down under reduced pressure and the residue was subjected to a reverse phase HPLC to give compound 27.7 (104 mg, 24% yield).

(E)-2-((2R,3R,4R,5R)-5-(7-amino-3H-[1,2,3]triazolo[4,5-d]pyrimidin-3-yl)-3,4-dihydroxy-4-methyl-tetrahydrofuran-2-yl)vinylphosphonic acid (27.8)

Compound 27.8 (37 mg, 72% yield) was synthesized from compound 27.7 (104 mg, 0.143 mmol) using the procedure described for the preparation of compound 10.2. $^1$HNMR (300 MHz, $D_2O$) δ 0.81 (s, 3H), 1.92 (s, 2H), 4.33 (d, J=8.4, 1H), 5.39 (t, 1H), J=9.0), 6.02 (t, 1H, J=39), 6.15-6.33 (m, 2H). 8.18 (s, 1H). $^{31}$PNMR: 9.22 ppm. LRMS [M–H]$^-$ $C_{11}H_{15}N_6O_6P$ requires 357.3. Found 357.0.

Bis-amidate prodrug 27.10

Compound 27.8 (10.0 mg, 0.027 mmol) was mixed together with HCl. AlaOBu (29 mg, 0.162 mmol), treated with 1 mL anhydrous pyridine and TEA (45 µL, 0.324 mmol). $Ph_3P$ (49 mg, 0.189 mmol) and 2,2'-dipyridyldisulfate (42 mg, 0.189 mmol) were dissolved in 0.5 mL pyridine in a separate flask, stirred for 15 min, and added to the previous mixture. The combined mixture was stirred at 60° C. for 7 h and concentrated under reduced pressure. The residue was subjected to a reverse phase HPLC to give compound 27.10 (4.3 mg, 26% yield). $^1$HNMR (300 MHz, $CDCl_3$) δ 0.91-1.34 (m, 9H), 1.36-1.47 (m, 10H), 1.58-1.71 (m, 4H), 3.38 (t, 2H, J=9.6), 3.95-4.19 (m, 6), 4.62 (d, 1H, J=6.6), 5.52 (t, 1H, J=7.5), 5.79-5.89 (m, 1H), 6.55 (s, 1H), 6.72-6.91 (m, 1H), 7.17 (s, 1H), 8.48 (s, 1H). $^{31}$PNMR: 17.03 ppm. LRMS (ESI) MH$^+$ $C_{25}H_{41}N_8O_8P$ requires 613.6. Found 613.1.

Example 15

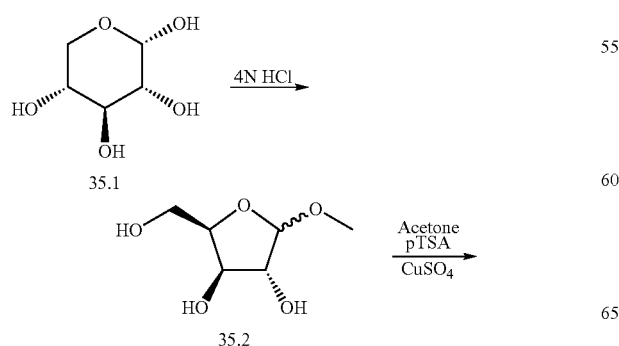

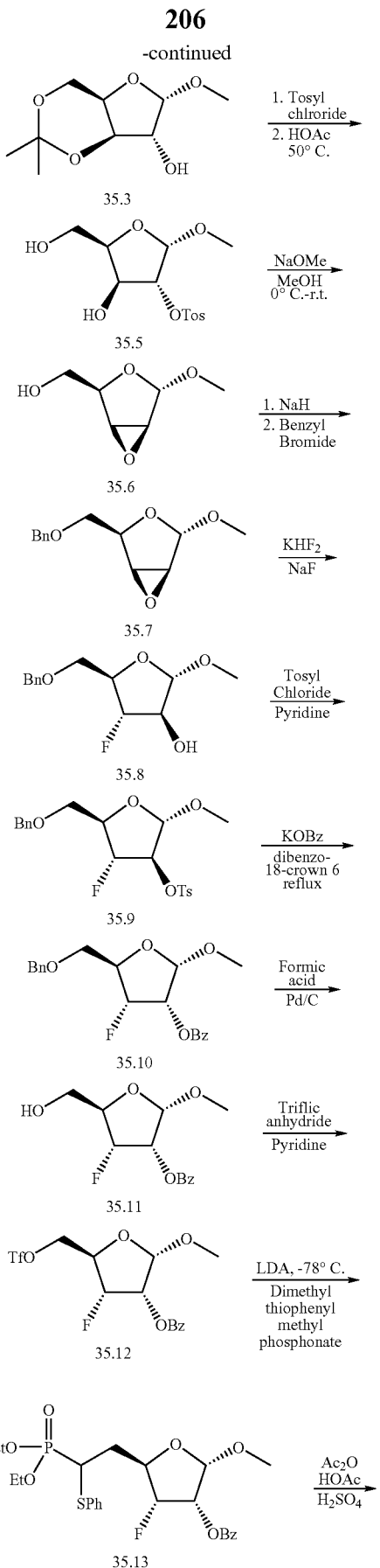

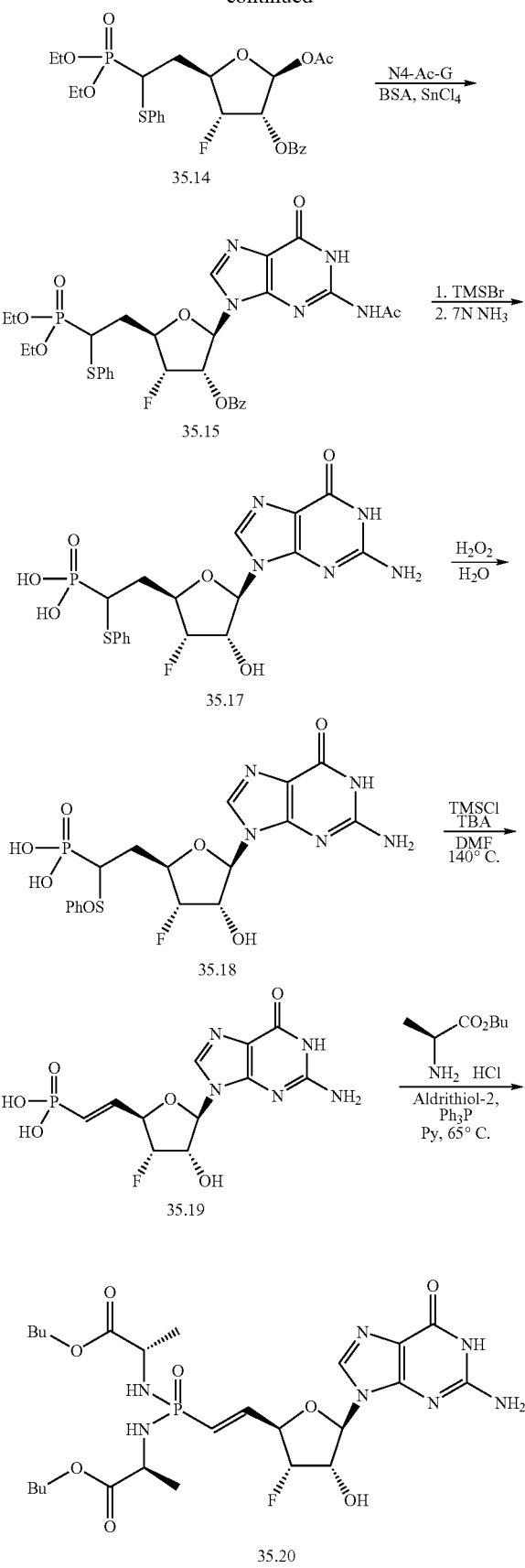

(2R,3R,4R)-2-(hydroxymethyl)-5-methoxy-tetrahydrofuran-3,4-diol (35.2)

Compound 35.1 (110 g, 734 mmol) was dissolved in 700 mL MeOH, and treated with 4N HCl in Dioxane (20 mL, 80 mmol). The mixture was stirred for 5 h and then neutralized with Dowex-1x-8 (OH⁻) anion exchange resin (600 mL). The mixture was then filtered and concentrated under reduced pressure. The residue (120.45 g, 100% yield) was used as it is for the next step reaction.

(4aR,7R,7aR)-6-methoxy-2,2-dimethyl-tetrahydro-4H-furo[3,2-d][1,3]dioxin-7-ol (35.3)

Compound 35.2 (120.45 g, 734 mmol) was dissolved in 1.5 L acetone, treated with p-toluene sulfonic acid monohydrate (0.6 g, 3.15 mmol) and $CuSO_4$ (225 g, 1.41 mol). The mixture was stirred for 60 h. The solid was removed by filtration and washed with (3×200 mL) acetone. The filtrate and the washings were combined and neutralized with 2.5 mL concentrated ammonium hydroxide. The solvent was removed by reduced pressure and the residue was dissolved in 750 mL $CH_2Cl_2$ and washed with 3'100 mL water. The water extracts were combined and extracted with 3×100 mL $CH_2Cl_2$. The $CH_2Cl_2$ extracts were combined, dried over $MgSO_4$, filtered and concentrated under reduced pressure. The residue was subjected to a silica gel column chromatography eluting with 0-3% MeOH in $CH_2Cl_2$ to give compound 35.3 (32.36 g, 21.6% yield).

(4aR,6S,7R,7aS)-6-methoxy-2,2-dimethyl-tetrahydro-4H-furo[3,2-d][1,3]dioxin-7-yl 4-methylbenzenesulfonate (35.4)

Compound 35.3 (35.42 g, 174 mmol) was dissolved in anhydrous pyridine, cooled to 0° C. and then treated with tosyl chloride (52.96 g, 278 mmol). The mixture was stirred at r.t. for 16 h and the solvent was removed under reduced pressure. The residue was dissolved in $CH_2Cl_2$, and washed with 3×100 mL water. The organic layer was collected, dried over $MgSO_4$, filtered and concentrated under reduced pressure. The residue was subjected to a reverse phase column chromatography eluting with 50% EtOAc in hexane to give compound 35.4 (57.88 g, 93% yield).

(2S,3R,4S,5R)-4-hydroxy-5-(hydroxymethyl)-2-methoxy-tetrahydrofuran-3-yl 4-methylbenzenesulfonate (35.5)

Compound 35.4 (32.18 g, 89.9 mmol) was dissolved in 400 mL of a 3:1 mixture of acetic acid and water. The mixture was heated to 50° C. for 2 h and the solvent was removed under reduced pressure. The residue was subjected to a column chromatography eluting with EtOAc to give compound 35.5.

((1R,2R,4S,5S)-4-methoxy-3,6-dioxa-bicyclo[3.1.0]hexan-2-yl)methanol (35.6)

Compound 35.5 (46.83 g, 147.26 mmol) was dissolved in anhydrous methanol 300 mL, cooled to 0° C. and treated with 25% NaOMe in MeOH. The mixture was allowed to rise to r.t. and stirred for 8 h. The mixture was then neutralized with acetic acid and the solvent was concentrated under reduced pressure. The residue was dissolved in EtOAc, filtered and the organic layer was washed with 200 mL water. The organic layer was collected and the aqueous layer was extracted with 4×100 mL ethyl acetate. The organic extracts were combined, dried over MgSO$_4$, filtered and concentrated under reduced pressure. The residue was subjected to a column chromatography to give compound 35.6 (18.18 g, 85% yield).

(1R,2R,4S,5S)-2-(benzyloxymethyl)-4-methoxy-3,6-dioxa-bicyclo[3.1.0]hexane (35.7)

Compound 35.6 (20 g, 137 mmol) was dissolved in 15 mL dioxane, cooled to 0° C. and treated with 60% NaH (6.0 g, 151 mmol). The mixture was stirred at 0° C. for 30 min and then treated with BnBr (18 mL, 151 mmol). The mixture was warmed to r.t., stirred for 3 h, and then quenched with 50 mL MeOH. The mixture was stirred for another 30 min and the solvent was evaporated under reduced pressure. The residue was subjected to a silica gel column chromatography eluting with 10-50% EtOAc in Hexane to give compound 35.7 (26.55 g, 82% yield).

(2S,3R,4S,5R)-5-(benzyloxymethyl)-4-fluoro-2-methoxy-tetrahydrofuran-3-ol (35.8)

Compound 35.7 (2.2 g, 9.32 mmol) was dissolved in 10 mL ethyleneglycol, and then treated with NaF (2.2 g), KHF$_2$ (2.2 g). The mixture was stirred at 200° C. for 4 h, cooled to r.t. and then treated with water (150 mL). The aqueous mixture was extracted twice with 200 mL EtOAc. The organic extracts were combined, dried over MgSO$_4$, filtered and concentrated down under reduced pressure. The residue was subjected to a silica gel column chromatography eluting with 20-100% EtOAc in hexane to give compound 35.8 (786 mg, 33% yield).

(2S,3R,4R,5R)-5-(benzyloxymethyl)-4-fluoro-2-methoxy-tetrahydrofuran-3-yl-4-methylbenzenesulfonate (35.9)

Compound 35.8 (13 g, 50.8 mmol) was dissolved in anhydrous pyridine (100 mL), and treated with tosyl chloride (22.5 g, 118 mmol). The mixture was stirred at rt for 1 h and then concentrated under reduced pressure. The residue was redissolved in DCM and washed with saturated NaHCO$_3$ twice; the organic layer was collected, dried over MgSO$_4$, filtered and concentrated under reduced pressure. The residue was subjected to a silica gel column chromatography eluting with 0-50% EtOAc in hexane to give compound 35.9 (20.49 g, 99% yield).

(2S,3S,4R,5R)-5-(benzyloxymethyl)-4-fluoro-2-methoxy-tetrahydrofuran-3-yl benzoate (35.10)

Compound 35.10 (1.0 g, 2.44 mmol), KOBz (1.95 g, 12.2 mmol) and dibenzo-18-crown-6 were added together. The mixture was suspended in 20 mL anhydrous DMSO and stirred at reflux for 8 h. The mixture was then cooled to r.t. and 150 mL CH$_2$Cl$_2$ was added. The organic layer was washed with 5×100 mL water, dried over MgSO$_4$, filtered and then concentrated under reduced pressure. The residue was subjected to a silica gel column chromatography eluting with 0-25% EtOAc in Hexane to give compound 35.10 (450 mg, 51.3% yield).

(2S,3S,4R,5R)-4-fluoro-5-(hydroxymethyl)-2-methoxy-tetrahydrofuran-3-yl benzoate (35.11)

A solution of 10% formic acid in MeOH (50 mL) was degassed under vacuum for 5 min, and then 20 mL of this solution was added under argon to Pd/C (450 mg). To this suspension, compound 35.10 (450 mg, 1.25 mmol) dissolved in 25 mL of the same solution was added dropwise while stirring. The reaction was monitored by LC-MS. When completed, 50 mL of water was added to the mixture. The catalyst was filtered off and the solvent was removed under reduced pressure. The residue was subjected to a silica gel column chromatography eluting with 0-50% EtOAc in Hexane to give compound 35.11 (270 mg, 80% yield).

(2S,3S,4R,5R)-4-fluoro-2-methoxy-5-(((trifluoromethylsulfonyloxy)methyl)-tetrahydrofuran-3-yl benzoate (35.12)

Compound 35.11 (270 mg, 1.0 mmol) was dissolved in 5 mL anhydrous CH2C12, cooled to 0° C. and then treated with triflic anhydride (0.252 mL, 1.5 mmol). The reaction was monitored by LC-MS. When the reaction was completed, 20 mL 1N HCl was added to quench the reaction. An additional 50 mL CH$_2$Cl$_2$ was added and the organic layer was separated. The organic layer was washed with an additional 20 mL 1N HCl, collected, dried over MgSO$_4$, filtered and concentrated under reduced pressure. The residue was subjected to a silica gel column chromatography eluting with 25% EtOAc in Hexane to give compound 35.12 (342 mg, 85% yield).

(2S,3S,4R,5R)-5-(2-(diethoxyphosphoryl)-2-(phenylthio)ethyl)-4-fluoro-2-methoxy-tetrahydrofuran-3-yl benzoate (35.13)

Diethylthiophenyl methyl phosphonate (0.554 mL, 2.5 mmol) was dissolved in 5 mL anhydrous THF. The solution was cooled to −78° C. under nitrogen and (1.8N in THF) LDA (1.4 mL, 2.5 mmol) was added dropwise. The mixture was stirred for 20 min. A solution of compound 35.12 (100 mg, 0.25 mmol) in 5 mL anhydrous THF was cooled to −78° C. for 5 min and then this solution was added dropwise to the reaction mixture. The mixture was then stirred at −78° C. for 1 h. Acetic acid was added to quench the reaction and the solvent was removed under reduced pressure. The residue was washed with 400 mL water to remove the starting phosphonate and the remaining residue was subjected to a silica gel column chromatography eluting with 75% EtOAc in Hexane to give compound 35.13 (68 mg, 53.2% yield).

(2S,3S,4R,5R)-2-acetoxy-5-(2-(diethoxyphosphoryl)-2-(phenylthio)ethyl)-4-fluoro-tetrahydrofuran-3-yl benzoate (35.14)

Compound 35.13 (50 mg, 0.1 mmol) was dissolved in a 10% solution of acetic anhydride in acetic acid (2.2 mL). Concentrated sulfuric acid was added and the mixture was stirred at r.t. for 2 h. The mixture was then poured into a 5% aqueous solution of NaHCO$_3$ (100 mL) containing 50 g of ice. The aqueous phase was then extracted with 2×100 mL CH$_2$Cl$_2$. The extracts were combined, dried over MgSO$_4$, filtered and concentrated under reduced pressure. The residue was subjected to a silica gel column chromatography to give compound 35.14 (60 mg, 95% yield).

(2R,3S,4R,5R)-2-(2-acetamido-6-oxo-1,6-dihydro-purin-9-yl)-5-(2-(diethoxyphosphoryl)-2-(phenylthio)ethyl)-4-fluoro-tetrahydrofuran-3-yl benzoate (35.15)

N-Acetyl Guanosine (108 mg, 0.56 mmol) was suspended in 10 mL anhydrous CH$_2$Cl$_2$. With stirring under nitrogen, BSA (345 mg, 1.4 mmol) was added to the suspension. The mixture was stirred at 80° C. for 2 h and cooled to r.t. Compound 35.14 (200 mg, 0.37 mmol) in 5 mL anhydrous DCE was added to the mixture, followed by SnCl$_4$ (64 mL, 0.55 mmol). The mixture was heated to 65° C. for 6 h and then cooled to r.t., diluted with 50 mL CH$_2$Cl$_2$ and poured onto a mixture of 50 g ice/50 mL saturated Rochelles Salt. The mixture was stirred for another 1 h. The organic layer was separated and the aqueous layer was extracted with 100 mL additional CH$_2$Cl$_2$. The organic extracts were combined, dried over MgSO$_4$, filtered and concentrated under reduced pressure. The residue was subjected to a silica gel column chromatography eluting with 5% MeOH in CH$_2$Cl$_2$ to give compound 35.15 (73 mg, 30% yield).

2-((2R,3R,4S,5R)-5-(2-acetamido-6-oxo-1,6-dihydropurin-9-yl)-4-(benzoyloxy)-3-fluoro-tetrahydrofuran-2-yl)-1-(phenylthio)ethylphosphonic acid (35.16)

Compound 35.16 (45 mg, 66% yield) was synthesized from compound 35.15 (77 mg, 0.11 mmol) using the procedure described for the preparation of compound 16.8.

2-((2R,3S,4S,5R)-5-(2-amino-6-oxo-1,6-dihydropurin-9-yl)-3-fluoro-4-hydroxy-tetrahydrofuran-2-yl)-1-(phenylthio)ethylphosphonic acid (35.17)

Compound 35.16 (12 mg, 0.019 mmol) was dissolved in 7 N NH$_3$ in MeOH (5 mL) and stirred for 12 h under nitrogen. The solvent was removed under reduced pressure and the residue was washed with 3×10 mL acetonitrile. The acetonitrile washings are filtered and the solid residue was redissolved in methanol, filtered and concentrated under reduced pressure. The residue gives compound 35.17 in greater than 90% purity (9.2 mg, 100% yield).

2-((2R,3S,4S,5R)-5-(2-amino-6-oxo-1,6-dihydropurin-9-yl)-3-fluoro-4-hydroxy-tetrahydrofuran-2-yl)-1-(phenylsulfinyl)ethylphosphonic acid (35.18)

Compound 35.17 (15 mg, 0.032 mmol) was suspended in 3 mL water, and treated with 30% hydrogen peroxide (100 mL). The mixture was heated to 90° C. for 3 h and sodium sulfite (113 mg, 0.9 mmol) was added to quench the peroxide. The solvent was removed under reduced pressure and the residue was subjected to a reverse phase HPLC to give compound 35.18 (12 mg, 77% yield).

(E)-2-((2R,3S,4S,5R)-5-(2-amino-6-oxo-1,6-dihydropurin-9-yl)-3-fluoro-4-hydroxy-tetrahydrofuran-2-yl)vinylphosphonic acid (35.19)

Compound 35.18 (12 mg, 0.025 mmol) was dissolved in anhydrous DMF (4 mL), treated with tributylamine (0.12 mL, 0.5 mmol) and TMSCl (0.063 mL, 0.5 mmol). The mixture was heated to 130° C. for 4 h, cooled to r.t., and then quenched with 2 mL water. The mixture was stirred at r.t for another 2 h and then the solvent was removed under reduced pressure. The residue was washed with 3×20 mL acetonitrile to remove TBA and TMSOH. The acetonitrile washes were discarded and the solid was dissolved in water, subjected to a reverse phase HPLC to give compound 35.19 (6.6 mg, 73% yield).
$^1$HNMR (D2O, 300 MHz) δ 8.40 (s, 1H), 6.57 (m, 1H), 6.13 (t, 1H), 5.92 (d, 1H), 4.90-5.20(m, 3H). $^{31}$PNMR (D$_2$O, 300 MHz): 11.815 ppm. LRMS (ESI) MH$^+$ C$_{11}$H$_{13}$FN$_5$O$_6$P requires 362.1. Found 362.0.

Bis-amidate prodrug 35.20

Compound 35.20 (0.7 mg, 7.6% yield) was synthesized from compound 35.19 (5.5 mg, 0.015 mmol) using the procedure described for the preparation of compound 9.11. $^1$HNMR (CD$_3$CN, 300 MHz) δ 0.85-0.9 (m, 6H), 1.32-1.38 (m, 10H), 1.62-1.65 (m, 4H), 3.61-4.18 (m, 8H), 4.60 (s, 1H), 4.90-5.23 (m, 3H), 5.62-6.29 (m, 4H), 6.61-6.6.79 (m, 1H), 7.42 (s, 1H). $^{31}$PNMR: 16.85 ppm. LRMS (ESI) MH$^+$ C$_{25}$H$_{39}$FN$_7$O$_8$P requires 616.3. Found 616.3.

Example 16

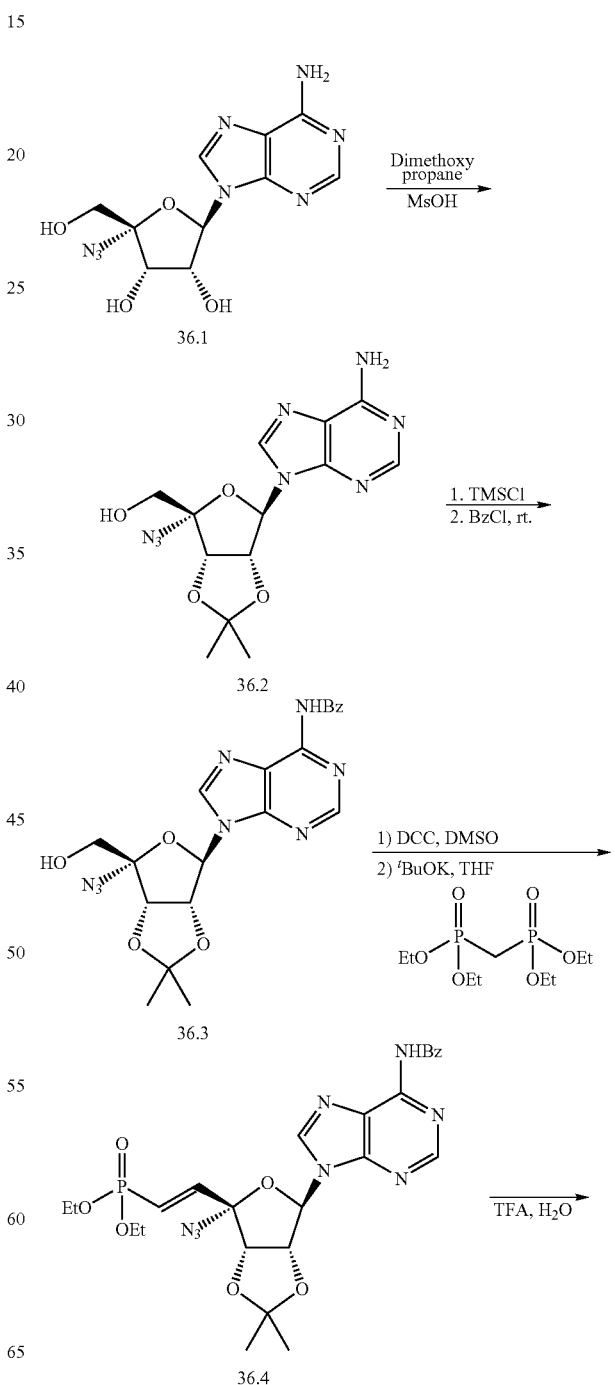

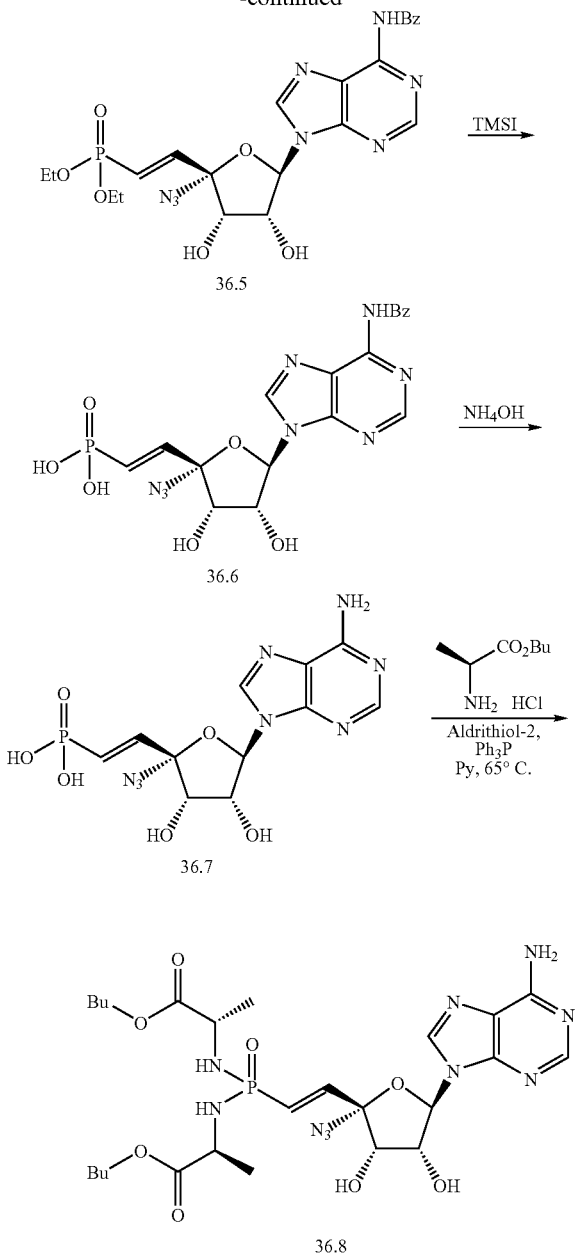

N-(9-((3aR,4R,6R,6aS)-6-azido-6-(hydroxymethyl)-2,2-dimethyl-tetrahydrofuro[3,4-d][1,3]dioxol-4-yl)-9H-purin-6-yl)benzamide (36.3)

Compound 36.2 (300 mg, 0.86 mmol) was dissolved in 8.6 mL anhydrous pyridine, and treated with TMSCl (1.09 mL, 8.6 mmol). The mixture was stirred for 1 h, and then treated with BzCl (1.0 mL, 8.6 mmol), stirred for overnight. MeOH was added to the mixture after the reaction was completed. The mixture was stirred for another 5 min and then concentrated under reduced pressure. The residue was dissolved in EtOAc, washed with sat. NaHCO₃ twice and the organic layer was dried over MgSO₄, filtered and concentrated under reduced pressure. The residue was subjected to a silica gel column chromatography eluting with 50% EtOAc in hexane to give compound 36.3 (357 mg, 74% yield).

diethyl (E)-2-((3aS,4R,6R,6aR)-4-azido-6-(6-benzamido-9H-purin-9-yl)-2,2-dimethyl-tetrahydrofuro[3,4-d][1,3]dioxol-4-yl)vinylphosphonate (36.4)

Compound 36.3 (129 mg, 0.22 mmol) was dissolved in 2.2 mL anhydrous DMSO, treated with TFA.Pyridine (11 mg, 0.056 mmol) and DCC (69 mg, 0.33 mmol). The mixture was stirred at r.t. for 14 h, and then cooled to 0° C. Premixed (EtO)$_2$P(O)CH$_2$P(O)(OEt)$_2$ with 1 M t-BuOK in THF (0.345 mL, 0.34 mmol) at 0° C., the mixture was stirred for 5 min and then added to the oxidized reaction mixture, warmed to r.t. and stirred for 3 h. The mixture was then cooled to 0° C., treated with 0.4 mL 1N HCl, diluted with EtOAc. The organic layer was washed with saturated NaHCO₃, brine, dried over MgSO₄, filtered and concentrated under reduced pressure. The residue was subjected to a silica gel column chromatography eluting with EtOAc to give compound 36.4 (124 mg, 81% yield).

diethyl (E)-2-((2R,3S,4R,5R)-2-azido-5-(6-benzamido-9H-purin-9-yl)-3,4-dihydroxy-tetrahydrofuran-2-yl)vinylphosphonate (36.5)

Compound 36.4 (122 mg, 0.18 mmol) was dissovled in a mixture of TFA in water (1.5 mL TFA in 0.2 mL water). The solution was stirred at r.t. for 30 min and then concentrated under reduced pressure. The residue was subjected to a silica gel column chromatography eluting with EtOAc to 20% MeOH in EtOAc to give compound 36.5 (68 mg, 70% yield).

(E)-2-((2R,3S,4R,5R)-2-azido-5-(6-benzamido-9H-purin-9-yl)-3,4-dihydroxy-tetrahydrofuran-2-yl)vinylphosphonic acid (36.6)

Compound 36.5 (261 mg, 0.48 mmol) was dissovled in CH₃CN (9.6 mL), treated with 2,6-lutidine (0.55 mL, 4.2 mmol) and TMSI (0.34 mL, 2.39 mmol). The mixture was stirred at r.t. for 30 min and concentrated under reduced pressure. Saturated NaHCO₃ was added to the residue and the mixture was stirred for 5 min. The solvent was then removed under redued pressure and CH₃CN was added, the mixture was filtered and concentrated under reduced pressure. The residue was used for the next step reaction without further purification.

(E)-2-((2R,3S,4R,5R)-5-(6-amino-9H-purin-9-yl)-2-azido-3,4-dihydroxy-tetrahydrofuran-2-yl)vinylphosphonic acid (36.7)

Compound 36.6 (crude 233 mg) was dissovled in 10 mL concentrated NH₄OH. The solution was stirred at r.t. for 24 h

((3aS,4R,6R,6aR)-6-(6-amino-9H-purin-9-yl)-4-azido-2,2-dimethyl-tetrahydrofuro[3,4-d][1,3]dioxol-4-yl)methanol (36.2)

Compound 36.1 (239 mg, 0.78 mmol) was dissolved in 15 mL acetone, treated with 2,2-dimethoxypropane (1.5 mL, 3.88 mmol) and MsOH (0.15 mL, 2.325 mmol). The mixture was stirred for overnight. TEA (3.1 eq) was added to the mixture and the mixture was concentrated under reduced pressure. The residue was triturated with CHCl₃ and water, extracted and the organic layer was separated, dried over MgSO₄, filtered and concentrated under reduced pressure. The residue was subjected to a silica gel column chromatography eluting with EtOAc to 20% MeOH in EtOAc to give compound 36.2 (144 mg, 53% yield).

and then concentrated under reduced pressure. The residue was subjected to a reverse phase HPLC eluting with 0-15% CH$_3$CN in water to give compound 36.7 (40 mg, 22% yield). $^1$H NMR (D$_2$O, 300 MHz) 8.12 (s, 1H), 8.03 (s, 1H), 6.14 (br m, 3H), 4.66 (m, 1H), 4.40 (d, J=6.0 Hz, 1H).; $^{31}$P NMR (D$_2$O 121.4 MHz) 7.1; MS (ESI) m/z 385 [M+H]$^+$.

Diphosphophosphonate of compound 36.7

This compound (7.5 mg, 44% yield) was synthesized from compound 36.7 (12 mg, 0.03 mmol) using the procedure described for the preparation of diphosphophosphoate of compound 1.11. $^1$H NMR (D$_2$O, 300 MHz) 8.26 (s, 1H), 8.09 (s, 1H), 6.36 (m, 3H), 4.66 (m, 1H), 4.48 (d, J=5.7 Hz, 1H), 3.00 (app quart, J=7.2 Hz, 24H), 1.07 (app t, J=7.2 Hz, 36H); $^{31}$P NMR (D$_2$O 121.4 MHz) 0.3 (d, J=22 Hz, 1P), −9.0 (d, J=22Hz, 1P), −24.3 (app t, J=53 Hz, 1P).

Bis-amidate prodrug 36.8

Compound 36.8 (3.3 mg, 14% yield) was synthesized from compound 36.7 (14 mg, 0.04 mmol) using the procedure described for the preparation of compound 9.11. $^1$H NMR (D$_2$O, 300 MHz) 8.35 (s, 1H), 8.27 (s, 1H), 6.70 (dd, J=21.0 Hz, 1H), 6.25 (dd, J=21.0 Hz, 1H), 6.26 (d, J=5.1 Hz, 1H), 4.95 (t, J=5.4 Hz, 1H), 4.53 (d, J=5.7 Hz, 1H), 4.03 (m, 6H), 3.90 (m, 4H), 1.57 (m, 4H), 1.32 (app t, J=5.4 Hz, 4H), 0.87 (m, 1H), $^{31}$P NMR (D$_2$O 121.4 MHz) 16.0; MS (ESI) m/z 639 [M+H]$^+$.

Example 17

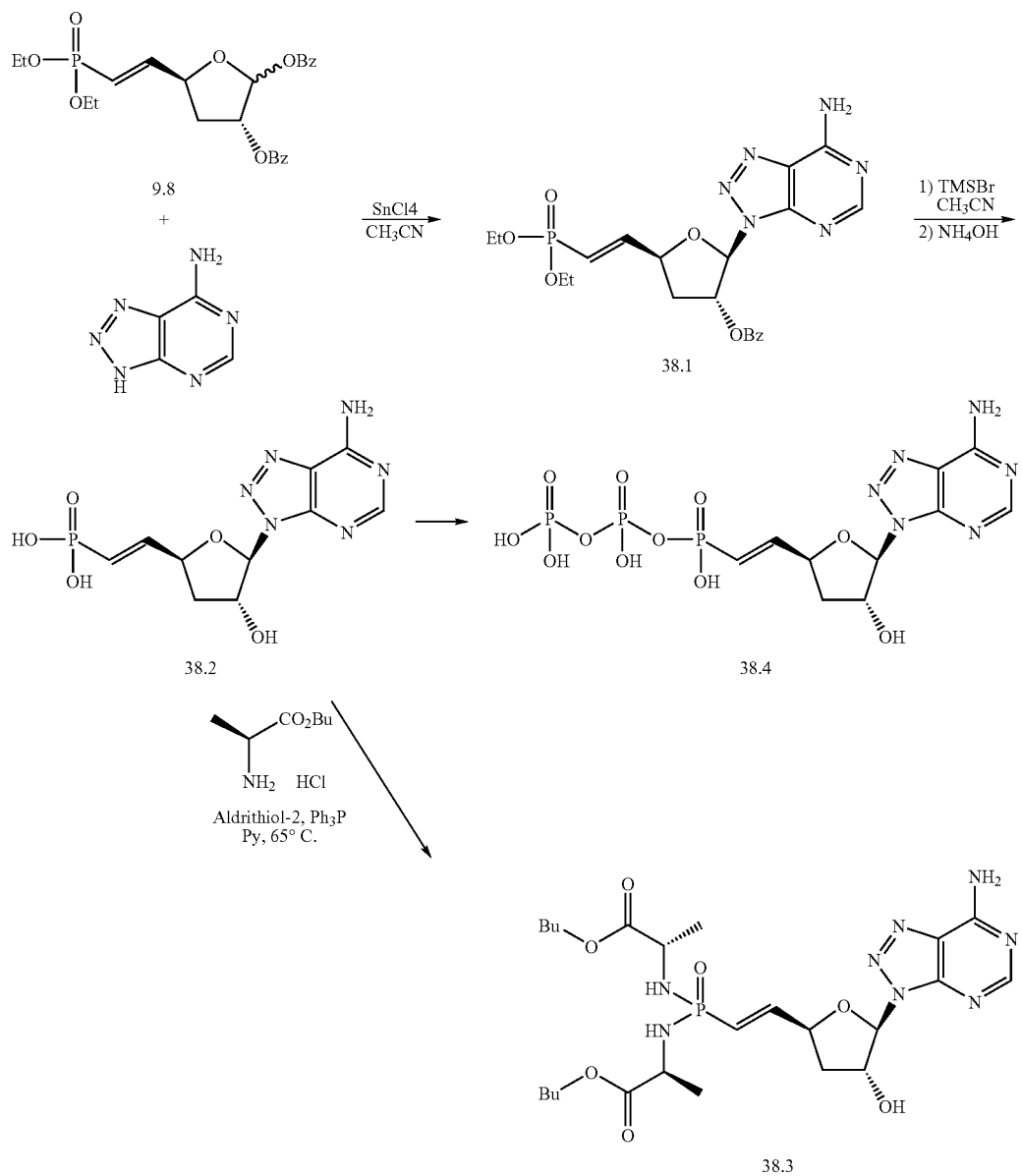

(2R,3R,5S)-2-(7-amino-3H-[1,2,3]triazolo[4,5-d]pyrimidin-3-yl)-5-((E)-2-(diethoxyphosphoryl)vinyl)-tetrahydrofuran-3-yl benzoate (38.1)

To a suspension of 8-azaadenine (204 mg, 1.5 mmol) in 8 mL CH$_3$CN was added BSA (0.73 mL, 3.0 mmol). The mixture was stirred at r.t. for 30 min till it became a clear solution.

To this mixture was added a solution of compound 38.1 (385 mg, 0.81 mmol) in 2 mL CH₃CN, followed by SnCl₄ (1M, CH₂Cl₂) (2.5 mL). The mixture was stirred at 50° C. for 22 h, cooled with ice-water bath, treated with NaHCO₃ (1 g solid+2 mL saturated solution) and stirred for 2 h. The mixture was then filtered and concentrated under reduced pressure. The residue was subjected to a silica gel column chromatography eluting with 20% EtOH in EtOAc to give compound 38.1 (50 mg, 13% yield).

(E)-2-((2S,4R,5R)-5-(7-amino-3H-[1,2,3]triazolo[4,5-d]pyrimidin-3-yl)-4-hydroxy-tetrahydrofuran-2-yl)vinylphosphonic acid (38.2)

Compound 38.2 (60 mg, 68% yield) was synthesized from compound 38.1 (115 mg, 0.24 mmol) using the procedure described for the preparation of compound 9.10. ¹H NMR (D₂O, 300 MHz): δ 2.31-2.55 (m, 2H), 4.78-4.98 (m, 2H), 5.78-5.88 (m, 1H), 5.94-6.08 (m, 1H), 6.23 (s, 1H). ³¹PNMR: 9.20 ppm. LRMS C₁₀H₁₃N₆O₅P requires 327.1. Found 327.0.

Bisamidate prodrug (38.3)

Compound 38.3 (8.3 mg, 44% yield) was synthesized from compound 38.2 (12 mg, 0.03 mmol) using the procedure described for the preparation of compound 9.11. ¹H NMR (CD₃OD, 400 MHz): δ 0.89-0.94 (m, 6H), 1.31-1.41 (m, 10H), 1.54-1.63 (m, 4H), 2.38-2.69 (m, 2H), 3.82-4.11 (m, 6H), 4.94-4.95 (m, 2H), 5.10 (s, 1H), 5.85-5.9 (m, 1H), 6.36 (s, 1H), 6.61-6.78 (m, 1H), 8.33 (s, 1H). ³¹PNMR: 19.73 ppm. LRMS (ESI) MH⁺ C₂₄H₃₉N₈O₇P requires 583.3. Found 583.1.

Diphosphophosphonate 38.4

This compound (13 mg, 39.7% yield) was synthesized from compound 38.2 (22 mg, 0.059 mmol) using the procedure described for the preparation of the diphosphophosphonate 6.8. ¹H NMR (D₂O, 300 MHz): δ 2.39-2.53 (m, 2H), 4.97-5.02 (m, 2H), 5.94-6.00 (m, 1H), 6.27-6.42 (m, 2H), 8.21 (s, 1H). 31PNMR: 4.35, 4.18, −5.42, −5.58, −21.44, −21.62 ppm. LRMS [M−H]⁻ C₁₀H₁₅N₆O₁₁P₃ requires 487.0. Found 486.9.

Example 18

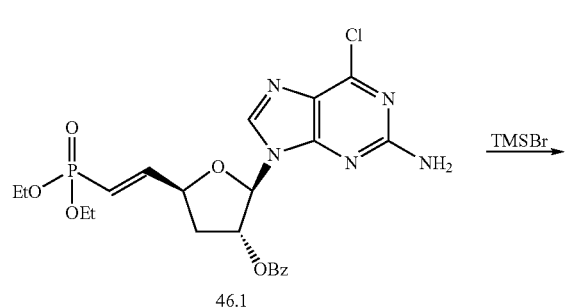

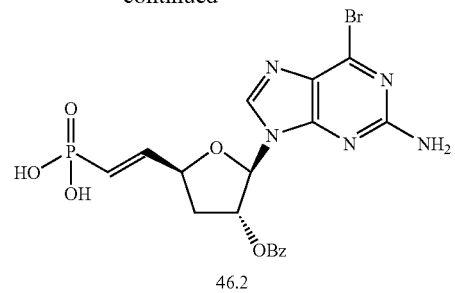

Benzoic acid 2-(2-amino-6-bromo-purin-9-yl)-5-(2-phosphono-vinyl)-tetrahydro-furan-3-yl ester (46.2)

Compound 46.2 was synthesized from compound 46.1 using the same procedure described for the preparation of compound 9.10.

{2-[5-(2-Amino-6-methylamino-purin-9-yl)-4-hydroxy-tetrahydro-furan-2-yl]-vinyl}-phosphonic acid (46.3)

Compound 46.2 (250 mg, crude) was dissolved in 40 wt % methylamine in water and stirred at rt for 3 h. The solution was concentrated under reduced pressure and the residue was subjected to a reverse phase HPLC to give compound 46.3 (60 mg, 35% yield). ¹H NMR (CDCl₃, 300 MHz): δ 2.05-2.18 (m, 2H), 2.83 (s, 3H), 4.54-4.55 (m, 1H), 4.84 (s, 1H), 5.73 (d, 1H, J=1.5), 5.89-5.95 (m, 1H), 6.22 (m, 1H), 7.64 (s, 1H). ³¹PNMR: 10.23 ppm. LRMS [M−H]⁻ C₁₂H₁₇N₆O₅P requires 355.1. Found 355.1.

Example 19

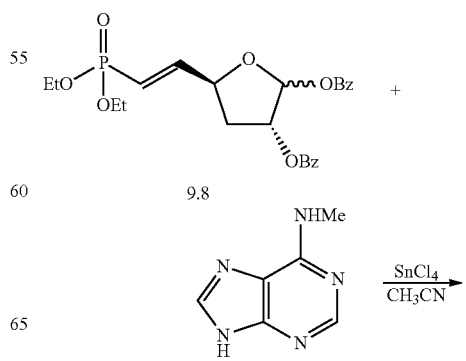

219
-continued

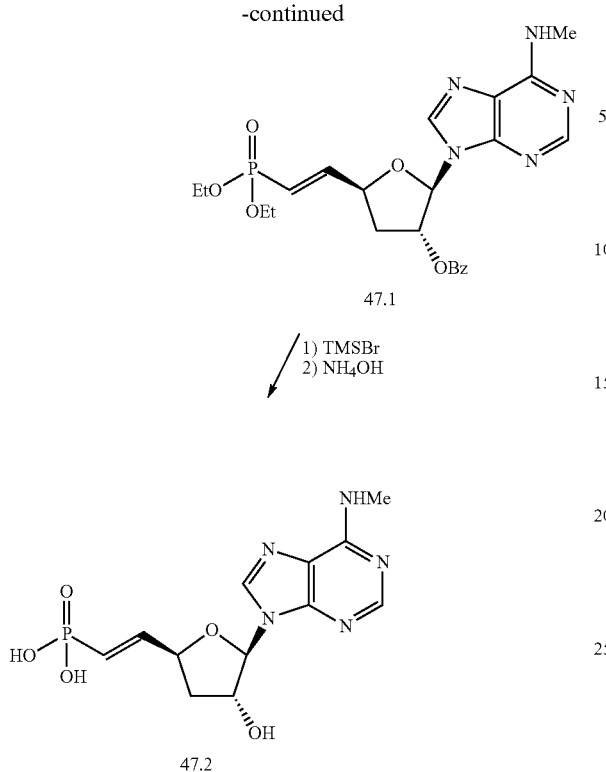

Benzoic acid 5-[2-(diethoxy-phosphoryl)-vinyl]-2-(6-methylamino-purin-9-yl)-tetrahydro-furan-3-yl ester (47.1)

Compound 9.8 (474 mg, 1 mmol) was dissolved in anhydrous $CH_3CN$ (10 mL) and treated with 6-aminomethylpurine (149 mg, 1 mmol). $SnCl_4$ (0.12 mL, 1 mmol) was added to the mixture dropwise and the mixture was stirred at rt for 16 h. The mixture was then concentrated under reduced pressure and the residue was dissolved in EtOAc. The organic phase was washed with saturated $NaHCO_3$, brine, dried over $MgSO_4$, filtered and concentrated under reduced pressure. The residue was subjected to a silica gel column chromatography eluting with 0-5% MeOH in DCM to give compound 47.1 (227 mg, 45% yield).

{2-[4-Hydroxy-5-(6-methylamino-purin-9-yl)-tetrahydro-furan-2-yl]-vinyl}-phosphonic acid (47.2)

Compound 47.1 (277 mg, 0.45 mmol) was dissovled in 4.5 mL anhydrous $CH_3CN$ and treated with TMSBr (0.9 mL, 6.8 mmol). The solution was stirred at rt for 3 h, and then concentrated under reduced pressure. The residue was dissolved in $NH_4OH$, stirred for another 2 h, and concentrated under reduced pressure. The residue was subjected to a reverse phase HPLC to give compound 47.2 (97 mg, 51% yield). $^1H$ NMR ($D_2O$, 300 MHz): δ 2.15-2.23 (m, 2H), 3.02 (s, 3H), 4.96 (s, 1H), 5.90-5.95 (m, 1H), 6.02 (d, 1H, J=1.2), 6.39 (m, 1H), 8.09 (s, 1H), 8.17 (s, 1H). $^{31}$PNMR: 11.34 ppm. LRMS [M−H]− $C_{12}H_{16}N_5O_5P$ requires 340.1. Found 340.0.

220

Example 20

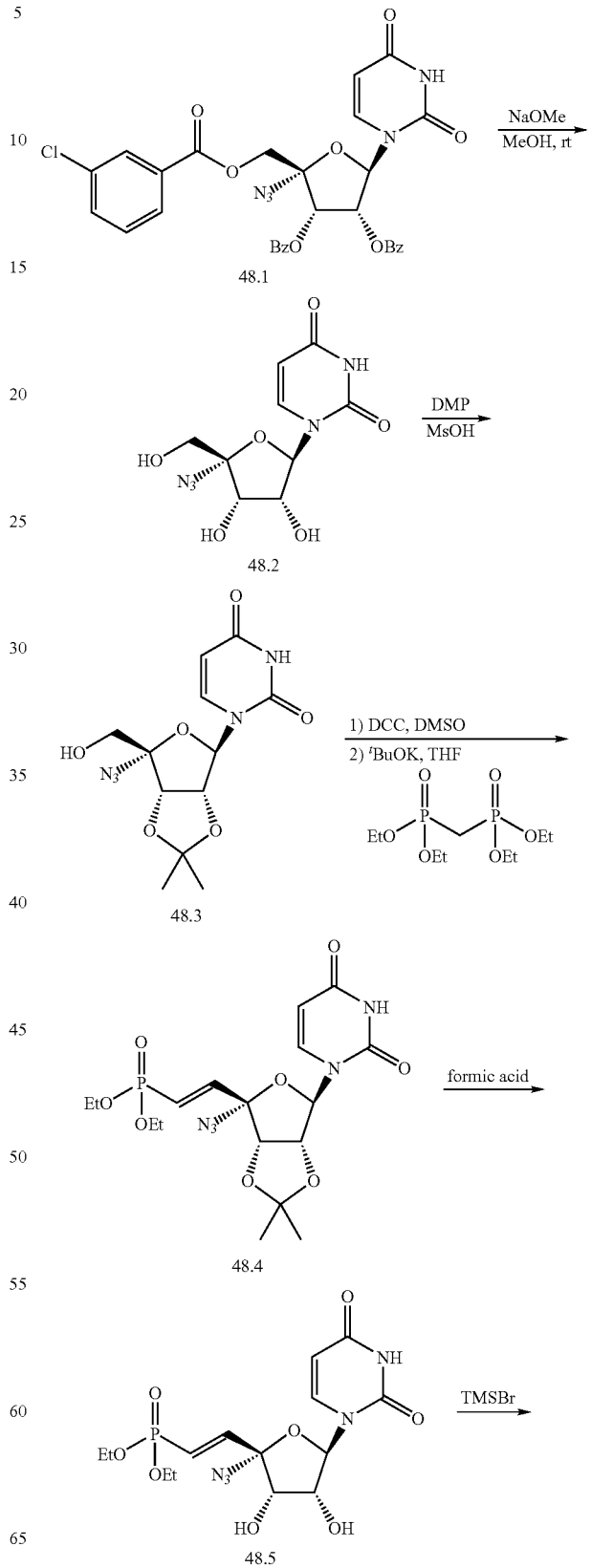

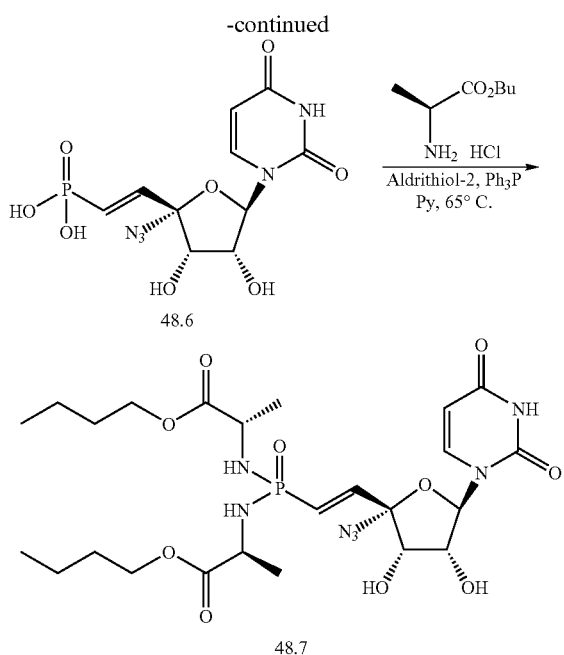

1-(5-Azido-3,4-dihydroxy-5-hydroxymethyl-tetrahydro-furan-2-yl)-1H-pyrimidine-2,4-dione (48.2)

Compound 48.1 (4 g, 6.33 mmol) was dissolved in 6.3 mL MeOH and treated with 25% NaOMe in MeOH (14 mL, 63.3 mmol). The solution was stirred at rt for 8 h, cooled to 0° C., treated with 4N HCl in dioxane (15 mL), stirred for another 5 min and then concentrated under reduced pressure. The residue was used in the next step reaction without further purification.

1-(6-Azido-6-hydroxymethyl-2,2-dimethyl-tetrahydro-furo[3,4-d][1,3]dioxol-4-yl)-1H-pyrimidine-2,4-dione (48.3)

Compound 48.2 (1.81 g, 6.35 mmol) was dissolved in 60 mL acetone, treated with 2,2-dimethoxypropane (60 mL) and MsOH (1.23 mL, 19.09 mmol). The mixture was stirred at rt for overnight. Triethylamine was added to quench the reaction and the mixture was concentrated under reduced pressure. The residue was partitioned between $CHCl_3$ and water; the organic layer was separated, dried over $MgSO_4$, filtered and concentrated under reduced pressure. The residue was subjected to a silica gel column chromatography eluting with 10% MeOH in EtOAc to give compound 48.3 (2.12 g, 100% yield).

{2-[4-Azido-6-(2,4-dioxo-3,4-dihydro-2H-pyrimidin-1-yl)-2,2-dimethyl-tetrahydro-furo[3,4-d][1,3]dioxol-4-yl]vinyl}-phosphonic acid diethyl ester (48.4)

Compound 48.3 (900 mg, 2.76 mmol) was dissolved in anhydrous DMSO (28 mL), treated with TFA.Pyridine (133 mg, 0.69 mmol) and DCC (859 mg, 4.14 mmol). The mixture was stirred at rt for overnight. In a separate flask, $(EtO)_2P(O)CH_2P(O)(EtO)_2$ (0.875 mL, 3.57 mmol) was premixed with 1M tBuOK solution in THF (4.28 mL, 4.28 mmol) at 0° C. and then added slowly to the mixture with compound 48.3. The resulting mixture was stirred at rt for 2 h, cooled to 0° C., treated with oxalic acid, 1N HCl, diluted with EtOAc and washed with saturated $NaHCO_3$, brine. The organic phase was separated, dried over $MgSO_4$, filtered, and concentrated under reduced pressure. The residue was subjected to a silica gel column chromatography eluting with Hexane to EtOAc to 20% MeOH in EtOAc to give compound 48.4 (131 mg, 10.4% yield).

{2-[2-Azido-5-(2,4-dioxo-3,4-dihydro-2H-pyrimidin-1-yl)-3,4-dihydroxy-tetrahydro-furan-2-yl]-vinyl}-phosphonic acid diethyl ester (48.5)

Compound 48.4 (130 mg, 0.29 mmol) was dissolved in 90% formic acid in water (2.8 mL). The solution was stirred at rt for 2 h and then concentrated under reduced pressure. The residue was used in the next step reaction without further purification.

{2-[2-Azido-5-(2,4-dioxo-3,4-dihydro-2H-pyrimidin-1-yl)-3,4-dihydroxy-tetrahydro-furan-2-yl]vinyl}-phosphonic acid (48.6)

Compound 48.5 (119 mg, 0.28 mmol) was dissolved in 2.6 mL CH3CN, treated with 2,6-lutidine (0.1 mL) and TMSBr (0.2 mL). The mixture was stirred at rt for 2 h and concentrated under reduced pressure. The residue was coevaporated with saturated NH4OH three times and the residue was subjected to a reverse phase HPLC to give compound 48.6 (100 mg, 92% yield). $^1$H NMR ($D_2O$, 300 MHz) 7.45 (d, J=8.1 Hz, 1H), 6.22 (app d, J=8.7 Hz, 1H), 6.16 (app d, J=5.7 Hz, 1H), 5.85 (d, J=3.0 Hz, 1H), 5.71 (d, J=8.1 Hz, 1H), 4.31 (m, 1H), 4.24 (m, 1H); $^{31}$P NMR ($D_2O$ 121.4 MHz) 7.3; MS (ESI) m/z 359 [M−2H]$^+$.

Bis-amidate prodrug 48.7

Compound 48.7 (0.5 mg, 3% yield) was synthesized from compound 48.6 (11.2 mg, 0.031 mmol) using the same procedure described for the preparation of compound 9.11. $^1$H NMR ($D_2O$, 300 MHz) 7.56 (m, 2H), 7.34 (d, J=7.8 Hz, 1H), 7.08 (m, 1H), 5.65 (m, 1H), 5.56 (d, J=7.8 Hz, 1H), 4.51 (m, 1H), 4.24 (m, 1H), 4.07 (m, 4H), 1/57 (m, 4H), 1.34 (m, 4H), 0.085 (m, 6H); $^{31}$P NMR ($D_2O$ 121.4 MHz) 22.1; MS (ESI) m/z 616 [M+1H]$^+$.

Example 21

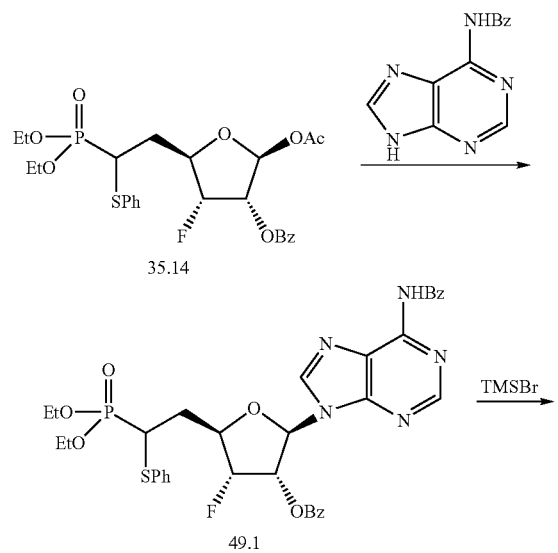

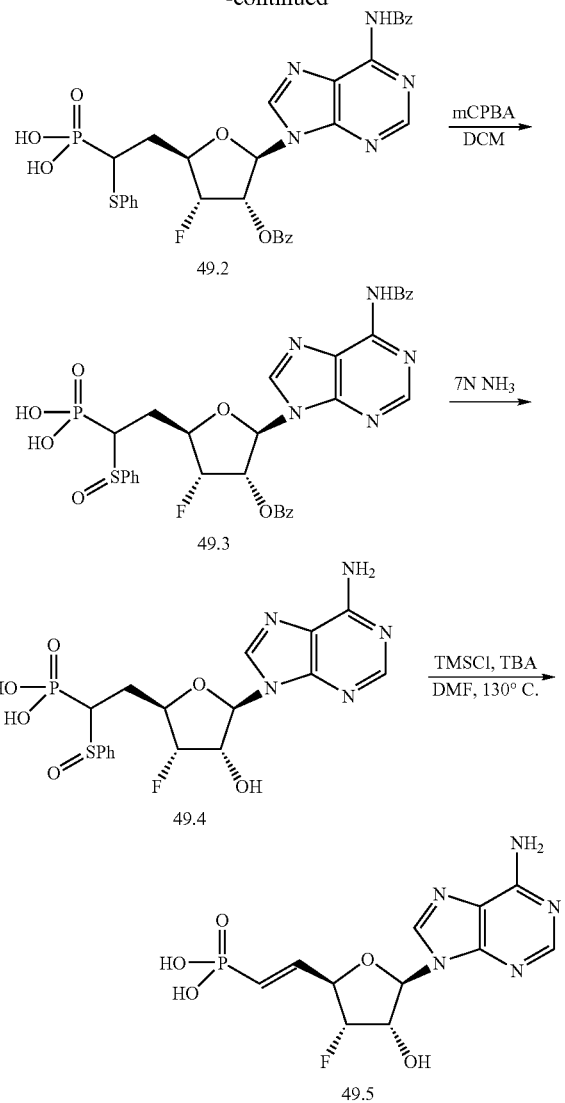

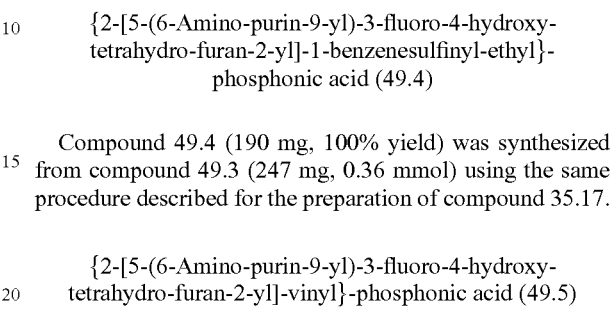

0.27 mmol) was dissolved in anhydrous DCM (2 mL). The solution of mCPBA was added in 200 µL aliquots. With each addition, the reaction was monitored by LC/MS to prevent overoxidation. When the starting material was gone by LC/MS, addition of mCPBA was stopped and the solvent was removed under reduced pressure. The residue was used in the next step reaction without further purification.

{2-[5-(6-Amino-purin-9-yl)-3-fluoro-4-hydroxy-tetrahydro-furan-2-yl]-1-benzenesulfinyl-ethyl}-phosphonic acid (49.4)

Compound 49.4 (190 mg, 100% yield) was synthesized from compound 49.3 (247 mg, 0.36 mmol) using the same procedure described for the preparation of compound 35.17.

{2-[5-(6-Amino-purin-9-yl)-3-fluoro-4-hydroxy-tetrahydro-furan-2-yl]-vinyl}-phosphonic acid (49.5)

Compound 49.4 (147 mg, 0.31 mmol) was dissolved in anhydrous DMF, treated with tributylamine (1.49 mL, 6.24 mmol) and TMSCl (0.79 mL, 6.24 mmol). The mixture was heated to 130° C. for 4 h and then cooled to rt. The reaction was quenched with water and stirred at rt for another 2 h. The mixture was concentrated under reduced pressure and the residue was washed with acetonitrile. The acetonitrile washes were discarded and the residue was dissolved in water, subjected to a reverse phase HPLC to give compound 49.5 (34 mg, 24% yield). $^1$H NMR (D$_2$O, 300 MHz): δ 4.91-5.17 (m, 3H), 5.92-5.95 (m, 1H), 6.07-6.59 (m, 2H), 8.37 (s, 1H). $^{31}$PNMR: 11.82 ppm. LRMS [M−H]$^−$ C$_{11}$H$_{13}$FN$_5$O$_5$P requires 344.1. Found 344.1.

Example 22

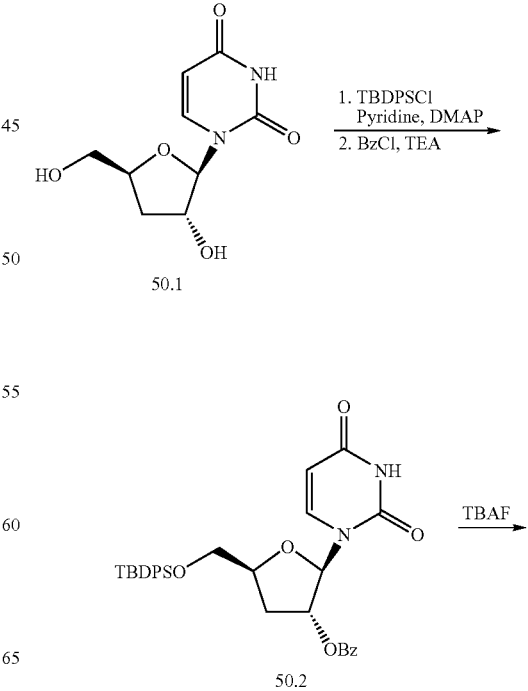

Benzoic acid 2-(6-benzoylamino-purin-9-yl)-5-[2-(diethoxy-phosphoryl)-2-phenylsulfanyl-ethyl]-4-fluoro-tetrahydro-furan-3-yl ester (49.1)

Compound 49.1 (347 mg, 79% yield) was synthesized from compound 35.14 (330 mg, 0.61 mmol) using the same procedure described for the preparation of compound 35.15.

Benzoic acid 2-(6-benzoylamino-purin-9-yl)-4-fluoro-5-(2-phenylsulfanyl-2-phosphono-ethyl)-tetrahydro-furan-3-yl ester (49.2)

Compound 49.1 (300 mg, 63% yield) was synthesized from compound 49.2 (515 mg, 0.72 mmol) using the same procedure described for the preparation of compound 35.16.

Benzoic acid 5-(2-benzenesulfinyl-2-phosphono-ethyl)-2-(6-benzoylamino-purin-9-yl)-4-fluoro-tetrahydro-furan-3-yl ester (49.3)

Compound 49.3 (180 mg, 0.27 mmol) was dissolved in anhydrous DCM. In a separate container, mCPBA (47 mg, -continued

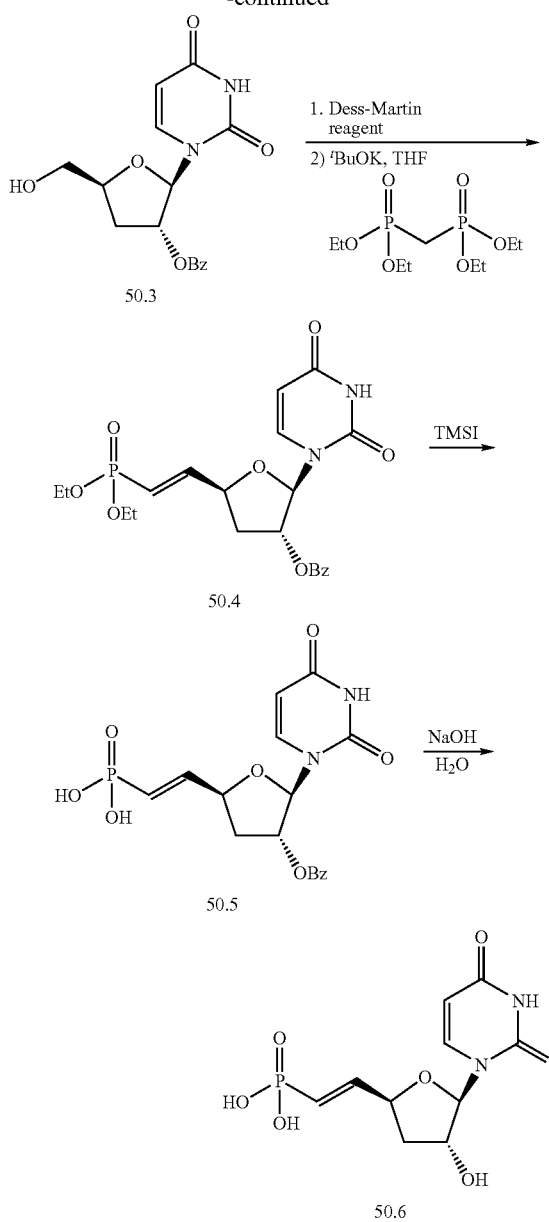

Benzoic acid 5-(tert-butyl-diphenyl-silanyloxymethyl)-2-(2,4-dioxo-3,4-dihydro-2H-pyrimidin-1-yl)-tetrahydro-furan-3-yl ester (50.2)

Compound 50.1 (0.300 g, 1.315 mmol) was dissolved in 3 ml anhydrous pyridine. Tert-butyldiphenylsilyl chloride (0.393 ml, 1.51 mmol) and dimethylaminopyridine (3.45 mg, 0.029 mmol) were added as solids under nitrogen. The reaction was stirred overnight at room temperature and monitored by LC/MS. When the reaction was complete the mixture was cooled to 0° C. and benzoyl chloride (0.337 ml, 2.9 mmol) was added drop wise. The mixture was allowed to rise to room temperature and stirred until complete by LC/MS. The solvent was removed under vacuum and the desired compound was purified by column chromatography. Yield 0.713 g, 80.6%. Anal.; mass spectrum (ESI) m/z 675 [M+H]+.

Benzoic acid 2-(2,4-dioxo-3,4-dihydro-2H-pyrimidin-1-yl)-5-hydroxymethyl-tetrahydro-furan-3-yl ester (50.3)

Compound 50.2 (0.713 g, 1.06 mmol) was dissolved in 10 ml anhydrous THF was cooled to 0° C. Tetrabutyl ammonium fluoride (1.11 ml, 1N in THF, 1.11 mmol) was added dropwise and the reaction mixture was allowed to rise to room temperature. The reaction was stirred for 4 hr at room temperature while monitoring by TLC. When the reaction was complete by TLC the, solvent was removed under vacuum. The residue was re-dissolved in ethyl acetate (4 ml) and purified by column chromatography. Yield 0.300 g, 65.0%. Anal. $^1$H-NMR (CD3CN): δ 2.2 m 1H; 2.45 m 1H; 3.37 t 1H; 3.7 dd 1H; 3.97 dd 1H; 4.53 m 1H; 5.62 m 1H; 5.87 d 1H; 6.06 s 1H; 7.49-7.70 m 5H; 7.79 t 1H; 8.05 t 4H; 8.19 d 1H.

Benzoic acid 5-[2-(diethoxy-phosphoryl)-vinyl]-2-(2,4-dioxo-3,4-dihydro-2H-pyrimidin-1-yl)-tetrahydro-furan-3-yl ester (50.4)

The procedure in step B should be started as the aldehyde prepared in step A was being filtered. The aldehyde was unstable and undergoes air oxidation in about 15 minutes.

Step A The starting alcohol compound 50.3 (0.150 g, 0.344 mmol) was dissolved in 5 ml anhydrous dichloromethane. The Dess-Martin Periodinane was added as a solid (0.146 g, 0.344) and the reaction was monitored by TLC. When the alcohol had disappeared the reaction was rapidly filtered through a small plug of silica gel to remove any solids. The silica plug was washed with ethyl acetate (2×50 mL). The ethyl acetate washes along with the dichloromethane reaction solvent were combined and evaporated to dryness. The residue was immediately take up into 10 ml anhydrous THF and added to stirred solution prepared as follows.

Step B In a round bottom under nitrogen dissolve tetraethylmethylenebisphosphonate (0.256 ml, 1.032 mmol) in anhydrous THF (5 ml). Cool this solution to 0° C. in an ice bath and add sodium hydride (0.041 g, 60% in mineral oil, 3 eq, 1.032 mmol) as a solid. Allow the mixture to rise to room temperature and stir for 15 minutes. After 15 minutes at room temperature add the freshly prepared aldehyde in THF and stir overnight at room temperature. Monitor the reaction by TLC. When the aldehyde had disappeared evaporate and purify the product by column chromatography. Yield 0.072 g, 37.0%. Anal. $^1$H-NMR (CD3CN): δ 1.30 t 6H; 2.35 m 1H; 2.50 dd 1H; 4.07 m 4H; 5.01 m 1H; 5.65 d 1H; 5.90 d 1H; 6.05 s 1H; 6.15 dd 1H; 6.86 dd 1H; 7.49-7.70 m 5H; 7.79 t 1H; 8.05 m 5H.

Benzoic acid 2-(3-benzoyl-2,4-dioxo-3,4-dihydro-2H-pyrimidin-1-yl)-5-(2-phosphono-vinyl)-tetrahydro-furan-3-yl ester (50.5)

Compound 50.4 (0.072, 0.127 mmol) was dissolved in 4 ml anhydrous acetonitrile, and 2,6-lutidine (0.0325 ml, 0.279 mmol) was added with stirring. Trimethylsilyl iodide (0.038 ml, 0.279 mmol) was added and the reaction was monitored by LC/MS. When complete the reaction was quenched by addition of triethylamine (2 equiv.) and methanol 1 ml. The solvents were removed under vacuum and the desired product was purified by reversed phase HPLC. Yield 0.065 g, 100.0%. Anal; mass spectrum (ESI) m/z 535 [M+Na]+.

{2-15-(2,4-Dioxo-3,4-dihydro-2H-pyrimidin-1-yl)-4-hydroxy-tetrahydro-furan-2-yl]-vinyl}-phosphonic acid (50.6)

Compound 50.5 (0.005 g, 0.01 mmol) was dissolved in 5 ml water and 1N sodium hydroxide (0.100 ml, 0.1 mmol) was added. The reaction was monitored by LC/MS. When complete the reaction was quenched by addition of glacial acetic acid (0.02 ml). The solvent was removed under vacuum and the final product was purified by reversed phase chromatography. Yield 0.0015 g, 50.5%. Anal. $^1$H-NMR (D2O): δ 1.85 dd 1H; 2.08 dd 1H; 4.40 d 2H; 4.83 m 1H; 5.67 s 1H; 5.72 d 1H; 5.99 m 1H; 6.18 m 1H; 7.58 d 1H.

Example 23

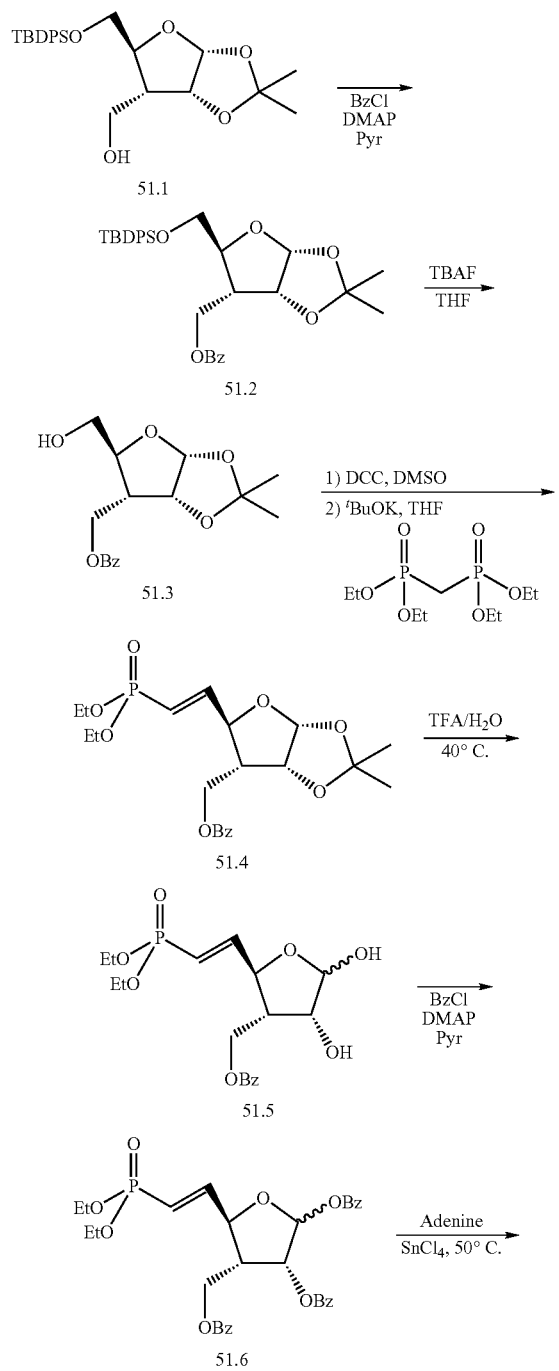

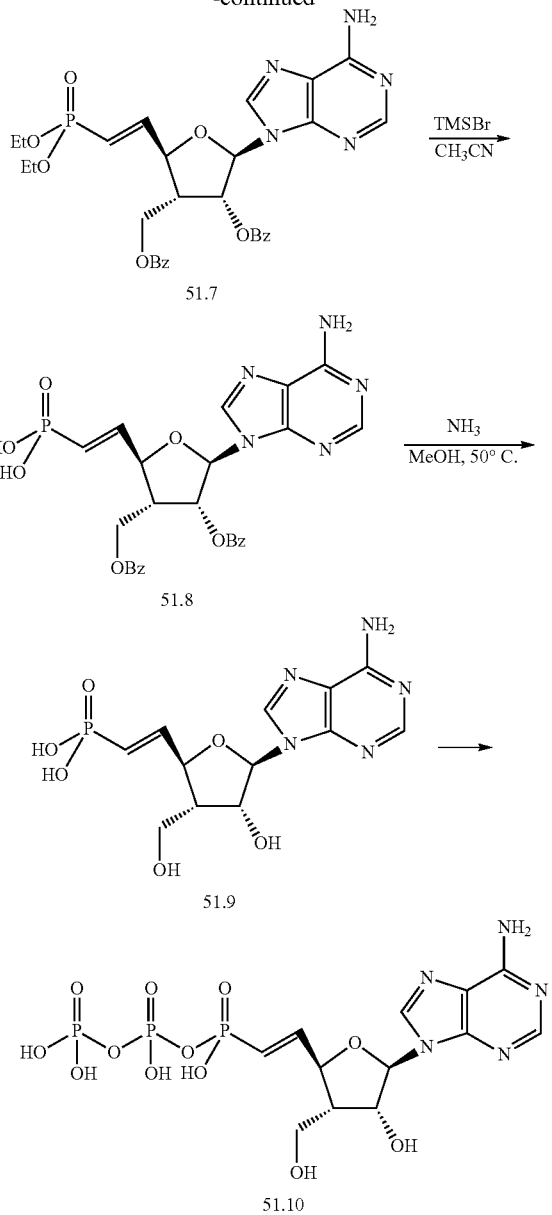

Compound 51.2 500 mg of 51.1 was dissolved in pyridine (4 mL). The solution was cooled to 0° C. and treated with BzCl (0.2 mL) and DMAP (42 mg). The reaction mixture was stirred for 2 h and diluted with EtOAc (10 mL), washed with brine (10 mL). The organic layer was dried over MgSO$_4$, filtered, evaporated under vacuum. The residue was subjected to silica gel chromatography eluting with 10% EtOAc in Hexane to give the product 51.2 (500 mg, 80% yield). $^1$H NMR (CD$_3$Cl, 300 MHz) δ 1.11 (s, 9H), 1.40 (s, 3H), 1.57 (s, 3H), 2.78-2.85 (m, 1H), 3.88 (dd, J=3.6, 11.7 Hz, 1H), 4.06 (dd, J=2.7, 11.4 Hz, 1H), 4.16-4.19 (m, 1H), 4.46 (dd, J=6.9, 11.1 Hz, 1H), 4.69 (dd, J=7.2, 11.1 Hz, 1H), 4.87 (t, J=4.2 Hz, 1H), 5.94 (d, J=3.6 Hz, 1H), 7.36-7.49 (m, 8H), 7.56-7.76 (m, 5H), 8.05-8.08 (m, 2H). LRMS (ESI) MH$^+$ C$_{32}$H$_{38}$O$_6$Si requires 547.7. Found 547.6.

Compound 51.3 245 mg of 51.2 was dissolved in THF (5 mL). The solution was cooled to 0° C. and treated with TBAF (0.58 mL, 1.0M in THF). The reaction mixture was stirred for 3 h and diluted with EtOAc (10 mL), washed with brine (10 mL). The organic layer was dried over MgSO$_4$, filtered, evaporated under vacuum. The residue was subjected to silica gel chromatography eluting with 40% EtOAc in Hexane to give the product 51.3 (112 mg, 81% yield). $^1$H NMR (CD$_3$Cl, 300 MHz) δ 1.32 (s, 3H), 1.51 (s, 3H), 2.47 (s, 1H), 2.54-2.59 (m, 1H), 3.67 (dd, J=3.6, 12.0 Hz, 1H), 3.96 (dd, J=2.1, 12.3 Hz, 1H), 4.08-4.14 (m, 1H), 4.46 (dd, J=7.2, 11.4 Hz, 1H), 4.60 (dd, J=7.2, 11.4 Hz, 1H), 4.78 (t, J=3.9 Hz, 1H), 5.85 (d, J=3.6 Hz, 1H), 7.40-7.57 (m, 3H), 8.00-8.04 (m, 2H). LRMS (ESI) MH$^+$ C$_{16}$H$_{20}$O$_6$ requires 309.1. Found 309.3.

Compound 51.4 4.3 g of 51.3 was dissolved in DMSO (80 mL), followed by addition of DCC (4.3 g) and pyridine trifluoroacetate(0.68 g). The reaction mixture was at RT overnight. The white solid generated in the reaction was then filtered to give the clear alderhyde solution. Potassium tert-butoxide (28 mL) was added to the solution of tetraethyl methylenediphosphonate (7 mL) in THF (50 mL) at 0° C. through dropping funnel slowly. The above solution was then added to the alderhyde solution via dropping funnel slowly at 0° C. The reaction mixture was stirred for 1 h before quenching with brine (30 mL). The quenched solution was extracted with EtOAc (2×40 mL), washed with sat. NaHCO$_3$ solution (30 mL) and brine (30 mL). The organic layer was dried over MgSO$_4$, filtered, evaporated under vacuum. The residue was subjected to silica gel chromatography eluting with 80% EtOAc in Hexane to give the product 51.4 (3.2 g, 52% yield). $^1$H NMR (CD$_3$Cl, 300 MHz) δ 1.24-1.30 (m, 6H), 1.35 (s, 3H), 1.54 (s, 3H), 2.28-2.37 (m, 1H), 3.99-4.08 (m, 4H), 4.42 (dd, J=6.9, 11.4 Hz, 1H), 4.56-4.59 (m, 1H), 4.66 (dd, J=7.2, 11.4 Hz, 1H), 4.50 (t, J=4.5 Hz, 1H), 5.93 (d, J=3.6 Hz, 1H), 6.08-6.15 (m, 1H), 6.78-6.93 (m, 1H), 7.44-7.60 (m, 3H), 8.04-8.07 (m, 2H). LRMS (ESI) MH$^+$ C$_{21}$H$_{29}$O$_8$P requires 441.2. Found 441.1.

Compound 51.5 Compound 51.4 (3.1 g) was dissolved in water (5 mL) and treated with TFA (5 mL). The reaction mixture was stirred at 40° C. overnight. The solvent was evaporated under vacuum and the residue was used in next step without purification.

Compound 51.6 Compound 51.5 (crude, 1.7 g) was dissolved in DCM (50 mL) and treated with Et$_3$N (2.38 mL), DMAP (0.26 g) and BzCl (2.04 mL). The reaction mixture was stirred for 3 h before quenching with MeOH (10 mL). The solution was diluted with DCM (20 mL) and washed with brine (20 mL). The organic layer was dried over MgSO$_4$, filtered, evaporated under vacuum. The residue was subjected to silica gel chromatography eluting with 65% EtOAc in Hexane to give the product 51.6 (2.6 g, 84% yield). $^1$H NMR (CD$_3$Cl, 300 MHz) δ 1.24-1.30 (m, 6H), 3.00-3.20 (m, 1H), 3.88-4.18 (m, 4H), 4.32 (dd, J=6.9, 11.4 Hz, 1H), 4.66-4.69 (m, 1H), 4.73 (dd, J=7.2, 11.4 Hz, 1H), 4.75 (t, J=4.5 Hz, 1H), 5.98 (d, J=3.6 Hz, 1H), 6.06-6.13 (m, 1H), 6.82-6.94 (m, 1H), 7.42-7.62 (m, 9H), 7.85-8.17 (m, 6H). LRMS (ESI) MH$^+$ C$_{32}$H$_{33}$O$_{10}$P requires 608.2. Found 608.1.

Compound 51.7 Compound 51.6 (460 mg) was dissolved in CH$_3$CN (15 mL) and treated with Adenine (153 mg) and SnCl$_4$ (0.14 mL). The reaction mixture was stirred for 10 h at 50° C. and cooled to RT. NaHCO$_3$ (2 g) and water (2 mL) was added to the solution and stirred for 4 h. The mixture was then filtered, concentrated and dissolved in EtOAc (30 mL). The solution was dried over MgSO$_4$, filtered, evaporated under vacuum. The residue was subjected to silica gel chromatography eluting with 10% EtOH in EtOAc to give the product 51.7 (260 mg, 55% yield). $^1$H NMR (CD$_3$CN, 300 MHz) δ 1.22-1.28 (m, 6H), 3.67-3.73 (m, 1H), 3.96-4.04 (m, 4H), 4.62 (dd, J=6.6, 11.4 Hz, 1H), 4.76 (dd, J=6.6, 11.4 Hz, 1H), 5.00-5.03 (m, 1H), 6.01-6.13 (m, 1H), 6.25 (d, J=6.6 Hz, 1H), 6.35 (d, J=1.8 Hz, 1H), 6.91-7.06 (m, 1H), 7.47-7.70 (m, 6H), 8.00-8.09 (m, 5H), 8.25 (s, 1H). LRMS (ESI) MH$^+$ C$_{30}$H$_{32}$N$_5$O$_8$P requires 621.2. Found 621.1.

Compound 51.8 Compound 51.7 was dissolved in CH$_3$CN (2 mL) and treated with 2,6-lutidine (47A) and TMSBr (0.26 mL). The reaction mixture was stirred at RT for 2 h and then quenched with 1N NH$_4$OH (3 mL). The solvent was evaporated under vacuum and the residue was purified with prep HPLC to give the product 51.8 (64 mg, 84%). $^1$H NMR (CD$_3$OD, 300 MHz) δ 3.42-3.53 (m, 1H), 3.84-3.91 (m, 1H), 4.60-4.65 (m, 2H), 6.03-6.26 (m, 2H), 6.30 (s, 1H), 6.53-6.67 (m, 1H), 7.34-7.54 (m, 6H), 7.89-7.99 (m, 4H), 8.17 (s, 1H), 8.31 (s, 1H). LRMS (ESI) MH$^+$ C$_{26}$H$_{24}$N$_5$O$_8$P requires 565.1. Found 565.1.

Compound 51.9 Compound 51.8 (61 mg) was dissolved in 7N NH$_3$ in MeOH (15 mL) and stirred at 50° C. overnight. The solvent was evaporated and the residue purified with prep HPLC to give product 9 (33 mg, 86%). $^1$H NMR (D$_2$O, 300 MHz) δ 2.44-2.47 (m, 1H), 3.52 (s, 1H), 3.66 (dd, J=5.7, 11.1 Hz, 1H), 3.81 (dd, J=7.8, 11.1 Hz, 1H), 4.55-4.60 (m, 1H), 4.72 (d, J=5.1 Hz, 1H), 5.93 (t, J=17.1 Hz, 1H), 6.03 (s, 1H), 6.30-6.44 (m, 1H), 8.11 (s, 2H). LRMS (ESI) MH$^+$ C$_{12}$H$_{16}$N$_5$O$_6$P requires 357.1. Found 357.2

Diphosphophosphonate 51.10 Compound 51.10 (14 mg, 46% yield) was synthesized from compound 51.9 (9.5 mg) using the procedure described for the preparation of diphosphophosphonate 6.8. $^1$HNMR (300 MHz, D$_2$O) δ 2.41-2.42 (m, 1H), 2.72-2.80 (m, 1H), 3.20-3.27 (m, 1H), 3.64 (dd, J=5.4, 11.7 Hz, 1H), 3.75 (dd, J=7.8, 11.7 Hz, 1H), 5.97-6.09 (m, 2H), 6.37-6.52 (m, 1H), 8.07 (s, 1H), 8.14 (s, 1H). LRMS [M−H]$^-$ C$_{12}$H$_{18}$N$_5$O$_{12}$P$_3$ requires 516.02. Found 516.08.

Example 24

Synthetic Scheme 52

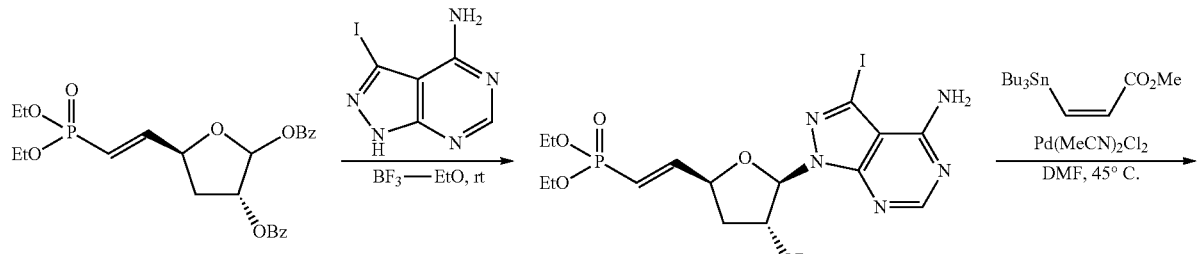

9.8         52.1

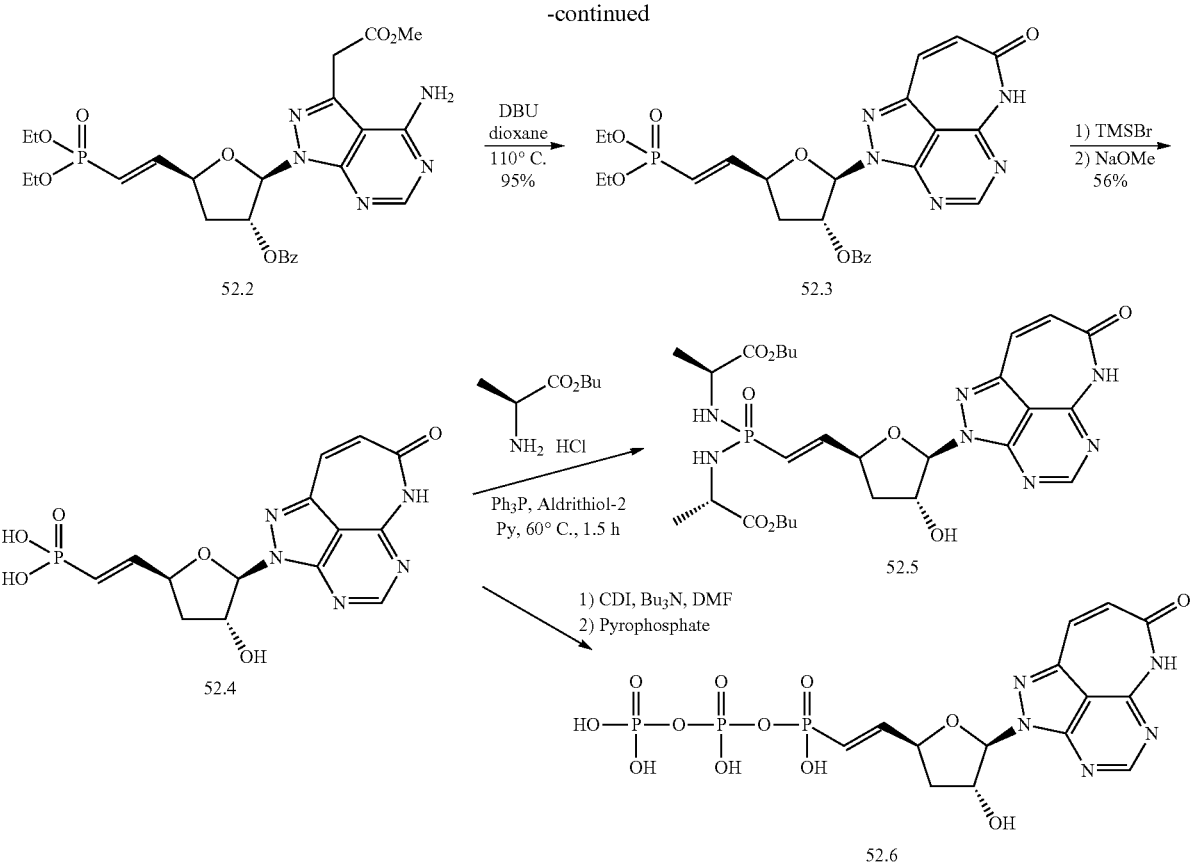

-continued

Compound 52.1

Compound 9.8 (1355 mg, 2.85 mmol) was dissolved in anhydrous $CH_3CN$ (25 mL), then treated with 7-deaza-7-iodo-8-aza-adenine (745 mg, 2.85 mmol) and $BF_3 \cdot OEt_2$ (2022 mg, 14.25 mmol). The mixture was stirred for 16 h, and concentrated under reduced pressure. The residue was dissolved in ethyl acetate and washed with saturated $NaHCO_3$ and Brine. The organic layer was separated, dried over $MgSO_4$, filtered and concentrated under reduced pressure. The residue was purified by a silica gel column chromatography eluting with 0-5% methanol in ethyl acetate to give compound 52.1 (910 mg, 52% yield).

Compound 52.2

To a solution of compound 52.1 (910 mg, 1.48 mmol) and methyl (Z)-3-tributylstannyl-acrylate (750 mg, 2.0 mmol) in DMF (10 mL) was added $Pd(MeCN)_2Cl_2$ (21 mg, 0.081 mmol) under argon. The reaction mixture was stirred at 45° C. for 20 h, then diluted with ethyl acetate and washed with NaHCO3 and brine. The organic phase was dried over $MgSO_4$, filtered and concentrated under reduced pressure. The residue was purified by a silica gel column chromatography eluting with 0-5% methanol in ethyl acetate to give compound 52.2 (705 mg, 83% yield).

Compound 52.3

Compound 52.2 (695 mg, 1.22 mmol) was dissolved in anhydrous dioxane (40 mL) and treated with DBU (185 mg, 1.22 mmol). The solution was stirred at 110° C. for 0.5 h, then cooled to 0° C. and treated with citric acid (10% water solution, 5 mL). The mixture was concentrated under reduced pressure. The residue was partitioned between ethyl acetate and water. The organic layer was separeady, dried over $MgSO_4$, filtered and concentrated under reduced pressure.

The residue was subjected to a silica gel column chromatography eluting with 0-5% methanol in ethyl acetate to give compound 52.3 (635 mg, 95% yield).

Compound 52.4

Compound 52.3 (630 mg, 1.16 mmol) was dissovled in anhydrous $CH_3CN$ (20 mL) and treated with 2,6-litidine (420 mg, 3.92 mmol) and TMSBr (1800 mg, 11.8 mmol). The solution was stirred at room temperature for 3 h, and then concentrated under reduced pressure. The residue was treated with diluted $NH_4OH$ and concentrated under reduced pressure, then dried in high vacuum. The residues was dissolved in anhydrous MeOH (10 mL) and treated with NaOMe (4.3 N, 1.5 mL). The solution was stirred for 0.5 h, and quenched with HCl (1N, 7 mL). The mixture was concentrated and purified by a reverse phase HPLC to give compound 52.4 (250 mg, 56% yield). $^1$H NMR (DMSO-d6, 300 MHz): δ 2.2 (m, 1H), 2.4 (m, 1H), 4.6 (m, 1H), 4.9 (m, 1H), 5.8 (dd, 1H, J1=J2=17.4), 6.22 (s, 1H), 6.32 (d, 1H, J=12.3), 6.4 (m, 1H), 7.35 (d, 1H, J=12), 8.6 (s, 1H), 11.6 (brs, 1H). $^{31}$PNMR: 11.88 ppm. LRMS [M+1]: 380.0.

Bis-amidate prodrug compound 52.5

Compound 52.5 (9 mg, 36% yield) was synthesized from compound 52.4 (15 mg, 0.0396 mmol) using the same procedure for the preparation of compound 9.11. $^1$H NMR (CD$_3$OD, 300 MHz): δ 0.90-0.98 (m, 6H), 1.30-1.35 (m, 10H), 1.54-1.64 (m, 4H), 2.35 (m, 1H), 2.6 (m, 1H), 3.85 (m, 2H), 4.08 (m, 4H), 4.8 (d, 1H, J=4.5), 5.9 (m, 1H), 6.4 (m, 3H), 6.7 (m, 1H), 7.3 (d, 1H, J=12), 8.56 (s, 1H). $^{31}$PNMR: 18.90 ppm. LRMS [M+1]: 634.0.

Diphosphophosphonate 52.6.

Compound 52.6 (12 mg, 32% yield) was synthesized from compound 52.4 (15 mg, 0.0396 mmol) using the procedure described for the preparation of the diphosphophosphonate of compound 6.8. ¹H NMR (300 MHz, D$_2$O): δ 2.3 (m, 1H), 2.5 (m, 1H), 4.8 (m, 1H), 4.9 (m, 1H), 5.9 (m, 1H), 6.2-6.5 (m, 3H), 7.25 (d, 1H, J=12), 8.4 (s, 1H). ³¹PNMR: 4.64, −10.6, −22.9. LRMS [M+1]: 539.9.

Example 25 solved in EtOAc. The organic phase was washed with saturated NaHCO$_3$, brine, dried over MgSO$_4$, filtered and concentrated under reduced pressure. The residue was subjected to a silica gel column chromatography eluting with 0-10% MeOH in DCM to give compound 53.1 (183 mg, 73% yield).

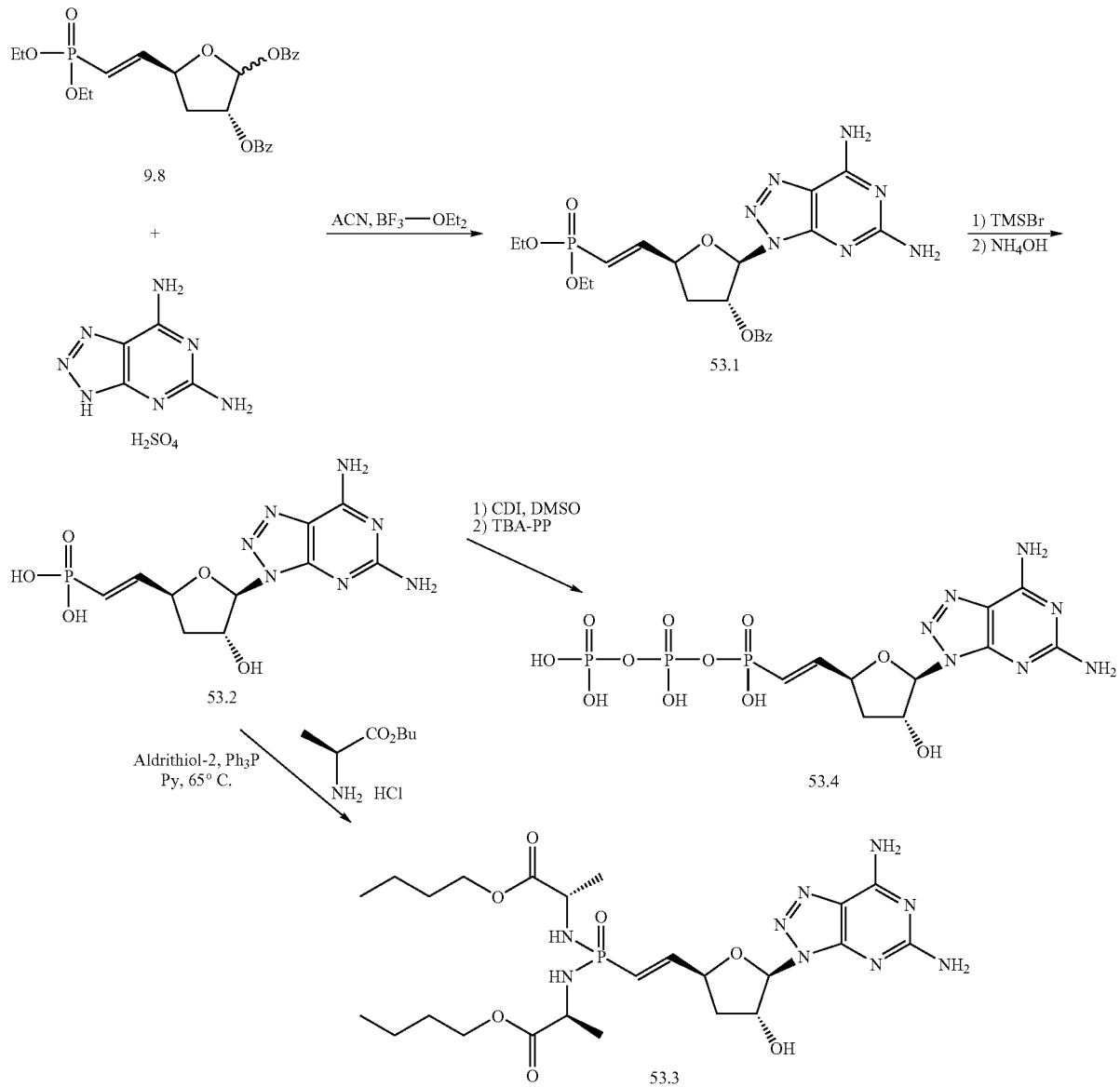

Synthetic Scheme 53

Benzoic acid 2-(5,7-diamino-[1,2,3]triazolo[4,5-d]pyrimidin-3-yl)-5-[2-(diethoxy-phosphoryl)-vinyl]-tetrahydro-furan-3-yl ester (53.1)

Compound 9.8 (237 mg, 0.5 mmol) was dissolved in anhydrous CH$_3$CN (10 mL) and treated with 8-aza-2,6-diaminopurine sulfate salt (125 mg, 0.5 mmol). Boron trifluoride-diethyl etherate (250 uL, 3 mmol) was added to the mixture which was then stirred at rt for 16 h. The mixture was concentrated under reduced pressure, and the residue was dis- {2-[5-(5,7-Diamino-[1,2,3]triazolo[4,5-d]pyrimidin-3-yl)-4-hydroxy-tetrahydro-furan-2-yl]-vinyl}-phosphonic acid (53.2)

Compound 53.1 (183 mg, 0.36 mmol) was dissolved in 7 mL of anhydrous CH$_3$CN and treated with TMS—Br (240 uL, 1.82 mmol). The solution was stirred at rt for 6 hrs. Added more TMS—Br (100 uL, 0.75 mmol) and stirred at room temperature for 16 hrs. Concentrated the reaction under reduced pressure. The residue was dissolved in methanol and added aqueous NH$_4$OH solution, stirred for another 3 hrs and concentrated under reduced pressure. The residue was subjected to a reverse phase HPLC to give compound 53.2 (110 mg, 81% yield). $^1$H NMR (D$_2$O, 300 MHz): δ 6.32 (m, 1H), 6.07 (s, 1H), 5.83 (m, 1H), 4.96 (m, 1H), 4.73 (m, 1H), 2.27 (m, 2H). $^{31}$P NMR: 11.17 ppm LC/MS: C$_{10}$H$_{14}$N$_7$O$_5$P Exact Mass: 343.08. Found: [M–H]$^-$ 342.0, [M+H]$^+$ 344.1.

Bisamidate prodrug (53.3)

Compound 53.3 (21 mg, 64% yield) was synthesized from compound 53.2 (20 mg, 0.055 mmol) using the procedure described for 52.5. $^1$H NMR (CD$_3$OD, 300 MHz): δ 6.77 (m, 1H), 6.15 (s, 1H), 6.01 (m, 1H), 5.07 (m, 1H), 4.71 (m, 1H), 4.06 (m, 4H), 3.89 (m, 2H), 2.55 (m, 1H), 2.31 (m, 1H), 1.59 (m, 4H), 1.35 (m, 10H), 0.92 (m, 6H). $^{31}$PNMR: 18.78 ppm. LC/MS: C$_{24}$H$_{40}$N$_9$O$_7$P Exact Mass: 597.28 Found: [M–H]$^-$ 596.0, [M+H]$^+$ 598.2.

Diphosphophosphonate (53.4)

Compound 53.4 (14.8 mg, 31% yield) was synthesized from compound 53.2 (30 mg, 0.083 mmol) using the procedure described for 6.8. $^1$HNMR (D$_2$O, 300 MHz): δ 6.49 (m, 1H), 6.12 (s, 1H), 6.06 (m, 1H), 5.03 (m, 1H), 2.32 (m, 2H). $^{31}$P NMR: 4.32 ppm, –5.46 ppm, –21.52 ppm. LC/MS: C$_{10}$H$_{16}$N$_7$O$_{11}$P$_3$ Exact Mass: 503.01. Found: [M–H]$^-$ 501.9, [M+H]$^+$ 504.0.

Example 26

Synthetic Scheme 54

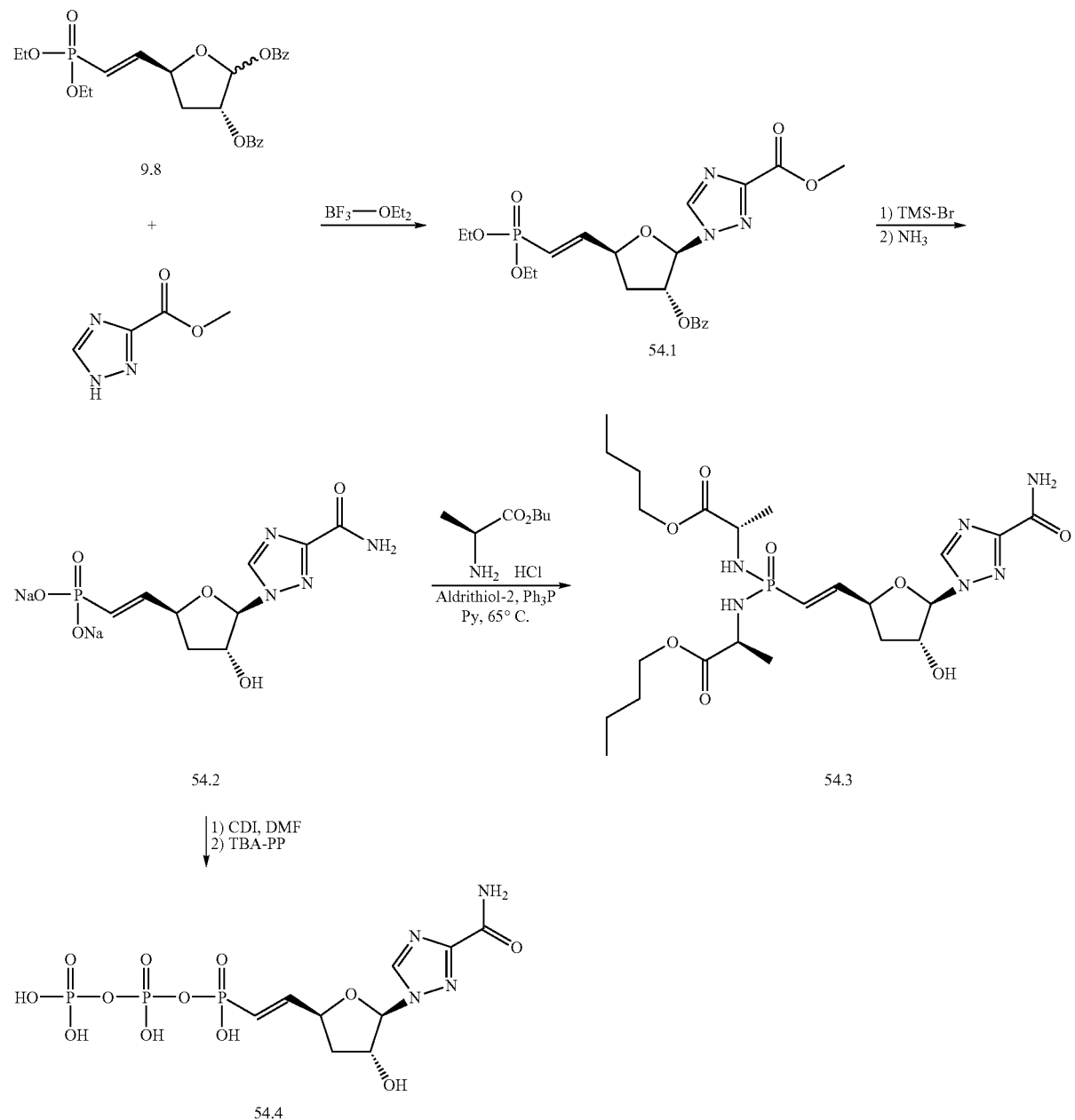

1-{3-Benzoyloxy-5-[2-(diethoxy-phosphoryl)-vinyl]-tetrahydro-furan-2-yl}-1H-[1,2,4]triazole-3-carboxylic acid methyl ester (54.1)

Compound 9.8 (474 mg, 1 mmol) was dissolved in anhydrous $CH_3CN$ (10 mL) and treated with 1,2,4-triazole-3-methyl carboxylate (191 mg, 1.5 mmol). Boron trifluoride-diethyl etherate (380 uL, 3 mmol) was added dropwise to the mixture which was then stirred at rt for 16 hrs. Added more Boron trifluoride-diethyl etherate (380 uL, 3 mmol) and stirred 10 hrs at rt. Added more Boron trifluoride-diethyl etherate (380 uL, 3 mmol) and stirred 14 hrs at rt. The mixture was concentrated under reduced pressure, and the residue was dissolved in EtOAc. The organic phase was washed with saturated $NaHCO_3$, brine, dried over $MgSO_4$, filtered and concentrated under reduced pressure. The residue was purified with reverse phase HPLC to give compound 54.1 (244 mg, 51% yield).

{2-[5-(3-Carbamoyl[1,2,4]triazol-1-yl)-4-hydroxy-tetrahydro-furan-2-yl]-vinyl}-phosphonic acid (460.2)

Compound 54.1 (244 mg, 0.51 mmol) was dissolved in 10 mL of anhydrous $CH_3CN$ and treated with TMS—Br (336 uL, 2.55 mmol). The solution was stirred at rt for 6 hrs. Stored reaction at −20° C. overnight. Stirred at rt for additional 3 hrs. Concentrated the reaction under reduced pressure. The residue was dissolved in water and $CH_3CN$ and then again concentrated under reduced pressure. The residue was mixed with 30 mL of 7N ammonia in methanol and stirred at rt for 16 hrs. Added another 20 mL of 7N ammonia in methanol and stirred at rt for 16 hrs. Concentrated under reduced pressure. Dissolved in aqueous $NaHCO_3$ solution and concentrated under reduced pressure. The residue was subjected to a reverse phase HPLC to give compound 54.2 (150 mg, 84% yield). $^1H$ NMR ($D_2O$, 300 MHz): δ 6.56 (s, 1H), 6.11 (m, 1H), 5.99 (m, 1H), 5.94 (s, 1H), 4.89 (m, 1H), 2.18 (m, 2H). $^{31}P$ NMR: 9.07 ppm. LC/MS: $C_9H_{13}N_4O_6P$ Exact Mass: 304.20. Found: $[M−H]^−$ 303.0, $[M+H]^+$ 305.0.

Bisamidate prodrug (54.3)

Compound 54.3 (15 mg, 38% yield) was synthesized from compound 54.2 (25 mg, 0.07 mmol) using the procedure described for 52.5. $^1H$ NMR ($CDCl_3$, 300 MHz): δ 8.44 (m, 1H), 7.44 (s, 1H), 6.70 (m, 2H), 6.03 (m, 2H), 5.59 (bs, 1H), 5.01 (m, 1H), 4.70 (m, 1H), 4.10 (m, 6H), 3.74 (m, 1H), 3.52 (m, 1H), 2.22 (m, 2H), 1.56 (m, 4H), 1.37 (m, 10H), 0.92 (m, 6H). $^{31}P$ NMR: 16.77 ppm. LC/MS: $C_{23}H_{39}N_6O_8P$ Exact Mass: 558.26 Found: $[(M+HOAc)−H]^−$ 617.0, $[M+H]^+$ 559.0.

Diphosphophosphonate (54.4)

Compound 54.4 (6.5 mg, 19% yield) was synthesized from compound 54.2 (13 mg, 0.04 mmol) using the procedure for 6.8. $^1H$ NMR ($D_2O$, 300 MHz): δ 8.57 (s, 1H), 6.46 (m, 1H), 6.07 (m, 1H), 6.95 (s, 1H), 4.98 (m, 1H), 3.07 (m, 18h), 2.25 (m, 2H) 1.14 (m, 27H). $^{31}P$ NMR: 4.16 ppm, −7.97 ppm, −23.09 ppm. LC/MS: $C_9H_{15}N_4O_{12}P_3$ Exact Mass: 464.16. Found: $[M−H]^−$ 462.9, $[M+H]^+$ 464.9.

Example 27

Synthesis Scheme 55

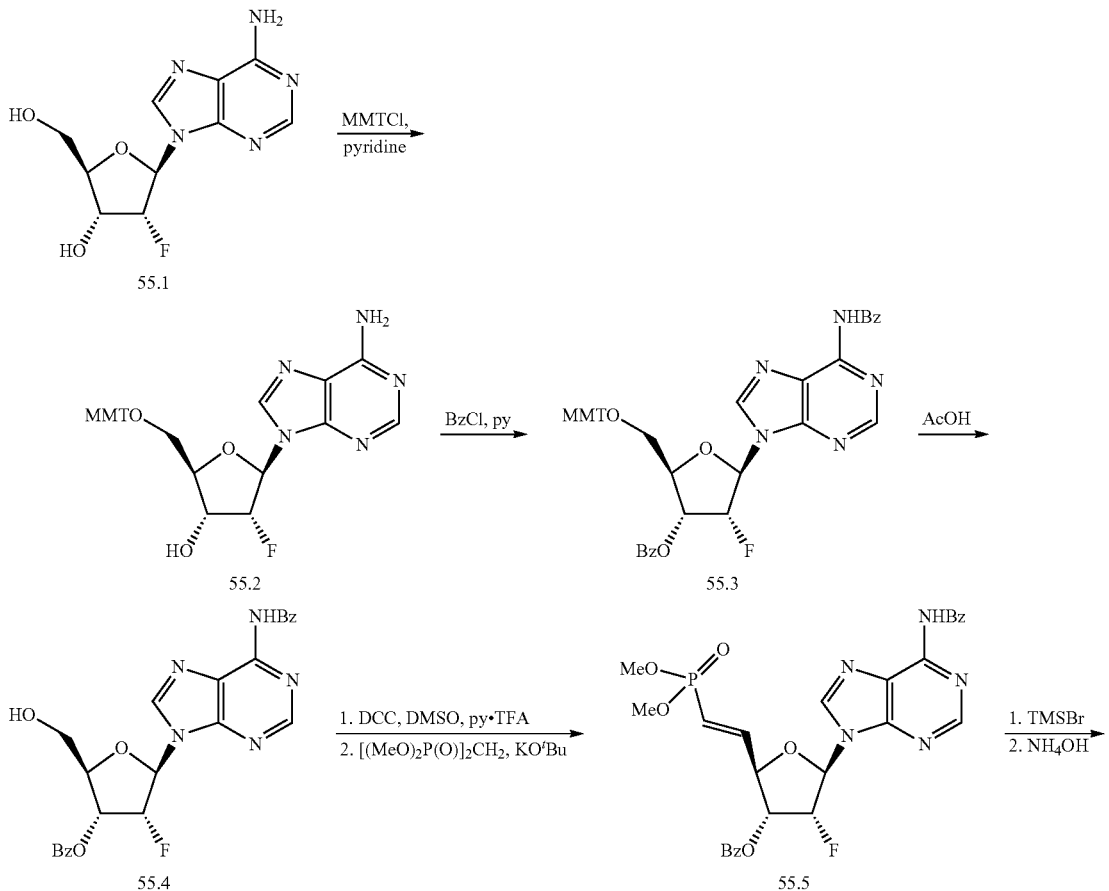

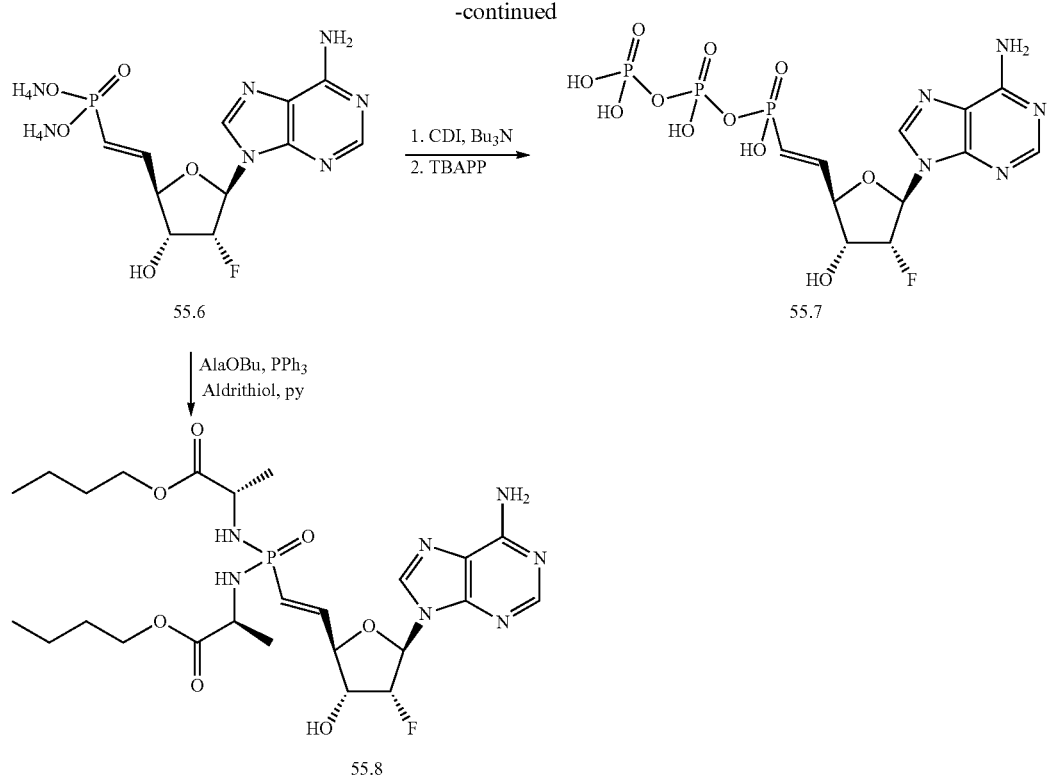

5-(6-Amino-purin-9-yl)-4-fluoro-2-trityloxymethyl-tetrahydro-furan-3-ol (55.2)

Compound 55.1 (4.9 g, 18.2 mmol) was dissolved in pyridine (180 mL) and treated with MMTCl (6.18 g, 20 mmol), which afforded 55.2 after stirring overnight. The mixture was used in pyridine without purification for the next reaction.

Benzoic acid 5-(6-benzoylamino-purin-9-yl)-4-fluoro-2-trityloxymethyl-tetrahydro-furan-3-yl ester (55.3)

Compound 55.2 (18.2 mmol) in pyridine (180 mL) was treated with BzCl (6.33 mL, 54.6 mmol) and stirred overnight. The solvent was removed in vacuo and the solid was dissolved in EtOAc (100 mL) and washed with $H_2O$ (2×50 mL). The solution was dried over $MgSO_4$, filtered, and subjected to Combiflash purification ($SiO_2$, 330 g, 0-100% EtOAc-hexanes gradient) which afforded 55.3 as a white solid (13.0 g, 96%, two steps).

Benzoic acid 5-(6-benzoylamino-purin-9-yl)-4-fluoro-2-hydroxymethyl-tetrahydro-furan-3-yl ester (55.4)

Compound 55.3 (13.0 g, 17.4 mmol) was treated with 80% AcOH (100 mL) and stirred at 40° C. for 5 h. The solvent was removed in vacuo and the mixture was subjected to Combiflash purification ($SiO_2$, 330 g, 0-100% EtOAc-hexanes gradient) which afforded 55.4 as a white solid (4.72 g, 45%).

Benzoic acid 5-(6-benzoylamino-purin-9-yl)-2-[2-(dimethoxy-phosphoryl)-vinyl]-4-fluoro-tetrahydro-furan-3-yl ester (55.5)

Compound 55.4 (2.59 g, 4.45 mmol) in anhydrous DMSO (40 mL) was treated with TFA•Pyridine (860 mg, 4.45 mmol) and DCC (1.38 g, 6.68 mmol). The mixture was stirred overnight, cooled to 0° C., and treated with a premixed solution of $[(MeO)_2P(O)]_2CH_2$ (1.32 g, 5.70 mmol) and 1 M $KO^tBu$ (6.90 mL, 6.90 mmol) in THF (40 mL). The mixture was stirred for 5 min and then warmed to r.t. and stirred for an additional 1.5 h. The mixture was cooled to 0° C., treated with saturated $NaHCO_3$ (25 mL), and diluted with EtOAc (100 mL). The solution was filtered, and the organic layer was separated and washed with $NaHCO_3$ (2×25 mL) and brine (25 mL). The solution was dried over $MgSO_4$, filtered and concentrated in vacuo. The residue was subjected to Combiflash purification ($SiO_2$, 120 g, 0-100% EtOAc-hexanes gradient) which afforded 55.5 as a white solid (900 mg, 30%).

{2-[5-(6-Benzoylamino-purin-9-yl)-4-fluoro-3-hydroxy-tetrahydro-furan-2-yl]-vinyl}-phosphonic acid bis-ammonium salt (55.6)

Compound 55.5 (92 mg, 0.16 mmol) in $CH_3CN$ (3.0 mL) was treated with 2,6-lutidine (183 μL, 1.6 mmol) and TMSBr (102 μL, 0.79 mmol) at 0° C. for 30 min. The mixture was warmed to r.t. and stirred for 30 min. The mixture was cooled to −40° C. and treated with triethylamine (446 μL, 3.2 mmol) in MeOH (2 mL). The mixture was warmed to r.t. and concentrated in vacuo. The residue was dissolved in concentrated $NH_4OH$ (1.5 mL) and warmed to 60° C. The solution was stirred for 2 h and then concentrated in vacuo. The residue was subjected to reverse phase HPLC eluting with 5-50% $CH_3CN$-water gradient to give 55.6 (26 mg, 48% yield): white solid (bis-ammonium salt); $^1H$ NMR ($D_2O$, 300 MHz) 8.01 (s, 1H), 7.96 (s, 1H), 6.24 (m, 2H), 6.01 (app t, J=16 Hz, 1H), 5.23 (d, J=52.2 Hz, 1H), 4.44 (m, 2H), 4.31 (m, 1H); $^{31}P$ NMR ($D_2O$ 121.4 MHz) 7.7; $^{19}F$ NMR ($D_2O$, 282 MHz) −203 (m, 1F); MS (ESI) m/z 345 $[M+H]^+$.

Diphosphophosphonate (55.7)

Compound 55.6 (12 mg, 0.035 mmol) in DMF (750 μL) was treated with tributylamine (25 μL, 0.10 mmol) followed by carbonyldiimidazole (56 mg, 0.34 mmol) and the mixture was stirred for 0.5 h. Tributyl ammonium pyrophosphate (TBAPP, 95 mg, 0.173 mmol) in DMF (0.4 mL) was added and the reaction mixture stirred for 2 h. The solvent was removed in vacuo and the crude product was purified by ion exchange HPLC (0-40% TEAB) to provide 55.7 (7.1 mg, 43% yield): white solid (tetra triethylammonium salt); $^1$H NMR (D$_2$O, 300 MHz) 8.39 (br s, 1H), 8.13 (s, 1H), 8.08 (s, 1H), 6.47 (m, 1H), 6.20 (m, 2H), 5.28 (d, J=51.6 Hz, 1H), 4.61 (m, 3H); $^{31}$P NMR (D$_2$O 121.4 MHz) 3.27 (d, 1P), −8.90 (d, 1P), −21.6 (s, 1P); $^{19}$F NMR (D$_2$O, 282 MHz) −203 (m, 1F); MS (ESI) m/z 504 [M−H]$^+$.

Bis-amidate prodrug (55.8)

Compound 55.6 (9.7 mg, 0.028 mmol) and L-alanine butyl ester hydrochloride (AlaOBu, 51 mg, 0.28 mmol) in anhydrous pyridine (1 mL) was treated with a premixed solution of Aldrithiol (43 mg, 0.20 mmol) and PPh$_3$ (51 mg, 0.20 mmol) in pyridine (1 mL). The mixture was stirred at 60° C. for 4 h. The solvent was removed in vacuo and residue was subjected to Combiflash purification (SiO$_2$, 4 g) followed by reverse phase HPLC with 5-50% CH$_3$CN-water gradient to provide 55.8 (7.9 mg, 47% yield): white solid; $^1$H NMR (CD$_3$OD, 300 MHz) 8.20 (s, 1H), 8.17 (s, 1H), 6.75 (app t, J=5.1, 17.0 Hz, 1H), 6.28 (d, J=19.5 Hz, 1H), 6.10 (app t, J=5.1, 17.0 Hz, 1H), 5.23 (d, J=3.6, 52.2 Hz, 1H), 4.68 (m, 2H), 4.52 (m, 1H), 4.04 (m, 6H), 3.90 (m, 4H), 1.55 (m, 4H), 1.40 (m, 4H), 0.88 (m, 6H); $^{31}$P NMR (D$_2$O 121.4 MHz) 16.6; $^{19}$F NMR (D$_2$O, 282 MHz) −204 (m, 1F); MS (ESI) m/z 602 [M+H]$^+$.

Example 28

Synthesis Scheme 56

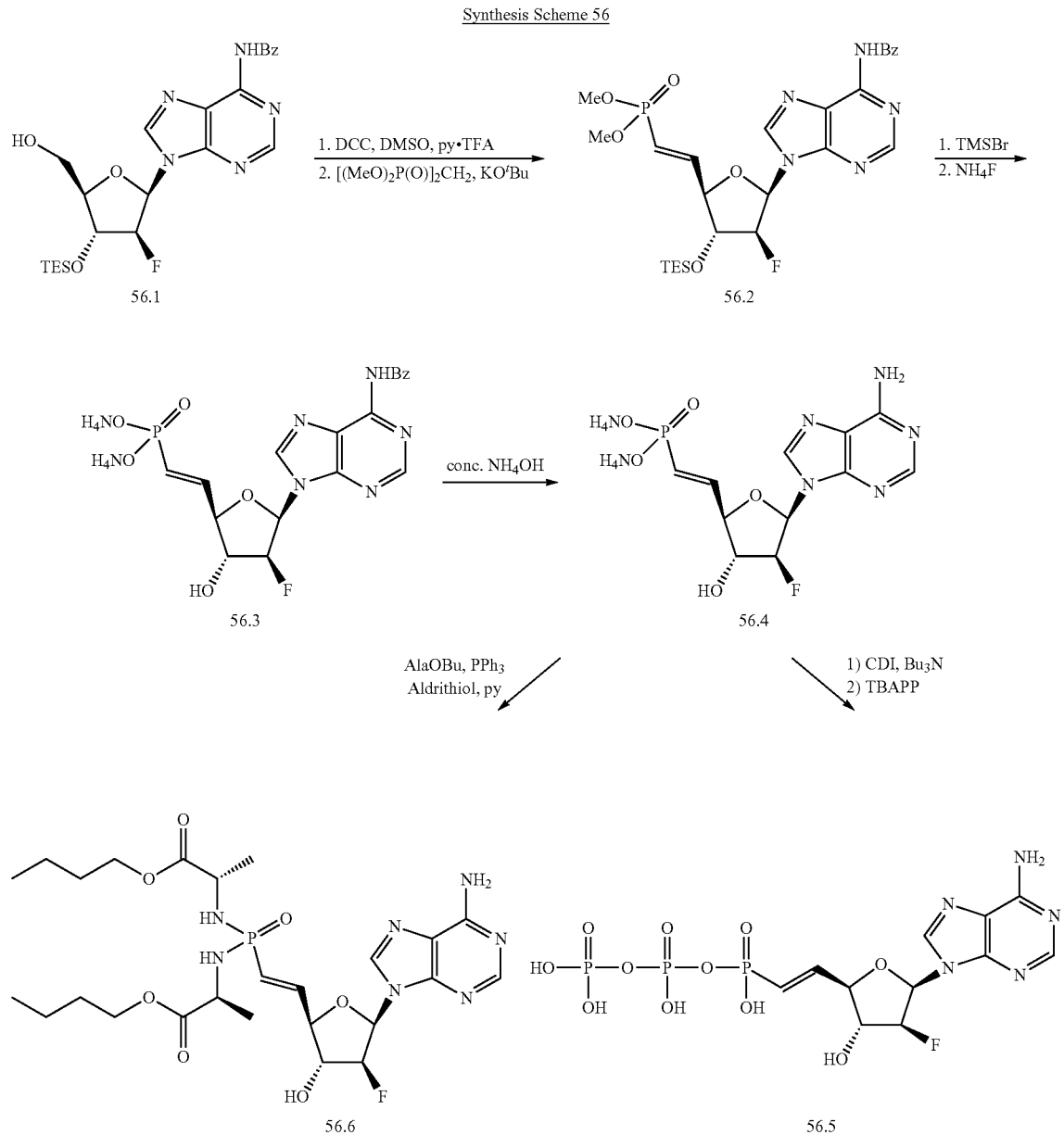

{2-[5-(6-Benzoylamino-purin-9-yl)-4-fluoro-3-triethylsilanyloxy-tetrahydro-furan-2-yl]-vinyl}-phosphonic acid dimethyl ester (56.2)

A similar procedure for the synthesis of 55.5 was followed for the preparation of 56.2 (338 mg, 23% yield).

{2-[5-(6-Benzoylamino-purin-9-yl)-4-fluoro-3-hydroxy-tetrahydro-furan-2-yl]-vinyl}-phosphonic acid bis ammonium salt (56.3)

Compound 56.2 (338 mg, 0.57 mmol) in $CH_3CN$ (6.0 mL) was treated with 2,6-lutidine (662 μL, 5.7 mmol) and TMSBr (368 μL, 2.9 mmol) at 0° C. for 30 min. The mixture was warmed to r.t. and stirred for 30 min. The mixture was cooled to −40° C. and treated with triethylamine (794 μL, 5.7 mmol) in MeOH (2 mL). The mixture was warmed to r.t. and concentrated in vacuo. The residue in DMF (2.0 mL) was treated with ammonium fluoride (1.06 g, 28.5 mmol) and heated to 80° C. for 5 h. The solvent was removed in vacuo and residue was subjected to reverse phase HPLC eluting with 5-50% $CH_3CN$-water gradient to give 56.3 (76 mg, 30% yield, 2 steps): white solid; $^1H$ NMR ($CD_3OD$, 300 MHz) 8.71 (s, 1H), 8.49 (s, 1H), 6.75 (d, J=8.1 Hz, 2H), 7.61 (app t, J=6.6 Hz, 1H), 7.52 (m, 2H), 6.71 (m, 2H), 6.15 (t, J=18.3 Hz, 1H), 5.17 (d, J=52.5 Hz, 1H), 4.50 (m, 2H); $^{31}P$ NMR ($D_2O$ 121.4 MHz) 12.2; $^{19}F$ NMR ($D_2O$, 282 MHz) −200 (m, 1F); MS (ESI) m/z 451 $[M+H]^+$.

{2-[5-(6-Amino-purin-9-yl)-4-fluoro-3-hydroxy-tetrahydro-furan-2-yl]-vinyl}-phosphonic acid bis ammonium salt (56.4)

Compound 56.3 (65 mg, 0.14 mmol) was dissolved in concentrated $NH_4OH$ (1.5 mL) and stirred for 24 h and then concentrated in vacuo. The residue was subjected to reverse phase HPLC eluting with 5-50% $CH_3CN$-water gradient to give 56.4 (52 mg, 93% yield): white solid (bis-ammonium salt); $^1H$ NMR ($D_2O$, 300 MHz) 8.11 (s, 1H), 7.89 (s, 1H), 6.20 (m, 2H), 5.86 (app t, J=16.0 Hz, 1H), 4.84 (d, J=52.8 Hz, 1H), 4.16 (m, 2H); $^{31}P$ NMR ($D_2O$ 121.4 MHz) 9.6; $^{19}F$ NMR ($D_2O$, 282 MHz) −195 (m, 1F); MS (ESI) m/z 346 $[M+H]^+$.

Diphosphophosphonate (56.5)

A similar procedure for the synthesis of 55.7 was followed for the preparation of 56.5 (4.3 mg, 58% yield): white solid (tetra triethylammonium salt); $^1H$ NMR ($D_2O$, 300 MHz): 8.29 (m, 1H), 8.13 (s, 1H), 6.45 (m, 2H), 6.20 (m, 2H), 5.29 (m, 1H) 4.51 (m, 1H). $^{31}P$ NMR: 3.6, −5.7, −21.7; MS (ESI) m/z 504 $[M-H]^-$; 506 $[M+H]^+$.

Bis-amidate prodrug (56.6)

A similar procedure for the synthesis of 56.8 was followed for the preparation of 56.6 (0.8 mg, 10% yield): white solid; $^1H$ NMR ($CD_3OD$, 300 MHz) 8.47 (s, 1H), 8.41 (s, 1H), 6.8 (m, 1H), 6.65 (d, J=18.9 Hz, 1H), 6.20 (app t, J=17.4 Hz, 1H), 5.19 (d, J=50.4 Hz, 1H), 4.32 (m, 2H), 4.04 (m, 6H), 3.90 (m, 4H), 1.55 (m, 4H), 1.40 (m, 4H), 0.88 (m, 6H); $^{31}P$ NMR ($D_2O$ 121.4 MHz) 18.3; MS (ESI) m/z 600 $[M+H]^+$.

Example 29

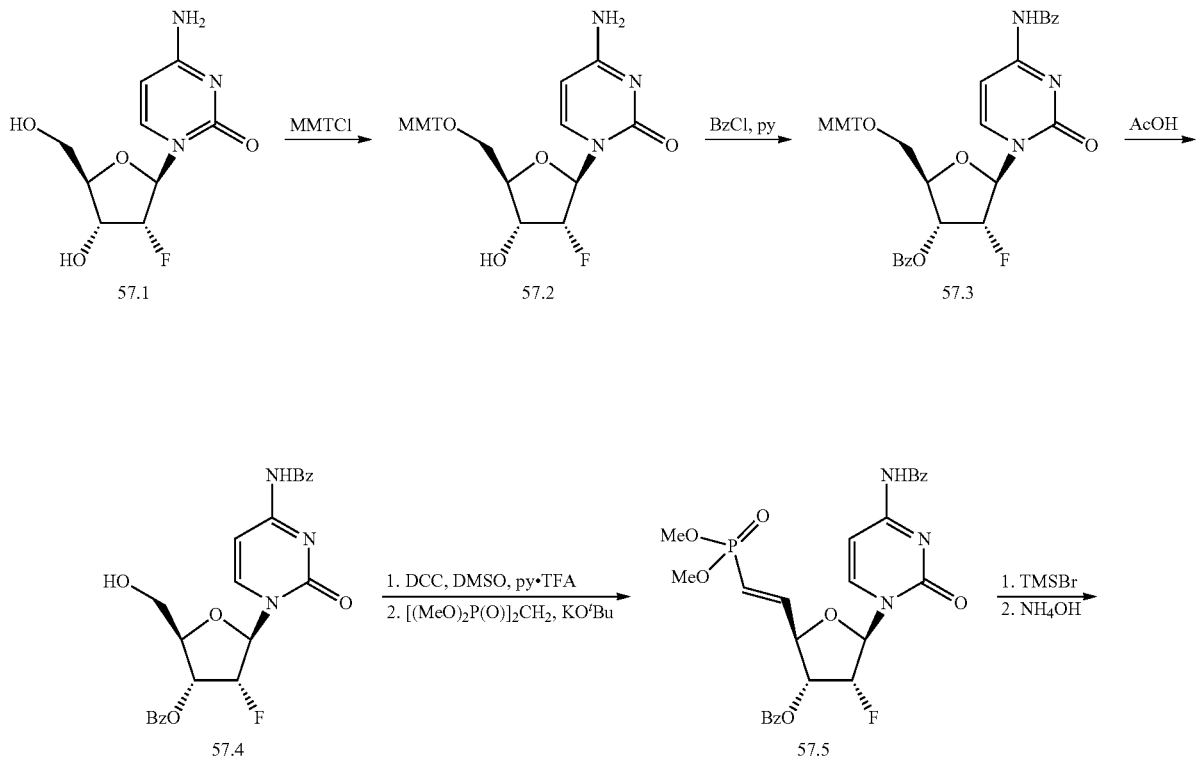

Synthesis Scheme 57

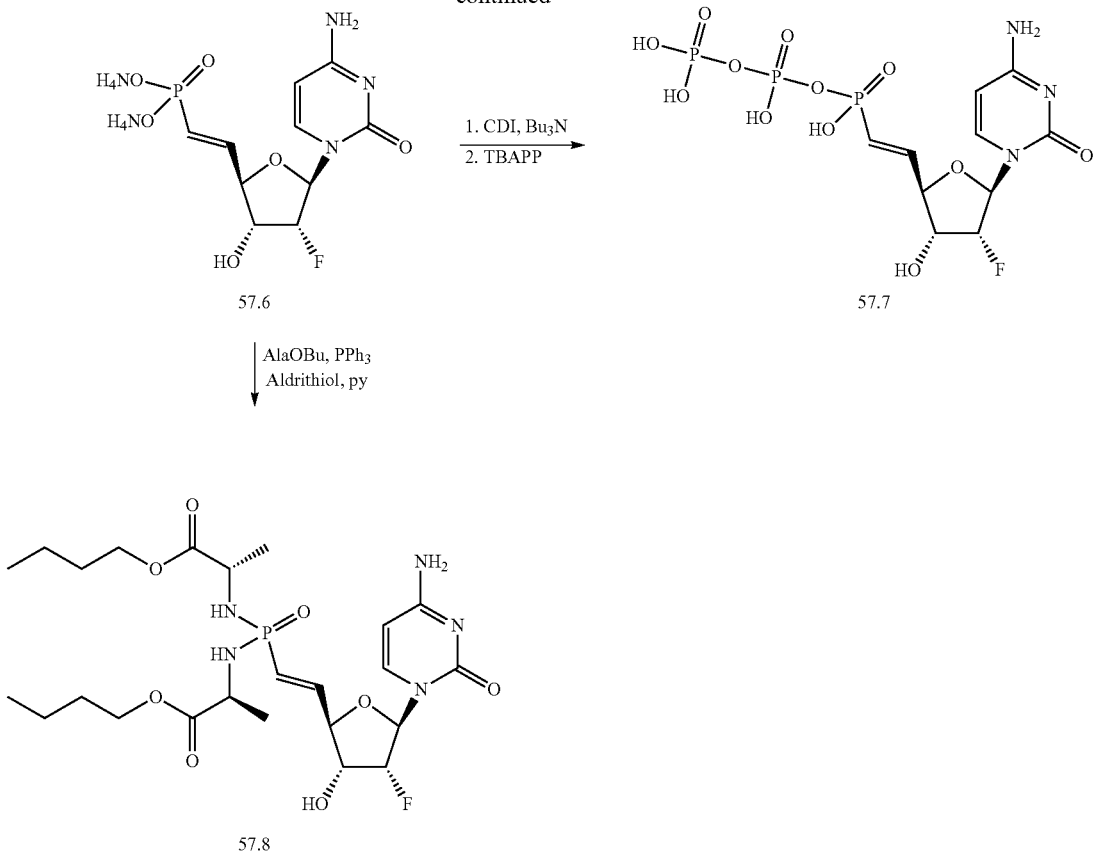

4-Amino-1-(3-fluoro-4-hydroxy-5-trityloxymethyl-tetrahydro-furan-2-yl)-1H-pyrimidin-2-one (57.2)

A similar procedure for the synthesis of 55.2 was followed for the preparation of 57.2.

Benzoic acid 5-(4-benzoylamino-2-oxo-2H-pyrimidin-1-yl)-4-fluoro-2-trityloxymethyl-tetrahydro-furan-3-yl ester (57.3)

A similar procedure for the synthesis of 55.3 was followed for the preparation of 57.3 (2.83 g, 91%).

Benzoic acid 5-(4-benzoylamino-2-oxo-2H-pyrimidin-1-yl)-4-fluoro-2-hydroxymethyl-tetrahydro-furan-3-yl ester (57.4)

A similar procedure for the synthesis of 55.4 was followed for the preparation of 57.4 (720 mg, 77%).

Benzoic acid 5-(4-benzoylamino-2-oxo-2H-pyrimidin-1-yl)-2-[2-(dimethoxy-phosphoryl)-vinyl]-4-fluoro-tetrahydro-furan-3-yl ester (57.5)

A similar procedure for the synthesis of 55.5 was followed for the preparation of 57.5 (214 mg, 24%, 2 steps).

{2-[5-(4-Amino-2-oxo-2H-pyrimidin-1-yl)-4-fluoro-3-hydroxy-tetrahydro-furan-2-yl]-vinyl}-phosphonic acid bis ammonium salt (57.6)

A similar procedure for the synthesis of 55.6 was followed for the preparation of 57.6 (88 mg, 72%, 2 steps): white solid (bis-ammonium salt); $^1$H NMR (D$_2$O, 300 MHz) 7.42 (d, J=7.8 Hz, 1H), 6.30 (app t, J=6.3, 18 Hz, 1H), 6.01 (app t, J=17.1 Hz, 1H), 5.83 (d, J=6.9 Hz, 1H), 5.73 (d, J=20.4 Hz, 1H), 4.94 (d, J=55.5 Hz, 1H), 4.33 (m, 1H), 4.04 (m, 1H); $^{31}$P NMR (D$_2$O 121.4 MHz) 10.5; $^{19}$F NMR (D$_2$O, 282 MHz) −200 (m, 1F); MS (ESI) m/z 320 [M−H]$^+$.

Diphosphophosphonate (57.7)

A similar procedure for the synthesis of 55.7 was followed for the preparation of 57.7: white solid (tetra triethylammonium salt); $^1$H NMR (D$_2$O, 300 MHz) 7.50 (m, 1H), 6.46 (m, 1H), 6.15 (m, 1H), 5.88 (m, 3H), 5.00 (m, 1H), 4.11 (m, 2H); $^{31}$P NMR (D$_2$O 121.4 MHz) 3.5 (d, 1P), −10.1 (d, 1P), −23.2 (t, 1P); MS (ESI) m/z 479 [M−H]$^+$.

Bis-amidate prodrug (57.8)

A similar procedure for the synthesis of 55.8 was followed for the preparation of 57.8 (13.7 mg, 49%): white solid; $^1$H NMR (CD$_3$OD, 300 MHz) 7.60 (d, J=7.5 Hz, 1H), 6.75 (app t, J=4.8, 18 Hz, 1H), 6.15 (app t, J=17.1 Hz, 1H), 5.91 (d, J=7.2 Hz, 1H), 5.84 (d, J=20.4 Hz, 1H), 5.04 (d, J=4.2, 54 Hz, 1H), 4.43 (m, 1H), 4.06 (m, 4H), 3.88 (m, 2H), 1.60 (m, 4H), 1.41 (m, 10H), 0.91 (m, 6H); $^{31}$P NMR (D$_2$O 121.4 MHz) 18.2; $^{19}$F NMR (D$_2$O, 282 MHz) −200 (m, 1F); MS (ESI) m/z 576 [M+H]$^+$.

Example 30
Synthesis Scheme 58
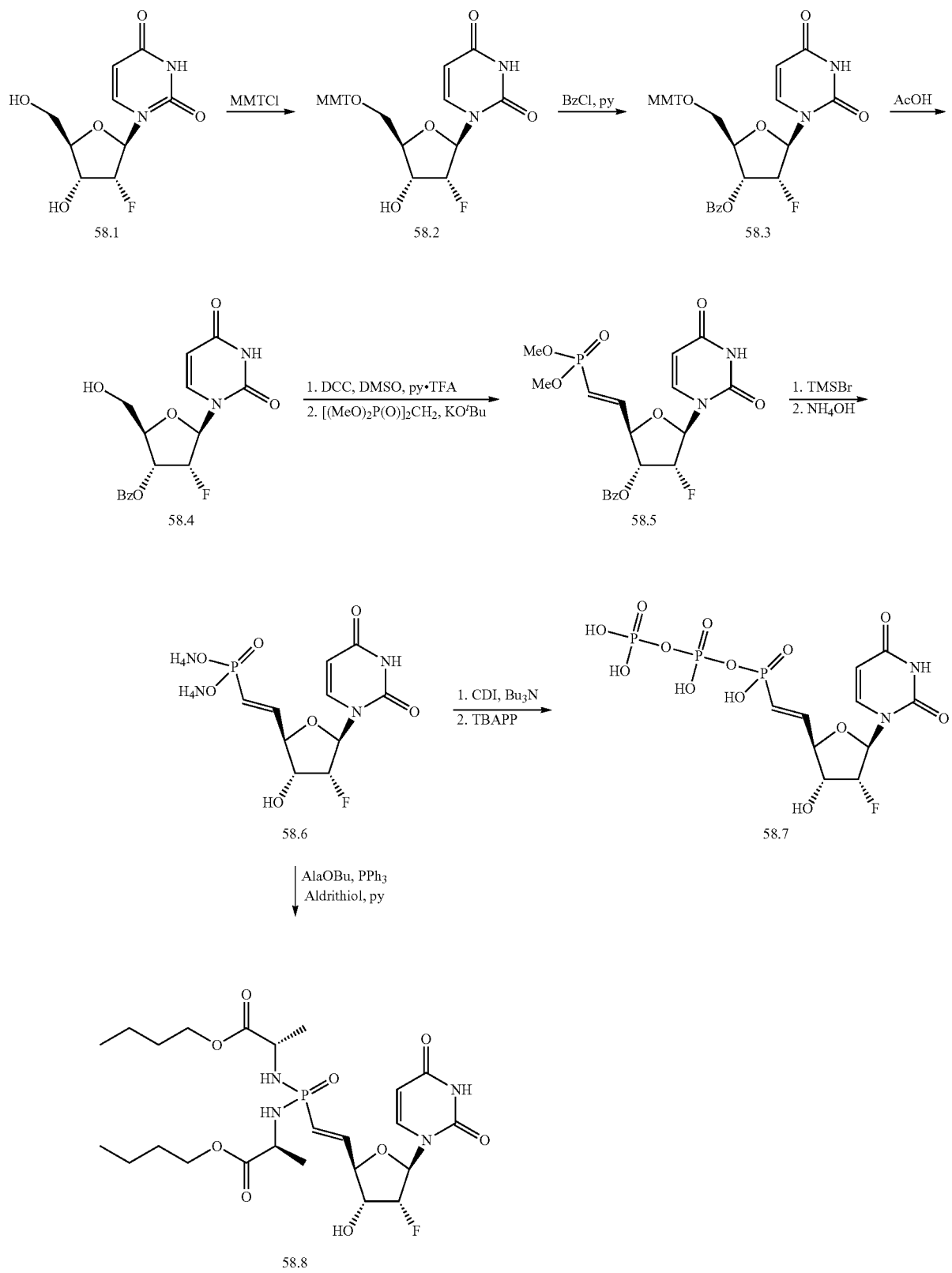

1-(3-Fluoro-4-hydroxy-5-trityloxymethyl-tetrahydro-furan-2-yl)-1H-pyrimidine-2,4-dione (58.2)

A similar procedure for the synthesis of 55.2 was followed for the preparation of 58.2.

Benzoic acid 5-(2,4-dioxo-3,4-dihydro-2H-pyrimidin-1-yl)-4-fluoro-2-trityloxymethyl-tetrahydro-furan-3-yl ester (58.3)

A similar procedure for the synthesis of 55.3 was followed for the preparation of 58.3 (2.36 g, 75% yield).

Benzoic acid 5-(2,4-dioxo-3,4-dihydro-2H-pyrimidin-1-yl)-4-fluoro-2-hydroxymethyl-tetrahydro-furan-3-yl ester (58.4)

A similar procedure for the synthesis of 55.4 was followed for the preparation of 58.4 (941 mg, 71% yield).

Benzoic acid 2-[2-(dimethoxy-phosphoryl)-vinyl]-5-(2,4-dioxo-3,4-dihydro-2H-pyrimidin-1-yl)-4-fluoro-tetrahydro-furan-3-yl ester (58.5)

A similar procedure for the synthesis of 55.5 was followed for the preparation of 58.5 (134 mg, 11% yield, 2 steps).

{2-[5-(2,4-Dioxo-3,4-dihydro-2H-pyrimidin-1-yl)-4-fluoro-3-hydroxy-tetrahydro-furan-2-yl]-vinyl}-phosphonic acid (58.6)

A similar procedure for the synthesis of 55.6 was followed for the preparation of 58.6 (102 mg, 57%, 2 steps): white solid (bis-sodium salt); $^1$H NMR (D$_2$O, 300 MHz) 7.46 (d, J=7.8 Hz, 1H), 6.04 (m, 2H), 5.69 (m, 2H), 5.05 (d, J=52.8 Hz, 1H), 4.14 (m, 1H), 4.03 (m, 1H); $^{31}$P NMR (D$_2$O 121.4 MHz) 8.7; $^{19}$F NMR (D$_2$O, 282 MHz) −200 (m, 1F); MS (ESI) m/z 324 [M+H]$^+$.

Diphosphophosphonate (58.7)

A similar procedure for the synthesis of 55.7 was followed for the preparation of 58.7 (2 mg, 7% yield): white solid (tetra triethylammonium salt); $^1$H NMR (D$_2$O, 300 MHz) 7.55 (d, J=8.1 Hz, 1H), 6.43 (m 1H), 6.14 (app t, J=18.0 Hz, 1H), 5.83 (m, 1H), 5.70 (d, J=8.1 Hz, 1H), 5.05 (d, J=52.5 Hz, 1H), 4.39 (m, 2H); $^{31}$P NMR (D$_2$O 121.4 MHz) −4.1 (m, 1P), −8.5 (m, 1P). −22 (m , 1P); MS (ESI) m/z 481 [M−H]$^+$.

Bis-amidate prodrug (58.8)

A similar procedure for the synthesis of 55.8 was followed for the preparation of 58.8 (7.7 mg, 37%): white solid; $^1$H NMR (CD$_3$OD, 300 MHz) 7.56 (d, J=7.8 Hz, 1H), 6.75 (m, 1H), 6.18 (m, 1H), 5.83 (d, J=21.0 Hz, 1H), 5.67 (d, J=8.1 Hz, 1H), 5.10 (J=52.8 Hz, 1H), 4.40 (m, 1H), 4.15 (m, 1H), 4.04 (m, 5H), 3.84 (m, 2H), 1.60 (m, 4H), 1.42 (m, 10H), 0.90 (m, 6H); $^{31}$P NMR (D$_2$O 121.4 MHz) 16.4; $^{19}$F NMR (D$_2$O, 282 MHz) −201 (m, 1F); MS (ESI) m/z 602 [M+H]$^+$.

Example 31

Synthetic Scheme 59

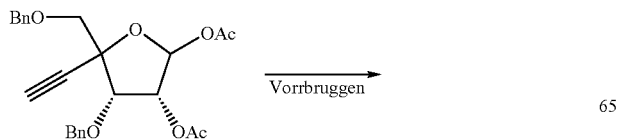

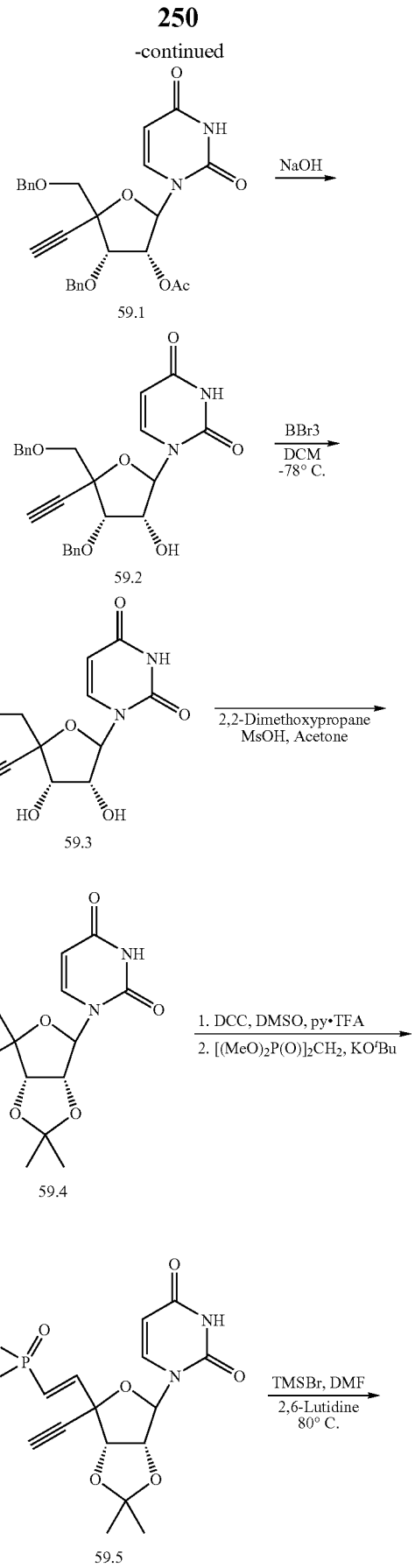

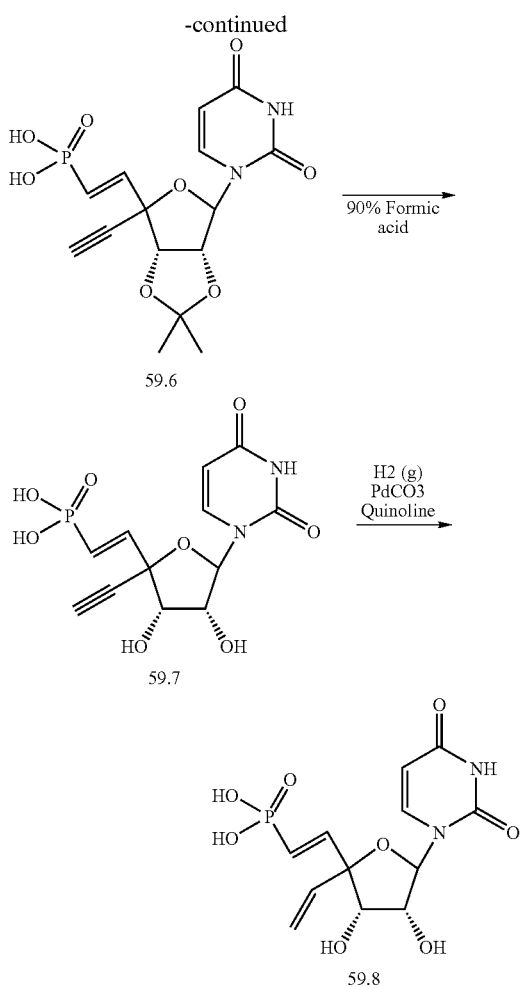

Compound 59.1

The starting sugar (Ohrui, H, et al.; J. Med. Chem.; EN; 43; 23; 2000; 4516-4525) (1.5 g, 3.42 mmol), uracil (0.767 g, 6.84 mmol) and BSA (5.0 ml, 20.52 mmol) were combined in anhydrous dichloroethane (50 ml) under nitrogen. The reaction was heated to 80° C. for 2 hr or until the solution became clear. The reaction was cooled to room temperature and trimethylsilyl trriflate was added. The reaction was heated to 80° C. for 16 hr. When the reaction was complete by LC/MS it was poured onto 100 ml saturated sodium bicarbonate. An additional 100 ml of dichloromethane was added. The mixture was stirred for 30 minutes. The organic layer was collected and the aqueous layer was extracted with 100 ml dichloromethane. The organic extracts were combined, dried over MgSO$_4$ (anh), filtered and then evaporated. The product was purified by column chromatography using ethyl acetate (0-100%) in hexanes to elute. Yield~78%. Anal. $^1$H-NMR (CD$_3$CN): δ 2.20 s 3H; 3.65-3.85 dd 2H; 4.41 d 1H; 4.50-4.7 m 4H; 5.38 m 2H; 6.08 d 1H; 7.40 m 10H; 7.63 d 1H; 9.00 s 1H.

Compound 59.2

The starting acetate 59.1 (1.3 g, 2.66 mmol), was dissolved in 1,4-dioxane (150 ml). Water (25 ml) and then 1 N sodium hydroxide (25 ml) were added. The reaction was monitored by LC/MS. When the reaction was complete, acetic acid (25 mmol) was added to neutralize. The solvents were removed under vacuum and the product was purified by column chromatography using ethyl acetate (0-100%) in hexanes to elute. Yield~100%. Anal. $^1$H-NMR (CD$_3$CN): δ 3.68-3.83 dd 2H; 4.20-4.35 m 2H; 4.57 s 2H; 4.79 s 2H; 5.38 d 2H; 5.94 d 1H; 7.40 m 10H; 7.61 d 1H; 8.97 s 1H.

Compound 59.3

The starting material 59.2 (0.100 g, 0.22 mmol), was dissolved in anhydrous dichloromethane (4 ml), and cooled to −78° C. under nitrogen. A solution of boron tribromide (1 N in DCM) (1.1 ml) was added and the reaction was stirred for 2 hr at −78° C. The reaction was then quenched by addition of a mixture of pyridine/methanol (7:10) vol/vol (5 ml). The reaction was stirred for 10 min at −78° C. then evaporated. The residue was taken up in 1 solution of 10% Methanol in dichloromethane and passed through a plug of silica gel using methanol (0-50%) in ethyl acetate to elute. This removed most of the boron salts and the crude material was taken forward without further purification, Verification was done by LS/MS Anal.; mass spectrum (ESI) m/z 269 [M+H]$^+$.

Compound 59.4

The crude starting material 59.3 (0.320 g, 1.2 mmol), was dissolved in acetone (40 ml) and 2,2-dimethoxy propane (6.7 ml, 54.31 mmol) was added under nitrogen with stirring. Methanesulfonic acid (0.234 ml, 3.6 mmol) was added and the reaction was stirred for 16 hr at room temperature. When the reaction was complete by LC/MS, triethylamine was added (4 mmol). Solvents were removed under high vacuum. The residue was re-dissolved in dichloromethane (200 ml) and extracted with 200 ml water. The organic layer was dried over MgSO$_4$ (anh). The product was purified by column chromatography using methanol (0-20%) in ethyl acetate to elute. Yield~40%. Anal. $^1$H-NMR (CD$_3$OD) δ 1.39 d 6H; 3.78 m 2H; 4.96 m 2H; 5.78 d 1H; 6.09 d 1H; 7.80 d 1H.

Compound 59.5

The starting material 59.4 (0.104 g, 0.34 mmol), was dissolved in anhydrous DMSO (5 ml). under nitrogen. Pyridine trifluoroacetate (0.0165 g, 0.085 mmol), and DCC (0.105 g, 0.51 mmol), were added and the reaction was stirred overnight. When the oxidation was complete the reaction was cooled to 0° C. A mixture of tetraethylmethylene bisphosphonate, (0.109 ml, 0.442 mmol), and potassium t-butoxide (1N in THF) (0.53 ml, 0.53 mmol), dissolved in anhydrous THF (0.5 ml) was added and the reaction was allowed to warm to room temperature and stir for 1 hr. When the reaction was complete by LC/MS it was cooled to 0° C. and 1 N HCl (1 ml) was added to quench. The reaction was diluted with 200 ml ethyl acetate and 100 ml water. The organic layer was separated and the aqueous extracted with 2×200 ml ethyl acetate. The organics were combined and washed with 2×100 ml brine. The organic was dried over MgSO$_4$ (anh). The final compound was purified by column chromatography using a gradient of ethyl acetate (0-100%) in hexanes to elute. Yield~43%. Anal. $^1$H-NMR (CD$_3$CN): δ 1.38 m 12H; 4.00-4.20 m 4H; 4.90 d 1H; 5.18 d 1H; 5.67 d 1H; 5.91 s 1H; 6.21 t 1H; 6.79 dd 1H; 7.43 d 1H; 9.39 s 1H. $^{31}$P-NMR (CD$_3$CN): δ 16.2 s 1P

Compound 59.6

The diethylphosphonate 59.5 (0.056 g, 0.127 mmol) was dissolved in 6 ml anhydrous DMF, and 2, 6-lutidine (0.074 ml, 0635 mmol) was added with stirring. Trimethylsilyl bromide(0.335 ml, 2.54 mmol) was added and the reaction was heated to 60° C. for 6 hr. When complete by LC/MS the reaction was quenched by addition of 1N ammonium hydroxide (3 ml) The solvents were removed under vacuum and the desired product was purified by reversed phase HPLC. Yield~71%. Anal. $^1$H-NMR (CD$_3$OD): δ 1.38 s 3H; 1.63 s 3H; 4.82 d 1H; 5.13 d 1H; 5.73 d 1H; 6.00 s 1H; 6.37 m 1H; 6.57 m 1H; 7.62 m 2H. $^{31}$P-NMR (CD$_3$OD): δ 11.09 s 1P

Compound 59.7

The phosphonic acid 59.6 (0.124 g, 0.32 mmol) was dissolved in a mixture of formic acid (18 ml) and water (2 ml) under nitrogen. The reaction was stirred for 2 hr at room temperature while monitoring by LC/MS. When the reaction was complete solvents were removed under high vacuum. The residue was dissolved in water and purified by prep-HPLC. Yield~59.4%. Anal. $^1$H-NMR (D$_2$O): δ 4.2 d 1H; 4.40 t 1H; 5.79 d 1H; 5.86 d 1H; 6.25-6.35 m 2H; 7.57 d 1H. $^{31}$P-NMR (D$_2$O): δ 10.74 s 1P Compound 59.8

The alkyne 59.7 (0.030 g, 0.087 mmol), Lindlar catalyst (15 mg) (Palladium, 5 wt. % calcium carbonate poisoned with lead) and quinoline (3 ul, 0.0045 mmol) were charged to a 25 ml flask. The mixture was suspended in methanol (7 ml) The flask was fitted with a hydrogen balloon. Air was removed by flushing 3 times with nitrogen. Hydrogen was then introduced by flushing 3 times. Hydrogenation was continued for 15 minutes. Hydogen was removed under vacuum and replaced by flushing with nitrogen. The reaction vessel was opened and an LC/MS taken. When the reaction was done by LC/MS catalyst was filtered off. Solvents were removed and the product purified by prep-HPLC. Yield~27%. Anal. $^1$H-NMR (D$_2$O): δ 4.23 d 1H; 4.40 t 1H; 5.22 s 1H; 5.29 d 1H; 5.80-6.00 m 3 H; 6.41 dd 1H; 7.57 d 1H. $^{31}$P-NMR (D$_2$O): δ0 11.58 s 1P.

Example 32

Compound 60.1

Intermediate 9.8 (0.8 g, 1.68 mmol) was added to acetonitrile (15 mL) followed by 6-chloropurine (0.29 g, 1.68 mmol), I-IMDS (0.33 mL, 1.6 mmol) and TMSCl (0.20 mL, 1.6 mmol). SnCl4 was then added (0.6 g, 2.3 mmol) and the mixture stirred at room temperature for 2 h. The mixture was treated with sodium hydrogen carbonate and water and then stirred for 1 h. The solid was removed by filtration and the filtrate concentrated to dryness under reduced pressure. The residue was subjected to flash column chromatography to isolate the product 60.1 (0.27 g, 32%).

Compound 60.2

Intermediate 60.1 (0.21 g, 0.41 mmol) was dissolved in THF (3 mL) and then treated with N-methyl hydrazine (0.2 mL, 8 mmol). The mixture was heated at 45 C for 5 min and then concentrated under reduced pressure. The crude residue was re-suspended in dichloromethane, washed with water, dried over sodium sulfate, filtered and concentrated to provide the crude product 60.2 (168 mg).

Crude product 60.2 (0.17 g, 0.31 mmol) was dissolved in THF (5 ml), and then treated with pyridine (0.12 g, 1.6 mmol) followed by methanesulphonyl chloride (55 mg, 0.38 mmol).

Synthetic Scheme 60

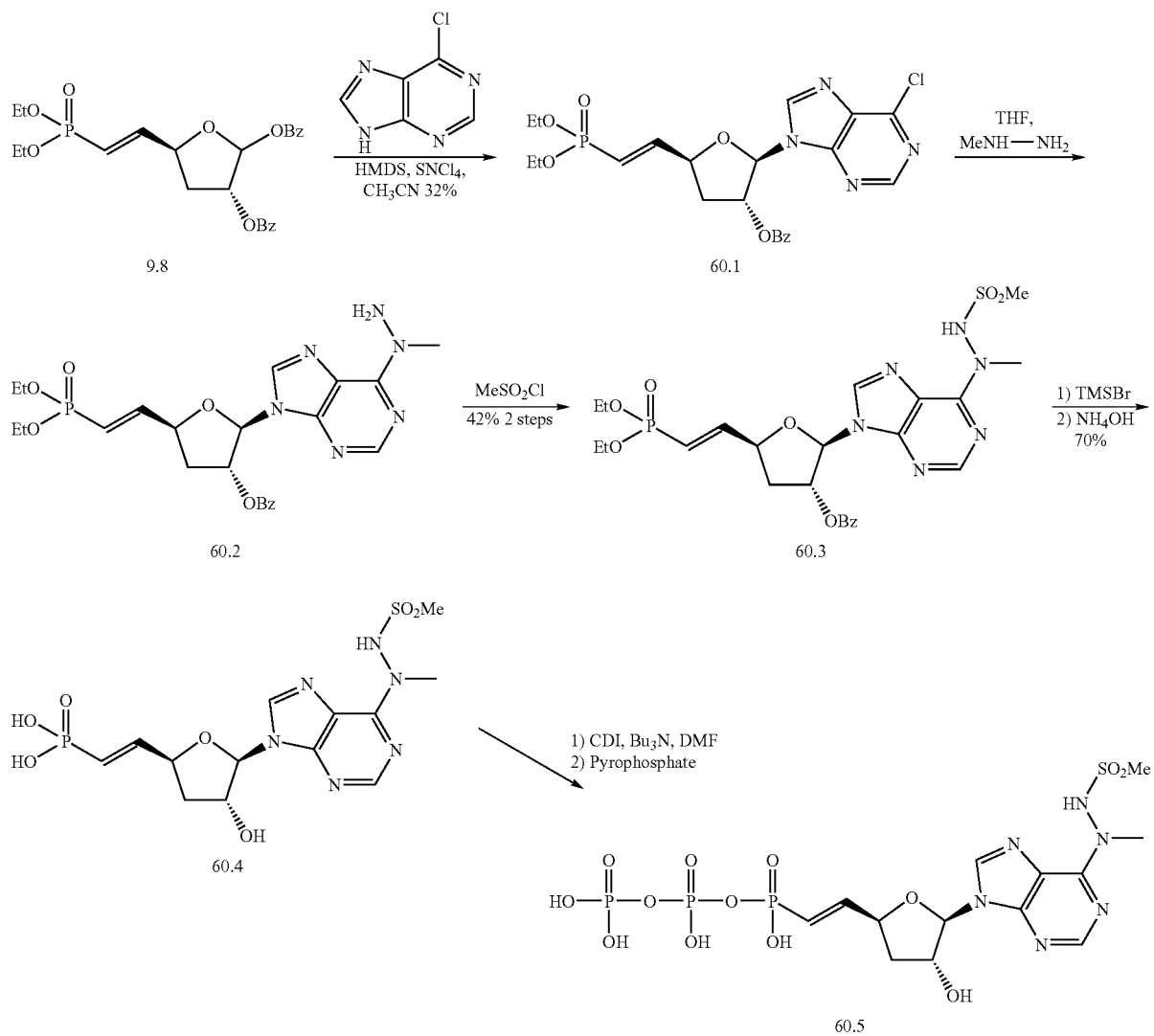

The mixture was stirred overnight and then treated with a further portion of methanesulphonyl chloride (50 mg, 0.42 mmol). The mixture was then stirred for 5 h at room temperature and then diluted with dichloromethane. The organic solution was washed with water, saturated brine, dried over sodium sulfate, filtered and concentrated under reduced pressure. The residue was subjected to silica gel chromatography to isolate the desired product 60.3 (155 mg, 84%).
Compound 60.4

Intermediate 60.3 (155 mg, 0.26 mmol) was dissolved in acetonitrile (15 mL) and then treated with 2,6-lutidine (0.14 g, 1.3 mmol) followed by TMSBr (0.55 g, 3.6 mmol). The mixture was stirred for 4 h and then concentrated to dryness under reduced pressure. The residue was azeotroped three times with concentrated ammonium hydroxide (3×10 mL) and the crude product that resulted was then dissolved in concentrated ammonium hydroxide (10 mL). The mixture was heated in a sealed tube at 45 C for 1 h before allowing to cool to room temperature. The reaction mixture was concentrated under reduced pressure to dryness and then redissolved in water (5 mL). Sodium hydrogen carbonate was added (100 mg) and the mixture then concentrated to dryness and purified by HPLC to isolate 60.4 as the sodium salt. (116 mg, 70%).
Compound 60.5

Compound 60.5 (14 mg, 40% yield) was synthesized from the diacid 60.4 (24 mg, 0.05 mmol) using the procedure described before. $^1$H NMR (D$_2$O, 300 MHz): δ 8.29 (m, 1H), 8.14 (m, 2H), 6.49 (m, 1H), 6.13 (m, 2H), 5.34 (m, 1H), 4.95 (m, 1H), 3.57 (s, 3H) 2.79 (s, 3H), 2.33 (m, 2H). $^{31}$P NMR: 4.08 ppm, −5.40 ppm, −21.40 ppm. LC/MS: C$_{13}$H$_{21}$N$_6$O$_{13}$P$_3$S Exact Mass: 594.01. Found: [M−H]$^-$ 593.0.

Example 33

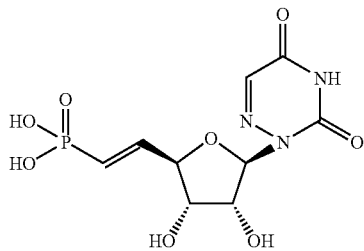

Compound 61 was synthesized using the procedures disclosed in the specific examples described. Mass Spec: 321.92 (ESI) $^1$H NMR: D2O 6.20-6.34 (1H, m), 5.86-6.05 (2H, m), 4.95-5.02 (1H, m), 4.40-4.44 (2H, m) 4.22 (1H, t, J=6 Hz). $^{31}$P NMR D2O: 10.96.
Antiviral Activity Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as an tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocol.
HCV IC$_{50}$ Determination Assay Protocol: NS5b polymerase assay (40 μL) was assembled by adding 28 μL polymerase mixture (final concentration: 50 mM Tris-HCl at pH 7.5, 10 mM KCL, 5 mM MgCl$_2$, 1 mM DTT, 10 mM EDTA, 4 ng/μL of RNA template, and 75 nM HCV Δ21 NS5b polymerase) to assay plates followed by 4 μL of compound dilution. The polymerase and compound were pre-incubated at 35° C. for 10 minute before the addition of 8 μL of nucleotide substrate mixture (33P-α-labeled competing nucleotide at K$_M$ and 0.5 mM of the remaining three nucleotides). The assay plates were covered and incubated at 35° C. for 90 min. Reactions were then filtered through 96-well DEAE-81 filter plates via vacuum. The filter plates were then washed under vacuum with multiple volumes of 0.125 M NaHPO$_4$, water, and ethanol to remove unincorporated label. Plates were then counted on TopCount to assess the level of product synthesis over background controls. The IC50 value was determined using Prism fitting program.

Preferably, compounds described herein inhibited NS5b polymerase with an IC50's below 1000 μM, more preferably below 100 μM, and most preferably below 10 μM. Representative activity of the compounds of the invention are shown in Table 2 wherein IC50's below 10 μM are designated A, IC50's between 10 and 100 μM are represented by B, and IC50's greater than 100 μM are represented by C.

TABLE 2

| NS5b polymerase inhibiting activity | |
|---|---|
| Compound Number | IC50 |
| 52.6 | A |
| 58.7 | B |
| 57.7 | A |
| 55.7 | A |
| 56.5 | C |
| 54.4 | C |
| 53.4 | C |
| 10.4 | C |
| 38.4 | B |
| 13.4 | C |
| 16.95 | B |
| 9.12 | C |
| 6.8 | C |
| 60.5 | C |

HCV EC$_{50}$ Determination

Replicon cells were seeded in 96-well plates at a density of $8\times10^3$ cells per well in 100 μL of culture medium, excluding Geneticin. Compound was serially diluted in 100% DMSO and then added to the cells at a 1:200 dilution, achieving a final concentration of 0.5% DMSO and a total volume of 200 μL. Plates were incubated at 37° C. for 3 days, after which culture medium was removed and cells were lysed in lysis buffer provided by Promega's luciferase assay system. Following the manufacturer's instruction, 100 μL of luciferase substrate was added to the lysed cells and luciferase activity was measured in a TopCount luminometer.

Preferably, compounds described herein had EC50's below 1000 μM, more preferably below 100 μM, and most preferably below 10 μM. Representative activity of the compounds of the invention are shown in Table 3 wherein EC50+s below 10 μM are designated A, EC50's between 10 and 100 μM are represented by B, and EC50's greater than 100 μM are represented by C.

Typically, compounds of the invention that were tested were found to have an EC$_{50}$ of less than about 1000 μM (Huh7). Some compounds demonstrated an EC$_{50}$ of less than about 10 μM (Huh7).

TABLE 3

Replicon inhibiting potency

| Compound Number | EC50 |
|---|---|
| 46.3 | C |
| 47.2 | C |
| 27.8 | C |
| 13.2 | C |
| 12.2 | A |
| 38.2 | C |
| 10.2 | B |
| 16.9 | C |
| 6.7 | C |
| 9.1 | B |
| 11.2 | C |
| 18.8 | B |
| 25.3 | C |
| 24.4 | C |
| 17.5 | C |
| 50.6 | C |
| 55.8 | B |
| 56.6 | A |
| 54.3 | C |
| 53.3 | B |
| 48.7 | B |
| 36.8 | C |
| 35.2 | C |
| 27.1 | A |
| 13.3 | B |
| 12.3 | A |
| 38.3 | A |
| 10.3 | C |
| 9.11 | A |
| 11.3 | C |
| 18.9 | C |

The cytotoxicity of a compound of the invention can be determined using the following general protocol.

Cytotoxicity Cell Culture Assay (Determination of CC50):

The assay is based on the evaluation of cytotoxic effect of tested compounds using a metabolic substrate.

Assay Protocol for Determination of CC50:

1. Maintain MT-2 cells in RPMI-1640 medium supplemented with 5% fetal bovine serum and antibiotics.
2. Distribute the cells into a 96-well plate (20,000 cell in 100 μl media per well) and add various concentrations of the tested compound in triplicate (100 μl/well). Include untreated control.
3. Incubate the cells for 5 days at 37° C.
4. Prepare XTT solution (6 ml per assay plate) in dark at a concentration of 2 mg/ml in a phosphate-buffered saline pH 7.4. Heat the solution in a water-bath at 55° C. for 5 min. Add 50 μl of N-methylphenazonium methasulfate (5 μg/ml) per 6 ml of XTT solution.
5. Remove 100 μl media from each well on the assay plate and add 100 μl of the XTT substrate solution per well. Incubate at 37° C. for 45 to 60 min in a $CO_2$ incubator.
6. Add 20 μl of 2% Triton X-100 per well to stop the metabolic conversion of XTT.
7. Read the absorbance at 450 nm with subtracting off the background at 650 nm.
8. Plot the percentage absorbance relative to untreated control and estimate the CC50 value as drug concentration resulting in a 50% inhibition of the cell growth. Consider the absorbance being directly proportional to the cell growth.

All publications, patents, and patent documents cited herein above are incorporated by reference herein, as though individually incorporated by reference.

The invention has been described with reference to various specific and preferred embodiments and techniques. However, it should be understood that many variations and modifications may be made while remaining within the spirit and scope of the invention.

What is claimed is:

1. A compound of Formula I:

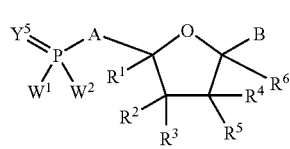

Formula I wherein:

A is —CR$^d$=CR$^d$— or

—C≡C—;

B is a nucleoside base which is optionally substituted;

each R$^1$, R$^2$, R$^3$, R$^4$, and R$^5$ is independently H, OR$^a$, N(R$^a$)$_2$, N$_3$, CN, NO$_2$, SR$^a$, halogen, C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, or C$_2$-C$_8$ substituted alkynyl; or R$^2$ and R$^4$ are taken together along with the atoms to which they are attached to form a double bond; or R$^2$ and R$^3$ taken together are =O, =NR$^b$, or =CR$^c$R$^d$; or R$^2$ and R$^3$ taken together with the carbon atom to which they are attached form a 3-7 membered carbocyclic ring wherein one carbon atom can optionally be replaced with —O—, —S— or —NR$^a$—;

R$^6$ is H, halogen, C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, or C$_2$-C$_8$ substituted alkynyl;

each R$^a$ is independently H, (C$_1$-C$_6$)alkyl, (C$_2$-C$_6$)alkenyl, (C$_2$-C$_6$)alkynyl or (C$_1$-C$_6$)alkanoyl;

each R$^b$ is independently H, (C$_1$-C$_6$)alkyl, (C$_2$-C$_6$)alkenyl, (C$_2$-C$_6$)alkynyl, O—(C$_1$-C$_6$)alkyl or OH;

each R$^c$ and R$^d$ is independently H, (C$_1$-C$_6$)alkyl, (C$_2$-C$_6$)alkenyl, (C$_2$-C$_6$)alkynyl or halo;

wherein each (C$_1$-C$_6$)alkyl, (C$_2$-C$_6$)alkenyl, or (C$_2$-C$_6$)alkynyl of R$^a$—R$^d$ is optionally substituted with one or more halo, hydroxy, or (C$_1$-C$_6$)alkoxy;

$Y^5$ is O, S, NR, $^+$N(O)(R), N(OR), $^+$N(O)(OR), or N—NR$_2$;

each $Y^1$ is independently O, S, NR, $^+$N(O)(R), N(OR), $^+$N(O)(OR), or N—NR$_2$;

$W^1$ and $W^2$ are each independently a group of the formula:

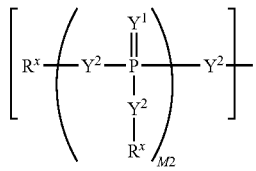

wherein:

each $Y^2$ is independently a bond, O, CR$_2$, NR, $^+$N(O)(R), N(OR), $^+$N(O)(OR), N—NR$_2$, S, S—S, S(O), or S(O)$_2$;

M2 is 0, 1 or 2;

each $R^y$ is independently H, F, Cl, Br, I, OH, R, —C(=Y$^1$)R, —C(=Y$^1$)OR, —C(=Y$^1$)N(R)$_2$, —N(R)$_2$, —$^+$N(R)$_3$, —SR, —S(O)R, —S(O)$_2$R, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, or —N(R)C(=Y$^1$)N(R)$_2$, amino (—NH$_2$), ammonium (—NH$_3$ $^+$), alkylamino, dialkylamino, trialkylammonium, C$_1$-C$_8$ alkyl, C$_1$-C$_8$ alkylhalide, carboxylate, sulfate, sulfamate, sulfonate, C$_1$-C$_8$ alkylsulfonate, C$_1$-C$_8$ alkylamino, C$_1$-$^C$$_8$ alkylhydroxyl, C$_1$-C$_8$ alkylthiol, alkylsulfone (—SO$_2$R), sulfonamide (—SO$_2$NR$_2$), alkylsulfoxide (—SOR), ester (—C(=O)OR), amido (—C(=O)NR$_2$), nitrile (—CN), azido (—N$_3$), nitro (—NO$_2$), C$_1$-C$_8$ alkoxy (—OR), C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, C$_2$-C$_8$ substituted alkynyl, a protecting group or W$^3$; or when taken together, two $R^y$ on the same carbon atom form a carbocyclic ring of 3 to 7 carbon atoms;

each $R^x$ is independently $R^y$, a protecting group, or the formula:

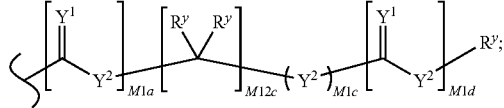

wherein:

M1a, M1c, and M1d are independently 0 or 1;

M12c is 0, 1, 2, 3, 4, 5, 6, 7, 8, 9, 10, 11 or 12; or when taken together, two $R^x$ are optionally substituted C$_2$-C$_4$ alkylene thereby forming a phosphorous-containing heterocycle;

each R is independently H, halogen, C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, C$_2$-C$_8$ substituted alkynyl, C$_6$-C$_{20}$ aryl, C$_6$-C$_{20}$ substituted aryl, C$_2$-C$_{20}$ heterocycle, C$_2$-C$_{20}$ substituted heterocycle, or a protecting group;

$W^3$ is $W^4$ or $W^5$; $W^4$ is R, —C(Y$^1$)R$^y$, —C(Y$^1$)W$^5$, —SO$_2$R$^y$, or —SO$_2$W$^5$; and $W^5$ is a carbocycle or a heterocycle wherein $W^5$ is independently substituted with 0 to 3 $R^y$ groups;

or a pharmaceutically acceptable salt, thereof;

provided that $W^1$ or $W^2$ is not an oxygen-linked 2'-deoxynucleoside;

provided that when

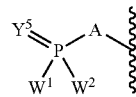

of Formula I is

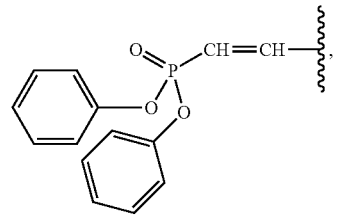

then

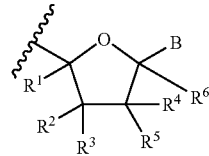

of Formula I is not:

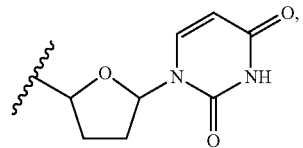

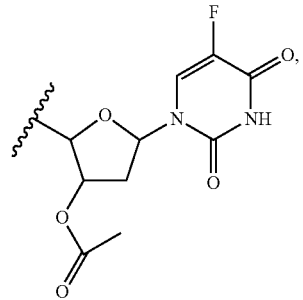

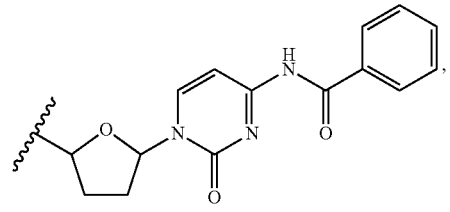

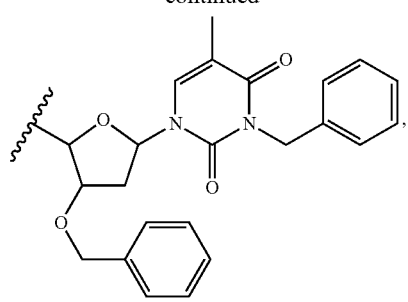
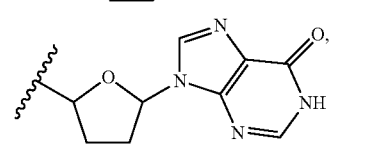
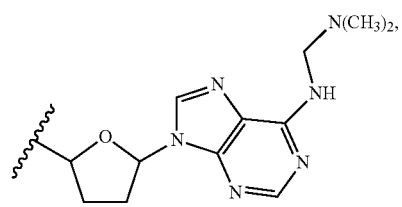
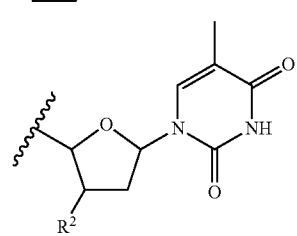
wherein R² is H, F or N₃,
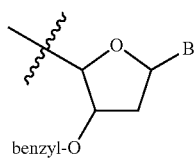
wherein B is N³-benzylthymine, or
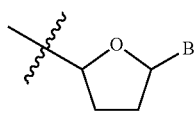
wherein B is N⁴-isobutyrylcytosin-1-yl, N²-isobutyrylguanin-9-yl or N⁶-benzoyladenin-9-yl;
provided that when
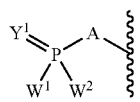
of Formula I is
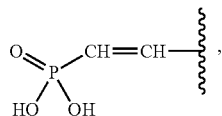
then
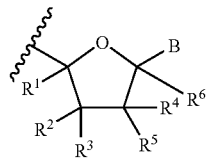
of Formula I is not:
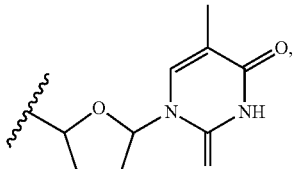
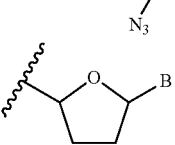
wherein B is adenine or cytidine, or
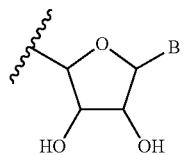
wherein B is
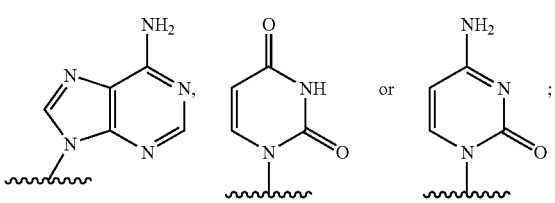
and
provided that the compound of Formula I is not:
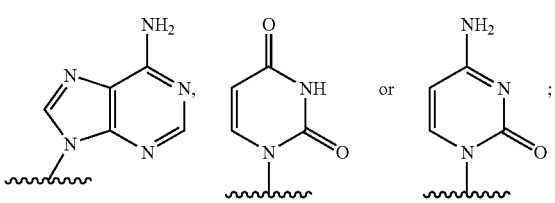

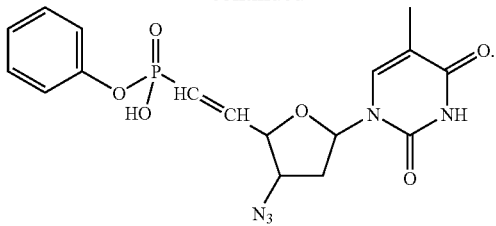

2. The compound according to claim 1, wherein $Y^5$ is O and A is —$CR^d$=$CR^d$—.

3. The compound according to claim 1, wherein B is selected from

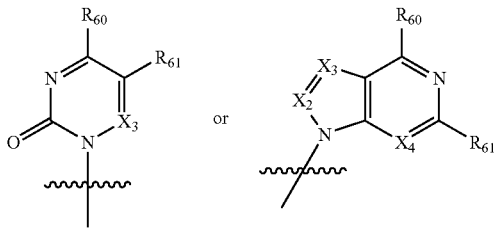

wherein:
$X_2$, $X_3$, and $X_4$ are each independently N, CH, or C—$R_{6a}$;
$R_{60}$, $R_{61}$, and $R_{6a}$ are each independently H, halo, $NR_{6b}R_{6c}$, hydroxyamino, $NR_{6b}NR_{6b}R_{6c}$, $N_3$, NO, $NO_2$, formyl, cyano, —C(=O)$NR_{6b}R_{6c}$, —C(=S)$NR_{6b}R_{6c}$, —C(=O)$OR_{6b}$, $R_{6b}$, $OR_{6b}$, or $SR_{6b}$; and
$R_{6b}$, and $R_{6c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, —S(O)$_2$($C_1$-$C_6$)alkyl or aryl($C_1$-$C_6$)alkyl;

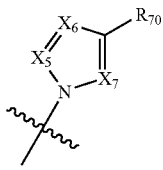

wherein:
$X_5$, $X_6$, and $X_7$, are each independently N, CH, or C—$R_{7a}$;
$R_{70}$ and $R_{7a}$ are each independently H, halo, $NR_{7b}R_{7c}$, hydroxyamino, $NR_{7b}NR_{7b}R_{7c}$, $N_3$, NO, $NO_2$, formyl, cyano, —C(=O)$NR_{7b}R_{7c}$, —C(=S)$NR_{7b}R_{7c}$, —C(=O)$OR_{7b}$, $R_{7b}$, $OR_{7b}$, or $SR_{7b}$; and
$R_{7b}$, and $R_{7c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, or aryl($C_1$-$C_6$)alkyl;

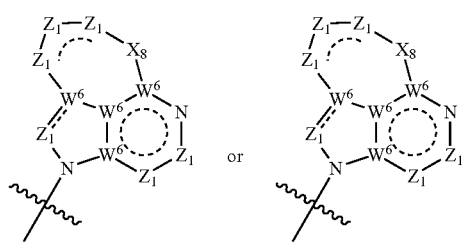

wherein:
each $Z_1$ is independently N, C—$R_{9a}$, O, S, $NR_{9b}$, >C=O, >C=S, >C=$NR_{9b}$, >S=O, >S(O)$_2$ or CH—$R_{9a}$; provided that if a $Z_1$ participates in an optional bond represented by a dotted line --- in the formula, then that $Z_1$ is N or C—$R_{9a}$; and provided that if a $Z_1$ does not participate in an optional bond represented by a dotted line --- in the formula, then that $Z_1$ is O, S, $NR_{9b}$, >C=O, >C=S, >C=$NR_{9b}$, >S=O, >S(O)$_2$ or CH—$R_{9a}$;

$X_8$ is O, S, SO, $SO_2$, Se, SeO, $SeO_2$ or $NR_{9b}$;
each $W^6$ is C, CH, or N; wherein if a $W^6$ participates in an optional bond represented by a dotted line --- in the formula, then that $W^6$ is C; and if a $W^6$ does not participate in an optional bond represented by a dotted line --- in the formula, then that $W^6$ is CH, or N;

each $R_{9a}$ is independently H, halo, $NR_{9c}R_{9d}$, hydroxyamino, $NR_{9c}NR_{9c}R_{9d}$, $N_3$, cyano, —C(=O)$NR_{9c}R_{9d}$, —C(=S)$NR_{9c}R_{9d}$, —C(=S)$NR_{9c}R_{9d}$, —C(=NH)$OR_{9c}$, $R_{9c}$, $OR_{9c}$, or $SR_{9c}$;

each $R_{9b}$ is independently H, ($C_1$-$C_6$)alkyl, ($C_1$-$C_6$)alkenyl, ($C_1$-$C_6$)alkynyl, aryl, ($C_1$-$C_6$)alkanoyl, or aryl($C_1$-$C_6$)alkyl; and $R_{9c}$, and $R_{9d}$ are each independently H, ($C_1$-$C_6$)alkyl, ($C_1$-$C_6$)alkenyl, ($C_1$-$C_6$)alkynyl, aryl, ($C_1$-$C_6$)alkanoyl, or aryl($C_1$-$C_6$)alkyl;

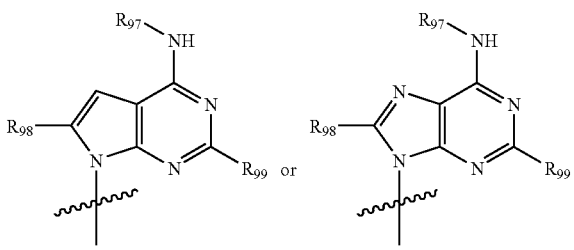

wherein:
$R_{97}$ is H, hydroxy, mercapto, ($C_1$-$C_6$)alkyl, ($C_1$-$C_6$)alkoxy, ($C_2$-$C_6$)alkenyl, ($C_3$-$C_8$)cycloalkyl, aryl($C_1$-$C_6$)alkyl, aryl or ($C_2$-$C_6$)alkynyl;

$R_{98}$ is H, hydroxy, mercapto, or ($C_1$-$C_6$)alkyl;

$R_{99}$ is H, halo, azido, cyano, nitro, $OR_{99a}$, $SR_{99a}$, $NR_{99b}R_{99c}$, ($C_1$-$C_6$)alkyl, ($C_2$-$C_6$)alkenyl, ($C_3$-$C_8$)cycloalkyl, aryl($C_1$-$C_6$)alkyl, aryl or ($C_2$-$C_6$)alkynyl;

each $R_{99a}$ is independently H, ($C_1$-$C_6$)alkyl, or ($C_1$-$C_6$)alkanoyl;

each $R_{99b}$ and $R_{99c}$ is independently H, ($C_1$-$C_6$)alkyl, or ($C_1$-$C_6$)alkanoyl;

wherein each ($C_1$-$C_6$)alkyl, ($C_1$-$C_6$)alkoxy ($C_1$-$C_6$)alkenyl, ($C_1$-$C_6$)alkynyl, ($C_3$-$C_8$)cycloalkyl, aryl, and aryl ($C_1$-$C_6$)alkyl of $R_{97}$, $R_{98}$, $R_{99}$, $R_{99a}$, $R_{99b}$, and $R_{99c}$, is optionally substituted with one or more ($C_1$-$C_6$)alkyl, ($C_1$-$C_6$)alkylthio, ($C_1$-$C_6$)alkoxy, ($C_1$-$C_6$)alkanoyl, ($C_1$-$C_6$)alkanoyloxy, ($C_1$-$C_6$)alkoxycarbonyl, $NH_2$, cyano, azido, halo, hydroxy, nitro, carboxy, trifluoromethoxy, aryl, or mercapto;

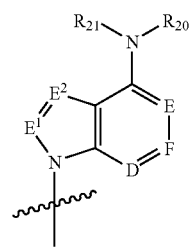

wherein:
R$_{20}$ is OH or (C$_1$-C$_6$)alkoxy that is optionally substituted with one or more R$_{22}$; and R$_{21}$ is H or (C$_1$-C$_6$)alkyl that is optionally substituted with one or more R$_{22}$; or R$_{20}$ and R$_{21}$ together with the nitrogen to which they are attached form a heterocyclic ring that is optionally subsitituted with one or more R$_{22}$;
each R$_{22}$ is independently (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NR$_{23}$R$_{24}$, —C(=O)NR$_{23}$R$_{24}$, aryl, heteroaryl, cyano, halo, hydroxy, nitro, carboxy, or (C$_3$-C$_8$)cycloalkyl;
R$_{23}$ and R$_{24}$ are each independently H, (C$_1$-C$_6$)alkyl or (C$_1$-C$_6$)alkanoyl;
wherein each aryl or heteroaryl of R$_{22}$ is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NR$_{23}$R$_{24}$, —C(=O)NR$_{23}$R$_{24}$, cyano, halo, hydroxy, nitro, carboxy, (C$_3$-C$_8$)cycloalkyl, trifluoromethoxy, mercapto, or trifluoromethyl; and
D, E, E$^1$, E$^2$, and F are each independently >N or >C—R$_{25}$;
each R$_{25}$ is independently H, cyano, nitro, (C$_1$-C$_6$)alkyl, (C$_1$-C$_6$)alkenyl, (C$_1$-C$_6$)alkynyl, —NHCONH$_2$, C(=O)NR$_{26}$R$_{27}$, COOR$_{28}$, hydroxy, (C$_1$-C$_6$)alkoxy, —NR$_{26}$R$_{27}$, halo, 1,3-oxazol-2-yl, 1,3-oxazol-5-yl, 1,3-thiazol-2-yl, imidazol-2-yl, 2-oxo-[1,3]dithiol-4-yl, furan-2-yl, or 2H-[1,2,3]triazol-4-yl;
each R$_{26}$ and R$_{27}$ is independently H, (C$_1$-C$_6$)alkyl, (C$_1$-C$_6$)alkenyl, (C$_1$-C$_6$)alkynyl, (C$_3$-C$_8$)cycloalkyl, aryl, heterocycle, hydroxy, (C$_1$-C$_6$)alkoxy; or R$_{26}$ and R$_{27}$ together with the nitrogen to which they are attached form a heterocycle; and
each R$_{28}$ is independently H, (C$_1$-C$_6$)alkyl, (C$_1$-C$_6$)alkenyl, (C$_1$-C$_6$)alkynyl, (C$_3$-C$_8$)cycloalkyl, aryl, or heterocycle;
wherein each (C$_1$-C$_6$)alkyl, (C$_1$-C$_6$)alkenyl, (C$_1$-C$_6$)alkynyl, (C$_3$-C$_8$)cycloalkyl, aryl, heterocycle, and (C$_1$-C$_6$)alkoxy of R$_{26}$ and R$_{27}$ is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NH$_2$, cyano, halo, hydroxy, nitro, carboxy, (C$_3$-C$_8$)cycloalkyl, (C$_3$-C$_8$)cycloalkoxy, trifluoromethoxy, or mercapto;

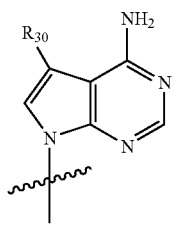

wherein:
R$_{30}$ is —C≡CR$_{31}$, —CH=CHR$_{32}$, formyl, —CH=NHNR$_{33}$, —CH=N(OR$_{33}$), —CH(OR$_{34}$), CN or —B(OR$_{33}$);
R$_{31}$ is H, tri(C$_1$-C$_6$)alkylsilyl, (C$_1$-C$_6$)alkoxy(C$_1$-C$_6$)alkyl, heteroaryl, aryl, carboxy, or (C$_1$-C$_6$)alkoxycarbonyl;
R$_{32}$ is hydrogen or cis-(C$_1$-C$_6$)alkoxy;
R$_{33}$ is H or (C$_1$-C$_6$)alkyl; and
R$_{34}$ is (C$_1$-C$_6$)alkyl;
wherein each aryl or heteroaryl of R$_{31}$ is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NR$_{35}$R$_{36}$, —C(=O)NR$_{35}$R$_{36}$, cyano, halo, hydroxy, nitro, carboxy, (C$_3$-C$_8$)cycloalkyl, (C$_3$-C$_8$)cycloalkoxy, guanidino, trifluoromethoxy, mercapto, —S(=O)$_m$R$_{37}$, or trifluoromethyl;
m is 0, 1, or 2;
R$_{35}$ and R$_{36}$ are each independently H, (C$_1$-C$_6$)alkyl or (C$_1$-C$_6$)alkanoyl;
R$_{37}$ is (C$_1$-C$_6$)alkyl, aryl, hetrocycle, or NR$_{38}$R$_{39}$; and
R$_{38}$ and R$_{39}$ are each independently H, (C$_1$-C$_6$)alkyl or (C$_1$-C$_6$)alkanoyl;
wherein each aryl or heterocycle of R$_{37}$ is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NR$_{35}$R$_{36}$, —C(=O)NR$_{35}$R$_{36}$, cyano, halo, hydroxy, nitro, carboxy, (C$_3$-C$_8$)cycloalkyl, (C$_3$-C$_8$)cycloalkoxy, guanidino, trifluoromethoxy, mercapto, or trifluoromethyl;

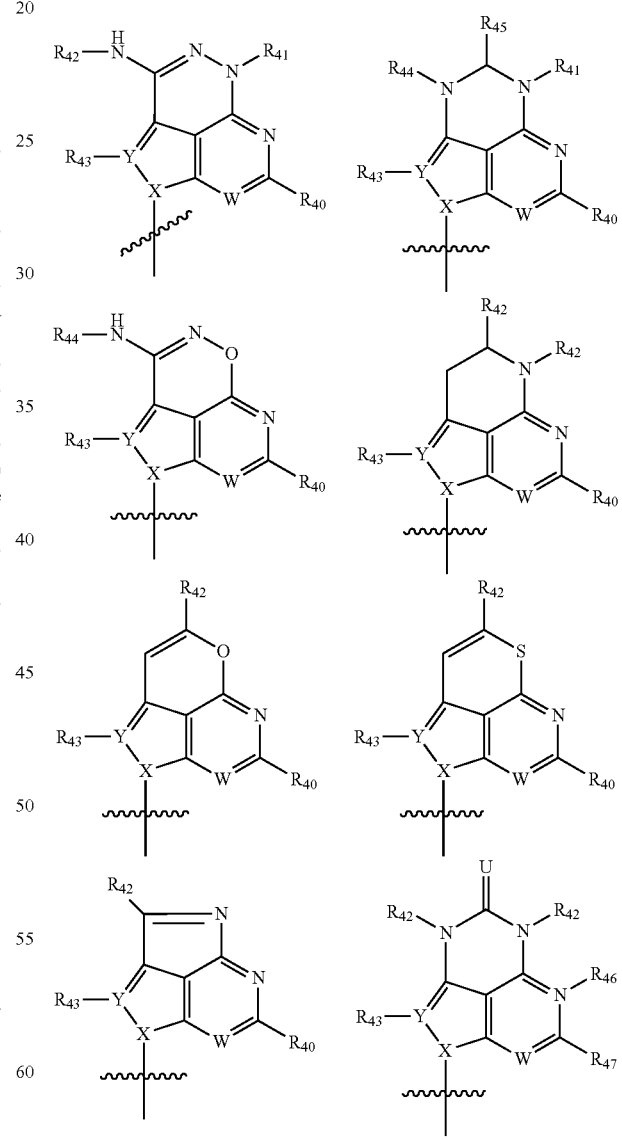

wherein:
R$_{40}$ is H, NR$_{4a}$R$_{4b}$, NHC(=O)R$_{4b}$, (C$_1$-C$_6$)alkylNR$_{4a}$R$_{4b}$, NHNH$_2$, cyano, (C$_1$-C$_6$)alkyl, (C$_2$-C$_6$)alkenyl, (C$_2$-C$_6$)

alkynyl, aryl($C_1$-$C_6$)alkyl, heterocycle($C_1$-$C_6$)alkyl, halo, ($C_1$-$C_6$)alkylthio, ($C_1$-$C_6$)alkoxy, hydroxy, or mercapto;

$R_{41}$ is H, ($C_1$-$C_6$)alkyl, hydroxy($C_1$-$C_6$)alkyl, ($C_2$-$C_6$)alkenyl, ($C_2$-$C_6$)alkynyl, heterocycle, aryl, aryl($C_1$-$C_6$)alkyl;

each $R_{42}$ is independently H, hydroxy, mercapto, cyano, —$SNR_{4c}R_{4d}$, —C(NH)$NR_{4c}R_{4d}$, —C(=NH)NHOH, —C(NH)$NHOR_{4c}$, —C(=NH)$NHNR_{4c}R_{4d}$, $NHCOR_{4c}$, $SR_{4c}$, $OR_{4c}$, $SOR_{4c}$, $SO_2R_{4c}$, —C(=O)$NR_{4c}R_{4d}$, —C(=S)$NR_{4c}R_{4d}$, or $R_{4c}$;

$R_{43}$ is H, hydroxy, $NR_{4c}R_{4d}$, NHC(=O)$NR_{4c}$, $NHNHR_{4c}$, ($C_1$-$C_6$)alkyl, ($C_2$-$C_6$)alkenyl, ($C_2$-$C_6$)alkynyl, heterocycle, aryl, aryl($C_1$-$C_6$)alkyl, halo, $COOR_{4c}$, $CONR_{4c}R_{4d}$, or absent when Y is N;

$R_{4a}$ and $R_{4b}$ are each independently hydrogen, ($C_1$-$C_6$)alkyl, ($C_2$-$C_6$)alkenyl, ($C_2$-$C_6$)alkynyl, heterocycle, or aryl;

$R_{4c}$, and $R_{4d}$ are each independently hydrogen, ($C_1$-$C_6$)alkyl, ($C_2$-$C_6$)alkenyl, ($C_2$-$C_6$)alkynyl, heterocycle, or aryl;

X, Y, and W are each independently N, C, $CR_{4c}$, S or P;

$R_{44}$ is H, hydroxy, mercapto, cyano, —$SNR_{4c}R_{4d}$, —C(NH)$NR_{4c}R_{4d}$, —C(=NH)NHOH, —C(NH)$NHOR_{4c}$, —C(=NH)$NHNR_{4c}R_{4d}$, $NHCOR_{4c}$, $SR_{4c}$, $OR_{4c}$, $SOR_{4c}$, $SO_2R_{4c}$, —C(=O)$NR_{4c}R_{4d}$, —C(=S)$NR_{4c}R_{4d}$, or $R_{4c}$;

$R_{45}$ is H, hydroxy, mercapto, cyano, —$SNR_{4c}R_{4d}$, —C(NH)$NR_{4c}R_{4d}$, —C(=NH)NHOH, —C(NH)$NHOR_{4c}$, —C(=NH)$NHNR_{4c}R_{4d}$, $NHCOR_{4c}$, $SR_{4c}$, $OR_{4c}$, $SOR_{4c}$, $SO_2R_{4c}$, —C(=O)$NR_{4c}R_{4d}$, —C(=S)$NR_{4c}R_{4d}$, or $R_{4c}$;

$R_{46}$, and $R_{47}$ together with the atoms to which they are attached form a heterocyclic ring; and U is S or O;

wherein each aryl or heterocycle is optionally substituted with one or more ($C_1$-$C_6$)alkyl, ($C_1$-$C_6$)alkylthio, ($C_1$-$C_6$)alkoxy, ($C_1$-$C_6$)alkanoyl, ($C_1$-$C_6$)alkanoyloxy, ($C_1$-$C_6$)alkoxycarbonyl, cyano, halo, hydroxy, nitro, carboxy, ($C_3$-$C_8$)cycloalkyl, ($C_3$-$C_8$)cycloalkoxy, trifluoromethoxy, mercapto, or trifluoromethyl;

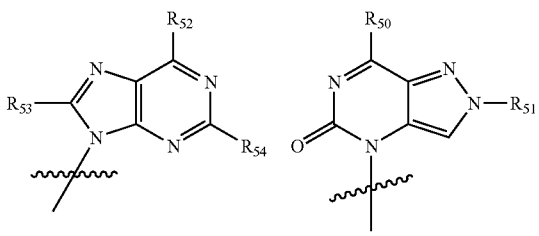

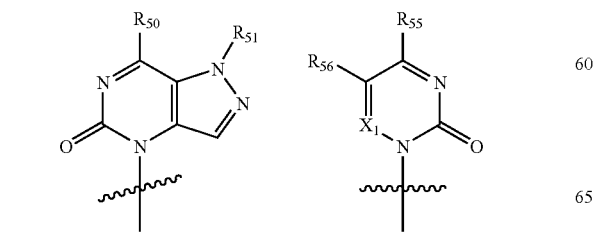

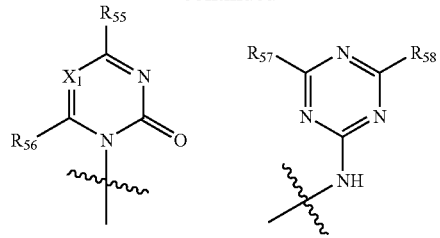

wherein:

$R_{50}$ is $NR_{5a}R_{5b}$, $ONR_{5a}R_{5b}$, $NR_{5a}NR_{5a}R_{5b}$, $SR_{5b}$, $OR_{5b}$, H, hydroxy, ($C_1$-$C_6$)alkyl, ($C_1$-$C_6$)alkenyl, ($C_1$-$C_6$)alkynyl, or aryl;

$R_{51}$ is ($C_1$-$C_6$)alkyl, ($C_1$-$C_6$)alkanoyl, or aryl;

$R_{52}$ is ($C_1$-$C_6$)alkyl, ($C_1$-$C_6$)alkenyl, ($C_1$-$C_6$)alkynyl, or aryl;

$R_{53}$ is H, halo, ($C_1$-$C_6$)alkyl, ($C_1$-$C_6$)alkenyl, ($C_1$-$C_6$)alkynyl, or aryl;

$R_{54}$ is H or $NH_2$;

$R_{55}$ is $NR_{5a}R_{5b}$, $ONR_{5a}R_{5b}$, $NR_{5a}NR_{5a}R_{5b}$, $SR_{5b}$, $OR_{5b}$, H, hydroxy, ($C_1$-$C_6$)alkyl, ($C_1$-$C_6$)alkenyl, ($C_1$-$C_6$)alkynyl, or aryl;

$R_{56}$ is H, halo, ($C_1$-$C_6$)alkyl, or ($C_1$-$C_6$)alkenyl;

$R_{57}$ and $R_{58}$ are each independently —L—$R_{5c}$;

each L is independently a direct bond, —N($R_{5a}$)—, O or S;

each $X_1$ is N or CH;

each $R_{5a}$ and $R_{5b}$ is independently H, hydroxy, ($C_1$-$C_6$)alkyl, ($C_1$-$C_6$)alkenyl, ($C_1$-$C_6$)alkynyl, or aryl; and each $R_{5c}$ is $NR_{5a}R_{5b}$, H, hydroxy, ($C_1$-$C_6$)alkyl, ($C_1$-$C_6$)alkenyl, ($C_1$-$C_6$)alkynyl, or aryl;

wherein each ($C_1$-$C_6$)alkyl, ($C_1$-$C_6$)alkenyl, ($C_1$-$C_6$)alkynyl, or aryl of $R_{50}$-$R_{58}$ and $R_{5a}$-$R_{5c}$ is optionally substituted with one or more ($C_1$-$C_6$)alkyl, ($C_1$-$C_6$)alkylthio, ($C_1$-$C_6$)alkoxy, ($C_1$-$C_6$)alkanoyl, ($C_1$-$C_6$)alkanoyloxy, ($C_1$-$C_6$)alkoxycarbonyl, cyano, halo, hydroxy, nitro, carboxy, ($C_3$-$C_8$)cycloalkyl, ($C_3$-$C_8$)cycloalkoxy, trifluoromethoxy, mercapto, or trifluoromethyl;

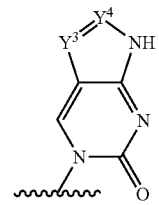

wherein:

$Y^3$=$Y^4$ is —N=N—, —CH=N—, —N=$CR_{8a}$—, or —CH=$CR_{8a}$—; and each $R_{8a}$ is independently H, halo, or ($C_1$-$C_6$)alkyl;

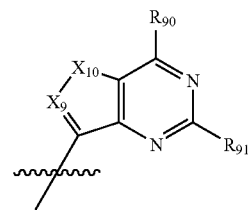

wherein:
- $X_9$ is $CR_{90a}$ or N;
- $X_{10}$ is O, S, or $NR_{91a}$;
- $R_{90}$ and $R_{91}$ are each independently H, halo, hydroxy, ($C_1$-$C_6$)alkoxy, $NR_{90b}R_{91b}$, or heterocycle;
- $R_{90a}$ is H, halo, methyl, azido, or amino;
- $R_{91a}$ is H, or ($C_1$-$C_6$)alkyl; and
- $R_{90b}$ and $R_{91b}$ are each independently H, ($C_1$-$C_6$)alkyl, ($C_3$-$C_8$)cycloalkyl, or aryl($C_1$-$C_6$)alkyl;
- wherein each ($C_1$-$C_6$)alkyl, ($C_3$-$C_8$)cycloalkyl, aryl($C_1$-$C_6$)alkyl, and heterocycle of $R_{90}$—$R_{91}$, $R_{91a}$, and $R_{90b}$-$R_{91b}$ are optionally substituted with one or more (e.g. 1, 2, 3, or 4) halo, hydroxy, amino, ($C_1$-$C_6$)alkyl, and ($C_1$-$C_6$)alkoxy;

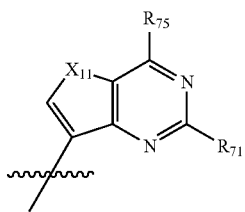

wherein:
- $X_{11}$ is O, S, or $NR_{70a}$;
- $R_{75}$ and $R_{71}$ are each independently H, halo, hydroxy, mercapto, aryl, heterocycle, ($C_1$-$C_6$)alkyl, ($C_1$-$C_6$)alkenyl, ($C_1$-$C_6$)alkynyl, ($C_1$-$C_6$)alkylthio, arylthio, —S(=O)($C_1$-$C_6$)alkyl, —S(=O)$_2$($C_1$-$C_6$)alkyl, —S(=O)$_2$$NR_{70b}R_{71b}$, $NR_{70b}R_{71b}$, ($C_1$-$C_6$) alkoxy, aryloxy, (heterocycle)oxy;
- $R_{70a}$ is H, methyl, ethyl, or acetyl; and
- $R_{70b}$ and $R_{71b}$ are each independently H, ($C_1$-$C_6$)alkyl, aryl, aryl($C_1$-$C_6$)alkyl, ($C_1$-$C_6$)alkanoyl, or aryl-C(=O)—; or

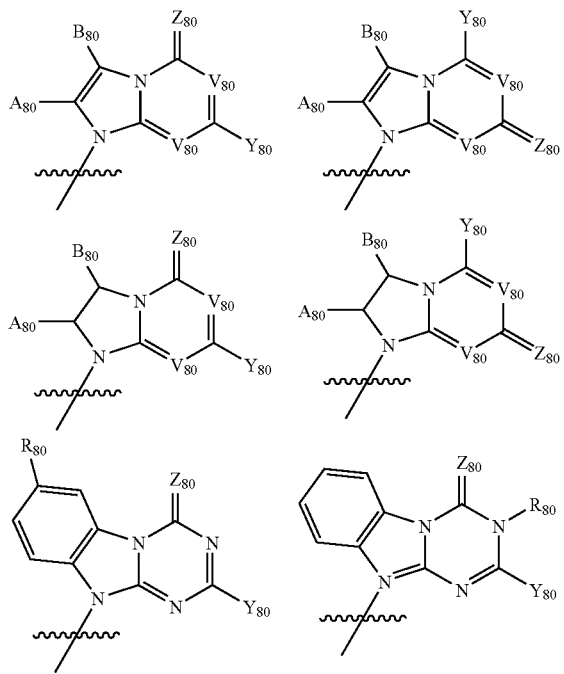

wherein:
- $A_{80}$, $B_{80}$, and $Y_{80}$, are each independently H, halo, $OR_{80}$, $S(O)R_{80}$, $NR_{80}R_{81}$, cyano, trifluoromethyl, C(=W)$OR_{80}$, C(=W)$SR_{80}$, C(=W)$NR_{80}R_{81}$, nitro, azido, carbocyclic, ($C_1$-$C_6$)alkyl, ($C_1$-$C_6$)alkenyl, ($C_1$-$C_6$)alkynyl, aryl, aryl($C_1$-$C_6$)alkyl, or heterocycle; or $A_{80}$ and $B_{80}$ taken together with the carbon atoms to which they are attached from a 4-7 membered carbocyclic or heterocyclic ring;
- n is 0, 1, or 2
- $Z_{80}$ is O, S, $NR_{80}$, or $CR_{80}R_{81}$;
- each $V_{80}$ is independently N or $CR_{80}$; and
- each $R_{80}$ and $R_{81}$ is independently H, carbocycle, ($C_1$-$C_6$) alkyl, ($C_1$-$C_6$)alkenyl, ($C_1$-$C_6$)alkynyl, halo, ($C_1$-$C_6$) alkoxy, amino, methylamino, dimethylamino, cyano, ($C_1$-$C_6$)alkanoyl, aryl, aryl($C_1$-$C_6$)alkyl, an amino acid residue (e.g. a naturally-occurring amino acid residue) or heterocycle; or $R_{80}$ and $R_{81}$ taken together with the atom(s) to which they are attached form a 3-7 membered carbocyclic or heterocyclic ring.

4. The compound according to claim 1, wherein B is

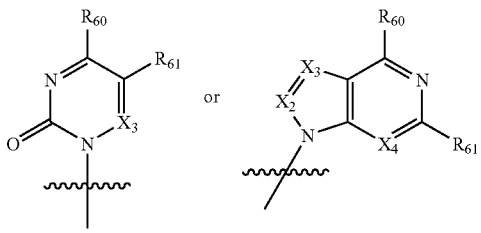

wherein:
- $X_2$, $X_3$, and $X_4$ are each independently N, CH, or C—$R_{6a}$;
- $R_{60}$, $R_{61}$, and $R_{6a}$ are each independently H, halo, $NR_{6b}R_{6c}$, hydroxyamino, $NR_{6b}NR_{6b}R_{6c}$, $N_3$, NO, $NO_2$, formyl, cyano, —C(=O)$NR_{6b}R_{6c}$, —C(=S)$NR_{6b}R_{6c}$, —C(=O)$OR_{6b}$, $R_{6b}$, $OR_{6b}$, or $SR_{6b}$; and
- $R_{6b}$, and $R_{6c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, —S(O)$_2$($C_1$-$C_6$)alkyl or aryl($C_1$-$C_6$)alkyl;

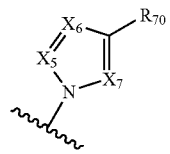

wherein:
- $X_5$, $X_6$, and $X_7$, are each independently N, CH, or C—$R_{7a}$;
- $R_{70}$ and $R_{7a}$ are each independently H, halo, $NR_{7b}R_{7c}$, hydroxyamino, $NR_{7b}NR_{7b}R_{7c}$, $N_3$, NO, $NO_2$, formyl, cyano, —C(=O)$NR_{7b}R_{7c}$, —C(=S)$NR_{7b}R_{7c}$, —C(=O)$OR_{7b}$, $R_{7b}$, $OR_{7b}$, or $SR_{7b}$; and
- $R_{7b}$, and $R_{7c}$ are each independently H, ($C_1$-$C_6$)alkyl, ($C_1$-$C_6$)alkenyl, ($C_1$-$C_6$)alkynyl, aryl, ($C_1$-$C_6$)alkanoyl, or aryl($C_1$-$C_6$)alkyl;

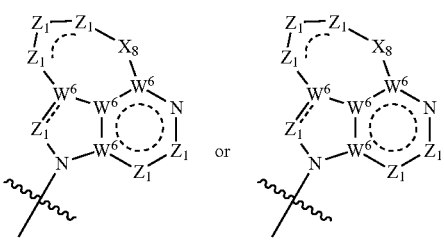

wherein:
each $Z_1$ is independently N, C—$R_{9a}$, O, S, $NR_{9b}$, >C=O, >C=S, >C=$NR_{9b}$, >S=O, >S(O)$_2$ or CH—$R_{9a}$; provided that if a $Z_1$ participates in an optional bond represented by a dotted line --- in the formula, then that $Z_1$ is N or C—$R_a$; and provided that if a $Z_1$ does not participate in an optional bond represented by a dotted line --- in the formula, then that $Z_1$ is O, S, $NR_{9b}$, >C=O, >C=S, >C=$NR_{9b}$, >S=O, >S(O)$_2$ or CH—$R_{9a}$;

$X_8$ is O, S, SO, SO$_2$, Se, SeO, SeO$_2$ or $NR_{9b}$;

each $W^6$ is C, CH, or N; wherein if a $W^6$ participates in an optional bond represented by a dotted line --- in the formula, then that $W^6$ is C; and if a $W^6$ does not participate in an optional bond represented by a dotted line --- in the formula, then that $W^6$ is CH, or N;

each $R_{9a}$ is independently H, halo, $NR_{9c}R_{9d}$, hydroxyamino, $NR_{9c}NR_{9c}R_{9d}$, N$_3$, cyano, —C(=O)$NR_{9c}R_{9d}$, —C(=S)$NR_{9c}R_{9d}$, —C(=S)$NR_{9c}R_{9d}$, —C(=NH)$OR_{9c}$, $R_{9c}$, $OR_{9c}$, or $SR_{9c}$;

each $R_{9b}$ is independently H, (C$_1$-C$_6$)alkyl, (C$_1$-C$_6$)alkenyl, (C$_1$-C$_6$)alkynyl, aryl, (C$_1$-C$_6$)alkanoyl, or aryl(C$_1$-C$_6$)alkyl; and $R_{9c}$ and $R_{9d}$ are each independently H, (C$_1$-C$_6$)alkyl, (C$_1$-C$_6$)alkenyl, (C$_1$-C$_6$)alkynyl, aryl, (C$_1$-C$_6$)alkanoyl, or aryl(C$_1$-C$_6$)alkyl; or

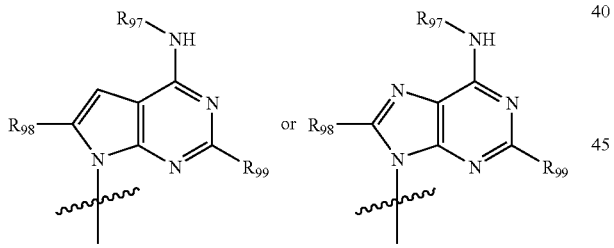

wherein:
$R_{97}$ is H, hydroxy, mercapto, (C$_1$-C$_6$)alkyl, (C$_1$-C$_6$)alkoxy, (C$_2$-C$_6$)alkenyl, (C$_3$-C$_8$)cycloalkyl, aryl(C$_1$-C$_6$)alkyl, aryl or (C$_2$-C$_6$)alkynyl;

$R_{98}$ is H, hydroxy, mercapto, or (C$_1$-C$_6$)alkyl;

$R_{99}$ is H, halo, azido, cyano, nitro, $OR_{99a}$, $SR_{99a}$, $NR_{99b}R_{99c}$, (C$_1$-C$_6$)alkyl, (C$_2$-C$_6$)alkenyl, (C$_3$-C$_8$)cycloalkyl, aryl(C$_1$-C$_6$)alkyl, aryl or (C$_2$-C$_6$)alkynyl;

each $R_{99a}$ is independently H, (C$_1$-C$_6$)alkyl, or (C$_1$-C$_6$) alkanoyl;

each $R_{99b}$ and $R_{99c}$ is independently H, (C$_1$-C$_6$)alkyl, or (C$_1$-C$_6$)alkanoyl;

wherein each (C$_1$-C$_6$)alkyl, (C$_1$-C$_6$)alkoxy (C$_1$-C$_6$)alkenyl, (C$_1$-C$_6$)alkynyl, (C$_3$-C$_8$)cycloalkyl, aryl, and aryl (C$_1$-C$_6$)alkyl of $R_{97}$, $R_{98}$, $R_{99}$, $R_{99a}$, $R_{99b}$, and $R_{99c}$, is optionally substituted with one or more (C$_1$-C$_6$)alkyl, (C$_1$-C$_6$)alkylthio, (C$_1$-C$_6$)alkoxy, (C$_1$-C$_6$)alkanoyl, (C$_1$-C$_6$)alkanoyloxy, (C$_1$-C$_6$)alkoxycarbonyl, NH$_2$, cyano, azido, halo, hydroxy, nitro, carboxy, trifluoromethoxy, aryl, or mercapto.

5. The compound according to claim 1, wherein B is

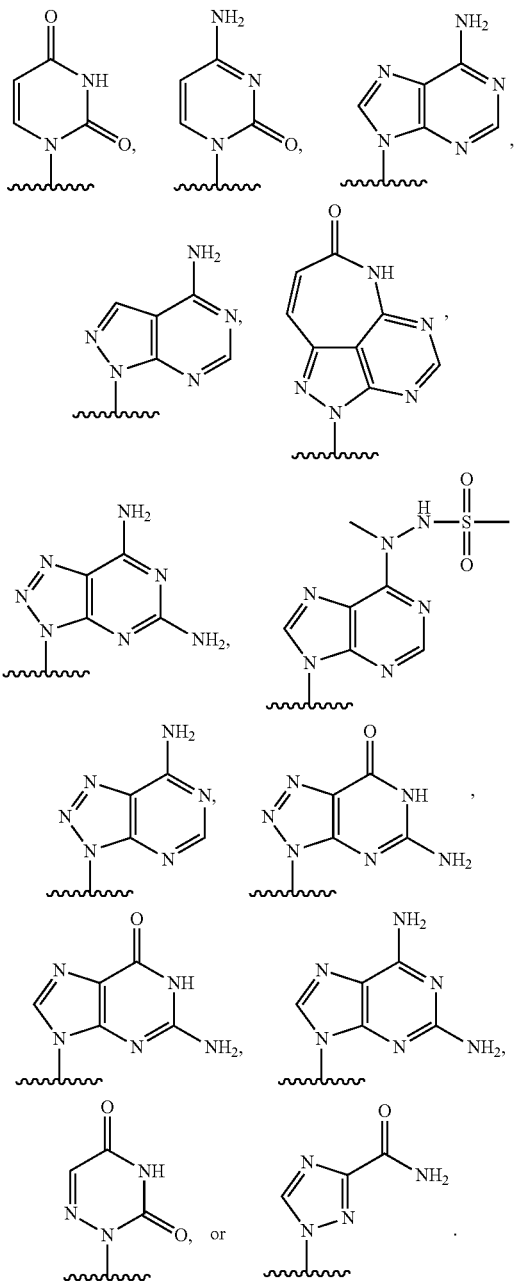

6. The compound according to claim 1, wherein $R^2$ and $R^3$ are both H and one of $R^4$ or $R^5$ is OH.

7. The compound according to claim 1, wherein each $R^3$ and $R^4$ is H and $R^2$ is H or F.

8. The compound according to claim 1, wherein $R^2$ and $R^4$ are H, $R^3$ is OH and $R^5$ is F.

9. The compound according to claim 1, wherein $R^1$ is CN, N$_3$, methyl, $OR^a$, ethenyl, or ethynyl.

10. The compound according to claim 1, wherein $R^1$ is $N_3$.

11. The compound according to claim 1, wherein

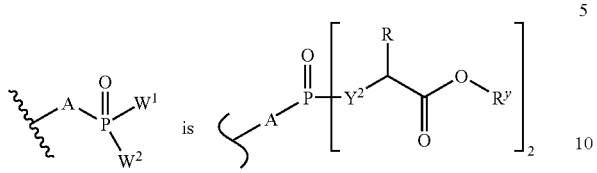

wherein each $Y^2$ is independently —O— or —NH—.

12. The compound according to claim 11, wherein each R is $CH_3$ and each $R^y$ is, independently, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, or $C_2$-$C_8$ substituted alkynyl.

13. The compound according to claim 11 or 12, wherein each $Y^2$ is —NH—.

14. The compound according to claim 1, wherein

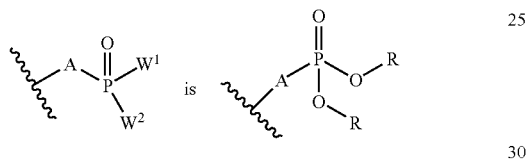

wherein each R is, independently, $C_1$-$C_8$ alkyl, $C_6$-$C_{20}$ aryl or $C_6$-$C_{20}$ substituted aryl.

15. A compound that is:

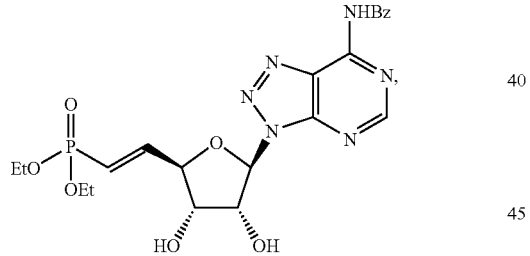

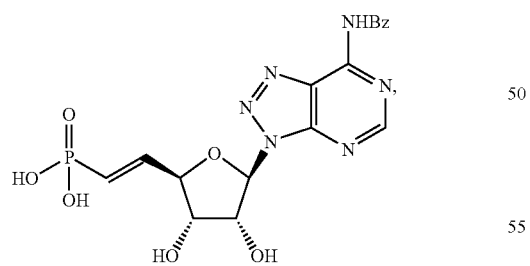

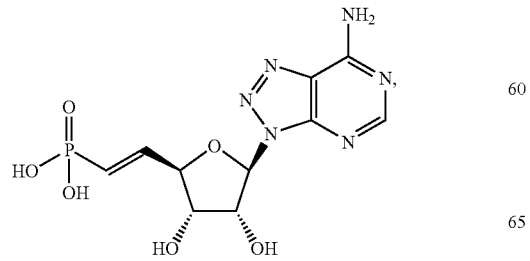

-continued

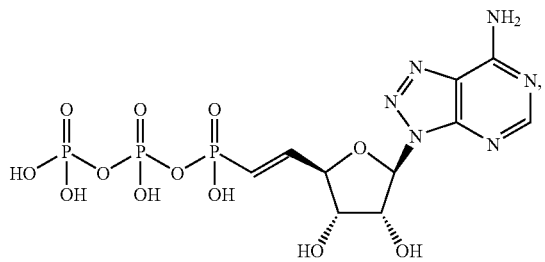

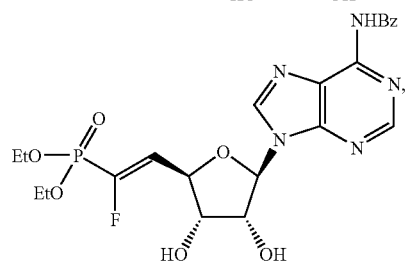

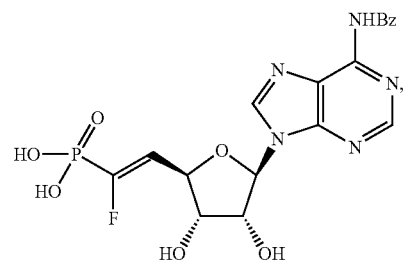

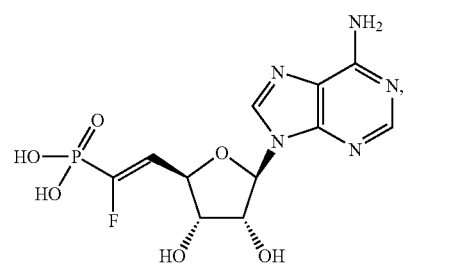

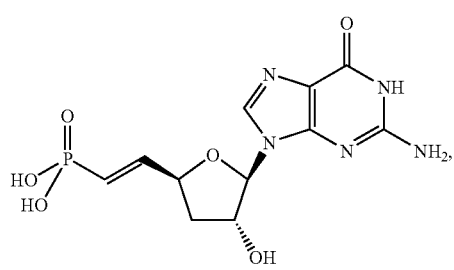

275
-continued
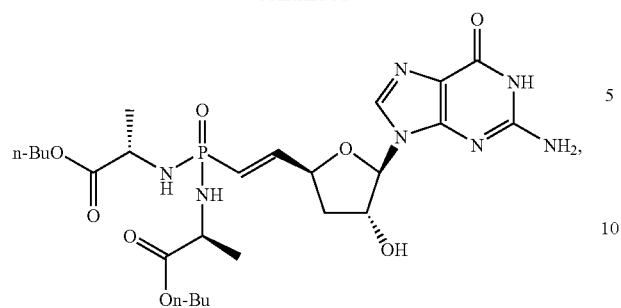
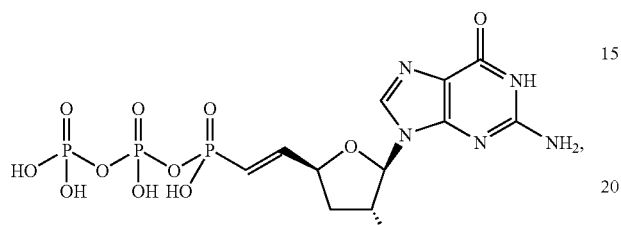
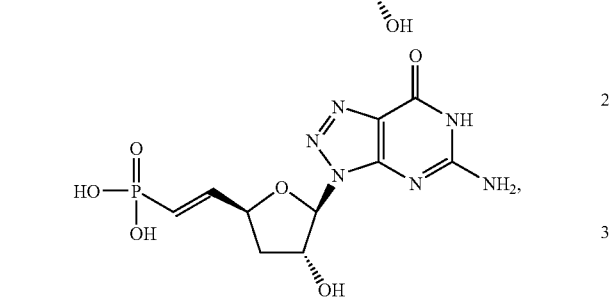
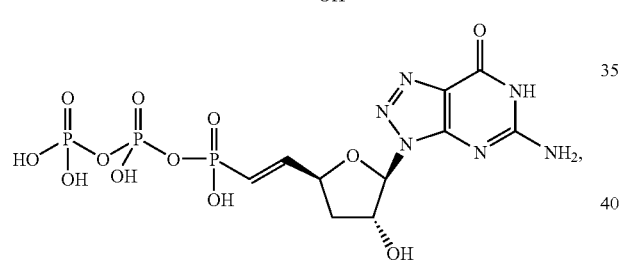
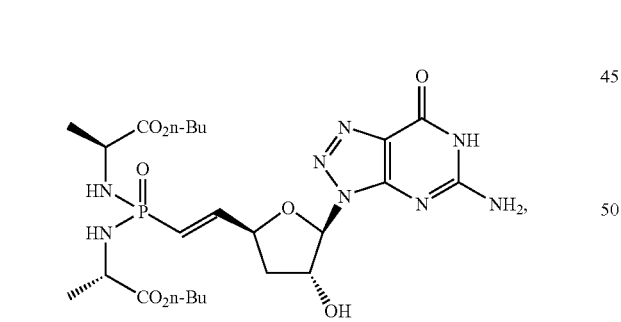
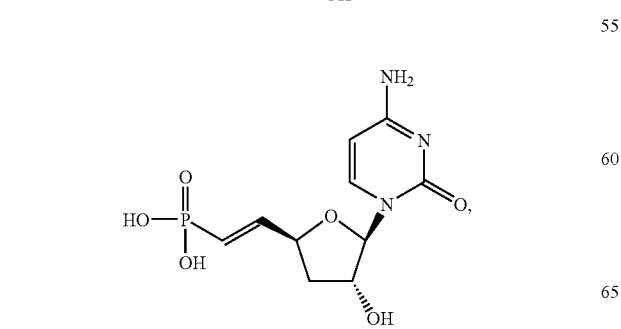
276
-continued
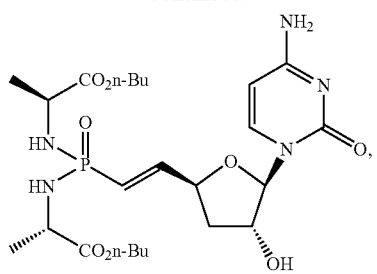
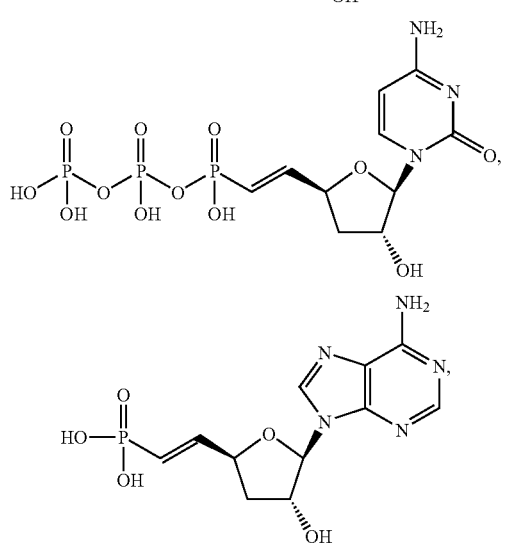
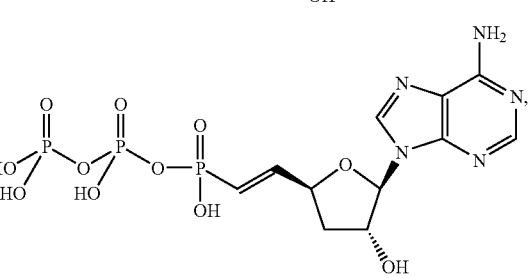
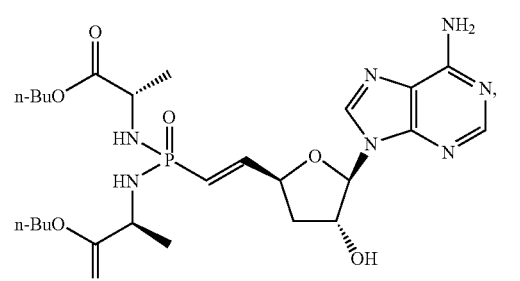
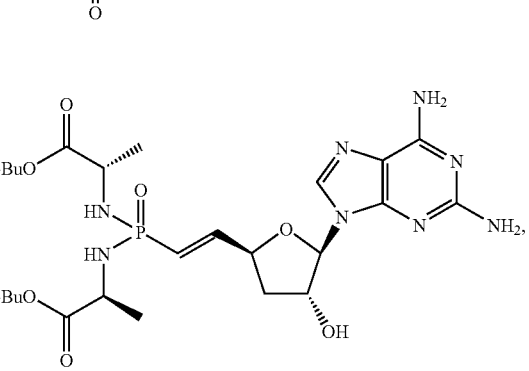

277
-continued
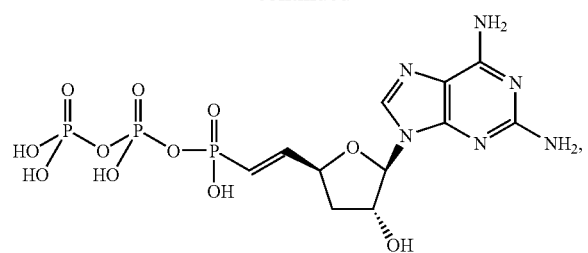
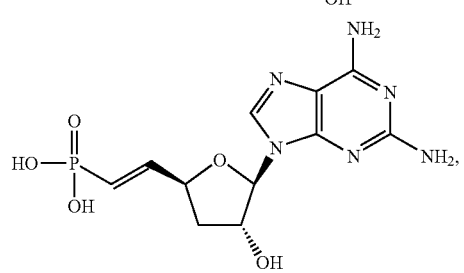
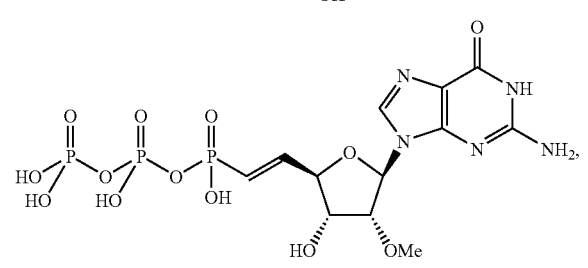
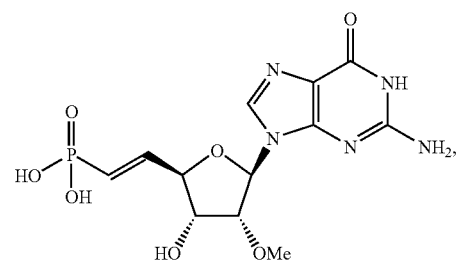
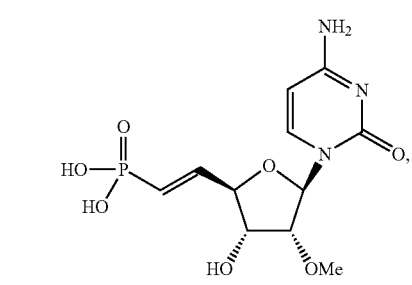
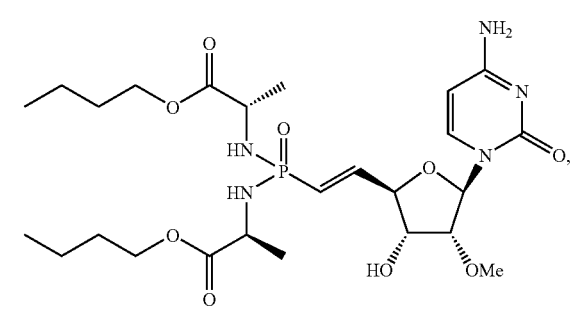
278
-continued
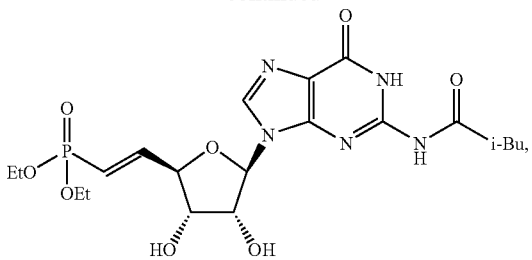
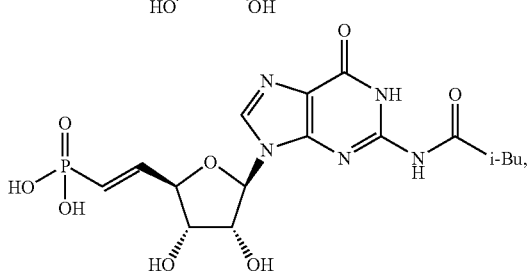
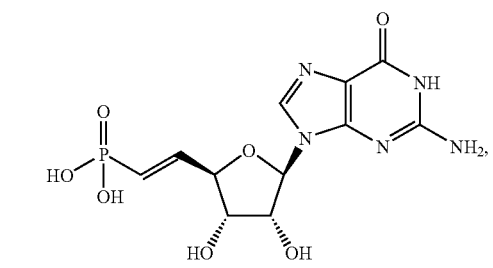
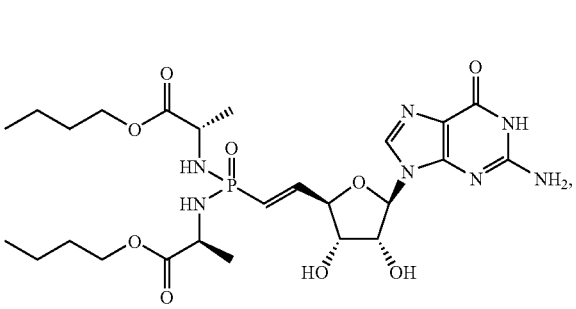
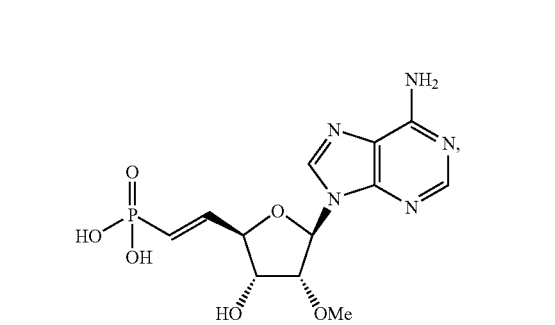
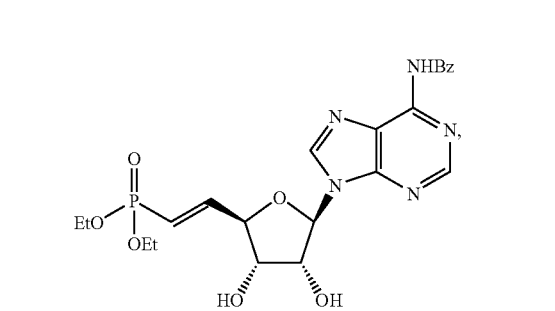

279
-continued
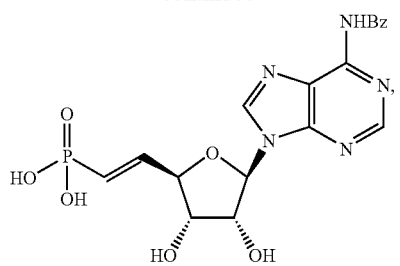
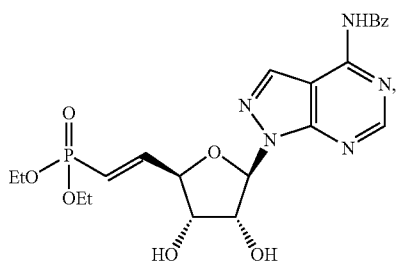
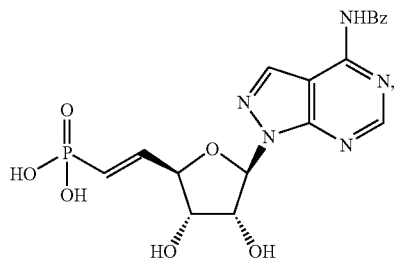
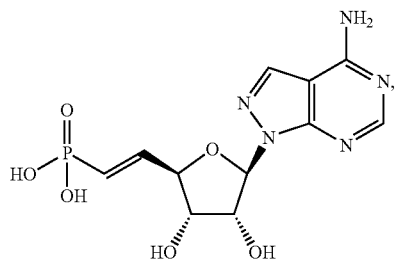
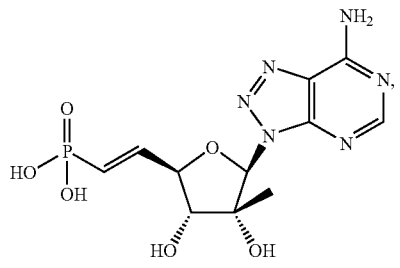
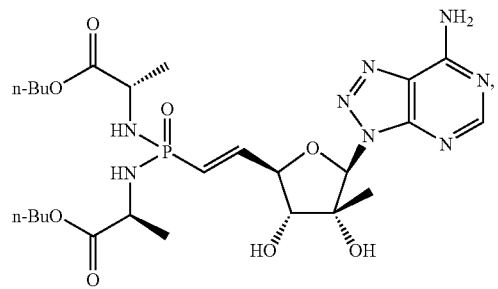
280
-continued
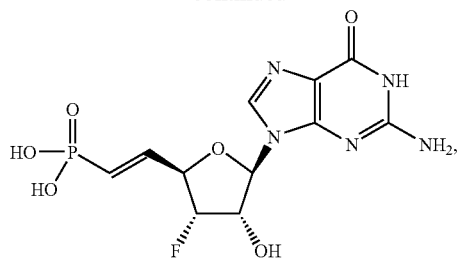
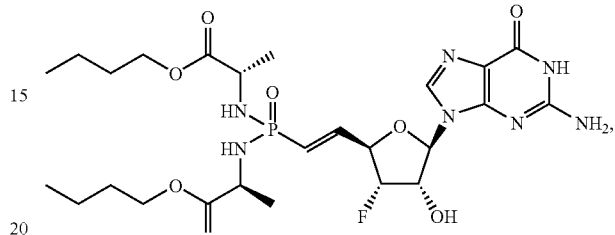
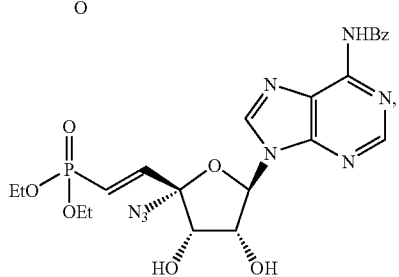
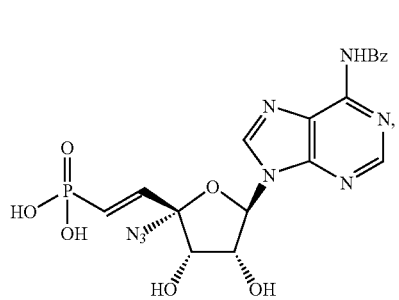
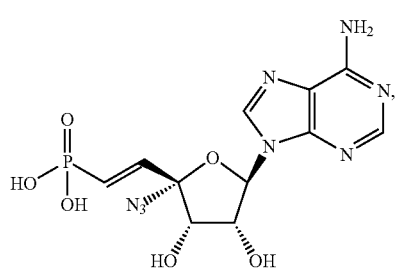
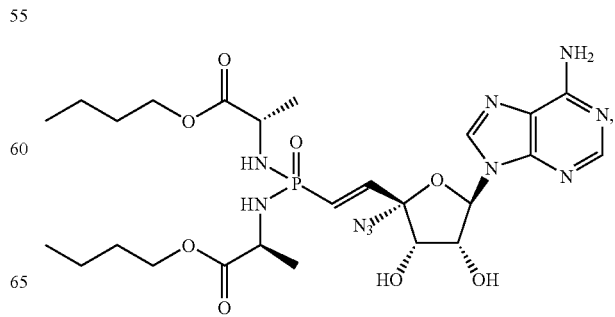

281
-continued
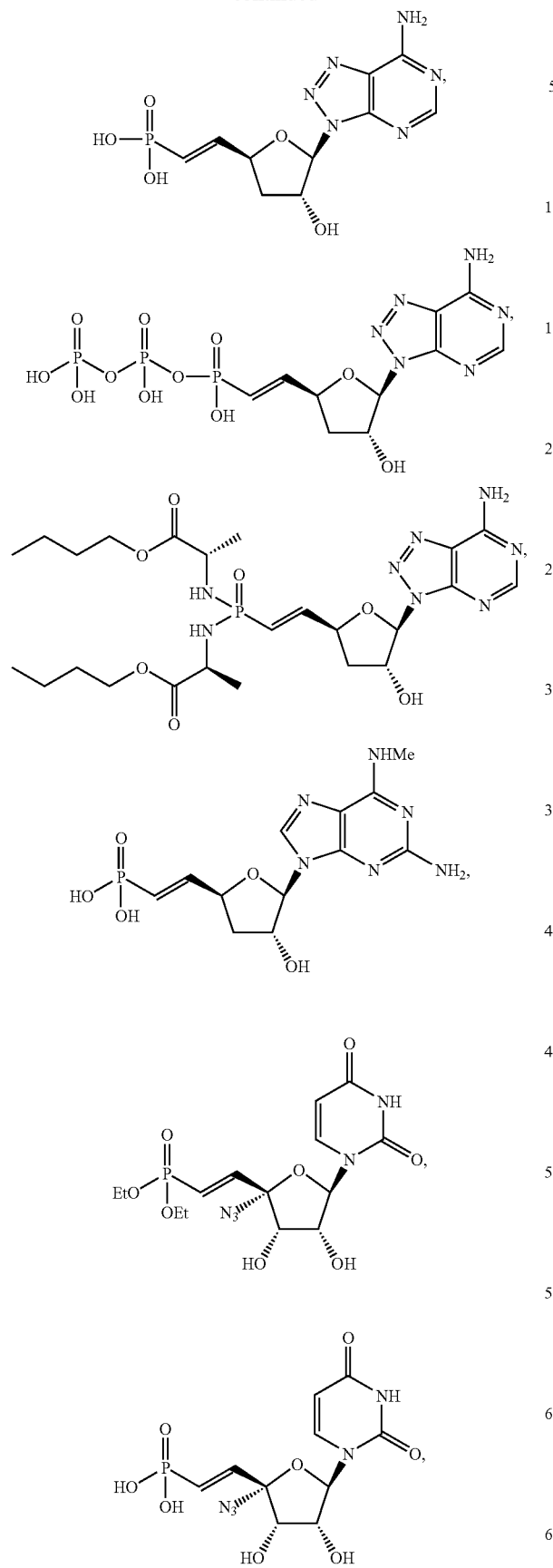
282
-continued
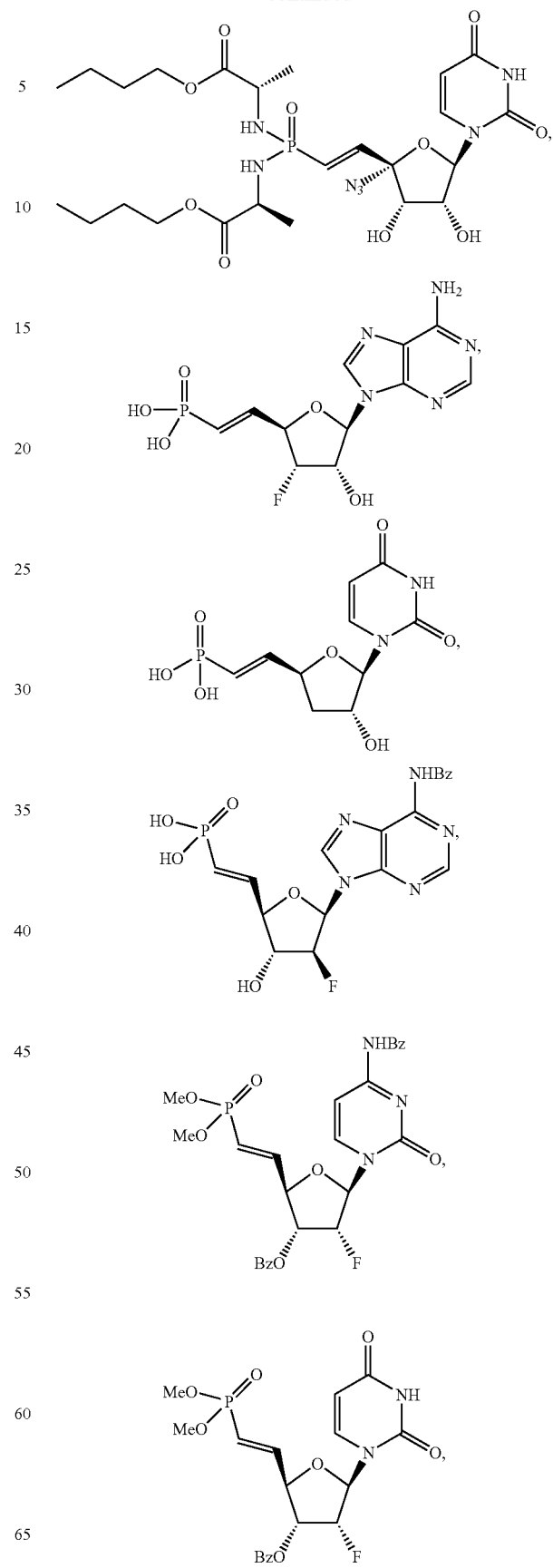

283 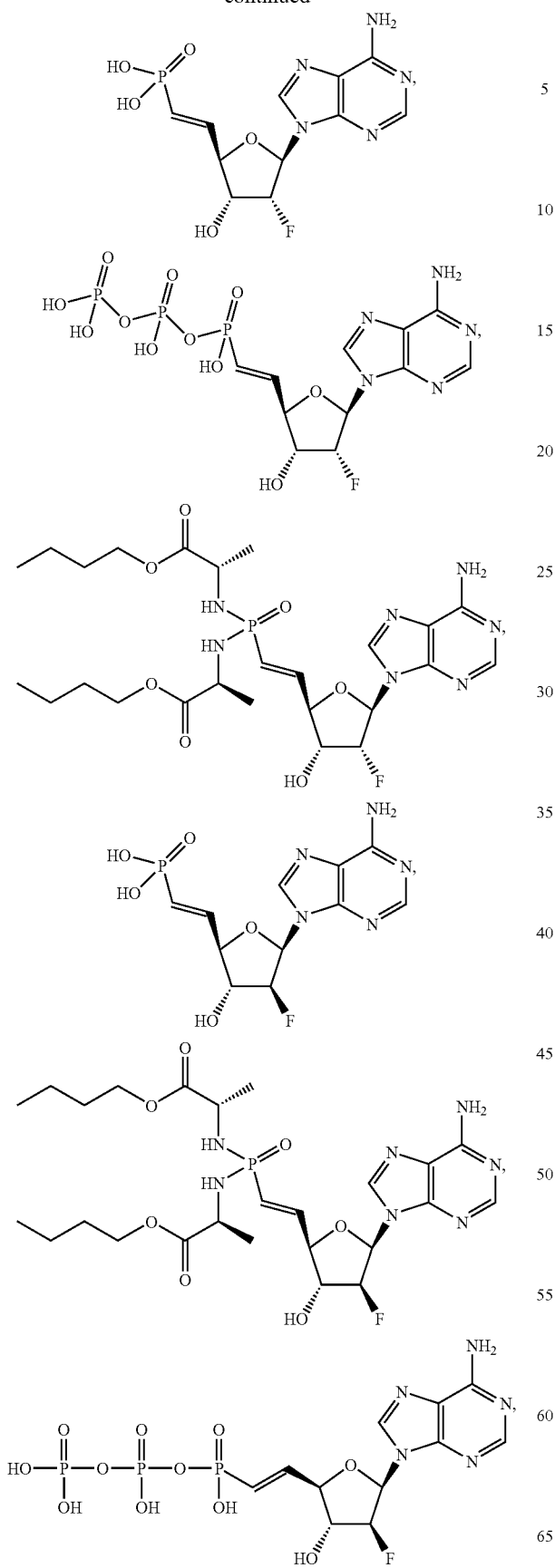
284 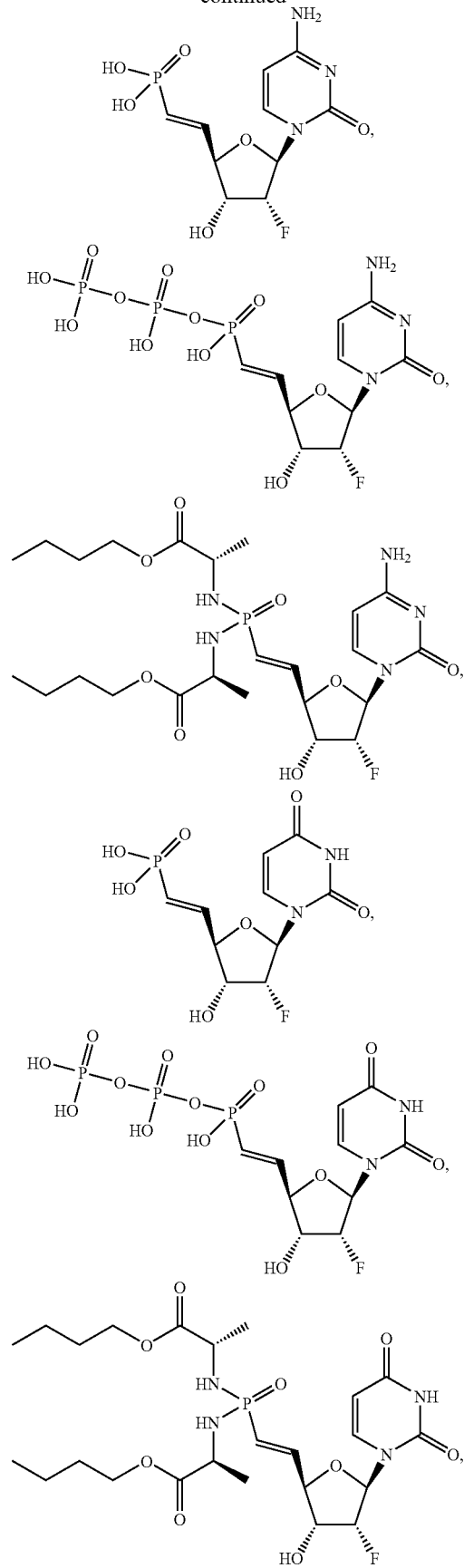

285
-continued
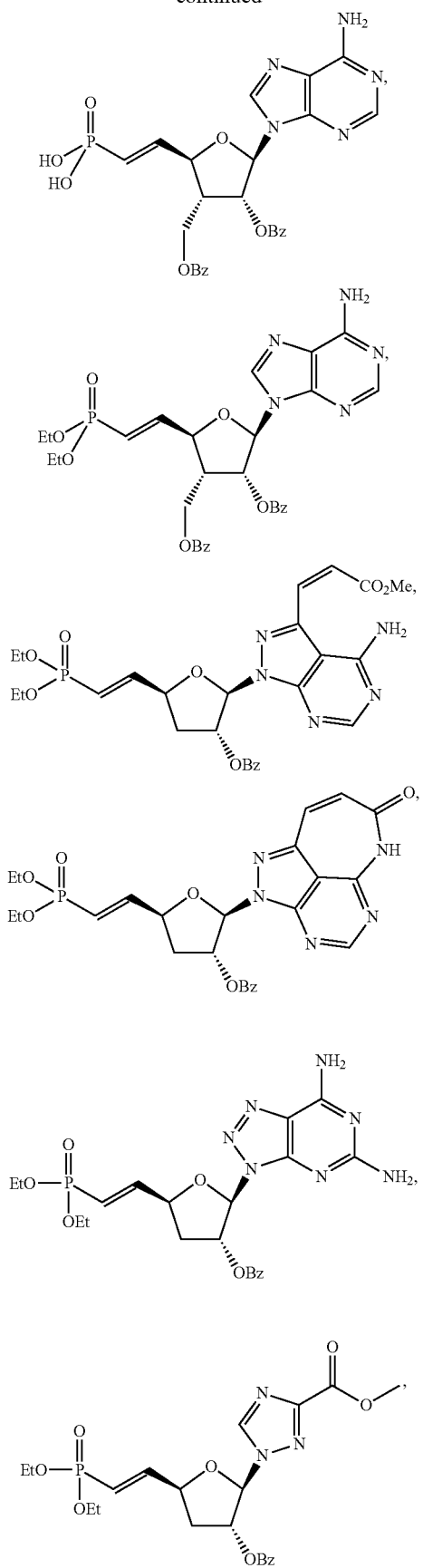
286
-continued
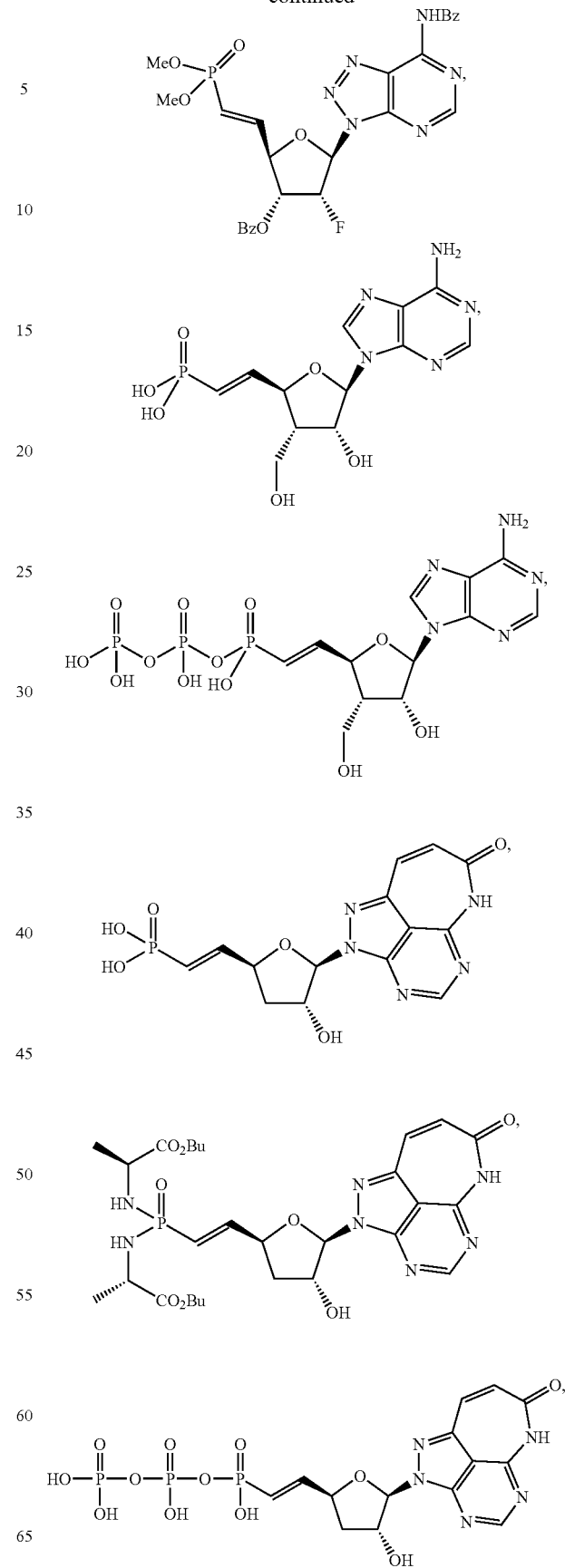

287
-continued

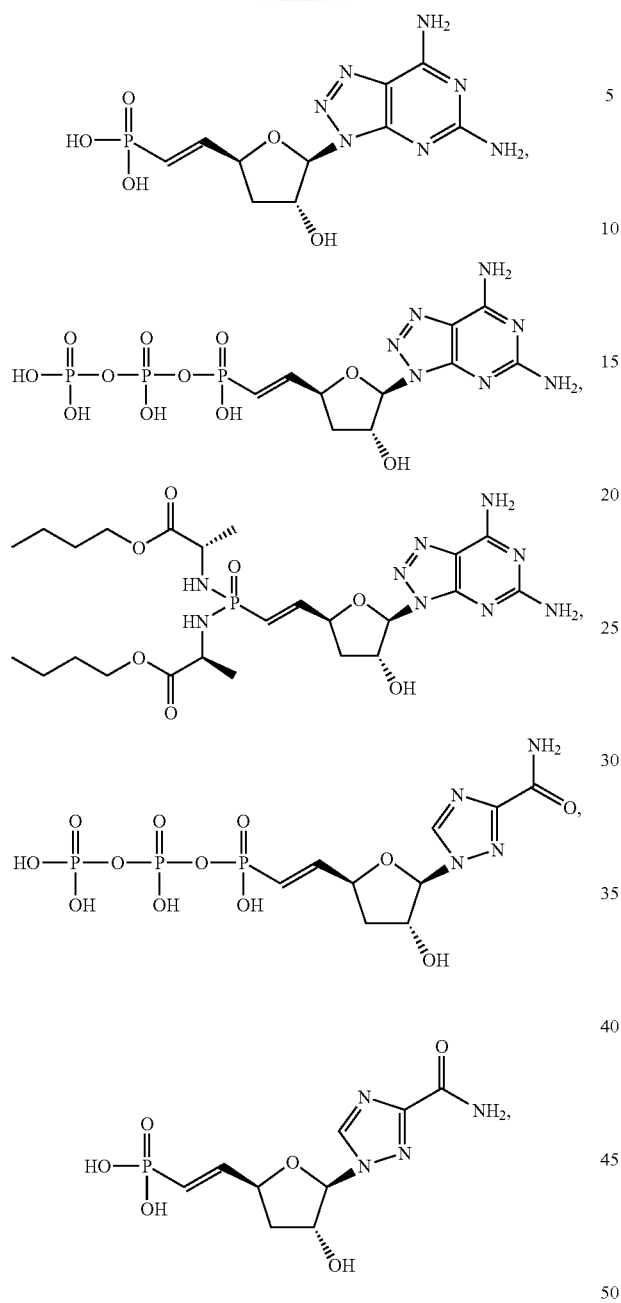

288
-continued

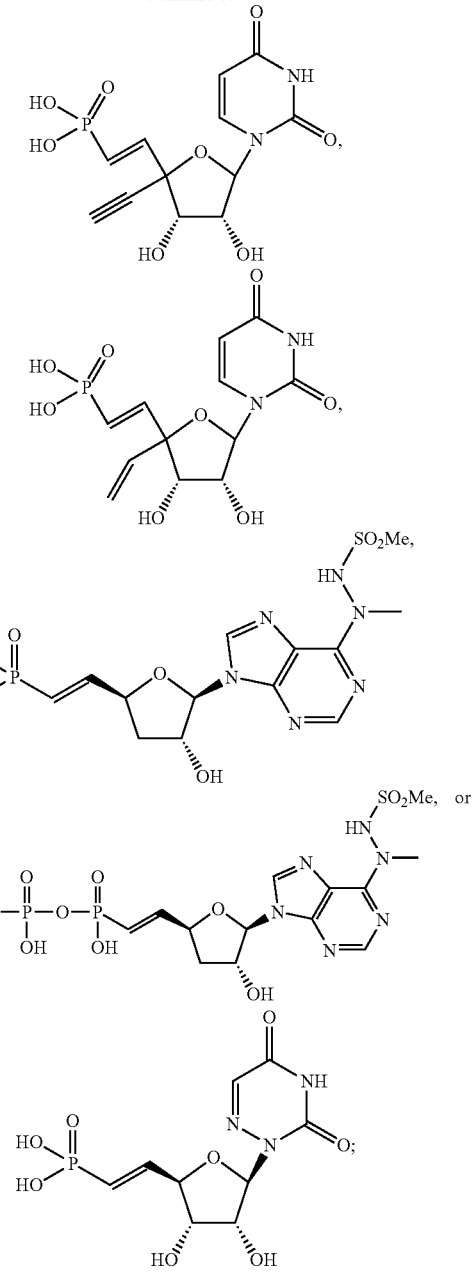

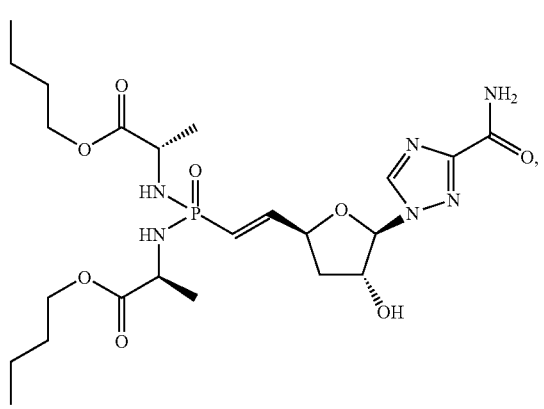

or a pharmaceutical acceptable salt thereof.

16. A pharmaceutical composition comprising a therapeutically effective amount of a compound as in claim 1 and a pharmaceutically acceptable carrier.

17. The pharmaceutical composition of claim 16 further comprising at least one additional therapeutic agent.

18. The pharmaceutical composition of claim 17, wherein said at least one additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

19. A method of inhibiting HCV polymerase comprising the administration to a mammal in need of such treatment a therapeutically effective amount of a compound of claim 1.

20. A method of treating infection by HCV comprising the administration to a mammal in need of such treatment a therapeutically effective amount of a compound of claim 1.

21. The method of claim 20, further comprising administering at least one additional therapeutic agent.

22. The method of claim 21, wherein said at least one additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

\* \* \* \* \*